US008771702B2

(12) United States Patent
Paterson et al.

(10) Patent No.: US 8,771,702 B2
(45) Date of Patent: Jul. 8, 2014

(54) NON-HEMOLYTIC LLO FUSION PROTEINS AND METHODS OF UTILIZING SAME

(75) Inventors: Yvonne Paterson, Philadelphia, PA (US); Paulo Cesar Maciag, Princeton, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 21 days.

(21) Appl. No.: 12/213,696

(22) Filed: Jun. 23, 2008

(65) Prior Publication Data

US 2009/0081248 A1 Mar. 26, 2009

(51) Int. Cl.
*A61K 39/02* (2006.01)
*C07K 2/00* (2006.01)
*C12N 15/64* (2006.01)

(52) U.S. Cl.
USPC .................. 424/192.1; 530/403; 435/320.1; 536/23.72

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,521,382 A | 6/1985 | Kessick et al. | |
| 4,567,041 A | 1/1986 | Likhite et al. | |
| 4,777,239 A | 10/1988 | Schoolnik et al. | |
| 4,816,253 A | 3/1989 | Likhite et al. | |
| 4,879,213 A | 11/1989 | Fox et al. | |
| 5,262,177 A | 11/1993 | Brown et al. | |
| 5,342,774 A | 8/1994 | Boon et al. | |
| 5,369,008 A | 11/1994 | Arlinghause et al. | |
| 5,643,599 A | 7/1997 | Lee et al. | |
| 5,679,356 A | 10/1997 | Bonnem et al. | |
| 5,681,570 A | 10/1997 | Yang et al. | |
| 5,719,054 A | 2/1998 | Boursnell et al. | |
| 5,728,399 A * | 3/1998 | Wu et al. ...................... | 424/450 |
| 5,824,538 A | 10/1998 | Branstrom et al. | |
| 5,830,702 A | 11/1998 | Portnoy et al. | |
| 5,858,682 A | 1/1999 | Gruenwald et al. | |
| 5,876,735 A | 3/1999 | Reed | |
| 5,877,159 A | 3/1999 | Powell et al. | |
| 6,015,567 A | 1/2000 | Hudziak et al. | |
| 6,051,237 A | 4/2000 | Paterson et al. | |
| 6,306,404 B1 | 10/2001 | LaPosta et al. | |
| 6,333,169 B1 | 12/2001 | Hudziak et al. | |
| 6,479,258 B1 | 11/2002 | Short et al. | |
| 6,521,449 B1 | 2/2003 | Polack et al. | |
| 6,565,852 B1 | 5/2003 | Paterson et al. | |
| 6,627,617 B1 | 9/2003 | Samulski et al. | |
| 6,767,542 B2 | 7/2004 | Paterson et al. | |
| 6,855,320 B2 | 2/2005 | Paterson et al. | |
| 7,135,188 B2 | 11/2006 | Paterson et al. | |
| 7,198,792 B2 | 4/2007 | Regts et al. | |
| 7,217,419 B2 | 5/2007 | Wettendorff | |
| 7,488,490 B2 * | 2/2009 | Davis et al. .................. | 424/278.1 |
| 2002/0025323 A1 | 2/2002 | Paterson et al. | |
| 2003/0028206 A1 | 2/2003 | Shiber et al. | |
| 2003/0202985 A1 | 10/2003 | Paterson et al. | |
| 2003/0220239 A1 | 11/2003 | Simard et al. | |
| 2004/0013690 A1 | 1/2004 | Portnoy et al. | |
| 2004/0197343 A1 | 10/2004 | Dubensky et al. | |
| 2004/0228877 A1 | 11/2004 | Dubensky et al. | |
| 2005/0118184 A1 | 6/2005 | Paterson et al. | |
| 2005/0129715 A1 | 6/2005 | Paterson et al. | |
| 2006/0051380 A1 | 3/2006 | Schulick et al. | |
| 2006/0093582 A1 | 5/2006 | Paterson et al. | |
| 2006/0104991 A1 | 5/2006 | Paterson et al. | |
| 2006/0121053 A1 | 6/2006 | Sweeney et al. | |
| 2006/0205067 A1 | 9/2006 | Paterson et al. | |
| 2006/0210540 A1 | 9/2006 | Paterson et al. | |
| 2006/0233835 A1 | 10/2006 | Paterson et al. | |
| 2006/0269561 A1 | 11/2006 | Paterson et al. | |
| 2008/0124354 A1 | 5/2008 | Paterson et al. | |

FOREIGN PATENT DOCUMENTS

| | | |
|---|---|---|
| CA | 2 109 176 | 4/1995 |
| EP | 0 902 086 | 3/1999 |
| JP | 63-173594 | 7/1988 |
| JP | 01 178592 | 7/1989 |
| WO | WO 90/12594 | 11/1990 |
| WO | WO 92/20356 | 11/1992 |
| WO | WO 93/15212 | 8/1993 |
| WO | WO 94/17192 | 8/1994 |
| WO | WO 96/14087 | 5/1996 |
| WO | WO 96/34631 | 11/1996 |
| WO | WO 97/35021 | 9/1997 |
| WO | WO 98/48026 | 10/1998 |
| WO | WO 99/06544 | 2/1999 |
| WO | WO 99/07861 | 2/1999 |

(Continued)

OTHER PUBLICATIONS

Gunn et al. (Journal of Immunology, 2001, vol. 167, p. 6471-6479).*
Mengaud et al. (Infection and Immunity, 1988, vol. 56, p. 766-772).*
S. Farzana Hussain and Yvonne Paterson "What is needed for effective antitumor immunotherapy? Lessons learned using *Listeria monocytogenes* as a live vector for HPV-associated tumors" Cancer Immunology, Immunotherapy vol. 54, No. 6, pp. 577-586, DOI: 10.1007/s00262-004-0600-2, Jun. 1, 2005.
Paterson Y. et al. "A vaccine comprising *Listeria monocytogenes* that expresses a bacterial PEST domain fused to human papilloma virus E7 induces regression of E7 expressing tumors" XP002593518, Database accession No. PREV200200343898, abstract, FASEB Journal, vol. 16, No. 4, Mar. 20, 2002, p. A665.
Paterson et al., "*Listeria*-based vaccines for cancer treatment", Current opinion in molecular therapeutics, Current drugs, vol. 7, No. 5, 2005, pp. 454-460.
Abachin et al., "Formation of D-alanyl-lipoteichoic acid is required for adhesion and virulence of *Listeria monocytogenes*", Molecular Microbiology, 2002, 43(1), 1-14.
Adams et al. (1992) "Cre-*lox* recombination in *Escherichia coli* cells. Mechanistic differences from the in vitro reaction." *J. Mol. Biol.* 226:661-673.

(Continued)

*Primary Examiner* — Agnieszka Boesen
(74) *Attorney, Agent, or Firm* — Mark S. Cohen; Pearl Cohen Zedek Latzer Baratz LLP

(57) ABSTRACT

The present invention provides recombinant proteins or peptides comprising a mutated listeriolysin O (LLO) protein or fragment thereof, comprising a substitution or internal deletion of the cholesterol-binding domain or a portion thereof, fusion proteins or peptides comprising same, nucleotide molecules encoding same, and vaccine vectors comprising or encoding same. The present invention also provides methods of utilizing recombinant proteins, peptides, nucleotide molecules, and vaccine vectors of the present invention to induce an immune response to a peptide of interest.

17 Claims, 51 Drawing Sheets

(56) References Cited

FOREIGN PATENT DOCUMENTS

| WO | WO 99/10496 | 3/1999 |
|---|---|---|
| WO | WO 99/25376 | 5/1999 |
| WO | WO 01/27295 | 4/2001 |
| WO | WO 01/72329 | 10/2001 |
| WO | WO 03/015716 | 2/2003 |
| WO | WO 03/092600 | 11/2003 |
| WO | WO 2004/006837 | 1/2004 |
| WO | WO 2006/036550 | 4/2006 |
| WO | WO 2007/061848 | 5/2007 |
| WO | WO 2007/106476 | 9/2007 |
| WO | WO 2007/130455 | 11/2007 |

OTHER PUBLICATIONS

Aggarwal et al., "Oral Salmonella: Malaria Circumsporozoite Recombinants Induce Specific CD8+ Cytotoxic T Cells", J. Exp. Med. 1990, 172, 1083-1090.

Alexander et al., "Characterization of an aromatic amino acid-dependent Listeria monocytogenes mutant: attenuation, persistance, and ability to induce protective immunity in mice", infection and immunity, May 1993, p. 2245-2248.

Allison et al. (1997) "Cloning and characterization of a Prevotella melaninogenica hemolysin." Infect Immun. 65(7):2765-71.

Alouf, "Cholesterol-binding cytolytic protein toxins" Int J Med Microbiol. Oct. 2000;290(4-5):351-6.

Amici et al., "DNA vaccination with full-length or truncated Neu induces protective immunity against the development of spontaneous mammary tumors in HER-2/neu transgenic mice", Gene Therapy, 2000, 7, 703-706.

An et al. (1996) "A recombinant minigene vaccine containing a nonameric cytoxic-T-Lymphocyte epitope confers limited protection against Listeria monocytogenes infection" Infect. Immun 64,(5):1685-1693.

Anderson (1998) "Human gene therapy." Nature. Apr. 30;392(6679 Suppl):25-30.

Angelakopoulos et al. (2002) "Safety and shedding of an attenuated strain of Listeria monocytogenes with a deletion of actA/plcB in adult volunteers: a dose escalation study of oral inoculation." Infect Immun. 70(7):3592-601.

Angelov et al., "Therapeutic vaccine for acute and chronic motor neuron diseases: Implications for amyotrophic lateral sclerosis", PNAS, Apr. 2003, vol. 100, No. 8, 4790-4795.

Anido et al., "Biosynthesis of tumorigenic HER2 C-terminal fragments by alternative initiation of translation", The EMBO Journal, 2006, 25, 3234-3244.

Attwood et al. (2000) "The Babel of Bioinformatics" Science 290(5491):471-473.

Awwad (1989) "Cyclophosphamide-induced immunologically mediated regression of a cyclophosphamide-resistant murine tumor: a consequence of eliminating precursor L3T4+ suppressor T-cells." Cancer Res. 49(7):1649-1654.

Bai et al., "Antigenic drift as a mechanism for tumor evasion of destruction by cytplytic T lymphocytes", J. Clin. Invest., 2003, 111, 1487-1496.

Bargmann et al., "The neu oncogene encodes an epiderman growth factor receptor-related protein" Nature, vol. 319, Jan. 1986, 226-230.

Bast et al., "Antitumor activity of bacterial infection, I. Effect of Listeria monocytogenes on growth of a murine fibrosarcoma", J. Natl. Cancer Inst., 54:749-756, 1975.

Baxeranis et al., Immunobiology of HER-2/neu oncoprotein and its potential application in cancer immunotherapy, Cancer Immunol. Immunother., 2004, 53, 166-175.

Bear (1986) "Tumor-specific suppressor T-cells which inhibit the in vitro generation of cytolytic T-cells from immune and early tumor-bearing host spleens." Cancer Res. Apr.;46(4 Pt 1):1805-12.

Beattie et al., "Cloning and characterization of T-cell-reactive protein antigens from Listeria monocytogenes", Infect. Immun., Sep. 1990; 58(9):2792-803.

Beatty, "A dual role for IFN-gamma in resolving the balance between tumor progression and regression", University of Pennsylvania, 2001, ii-xiii, pp. 1-10, AAT 9989567, UMI No. 9989567, Bell and Howell Information and Learning Company, Ann Arbor, Michigan.

Beatty, "A dual role for IFN-gamma in resolving the balance between tumor progression and regression" Dissertation Abstracts International, 2000, 61/10B:5224 Abstract only.

Bernhard et al. (2002) "Vaccination against the HER-2/neu oncogenic protein." Endocrine-Related Cancer, 9:33-44.

Bielecki et al. (1990) "Bacillus subtilis expressing a haemolysin gene from Listeria monocytogenes can grow in mammalian cells" Nature 354:175-176.

Billington et al. (1997) "The Arcanobacterium (Actinomyces) pyogenes hemolysin, pyolysin, is a novel member of the thiol-activated cytolysin family." J Bacteriol. Oct.;179(19):6100-6.

Biragyn et al., "Models for Lymphoma", Current Protocols in Immunology, 2001, 20.6.1-20.6.30.

Bodmer et al. (1988) "Enhanced recognition of a modified peptide antigen by cytotoxic T cells specific for influenza nucleoprotein." Cell 52: 253-258.

Boon et al. (2006) "Human T cell responses against melanoma" Annu Rev Immunol. 24:175-208.

Boon et al., "Tumor Antigens Recognized by T Lymphocytes", Annu. Rev. Immunol. 1994,12, 337-365.

Borysiewicz et al. "A recombinant vaccinia virus encoding Human Papillomavirus Types 16 and 18, E6 and E7 proteins as immunotherapy for Cervical Cancer" Lancet, 0099-5355, Jun. 1, 1996, vol. 347, Issue 9014.

Bourquin et al. (2000) "Myelin oligodendrocyte glycoprotein-DNA vaccination induces antibody-mediated autoaggression in experimental autoimmune encephalomyelitis" Eur J Immunol 30:3663-3671.

Bouwer et al., "Acquired immunity to an intracellular pathogen: immunologic recognition of L. monocytogenes-infected cells", Aug. 1997;158:137-46.

Bouwer et al., "Cytotoxic-T-lymphocyte responses to epitopes of listeriolysin O and p60 following infection with Listeria monocytogenes", Infect. Immun., Jul. 1996; 64(7):2515-22.

Bowie et al., "Deciphering the message in protein sequences: tolerance to amino acid substitutions", Science 247:1306-1310, 1990.

Boyer et al. (2005) "DNA prime Listeria boost induces a cellular immune response to SIV antigens in the rhesus macaque model that is capable of limited suppression of SIV239 viral replication." Virology. Mar. 1;333(1):88-101.

Brasseur et al. (1992) "Human gene MAGE-1, which codes for a tumor-rejection antigen, is expressed by some breast tumors." Int. J Cancer 52(5):839-841.

Brockstedt et al. (2004) "Listeria-based cancer vaccines that segregate immunogenicity from toxicity." Proc Natl Acad Sci USA. 101(38):13832-7.

Bron et al. (2004) "Identification of Lactobacillus plantarum genes that are induced in the gastrointestinal tract of mice." J Bacteriol. Sep.;186(17):5721-9.

Bron et al., "Use of the alr gene as a food-grade selection marker in lactic acid bacteria", Applied and Environmental Microbiology, Nov. 2002, vol. 68, No. 11, p. 5663-5670.

Brown et al. (1988) "Site-specific integration in Saccharopolyspora erythraea and multisite integration in Streptomyces lividans of actinomycete plasmid pSE101." J. Bacteriology 170: 2287-2295.

Brown et al. "Chemical synthesis and cloning of a tyrosine tRNA gene" (1979, Meth. Enzymol 68:109-151).

Bruder et al., "Efficient induction of cytotoxic CD8+ T cells against exogenous proteins: establishment and charcterization of a T cell line specific for the membrane protein ActA of Listeria monocytogenes", Eur. J. Immunol., Sep. 1998, 28(9):2630-9.

Bruhn et al. (2005) "Characterization of anti-self CD8 T-cell responses stimulated by recombinant Listeria monocytogenes expressing the melanoma antigen TRP-2." Vaccine. Jul. 21;23(33):4263-72.

Brundage et al. (1993) "Expression and phosphorylation of the Listeria monocytogenes ActA protein in mammalian cells." Proc. Natl. Acad. Sci. USA 90: 11890-11894.

Brunner et al., "Quantitative assay of the lytic action of immune lymphoid cells on cr-labelled allogeneic target cells in vitro; inhibition by isoantibody and by drugs", Immunology, 1968, 14, 181-196.

(56) References Cited

OTHER PUBLICATIONS

Bu et al., "Enhancement of Immune Response to an HIV env DNA Vaccine by a C-Terminal segment of listeriolysin O", Aids Research and Human Retroviruses, vol. 19 (5), 2003, pp. 409-420.
Bubert et al. (1997) "The *Listeria monocytogenes* iap gene as an indicator gene for the study of PrfA-dependent regulation." *Mol Gen Genet*. Sep.;256(1):54-62.
Burnham (2003) "Bad bugs: good for cancer therapy?" *Drug Discovery Today* 8(2):54-55.
Buske C et al "Current status and perspective of antibody therapy in follicular lymphoma" Haematologica. Jan. 2006;91(1):104-12.
Calendar et al. Poster presented at the ISOPOL Meeting 2001, http://64.233.169.104/search?q=cache:mA__uJpQsCrcJ:www.ma.uni-heidelberg.de/inst/imh/download/isopol.doc+Portnoy+Isopol+2001& hl=en&ct=clnk&cd=3&gl=us.
Camilli et al. (1993) "Dual roles of plcA in *Listeria monocytogenes* pathogenesis." *Mol. Microbiol*. 8:143-157.
Camilli et al., "*Listeria monocytogenes* mutants lacking phosphatidylinositol-specific phospholipase C are avirulent", J. Exp. Med., vol. 173, 751-754, Mar. 1991.
Carbone (1989) "Induction of ovalbumin-specific cytotoxic T cells by in vivo peptide immunization." *J Exp Med* 169:603-612.
Carbone (1990) "Class I-restricted processing and presentation of exogenous cell-associated antigen in vivo." *J Exp Med* 171:377-387.
Catic et al., "Introduction of protein or DNA delivered via recombinant *Salmonella typhimurium* into the major histocompatibility complex class I pesentation pathway of macrophages", Microbes Infect., Feb. 1999, 1(2):113-21.
Chamberlain et al. (2000) "Innovations and strategies for the development of anticancer vaccines." *Expert Opinion on Pharmacotherapy* 1(4):603-614.
Chazin et al., "Transformation mediated by the human HER-2 gene independent of the epidermal growth factor receptor", Oncogene, 1992, 7, 1859-1866.
Cheever et al., "T-Cell Immunity to Oncogeneic Proteins Including Mutated RAS and Chimeric BCR-ABL", Ann. N.Y. Acad. Sci. 1993, 690:101-112.
Chen et al., "DNA Vaccines Encoding Full-Length or Truncated Neu Induce Protective Immunity against Neu-expressing Mammary Tumors", Cancer Research 58, 1965-1971, May 1, 1998.
Cho et al., "Structure of the extracellular region of HER2 alone and in complex with the herceptin Fab", Nature, vol. 421, Feb. 2003, 756-760.
Ciurea et al., "Viral persistence in vivo through selection of neutralizing antibody-escape variants", PNAS, Mar. 2000, vol. 97, No. 6, 2749-2754.
Cohen, J. "Cancer vaccines get a shot in the arm", Science 262:841-843, Nov. 1993.
Concetti et al., "Autoantibody to P185$^{erbB2/neu}$ oncoprotein by vaccination with xenogenic DNA", Cancer Immunol. Immunother., 1996, 43, 307-315.
Courvalin et al. (1995) "Gene transfer from bacteria to mammalian cells." *C R Acad Sci III*. Dec.;318(12):1207-12.
Coussens et al., "Tyrosine kinase receptor with extansive homology to EGF receptor shares chromosomal location with neu oncogene", Sceince, vol. 230, 1132-1139, Dec. 1985.
Cunto-Amesty et al. (2003) "Strategies in cancer vaccines development." *Int J Parasitol*. 33(5-6):597-613.
Dakappagari et al. (2000) "Prevention of mammary tumors with a chimeric HER-2 B-cell epitope peptide vaccine." *Cancer Res*. Jul. 15;60(14):3782-9.
Dancz CE et al "Inducible control of virulence gene expression in *Listeria monocytogenes*: temporal requirement of listeriolysin O during intracellular infection" (J Bacteriol. 184: 5935-5945, 2002).
Darji et al. (1995) "Hyperexpression of listeriolysin in the nonpathogenic species *Listeria innocua* and high yield purification." *J Biotechnol*. Dec. 15;43(3):205-12.
Darji et al. (1995) "Listeriolysin generates a route for the presentation of exogenous antigens by major histocompatibility complex class I." *Eur J Immunol*. Oct.;25(10):2967-71.
Darji et al. (1997) "Oral somatic transgene vaccination using attenuated *S. typhimurium*" Cell 91:765-775.
Darji et al. (1997) "TAP-dependent major histocompatibility complex class I presentation of soluble proteins using listeriolysin." *Eur J Immunol*. Jun.;27(6):1353-9.
Darji et al. (2003) "Induction of immune responses by attenuated isogenic mutant strains of *Listeria monocytogenes*." *Vaccine* 1;21 Suppl 2:S102-9.
Darji et al., "Antigen-specific T cell receptor antagonism by antigen-presenting cells treated with the hemolysin of *Lestria monocytogenes*: a novel type of immune escape", Eur. J. Immunol., Jul. 1997; 27(7):1696-703.
Darji et al., "T-cell anergy induced by antigen presenting cells treated with the hemolysin of *Listeria monocytogenes*", Immunol. Lett., Jun. 1997; 57(1-3):33-7.
Darji et al., "The role of the bacterial membrane protein ActA in immunity and protection against *Listeria monocytogenes*", J. Immunol., Sep. 1, 1998; 161(5):2414-20.
Decatur et al. (2000) "A PEST-like sequence in Listeriolysin O essential for *Listeria monocytogenes* pathogenicity" *Science* 290(5493):992-995.
Dermime et al. (2004) "Vaccine and antibody-directed T cell tumour immunotherapy." *Biochim Biophys Acta*. 1704(1):11-35.
Deshpande et al. (1997) "Isolation of a contact-dependent haemolysin from *Mycobacterium tuberculosis*." *J Med Microbiol*. Mar.;46(3):233-8.
Di Carlo et al., "Inhibition of Mammary Carcinogenesis by systemic interleukin 12 or P185$^{neu}$ DNA vaccination in HER-2/neu transgenic BALB/c mice", Clinical Cancer Research, Mar. 2001, vol. 7, 830s-837s.
Dietrich et al. (1998) "Delivery of antigen-encoding plasmid DNA into the cytosol of macrophages by attenuated suicide Listeria monocytogenes" *Nature Biotechnology* 15:181-185.
Dietrich et al. (2001) "From evil to good: a cytolysin in vaccine development." *Trends Microbiol*. Jan;9(1):23-8.
Disis et al., "Effect of dose on immune response in patients vaccinated with an her-2/neu intracellular domain protein-based vaccine", Journal of Clinical Oncology, vol. 22, No. 10, May 2004, 1916-1925.
Disis et al., "Generation of T-cell Immunity to the HER-2/neu Protein After Active Immunization with HER-2/neu Peptide-Based Vaccines", J. Clin. Oncol. 20:2624-2632, 2002.
Disis et al., "HER-2/neu protein: A target for antigen-specific immunotherapy of Human Cancer", Adv Cancer Res 71:343-371,1997.
Disis et al., "Immunity to the HER-2/neu oncogenic protein", Ciba Found. Symp. 1994 187:198-211.
Disis et al., "Peptide-Based, but not whole protein, vaccines elicit immunity to HER-2/neu, an oncogenic self-protein", The Journal of Immunology, 1996, 156:3151-3158.
Doling et al., "Cytotoxic T-lymphocyte epitopes fused to anthrax toxin induce protective antiviral immunity", Infect. Immun., Jul. 1999, 67(7):3290-6.
Dramsi et al. (1995) "Entry of *Listeria monocytogenes* into hepatocytes requires expression of inIB, a surface protein of the internalin multigene family." *Mol Microbiol*. 16(2):251-61.
Dumitrescu et al., "Understanding breast cancer risk—where do we stand in 2005?", J. Cell. Mol. Med., vol. 9, No. 1, 2005, pp. 208-221.
Dunn et al. (1991) "Selective radiation resistance of immunologically induced T cells as the basis for irradiation-induced T-cell-mediated regression of immunogenic tumor." *J Leukoc Biol*. 49(4): 388-396.
Dunn et al., "A critical function for type I interferons in cancer immunoediting", vol. 6, No. 7, Jul. 2005, Nature Immunology, 722-729.
Dunn et al., "Cancer immunoediting from immunosurveillance to tumor escape", Nature Immunology, vol. 3, No. 11, Nov. 2002, 991-998.
Dunn et al., "Interferon-65 and cancer Immunoediting", Immunologic Research, 2005, 32/1-3: 231-245.
Dunn, "The Immunobiology of cancer Immunosurveillance and Immunoediting", Immunity, Aug. 2004, vol. 21, 137-148.
Ebert et al. (1990) "Selective immunosuppressive action of a factor produced by colon cancer cells." *Cancer Res*. 50(19): 6158-6161.

(56) References Cited

OTHER PUBLICATIONS

Einstein et al. "Heat shock fusion protein-based immunotherapy for treatment of cervical intraepithelial neoplasia III" Gynecologic Oncology 106 (2007) 453-460.
Ercolini et al., "Recruitment of latent pools of high-avidity CD8+ T cells to the antitumor immune response", JEM, vol. 201, No. 10, May 2005, 1591-1602.
Esserman et al., "Vaccination with the extracellular domain of P185$^{neu}$ prevents mammary tumor development in neu transgenic mice", Cancer Immunol. Immunother., 1999, 47, 337-342.
Ezzel (1995) "Cancer Vaccines: An Idea Whose Time Has Come?" J. NIH Res., 7:46-49.
Falk et al. (1991) "Identification of naturally processed viral nonapeptides allows their quantification in infected cells and suggests an allele-specific T cell epitope forecast." *J Exp Med.* 174(2):425-434.
Fields, "Preparation of antipeptide antibodies—Introduction to peptide synthesis", Current Protocols in Molecular Biology, 2002, 11.15.1-11.15.9.
Finn et al. (2003) "Cancer vaccines: between the idea and the reality." Nature Reviews Immunology 3:630-641.
Finn et al., "MUC-1 Epithelial Tumor Mucin-Based Immunity and Cancer Vaccines", Immuno. Rev. 1995, 145:61-89.
Foy et al., "Vaccination with HER-2/neu DNA or protein subunits protects against growth of HER-2/neu—expressing murine tumor", Vaccine, 19, 2001, 2598-2606.
Frankel et al. (1995) "Induction of cell-mediated immune responses to human immunodeficiency virus type 1 Gag protein by using *Listeria monocytogenes* as a live vaccine vector." *J. Immunol.* 155:4775-4782.
Freshney, "Culture of animal cells—a manual of basic technique", Chapter 1, Second Edition, 1983, 1-6.
Frey (1993) "Rat adenocarcinoma 13762 expresses tumor rejection antigens but tumor-bearing animals exhibit tumor-specific immunosuppression." *Clin Immunol Immunopathol.* 69(2):223-233.
Friedman et al. (2000) "Induction of human immunodeficiency virus (HIV)-specific CD8 T-cell responses by *Listeria monocytogenes*and a hyperattenuated *Listeria* strain engineered to express HIV antigens." *J. Virology* 74 9987-9993.
Fu et al. (1990) "Expansion of immunoregulatory macrophages by granulocyte-macrophage colony-stimulating factor derived from a murine mammary tumor." *Cancer Res.* 50(2):227-234.
Fujii (1987) "Significance of suppressor macrophages for immunosurveillance of tumor-bearing mice." *J Natl Cancer Inst.* 78(3):509-517.
Furukawa (1993) "Nude mouse metastatic models of human stomach cancer constructed using orthotopic implantation of histologically intact tissue." *Cancer Res.* 53(5):1204-1207.
Galen et al. (2001) "Can a 'flawless' live vector vaccine strain be engineered?" *Trends Microbiol.* 9(8):372-6.
Gallo et al., "Xenogeneic immunization in mice using HER2 DNA delivered by an adenoviral vector", Int. J. Cancer, 113, 67-77, 2005.
Gansbacher et al., "Interleukin 2 Gene Transfer into Tumor Cells Abrogates Tumorigenicity and Induces Protective Immunity", J. Exp. Med. 1990, 172, 1217-1224.
Garay-Malpartida et al., "Caspredictor: a new computer-based tool for caspase substrate prediction", Bioinformatics, vol. 21, suppl. 1, 2005, p. 169-176.
Garcia-Lora et al., "MHC class I-deficient metastatic tumor variants immunoselected by T lymphocytes originate from the corrdinated downregulation of Apm components", Int. J. Cancer, 106, 521-527, 2003.
Gentschev et al. (1995) "*Salmonella* strain secreting active Listeriolysin changes its intracellular localization" *Infect. Immun.* 63:4202-4205.
Gentschev et al. (1996) "Development of antigen-delivery systems, based on the *Escherichia coli* hemolysin secreatiohn pathway." *Gene* 179:133-140.
Gillespie et al., "The potential of melanoma antigen expression in cancer therapy", Cancer Treat. Rev. 1999, 25(4):219-27.

Gilmore et al. (1989) "A *Bacillus cereus* cytolytic determinant, cereolysin AB, which comprises the phospholipase C and sphingomyelinase genes: nucleotide sequence and genetic linkage." *J Bacteriol.* Feb.;171(2):744-53.
Glenting et al., "A plasmid selection system in *Lactococcus lactis* and its use for gene expression in *L. lactis* and human kidney fibroblasts", Applied and Environmental Microbiology, Oct. 2002, vol. 68, No. 10, p. 5051-5056.
Glomski et al. (2002) "The *Listeria monocytogenes* hemolysin has an acidic pH optimum to compartmentalize activity and prevent damage to infected host cells." *J Cell Biol.* Mar. 18;156(6):1029-38.
Goebel et al. (1993) "*Listeria monocytogenes*—a model system for studying the pathomechanisms of an intracellular microorganism." *Zbl. Bakt.* 278:334-347.
Goedegeburre et al., "Vaccine trials for the Clinician: Prospects for viral and non-viral vectors" The Oncologist 1997;2 (5):300-310.
Golsteyn et al., "Structural and functional similarities between the human cytoskeletal protein zyxin and the ActA protein of *Listeria monocytogenes*", J. Cell Sci. 110:1893-1906, 1997.
Golumbek et al., "Treatment of Established Renal Cancer by Tumor Cells Engineered to Secrete Interleukin-4", Science 1991, 254, 713-716.
Goossens et al. (1992) "Induction of protective CD8+ T lymphocytes by an attenuated *Listeria monocytogenes* actA mutant." *Int Immunol.* Dec.;4(12):1413-8.
Goossens et al. (1995) "Attenuated *Listeria monocytogenes* as a live vector for induction of CD8+ T cells in vivo: a study with the nucleoprotein of the lymphocytic choriomeningitis virus." *Int Immunol.* May;7(5):797-805.
Gregory et al., 1997, "Internalin B promotes the replication of *Listeria monocytogenes* in mouse hepatocytes", Infect. Immun. 65(12):5137-41.
Gritzapis et al., "Vaccination with Human HER-2/neu (435-443) CTL peptide induces effective antitumor immunity against HER-2/ neu -expressing tumor cells in vivo", Cancer Res., 66, 10, May 2006, 5452-5460.
Gunn (2001) "Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16." *J Immunol.* 167(11) 6471-6479.
Gunn et al. (2001) "Listeriolysin—a useful cytolysin." Trends Microbio1.9(4):161-162.
Gunn et al. (2002) "Recombinant Intra-cellular Bacteria as Carriers for Tumor Antigens." In *Vaccine Delivery Strategies*, Chapter 14, Eds. Guido Dietrich and Werner Goebel, Horizon Scientific Press, UK.
Gunn, "Recombinant *Listeria monocytogenes* as a tumor therapeutic", *Univ. of Pennsylvania—Electronic Dissertations*. Paper AAI3015316, UMI Microform 3015316, 2001, pp. v-vi, Bell and Howell Information and Learning Company, Ann Arbor, Michigan, abstract.
Gunn, "Recombinant *Listeria monocytogenes* as a tumor therapeutic" Dissertation Abstracts International, 2001, 62/5B:2244 Abstract Only.
Guy et al., "Expression of the neu proto oncogene in the mammary epithelium of transgenic mice induces metastatic disease", Proc. Natl. Acad. Sci. USA, Nov. 1992, vol. 89, pp. 10578-10582.
Guzman et al. (1998) "Attenuated *Listeria monocytogenes* carrier strains can deliver an HIV-1 gp120 T helper epitope to MHC class II-restricted human CD4+ T cells" *European Journal of Immunology* 28:1807-1814.
Harris et al., "Molecular Basis for Hetreogeneity of the Human p53 protein", Molecular and Cellular Biology, Dec. 1986, vol. 6, No. 12, p. 4650-4656.
Harty et al. (1996) "Primary and secondary immune responses to *Listeria monocytogenes.*" *Curr Opin Immunol.* 8:526-530.
Harty et al., "CD8 T lymphocytes specific for the secreted p60 antigen protect against *Listeria monocytogenes* infection", J. Immunol., May 1, 1995; 154(9):4642-50.
Hassan et al. (2004) "Mesothelin: a new target for immunotherapy." *Clin Cancer Res.* 10(12 Pt 1):3937-42.

(56) References Cited

OTHER PUBLICATIONS

Hauf et al. (1997) "*Listeria monocytogenes* infection of P388D1 macrophages results in a biphasic NF-kappaB (RelA/p50) activation induced by lipoteichoic acid and bacterial phospholipases and mediated by IkappaBalpha and IkappaBbeta degradation." *Proc Natl Acad Sci U S A*. Aug. 19;94(17):9394-9.

Hausen et al. "Papillomaviruses causing cancer: evasion from host-cell control in early events in carcinogenesis." J Natl Cancer Inst. May 3, 2000;92(9):690-8.

Hess et al. (1995) "*Listeria monocytogenes* p60 supports host cell invasion by and in vivo survival of attenuated *Salmonella typhimurium*." *Infect Immun*. May;63(5):2047-53.

Hess et al. (1996) "*Salmonella typhimurium* aroA- infection in gene-targeted immunodeficient mice: major role of CD4+ TCR-alpha beta cells and IFN-gamma in bacterial clearance independent of intracellular location." *J Immunol*. May 1;156(9):3321-6.

Hess et al. (1996) "Superior efficacy of secreted over somatic antigen display in recombinant *Salmonella* vaccine induced protection against listeriosis" *Proc. Nat. Acad. Sci*. 93:1458-1463.

Hess et al. (1997) "Protection against murine listeriosis by an attenuated recombinant *Salmonella typhimurium* vaccine strain that secretes the naturally somatic antigen superoxide dismutase." *Infect Immun*. Apr;65(4):1286-92.

Hess et al. (1998) "*Mycobacterium bovis* bacilli Calmette-Guerin strains secreting listeriolysin of *Listeria monocytogenes*" *Proc. Natl. Acad. Sci*. 95:5299-5304.

Hess et al., "Live antigen carriers as tools for improved anti-tuberculosis vaccines", FEMS Immunol. Med. Microbiol., Feb. 1999, 23(2), 165-73.

Higgins et al. (1998) "Bacterial delivery of DNA evolves." *Nat Biotechnol*. Feb.;16(2):138-9.

Higgins et al., "Delivery of protein to the cytosol of macrophages using *Escherichia coli* K-12", Mol. Microbiol., Mar. 1999, 31(6):1631-41.

Hiltbold et al., "Mechanisms of processing and presentation of the antigens of *Listeria monocytogenes*", Infect. Agents Dis., Oct. 1993; 2(5):314-23.

Hiltbold et al., "The presentation of class I and class II epitopes of listeriolysin O is regulated by intracellular localization and by intracellular localization and by intercellular spread of *Listeria monocytogenes*", J. Immunol., Aug. 1996; 157(3):1163-75.

Hodgson (2000) "Generalized transduction of serotype 1/2 and serotype 4b strains of *Listeria monocytogenes*." Mol Microbiol. 35(2):312-23.

Hoogenboom et al., "By passing Immunisation—human antibodies from synthetic repertoires of germline $V_H$ gene segments rearranged in vitro", J. Mol. Biol., 1992, 227, 381-388.

Hu et al. (2004) "*Escherichia coli* expressing recombinant antigen and listeriolysin O stimulate class I-restricted CD8+ T cells following uptake by human APC." *J. Immunology* 172:1595-1601.

Huang et al. (1994) "Role of bone marrow-derived cells in presenting MHC class I-restricted tumor antigens." Science 264961-965.

Hueman et al., "Phase I clinical trial of a HER-2/neu peptide (E75) vaccine for the prevention of prostate—specific antigen recurrence in high-risk prostate cancer patients", Clin. Cancer Res., 11(20), Oct. 2005, 7470-7479.

Hussain et al. (2004) "CD4+CD25+ regulatory T cells that secrete TGFbeta and IL-10 are preferentially induced by a vaccine vector." *J Immunother*. Sep.-Oct.;27(5):339-46.

Ikonomidis et al. (1994) "Delivery of a viral antigen to the class I processing and presentation oathway by *Listeria monocytogenes*" *Journal of Experimental Medicine* 180(6):2209-2218.

Ikonomidis et al. (1994) Abstract E-90, Abstracts, 94th General Meeting of the American Society for Microbiology, May 23-27.

Ikonomidis et al., "Influenza-specific immunity induced by recombinant *Listeria monocytogenes* vaccines", Vaccine, vol. 15, No. 4, pp. 433-440, 1997.

Ikonomidis et al., "Recombinant *Listeria Monocytogenes* Cancer Vaccines", Vaccine 95, 1995, 95:317-326.

Ikonomidis et al., ASM Las Vegas, The 94th General Meeting of the American Society for Microbiology, May 23-27, 1994, Las Vegas Convention Center, Las Vages, Nevada, p. 29, 159, 662, 664.

International Search Report of Application No. PCT/US01/09736 dated Jul. 27, 2001.

International Search Report of Application No. PCT/US05/32682 dated Jun. 1, 2006.

International Search Report of Application No. PCT/US07/06292 dated Jun. 17, 2008.

International Search Report of Application No. PCT/US07/10635 dated Sep. 11, 2008.

International Search Report of Application No. PCT/US08/03067 dated Aug. 29, 2008.

International Search Report of Application No. PCT/US08/06048 dated Nov. 20, 2008.

International Search Report of Application No. PCT/US95/14741 dated Feb. 15, 1996.

Jager et al. "Identification of NY-ESO-1 epitopes presented by human histocompatibility antigen (HLA)-DRB4*0101-0103 and recognized by CD4(+) T lymphocytes of patients with NY-ESO-1-expressing melanoma" J Exp Med. Feb. 21, 2000 ;191(4):625-30.

Jensen (1997) "Recombinant Listeria monocytogenes vaccination eliminates papillomavirus-induced tumors and prevents papilloma formation from viral DNA." *J Virol*. 71(11):8467-8474.

Jenson et al., "Recombinant *Listeria monocytogenes* as a live vaccine vehicle and a probe for studying cell-mediated Immunity", Immunological Review, vol. 158, 147-157, Aug. 1997.

Jones et al. (1994) "Characterization of *Listeria monocytogenes* pathogenesis in a strain expressing perfringolysin O in place of listeriolysin O." *Infect. Immun*. 62:5608-5613.

Kaufman et al. (1999) "Impact of intracellular location of and antigen display by intracellular bacteria: implications for vaccine development" *J Immunol. Lett*, 65(1-2):81-84.

Kawashima et al., "The Multi-epitope Approach for Immunotherapy for Cancer: Identification of Several CTL Epitopes from Various Tumor-Associated Antigens Expressed on Solid Epithelial Tumors", Hum. Immunol. 1998 59:1-14.

Kerksiek (1999) "T cell responses to bacterial infection"*Curr Opin. Immunol*. 1(4):400-405.

Khong et al., "Identification of multiple antigens recognized by tumor-infiltrating lymphocytes from a single patient: Tumor escape by antigen loss and loss of MHC expression", J. Immunother., 2004, 27, 184-190.

King et al., "Amplification of a Novel v-erbB-related gene in a human mammary carcinoma", Science, Sep. 1985, vol. 229, 974-976.

Kocks et al. (1992) "*L. monocytogenes*-induced actin assembly requires the ActA gene product" *Cell* 68(3):521-531.

Kohler et al., "Expression of the iap gene coding for protein p60 of *Listeria monocytogenes* is controlled on the posttranscriptional level", Journal of Bacteriology, Aug. 1991, vol. 173, No. 15, p. 4668-4674.

Kovacsovics-Bankowski et al. (1993) "Efficient major histocompatibility complex class I presentation of exogenous antigen upon phagocytosis by macrophages." *Proc. Natl. Acad. Sci. USA* 90:4942-4946.

Kruisbeek, "In vivo depletion of CD4– and CD8-specific T cells" Current Protocols in Immunology, John Wiley & Sons, Inc., eds., 1991, V.1, 4.1.1-4.1.2.

Kumar et al., "Amino acid variations at a single residue in an autoimmune peptide profoundly affect its properties: T-cell activation, major histocompatibility complex binding, and ability to block experimental allergic encephalomyelitis", PNAS, 87:1337-1341, 1990.

Kuntson et al., "Immunization with a HER-2/neu helper peptide vaccine generates HER-2/neu CD8 T-cell immunity in cancer patients", The Journal of Clinical Investigation, 107:477-484,2001.

Kuntson et al., "Neu antigen negative variants can be generated after neu-specific antibody therapy in neu transgenic mice", Cancer Research 64, Feb. 2004, 1146-1151.

Kyte et al., "A simple method for displaying the hydropathic character of a protein", J. Mol. Biol., 1982, 157, 105-132.

(56) References Cited

OTHER PUBLICATIONS

Lacey et al., "Phase IIa safety and immunogenicity of a therapeutic vaccine, TA-GW, in persons with genital warts", The Journal of Infectious Diseases, 1999, 179:612-8.

Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site." *J. Virology* 75(20) :9654-9664.

Lampson et al. (1993) "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ." *Cancer Research* 53:176-182.

Lara-Tejero et al. (2004) "T cell responses to *Listeria monocytogenes*." *Curr Opin Microbiol.* 7(1):45-50.

Lasa et al. (1997) "Identification of two regions in the N-terminal domain of ActA involved in the actin comet tail formation by *Listeria monocytogenes*" *EMBO* 16(7):1531-40.

Lauer et al. (2002) "Construction, characterization, and use of two *Listeria monocytogenes* site-specific phage integration vectors." *J. Bacteriology* 184: 4177-4186.

Lauer et al. "Characterization of the Attachment Site of Bacteriophage U153 within the *Listeria monocytogenes* comK Gene " ASM Meeting, Abstract 1999.

Lauer et al., "Systematic mutational analysis of the amino-terminal domain of the *Listeria monocytogenes* ActA protein reveals novel functions in actin-based motility", Molecular Microbiology 42(5):1163-1177, 2001.

Leâd et al. (1995) "A species-specific nucleotide sequence of *Mycobacterium tuberculosis* encodes a protein that exhibits hemolytic activity when expressed in *Escherichia coli*." *Infect Immun.* Nov;63(11):4301-6.

Lebrun et al. (1996) "Internalin must be on the bacterial surface to mediate entry of *Listeria monocytogenes* into epithelial cells" *Molecular Microbiology* 21(3):579-592.

Lee et al. (1991) "Construction of single-copy integration vectors for *Staphylococcus aureus*." *Gene* 103:101-5.

Lee et al., "Delivery of macromolecules into cytosol using liposomes containing hemolysin from *Listeria monocytogenes*", J. Biol. Chem., Mar. 29, 1996; 271(13):7249-52.

Lee et al., "The murine MHC class I genes, H-2D and H-2L, and two genes reported to encode tumor-specific antigens", J. Exp. Med., Nov. 1988, vol. 168, 1719-1739.

Lehner et al. (1996) "Processing and delivery of peptides presented by MHC class I molecules." *Curr Opin Immunol.* 8(1):59-67.

Leitner et al., "DNA and RNA-based vaccines: prinicples, progress and prospects", Vaccine, Dec. 1999, 18(9-10):765-777.

Lejeune (1994) "Nitric oxide involvement in tumor-induced immunosuppression." *J Immunol.* 152(10):5077-5083.

Liau et al. (2002) "Tumor immunity within the central nervous system stimulated by recombinant *Listeria monocytogenes* vaccination." *Cancer Res.* 62(8)2287-93.

Lin et al. (1996) Treatment of established tumors with a novel vaccine that enhances Major Histocompatibility Class II presentation of tumor antigen *Cancer Res.* 56:21-26.

Lin et al. (2002) "Oral vaccination with recombinant *Listeria monocytogenes* expressing human papillomavirus type 16 E7 can cause tumor growth in mice to regress." *Int J Cancer.* Dec. 20;102(6):629-37.

Lingnau et al. (1995) "Expression of the *Listeria monocytogenes* EGD inlA and inlB genes, whose products mediate bacterial entry into tissue culture cell lines, by PrfA-dependent and -independent mechanisms." *Infect Immun.* Oct.;63(10):3896-903.

Lipford et al., "Vaccination with immunodominant peptides encapsulated in Quil A-containing liposomes induces peptide-specific primary CD8+ cytotoxic T cells", Vaccine, Jan. 1994; 12(1):73-80.

Liu, "Vaccine developments", Nature Medicine Vaccine Supplement, May 1998, vol. 4, No. 5, 515-519.

Loeffler et al. (2006) "Comparison of different live vaccine strategies in vivo for delivery of protein antigen or antigen-encoding DNA and mRNA by virulence-attenuated *Listeria monocytogenes*." *Infect Immun.* Jul.;74(7):3946-57.

Loessner et al. (1995) "Heterogeneous endolysins in *Listeria monocytogenes* bacteriophages: a new class of enzymes and evidence for conserved holin genes within the siphoviral lysis cassettes." *Mol Microbiol.* Jun.;16(6):1231-41.

Loessner et al. (2000) "Complete nucleotide sequence, molecular analysis and genome structure of bacteriophage A118 of *Listeria monocytogenes*: implications for phage evolution." *Molecular Microbiology* 35(2):324-40.

Maciag et al., "The first clinical use of a live-attenuated *Listeria monocytogenes* vaccine: a Phase I safety study of Lm-LLO-E7 in patients with advanced carcinoma of the cervix" Vaccine. Jun. 19, 2009;27(30):3975-83.

Mahdavi et al., "Vaccines against Human Papillomavirus and Cervical Cancer: Promises and Challenges" The Oncologist 2005; 10:528-538.

Makela et al. (1987) Hand Book of Experimental Immunology, vol. 1, chapter 3, pp. 3.1-3.13.

Mandal et al. (2002) "Listeriolysin O-liposome-mediated cytosolic delivery of macromolecule antigen in vivo: enhancement of antigen-specific cytotoxic T lymphocyte frequency, activity, and tumor protection." *BBA* 1563 7-17.

Manjili et al. (2003) "HSP110-HER2/neu chaperone complex vaccine induces protective immunity against spontaneous mammary tumors in HER-2/neu transgenic mice." *J lmmunol.* Oct. 15;171(8):4054-61.

Marks et al., "By-Passing immunization human antibodies from V-gene libraries displayed on phage", J. Mol. Biol. 1991, 222, 581-597.

Marquis et al. (1997) "Proteolytic pathways of activation and degradation of a bacterial phospholipase C during intracellular infection by *Listeria monocytogenes*." *J. Cell Biol.* 137:1381-1392.

Martin et al. (1986) "Nucleotide sequence of the tetM tetracycline resistance determinant of the streptococcal conjugative shuttle transposon Tn1545." *Nucleic Acid Res.* 14:7047-7058.

Marx et al. (2002) "Broad-host-range cre-lox system for antibiotic marker recycling in gram-negative bacteria." *Biotechniques.* Nov. ;33(5):1062-7.

Mata et al., "Evolution of a recombinant *Listeria monocytogenes* expressing an HIV protein that protects mice against viral challenge", Vaccine, 19, 2001, 1435-1445.

Mazzaccaro et al., "Major histocompatibility Class I presentation of soluble antigen facilitated by *Mycobacterium tuberculosis* infection", Proc. Natl. Acad. Sci. USA; Oct. 15, 1996; 93(21):11786-91.

McCarty et al., "Targeting p53 for Adoptive T-Cell Immunotherapy", Cancer Research 1998, 15:58 2601-5.

McKaig et al., "Human Papillomavirus and Head and Neck Cancer: Epidemiology and Molecular Biology", Head Neck 1998, 20 (3):250-65.

McLaughlan et al. (1998) "Molecular characterization of an autolytic amidase of *Listeria monocytogenes* EGD." *Microbiology.* May;144(Pt 5):1359-67.

Meneguzzi et al., "Immunization against human papillomavirus type 16 tumor cells with recombinant vaccinia viruses expressing E6 and E7", Virology 181(1), 62-69 (1991).

Mengaud et al. (1988) "Expression in *Escherichia coli* and sequence analysis of the Listeriolysin O determinant of *Listeria monocytogenes*" *Infection and Immunity* 56(4):766-772.

Michel et al., "Attenuated mutants of the intracellular bacterium *Listeria monocytogenes* obtained by single amino acid substitutions in listeriolysin O", Molecular Microbiology (1990), 4 (12), pp. 2167-2178.

Mikayama et al. (1993) "Molecular cloning and functional expression of a CDNA encoding gycosylation-inhibiting factor" *Proc. Natl. Acad. Sci. USA* 90:10056-10060.

Miller et al., "Targeted vectors for gene therapy", The FASEB Journal, Feb. 1995, vol. 9, p. 190-199.

Mlynárová et al. (2002) "The promiscuity of heterospecific lox sites increases dramatically in the presence of palindromic DNA." *Gene.* Aug. 21;296(1-2):129-37.

(56) References Cited

OTHER PUBLICATIONS

Mollet et al. (1993) "Directed genomic integration, gene replacement, and integrative gene expression in *Streptococcus thermophilus*." *J. Bacteriology* 175:4315-4324.

Moriishi et al. (1998) "Sequence analysis of the actA gene of *Listeria monocytogenes* isolated from human" *Microbiol. Immunol.* 42(2):129-132.

Muller, "Expression of activated oncogenes in the murine mammary gland: transgenic models for human breast cancer", Cancer and Metastasis Reviews, 10:217-227, 1991.

Murali et al., "Structural analysis of P185$^{C-neu}$ and epidermal growth factor receptor tyrosine kinases: oligomerization of kinase domains", Proc. Natl. Acad. Sci. USA vol. 93, pp. 6252-6257, Jun. 1996, Biochemistry.

Naz et al., "Novel human prostate-specific cDNA: molecular cloning, expression, and immunobiology of the recombinant protein", Biochemical and Biophysical Research Communications 297, 2002, 1075-1084.

Narang et al. "Improved phosphotriester method for the synthesis of gene fragments" (1979, Meth. Enzymol. 68: 90-99).

Neeson et al., "A DNA prime-oral listeria boost vaccine in rhesus macaques induces a SIV-specific CD8 T cell mucosal response characterized by high levels of α4β7 integrin and an effector memory phenotype", Virology, Oct. 2006, 354(2), 299-315.

Neeson et al., "Listeriolysin O is an improved protein carrier for lymphoma immunoglobulin idiotype and provides systemic protection against 38c/3 lymphoma", Cancer Immunol. Immunother., 2007, 13 pages.

Ngo et al. (1994) The Protein Folding Problem and Tertiary Structure Prediction 492-495.

Nielsen et al., "Peptide nucleic acids as therapeutic agents", Nucleic acids, p. 353-357, Curr Opinion Struc Biol 9(3): 353-7, Jun. 1997.

Ochsenbein et al. (1999) "A comparison of T cell memory against the same antigen induced by virus versus intracellular bacteria." *Proc Natl Acad Sci U S A*. Aug. 3;96(16):9293-8.

Oscarsson et al. (1996) "Induction of haemolytic activity in *Escherichia coli* by the slyA gene product." *Mol Microbiol.* Apr;20(1):191-9.

Pagano, J.S., "Epstein-Barr Virus: The First Human Tumor Virus and its Role in Cancer", Proc. Assoc. Am. Physicians 1999 111(6):573-80.

Paglia et al. (1997) "The defined attenuated *Listeria monocytogenes* delta mp12 mutant is an effective oral vaccine carrier to trigger a long-lasting immune response against a mouse fibrosarcoma" *Eur J Immunol* 27:1570-1575.

Palmeros et al. (2000) "A family of removable cassettes designed to obtain antibiotic-resistance-free genomic modifications of *Escherichia coli* and other bacteria." *Gene*. Apr. 18;247(1-2):255-64.

(1999) "Regression of established B16F10 melanoma with a recombinant *Listeria monocytogenes* vaccine." *Cancer Res* 59(20):5264-5269.

Pan et al. (1995) "A recombinant *Listeria monocytogenes* vaccine expressing a model tumour antigen protects mice against lethal tumour cell challenge and causes regression of established tumours." *Nature Med*. 1:471-477.

Pan et al. (1995) "Regression of established tumors in mice mediated by the oral administration of a recombinant *Listeria monocytogenes* vaccine" *Cancer Res* 55:4776-4779.

Pardoll, "Cancer Vaccines", Nature Medicine Vaccine Supplement, May 1998, vol. 4, No. 5, 525-531.

Parida et al. (1998) "Internalin B is essential for adhesion and mediates the invasion of *Listeria monocytogenes* into human endothelial cells." *Mol Microbiol.* Apr.;28(1):81-93.

Paterson et al., "Recombinant *Listeria monocytogenes* cancer vaccines", Curr Opin Immunol. Oct. 1996;8(5) 664-669.

Paterson et al., Proceedings of the American Association for Cancer Research, Mar. 2000, 41:890, abstract # S25.

Paterson, "Rational approaches to immune regulation", Immunogenic Research, 27(2-3):451-462, Jun. 2003.

Paul et al. (1989) "Fundamental Immunology", Second Edition, Raven Press, 987-988.

Peng et al. "Adjuvant properties of listeriolysin O protein in a DNA vaccination strategy" Cancer Immunol Immunother. Jun. 2007;56(6):797-806.

Peng et al. (2004) "The ability of two *Listeria monocytogenes* vaccines targeting human papillomavirus-16 E7 to induce an antitumor response correlates with myeloid dendritic cell function." *J. Immunol*. 172:6030-6038.

Penichet et al. (2001) "Antibody-cytokine fusion proteins for the therapy of cancer." *J. Immunological Methods* 248:91-101.

Peters et al. (2003) "Tailoring host immune responses to *Listeria* by manipulation of virulence genes—the interface between innate and acquired immunity." *FEMS Immunol Med Microbiol*. Apr. 1;35(3):243-53.

Pfeifer et al. (1993) "Phagocytic processing of bacterial antigens for class I MHC presentation to T cells." *Nature*. Jan. 28;361(6410):359-62.

Piechocki et al., "Complementary Antitumor Immunity Induced by Plasmid DNA Encoding Secreted and Cytoplasmic Human ErbB-2", The Journal of Immunology, 2001, 167:3367-3374.

Pilgrim et al., "Bactofection of mammalian cells by *Listeria monocytogenes*: improvement and mechanism of DNA delivery", Gene Therapy, 2003, 10, 2036-2045.

Pilon et al., "Vaccination with Crytoplasmic ErbB-2 DNA Protects Mice from Mammary Tumor Growth Without Anti-ErbB-2 Antibody", The Journal of Immunology, 2001, 167:3201-3206.

Portnoy et al. "Molecular determinants of *Listeria Monocytogenes* pathogenesis", Infection and Immunity, Apr. 1992, p. 1263-1267.

Portnoy et al, "Role of hemolysin for the intracellular growth of *Listeria monocytogenes*" (J Exp Med vol. 167:1459-1471, 1988).

Pricher et al., "Viral escape by selection of cytotoxic T cell-resistant virus variants in vivo", Nature, vol. 346, Aug. 1990, 629-633.

Pucci et al., "*Straphylococcus hameolyticus* contains two D-glutamic acid biosynthetic activities, a glutamate racemase and a D-amino acid transaminase", Journal of Bacteriology, Jan. 1995, vol. 177, No. 2, p. 336-342.

Punwaney et al., "Human Papillomavirus May be Common within Nasopharyngeal Carcinoma of Caucasian Americans: investigation of Epstein-Barr virus and human papillomavirus in Eastern and Western Nasopharyngeal Carcinoma using Ligation-Dependent polymerase chain reaction", Head Neck, 1999, 21(1):21-9.

Pupa et al. (2001) "Prevention of spontaneous neu-expressing mammary tumor development in mice transgenic for rat proto-neu by DNA vaccination." *Gene Ther*. Jan.;8(1):75-9.

Quénée et al. (2005) "Combined sacB-based negative selection and cre-lox antibiotic marker recycling for efficient gene deletion in *Pseudomonas aeruginosa.*" *Biotechniques*. Jan.;38(1):63-7.

Radford et al. (2002) "A recombinant *E. coli* vaccine to promote MHC class I-dependent antigen presentation: application to cancer immunotherapy." *Gene Therapy* 9:1455-1463.

Radford et al. (2003) "Recombinant *E. coli* efficiently delivers antigen and maturation signals to human dendritic cells: presentation of MART1 to CD8+ T cells." *Int. J. Cancer* 105:811-819.

Raffaghello et al., "Multiple defects of the antigen-processing machinery components in human neuroblastoma: immunotherapeutic implications", Oncogene, 2005, 24, 4634-4644.

Raveneau et al. (1992) "Reduced virulence of a *Listeria monocytogenes* phospholipase-deficient mutant obtained by transposon insertion into the zinc metalloprotease gene." *Infect. Immun*. 60: 916-921.

Realini et al. (1994) "KEKE motifs. Proposed roles in protein-protein association and presentation of peptides by MHC class I receptors" *FEBS Letters* 348:109-113.

Rechsteiner et al. (1996) "PEST sequences and regulation by proteolysis" *TIBS* 21:267-271.

Reilly et al., "HER-2/neu is a tumor rejection target in tolerized HER-2/neu transgenic mice", Cancer Research 60, 3569-3576, Jul. 2000.

Reiter et al. (1989) "Transfer RNA genes frequently serve as integration sites for prokaryotic genetic elements." *Nucleic Acids Research* 17(5)1907-14.

(56) References Cited

OTHER PUBLICATIONS

Renard et al. (2003) "HER-2 DNA and protein vaccines containing potent Th cell epitopes induce distinct protective and therapeutic antitumor responses in HER-2 transgenic mice." *J Immunol.* 171(3):1588-95.

Repique (1992) "Immunosuppression derived from human B-lymphoblastoid and melanoma cell lines." *Cancer Invest.* 10(3):201-208.

Restifo et al., "Identification of Human Cancers Deficient in Antigen Processing", J. Exp. Med. 1993, 177, 265-272.

Restifo et al., "The promise of nucleic acid vaccines", Gene Ther., Jan. 2000, 7(2): 89-92.

Roden et al. (2004) "Vaccination to prevent and treat cervical cancer." *Hum Pathol* 35(8):971-82.

Rogers et al., "Amino acid sequences common to rapidly degraded proteins: the PEST hypothesis", Science, Reports, Oct. 1986, vol. 234, 364-368.

Romero et al., "Coordinated downregulation of the anti gen presentation machinery and HLA class I/β2-microglobulin complex is responsible for HLA-ABC loss in bladder cancer", Int. J. Cancer, 2005, 113, 605-610.

Rovero et al., "DNA Vacciniation Against Rat Her-2/Neu p185 More Effectively Inhibits Carcinogenesis Than Transplantable Carcinomas in Transgenic BALB/c Mice", The Journal of Immunology, 2000, 165:5133-5142.

Rüssmann et al. (1998) "Delivery of epitopes by the *Salmonella* type III secretion system for vaccine development." *Science.* Jul. 24;281(5376):565-8.

Safley et al. (1991) "Role of Listeriolysin-o (LLO) in the T Lymphocyte response to infection with *Listeria Monocytogenes*" *J Immunol.* 146(10):3604-3616.

Scardino et al., "HER-2/neu and hTERT cryptic epitopes as Novel targets for broad spectrum tumor Immunotherapy", The Journal of Immunology, 2002, 168:5900-5906.

Schafer et al. (1992) "Induction of a cellular immune response to a foreign antigen by a recombinant *Listeria monocytogenes* vaccine." *J. Immunol.* 149(1):53-59.

Scheirlinck et al. (1989) "Integration and expression of alpha-amylase and endoglucanase genes in the *Lactobacillus plantarum* chromosome." *Appl Environ Microbiol* 55(9) :2130-7.

Schlom et al., "Cancer Vaccines:Moving Beyond Current Paradigms", Clin. Cancer Res. 2007; 13(13), Jul. 1, 2007.

Schneider et al., "Induction of pulmonary allergen-specific IgA responses or airway hyperresponsiveness in the absence of allergic lung disease following sensitization with limiting doses of ovalbumin-alum", Cellular Immunology, 212, 101-109, 2001.

Schnupf et al., "Phosphorylation, ubiquitination and degradation of listeriolysin O in mammalian cells: role of the PEST-like sequence", Cellular Microbiology 8(2):353-364, 2006.

Schwartz, "T cell anergy", Annu. Rev. Immunol., 2003, 21, 305-34.

Scortti et al., "The PrfA virulence regulon", Microbes Infect. Aug. 2007;9(10):1196-207. Epub May 7, 2007.

Seffernick et al., "Melamine deaminase and atrazine chlorohydrolase: 98 percent identical but functionally different", J. Bacteriol. 183(8):2405-10, Apr. 2001.

Serth et al., "Increased Levels of Human Papillomavirus Type 16 DNA in a Subset of Prostate Cancers", Cancer Res. 1999 15:59(4):823-5.

Sewell et al. (2004) "Recombinant *Listeria* vaccines containing PEST sequences are potent immune adjuvants for the tumor-associated antigen human papillomavirus-16 E7." *Cancer Res.* Dec. 15;64(24):8821-5.

Sewell et al., "Regression of HPV-positive tumors treated with a new *Listeria monocytogenes* vaccine", Arch Otolaryngol Head Neck Surg, Jan. 2004, vol. 130, 92-97.

Shen et al. (1998) "Compartmentalization of bacterial antigens: differential effects on priming of CD8 T cells and protective immunity." *Cell.* Feb. 20;92(4):535-45.

Shen et al. (1998) "*Listeria monocytogenes* as a probe to study cell-mediated immunity" *Curr. Opin. Immunol.* 10(4):450-458.

Shen et al., "Recombinant *Listeria monocytogenes* as a Live Vaccine Vehicle for the Induction of Protective Anti-Viral Cell-Mediated Immunity", Proc. Natl. Acad. Sci., USA, 92:3987-3991, Apr. 25, 1995.

Shetron-Rama et al. (2002) "Intracellular induction of *Listeria monocytogenes* actA expression." *Infect. Immun.* 70:1087-1096.

Shimizu et al. (1994) "Effects of CD4+ and CD8+ T cells in tumor-bearing mice on antibody production." *Cancer Immunol Immunother.* 38(4):272-276.

Shrikant et al., "CTLA-4 blockade reverses CD8+ T cell tolerance to tumor by a CD4+ T cell-and IL-2-dependent mechanism", Immunity, Oct. 1999, vol. 11, 483-493.

Silverman et al., "Expression of c-myc, c-raf-1, and c-Ki-ras in azaserine-induced pancreatic carcinomas and growing pancreas in rats" Mol. Carcinog 3(6):379-86, 1990.

Singh et al. (2005) "Fusion to Listeriolysin O and delivery by *Listeria monocytogenes* enhances the immunogenicity of HER-2/neu and reveals subdominant epitopes in the FVB/N mouse." *J Immunol.* Sep. 15;175(6):3663-73.

Singh et al., "Structure-Based design of a potent, selective and irreversible inhibitor of the catalytic domain of the erbb receptor subfamily of protein tyrosine kinases", J. Med. Chem., 1997, 40, 1130-1135.

Singh et al., "Vaccination strategy determines the emergence and dominance of CD8+ T-cell epitopes in a FVB/N Rat HER-2/neu mouse model of breast cancer", Cancer Res., 66, 15, Aug. 2006, 7748-7757.

Sirard et al. (1997) "Intracytoplasmic delivery of Listeriolysin O by a vaccinal strain of *Bacillus anthracis* induces CD8-mediated protection against *Listeria monocytogenes*" *J Immun.* 159:4435-4443.

Skoble, J. et al. (2000). "Three regions within acta promote arp2/3 complex-mediated actin nucleation and *Listeria monocytogenes* motility" *The Journal of Cell Biology* 150(3):527-537.

Skolnick et al. (2000) "From genes to protein structure and function: novel applications of computational approached in the genomic era" *Trends in Biotech.* 18(1):34-39.

Slifka et al. (1996) "Antiviral cytotoxic T-cell memory by vaccination with recombinant *Listeria monocytogenes.*" *J. Virol.* 70(5):2902-10.

Smith et al. (1995) "Asymmetric Distribution of the *Listeria monocytogenes* ActA Protein is Required and Sufficient to Direct Actin-Based Motility" *Molecular Microbiology* 17:945-951.

Smith et al. (1995) "The two distinct phospholipases C of *Listeria monocytogenes* have overlapping roles in escape from a vacuole and cell-to-cell spread." *Infect. Immun.* 63 4231-4237.

Souders et al. (2006) "In vivo bactofection: *Listeria* can function as a DNA-cancer vaccine." *DNA Cell Biol.* Mar.;25(3):142-51.

Stahl et al. (1984) "Replacement of the *Bacillus subtilis* subtilisin structural gene with an in vitro-derived deletion mutation." *J. Bacteriol* 158:411-418.

Starks et al. (2004) "*Listeria monocytogenes* as a vaccine vector: virulence attenuation or existing antivector immunity does not diminish therapeutic efficacy." *J. Immunology* 173:420-427.

Stitz et al. (1990) "Characterization and immunological properties of influenza A virus nucleoprotein (NP): cell-associated NP isolated from infected cells or viral NP expressed by vaccinia recombinant virus do not confer protection." *J Gen Virol.* 71(Pt 5):1169-1179.

Stover et al., "New Use of BCG for Recombinant Vaccines", Nature 1991, 351, 456-460.

Strugnell et al. (1990) "Stable expression of foreign antigens from the chromosome of *Salmonella typhimurium* vaccine strains." *Gene* 88:57-63.

Strych et al., "Mutant analysis shows that alanine racemases from *Pseudomonas aeruginosa* and *Escherichia coli* are dimeric", Journal of Bacteriology, Aug. 2002, p. 4321-4325.

Stryer et al. (1998) Biochemistry, Third Edition, WH Freeman Company, New York, 31-33.

Sun et al. (1990) "Isolation of *Listeria monocytogenes* small-plaque mutants defective for intracellular growth and cell-to-cell spread." *Infect. Immun.* 58 3770-3778.

Szalay et al., "Presentation of *Listeria monocytogenes* antigens by major histocompatibility complex class I molecules to CD8 cytotoxic T lymphocytes independent of listeriolysin secretion and virulence", Eur. J. Immunol., Jul. 1994; 24(7):1471-7.

(56) References Cited

OTHER PUBLICATIONS

Tanabe et al. (1999) "Induction of Protective T Cells against *Listeria monocytogenes* in Mice by Immunization with a Listeriolysin O-Negative Avirulent Strain of Bacteria and Liposome-Encapsulated Listeriolysin O" *Infect. Immun.* 67(2):568-575.

Teitelbaum et al., "Mycobacterial infection of macrophages results in membrane-permeable phagosomes", Proc. Natl. Acad. Sci. USA, Dec. 1999; 96(26):15190-5.

Thompson et al., "Pathogenicity and Immunogenicity of a *Listeria monocytogenes* strain that requires D-alaninc for growth", Infection and Immunity, Aug. 1998, vol. 66, No. 8, p. 3552-3561.

Thull et al., "Recognition and management of hereditary breast cancer syndromes", The Oncologist, 2004; 9:13-24.

Tilney et al. (1989) "Actin filaments and the growth, movement, and spread of the intracellular bacterial parasite, *Listeria monocytogenes.*" *J Cell Biol.* Oct.;109(4 Pt 1):1597-608.

Townsend et al., "Tumor Rejection after Direct Costimulation of CD8+ T Cells by B7-Transfected Melanoma Cells", Science 1993, 259, 368-370.

Travis, "A Stimulating New Approach to Cancer Treatment", Science 1993, 259, 310-311.

Ulmanen et al., "Transcription and Translation of Foreign genes in *Bacillus subtilis* by the aid of a secretion vector", Journal of Bacteriology, Apr. 1985, vol. 162, No. 1, p. 176-182.

Uyttenhove et al., "Escape of mouse mastocytoma P815 after Nearly complete rejection is due to antigen-loss variants rather than immunosuppression", J. Exp. Med., vol. 157, Mar. 1983, 1040-1052.

Vasil et al. (1982) "Cloning of a phosphate-regulated hemolysin gene (phospholipase C) from *Pseudomonas aeruginosa.*" *J Bacteriol.* Oct. ;152(1):431-40.

Vazquez et al., "Differerential regulation of la expression and antigen presentation by listeriolysin-producing versus non-producing strains of *Listeria monocytogenes*", J. Leukoc Biol., May 1996; 59(5):683-90.

Vazquez-Boland et al. (1992) "Nucleotide sequence of the lecithinase operon of *Listeria monocytogenes* and possible role of lecithinase in cell-to-cell spread." *Infect. Irnmun.* 60:219-230.

Verch et al. (2004) "*Listeria monocytogenes*-based antibiotic resistance gene-free antigen delivery system applicable to other bacterial vectors and DNA vaccines." *Infect Immun.* Nov.;72(11):6418-25.

Verma et al. (1995) "Delivery of class I and class II MHC-restricted T-cell epitopes of listeriolysin of *Listeria monocytogenes* by attenuated *Salmonella*", Vaccine 13(2):142-150.

Villanueva et al., "Listeriolysin is processed efficiently into an MHC class I-associated epitope in *Listeria monocytogenes*-infected cells", J. Immunol., Dec. 1, 1995; 155(11):5227-33.

Vines et al., "Identification and charcterization of nucleotide sequence difference in there virulence-associate genes of *Listeria monocytogenes* strains representing clinically important serotypes", Current Microbiology, May 1998, vol. 36, No. 5, pp. 309-318.

Vitiello et al., "Development of a Lipopeptide-based Therapeutic Vaccine to treat chronic HBV infection", J. Clin. Invest., vol. 95, Jan. 1995, 341-349.

Walker et al. (1994) "Tumor growth alters T cell and macrophage production of and responsiveness to granulocyte-macrophage colony-stimulating factor: partial dysregulation through interleukin-10." *Cell Immunol.* 154(1):342-357.

Watson et al. (1991) "Splenic macrophages from tumor-bearing mice co-expressing MAC-1 and MAC-2 antigens exert immunoregulatory functions via two distinct mechanisms." *J Leukoc Biol.* 49(2): 126-138.

Watson et al., "Immunosurveillance is active in colorectal cancer as downregulation but not complete loss of MHC class I expression correlates with a poor prognosis", Int. J. Cancer, 2006, 118, 6-10.

Wei et al. (2005) "*Listeria monocytogenes* phosphatidylinositol-specific phospholipase C has evolved for virulence by greatly reduced activity on GPI anchors." *Proc. Natl. Acad. Sci. USA* 102: 12927-12931.

Wei et al., "Protection against mammary tumor growth by vaccination with full-length, modified human ErbB-2 DNA", Int. J. Cancer, 81, 748-754, 1999.

Weidt et al. (1994) "CD8+ T lymphocyte-mediated antiviral immunity in mice as a result of injection of recombinant viral proteins." *J Immunol.* Sep. 15;153(6):2554-61.

Weiskirch et al. (1997) "*Listeria monocytogenes*: a potent vaccine vector for neoplastic and infectious disease." *Immunological Reviews* 158:159-169.

Welch et al. (1998) "Interaction of Human Arp2/3 Complex and the *Listeria monocytogenes* ActA Protein in Actin Filament Nucleation" *Science* 281:105-108.

Wilson et al., "Transient expression of bacterial gene fragments in eukaryotic cells: implications for CD8(+) T cell epitope analysis", J. Immunol. Methods, Feb. 2000, 234(1-2):137-47.

Wingens et al., "Structural analysis of an epidermal growth factor / transforming growth factor-α chimera with uniqe ErbB binding specificity", The Journal of Biological Chemistry, vol. 278, No. 40, Issue of Oct. 3, pp. 39114-39123, 2003.

Winter JN et al "Low-grade lymphoma" Hematology Am Soc Hematol Educ Program. 2004; 203-20.

Wirth et al. (1986) "Highly efficient protoplast transformation system for *Streptococcus faecalis* and a new *Escherichia coli-S. faecalis* shuttle vector." *J Bacteriol.* 165(3):831-6.

Witkowski et al., "Conversion of a beta-ketoacyl synthase to a malonyl decarboxylase by replacement of the active-site cysteine with glutamine", Biochemistry 38(36):11643-50, Sep. 7, 1999.

Wu et al. (1995) "Engineering an intracellular pathway for major histocompatibility complex class II presentation of antigens" *Cancer Res.* 56:21-26.

Wu et al., "Engineering an intracellular pathway for major histocompatibility complex class II presentation of antigens", Proc. Natl. Acad. Sci. USA, 1995, 92:11671-5.

Wunderlich et al., "Assays for T cell function: induction and measurement of cytotoxic T lymphocyte activity", Current Protocols in Immunology, 1997, vol. 3, p. 3.11.1-3.11.20.

Yaghmai et al., "Optimized regulation of gene expression using artificial transcription factors", Molecular Therapy, Jun. 2002, vol. 5, No. 6, 685-694.

YE et al., "Enhanced immunogenicity of SIV Gag DNA vaccines encoding chimeric proteins containing a C-terminal segment of Listeriolysin O" Virus Research 97 (2003) 7-16.

Young et al. (1992) "Tumor-derived cytokines induce bone marrow suppressor cells that mediate immunosuppression through transforming growth factor beta." *Cancer Immunol Immunother.* 35(1): 14-18.

Young et al. (1995) "Holins: form and function in bacteriophage lysis." *FEMS Microbiol Rev.* Aug.;17(1-2):191-205.

Young et al., "Cloning and Expression of Influenza Virus Genes", The Origin of Pandemic Influenza Viruses, W.G. Laver, eds., Elsevier Science Publishing Co., Inc., NY, 1983, p. 129.

Zhang et al. (1993) "Functional replacement of the hemolysin A transport signal by a different primary sequence." *Proc Natl Acad Sci U S A.* May 1;90(9):4211-5.

Zhang et al., "Selection of Tumor Antigens as Targets for Immune Attack Using Immunohistochemistry: Protein Antigens", Clin. Cancer Res. 1998 4:2669-2676.

Zubair et al., "Live recombinant vaccine vectors for HPV antigens associated with infection and malignancy", In: Vaccines for Human Papillomavirus Infection and Anogential Disease (ed. Robert W. Tindle), 1999, pp. 173-192.

Zwickey et al., "Peptide epitopes from noncytosolic *Listeria monocytogenes* can be presented by major histocompatibiity complex class I molecules", Infect. Immun., May 1996; 64(5):1870-2.

Zwickey et al.,"Antigen secreted from noncytosolic *Listeria monocytogenes* is processed by the classical MHC class I processing pathway", J. Immunol., Jun. 1999, 162(11):6341-50.

Higgens et al., "Delivery of protein to the cytosol of macrophages using *Escherichia coli* K-12" Molecular Microbiology (1999) 31(6), 1631-1641.

Bouwer et al., "Directed antigen delivery as a vaccine strategy for an intracellular bacterial pathogen" PNAS Mar. 28, 2006 vol. 103, No. 13, 5102-5107.

Dubail et al., "Functional assembly of two membrane-binding domains in listeriolysin O, the cytolysin of *Listeria monocytogenes*" *Microbiology* (2001), 147, 2679-2688.

Gene Bank Accession No. AA 435505 (1999, p. 1-4).

\* cited by examiner

LLO-His is purified from BL21 soluble proteins by Ni-NTA agarose

Conjugation of 38C13 Idiotype protein to KLH or LLO is complete

38C13 lymphoma tumor protection study shows the anti-tumor efficacy of the Id-LLO vaccine is equivalent to that of Id-KLH Id-LLO vaccine induces a Th1 response Id-KLH and Id-LLO vaccines induce a low frequency Th2 response Id-LLO vaccine induces expansion of LLO-specific CD8 T cells Id-LLO vaccine induces a CD4 proliferative response to LLO and the 38C13 idiotype protein Proliferative index = average no of divisions that the dividing cell population underwent ID NO: 37 or a combination thereof, wherein said

SEQUENCE LISTING

```
<160> NUMBER OF SEQ ID NOS: 63

<210> SEQ ID NO 1
<211> LENGTH: 180
<212> TYPE: PRT
<213> ORGANISM: Homo sapiens

<400> SEQUENCE: 1

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80
```

```
Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 2
<211> LENGTH: 9
<212> TYPE: PRT
<213> ORGANISM: Homo sapiens

<400> SEQUENCE: 2

Ser Leu Leu Met Trp Ile Thr Gln Cys
1               5

<210> SEQ ID NO 3
<211> LENGTH: 11
<212> TYPE: PRT
<213> ORGANISM: Homo sapiens

<400> SEQUENCE: 3

Ser Leu Leu Met Trp Ile Thr Gln Cys Phe Leu
1               5                   10

<210> SEQ ID NO 4
<211> LENGTH: 12
<212> TYPE: PRT
<213> ORGANISM: Homo sapiens

<400> SEQUENCE: 4

Ser Leu Leu Met Trp Ile Thr Gln Cys Phe Leu Pro
1               5                   10

<210> SEQ ID NO 5
<211> LENGTH: 13
<212> TYPE: PRT
<213> ORGANISM: Homo sapiens

<400> SEQUENCE: 5

Ser Leu Leu Met Trp Ile Thr Gln Cys Phe Leu Pro Val
1               5                   10

<210> SEQ ID NO 6
<211> LENGTH: 14
<212> TYPE: PRT
<213> ORGANISM: Homo sapiens

<400> SEQUENCE: 6

Ser Leu Leu Met Trp Ile Thr Gln Cys Phe Leu Pro Val Phe
1               5                   10

<210> SEQ ID NO 7
<211> LENGTH: 15
```

```
<212> TYPE: PRT
<213> ORGANISM: Homo sapiens

<400> SEQUENCE: 7

Ser Leu Leu Met Trp Ile Thr Gln Cys Phe Leu Pro Val Phe Leu
1               5                   10                  15

<210> SEQ ID NO 8
<211> LENGTH: 20
<212> TYPE: PRT
<213> ORGANISM: Homo sapiens

<400> SEQUENCE: 8

Trp Ile Thr Gln Cys Phe Leu Pro Val Phe Leu Ala Gln Pro Pro Ser
1               5                   10                  15

Gly Gln Arg Arg
            20

<210> SEQ ID NO 9
<211> LENGTH: 20
<212> TYPE: PRT
<213> ORGANISM: Homo sapiens

<400> SEQUENCE: 9

Tyr Leu Ala Met Pro Phe Ala Thr Pro Met Glu Ala Glu Leu Ala Arg
1               5                   10                  15

Arg Ser Leu Ala
            20

<210> SEQ ID NO 10
<211> LENGTH: 10
<212> TYPE: PRT
<213> ORGANISM: Homo sapiens

<400> SEQUENCE: 10

Ala Ser Gly Pro Gly Gly Gly Ala Pro Arg
1               5                   10

<210> SEQ ID NO 11
<211> LENGTH: 9
<212> TYPE: PRT
<213> ORGANISM: Homo sapiens

<400> SEQUENCE: 11

Met Pro Phe Ala Thr Pro Met Glu Ala
1               5

<210> SEQ ID NO 12
<211> LENGTH: 9
<212> TYPE: PRT
<213> ORGANISM: Homo sapiens

<400> SEQUENCE: 12

Leu Ala Met Pro Phe Ala Thr Pro Met
1               5

<210> SEQ ID NO 13
<211> LENGTH: 9
<212> TYPE: PRT
<213> ORGANISM: Homo sapiens

<400> SEQUENCE: 13

Ala Arg Gly Pro Glu Ser Arg Leu Leu
1               5
```

<210> SEQ ID NO 14
<211> LENGTH: 9
<212> TYPE: PRT
<213> ORGANISM: Homo sapiens

<400> SEQUENCE: 14

Leu Leu Met Trp Ile Thr Gln Cys Phe
1               5

<210> SEQ ID NO 15
<211> LENGTH: 9
<212> TYPE: PRT
<213> ORGANISM: Homo sapiens

<400> SEQUENCE: 15

Ser Leu Leu Met Trp Ile Thr Gln Val
1               5

<210> SEQ ID NO 16
<211> LENGTH: 9
<212> TYPE: PRT
<213> ORGANISM: Homo sapiens

<400> SEQUENCE: 16

Ser Leu Leu Met Trp Ile Thr Gln Val
1               5

<210> SEQ ID NO 17
<211> LENGTH: 98
<212> TYPE: PRT
<213> ORGANISM: Human papillomavirus

<400> SEQUENCE: 17

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 18
<211> LENGTH: 11
<212> TYPE: PRT
<213> ORGANISM: Listeria monocytogenes

<400> SEQUENCE: 18

Glu Cys Thr Gly Leu Ala Trp Glu Trp Trp Arg
1               5                   10

<210> SEQ ID NO 19
<211> LENGTH: 9
<212> TYPE: PRT
<213> ORGANISM: Human papillomavirus

```
<400> SEQUENCE: 19

Arg Ala His Tyr Asn Ile Val Thr Phe
1               5

<210> SEQ ID NO 20
<211> LENGTH: 105
<212> TYPE: PRT
<213> ORGANISM: Human papillomavirus

<400> SEQUENCE: 20

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
        50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 21
<211> LENGTH: 8
<212> TYPE: PRT
<213> ORGANISM: Human papillomavirus

<400> SEQUENCE: 21

Thr Leu Gly Ile Val Cys Pro Ile
1               5

<210> SEQ ID NO 22
<211> LENGTH: 9
<212> TYPE: PRT
<213> ORGANISM: Human papillomavirus

<400> SEQUENCE: 22

Leu Leu Met Gly Thr Leu Gly Ile Val
1               5

<210> SEQ ID NO 23
<211> LENGTH: 10
<212> TYPE: PRT
<213> ORGANISM: Human papillomavirus

<400> SEQUENCE: 23

Tyr Met Leu Asp Leu Gln Pro Glu Thr Thr
1               5                   10

<210> SEQ ID NO 24
<211> LENGTH: 158
<212> TYPE: PRT
<213> ORGANISM: Human papillomavirus

<400> SEQUENCE: 24

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
```

```
            20                  25                  30
Ile Ile Leu Glu Cys Val Tyr Cys Lys Gln Gln Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 25
<211> LENGTH: 158
<212> TYPE: PRT
<213> ORGANISM: Human papillomavirus

<400> SEQUENCE: 25

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val
145                 150                 155

<210> SEQ ID NO 26
<211> LENGTH: 145
<212> TYPE: PRT
<213> ORGANISM: Mus musculus

<400> SEQUENCE: 26

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Ser Leu Ser Cys Ala Ala Ser Gly Phe Thr Phe
```

```
            35                  40                  45
Thr Asp Tyr Tyr Met Ser Trp Val Arg Gln Pro Gly Lys Ala Leu
 50                  55                  60
Glu Trp Leu Ala Leu Ile Arg Asn Lys Ala Asn Gly Tyr Thr Thr Glu
 65                  70                  75                  80
Tyr Ser Ala Ser Val Lys Gly Arg Phe Thr Ile Ser Arg Asp Asn Ser
                 85                  90                  95
Gln Ser Ile Leu Tyr Leu Gln Met Asn Ala Leu Arg Ala Glu Asp Ser
                100                 105                 110
Ala Thr Tyr Tyr Cys Ala Arg Asp Pro Asn Tyr Tyr Asp Gly Ser Tyr
                115                 120                 125
Glu Gly Tyr Phe Asp Tyr Trp Ala Gln Gly Thr Thr Leu Thr Val Ser
        130                 135                 140
Ser
145

<210> SEQ ID NO 27
<211> LENGTH: 124
<212> TYPE: PRT
<213> ORGANISM: Mus musculus

<400> SEQUENCE: 27

Leu Leu Leu Ile Ser Val Thr Val Ile Val Ser Asn Gly Glu Ile Val
 1               5                  10                  15
Leu Thr Gln Ser Pro Thr Thr Met Ala Ala Ser Pro Gly Glu Lys Ile
                 20                  25                  30
Thr Ile Thr Cys Ser Ala Ser Ser Ile Ser Ser Asn Tyr Leu His
             35                  40                  45
Trp Tyr Gln Gln Lys Pro Gly Phe Ser Pro Lys Leu Leu Ile Tyr Arg
 50                  55                  60
Thr Ser Asn Leu Ala Ser Gly Val Pro Ala Arg Phe Ser Gly Ser Gly
 65                  70                  75                  80
Ser Gly Thr Ser Tyr Ser Leu Thr Ile Gly Thr Met Glu Ala Glu Asp
                 85                  90                  95
Val Ala Thr Tyr Tyr Cys Gln Gln Gly Ser Ser Ile Pro Arg Gly Val
                100                 105                 110
Thr Phe Gly Ser Gly Thr Lys Leu Glu Ile Lys Arg
            115                 120

<210> SEQ ID NO 28
<211> LENGTH: 132
<212> TYPE: PRT
<213> ORGANISM: Mus musculus

<400> SEQUENCE: 28

Gly Phe Leu Leu Ile Ser Val Thr Val Ile Leu Thr Asn Gly Glu Ile
 1               5                  10                  15
Phe Leu Thr Gln Ser Pro Ala Ile Ile Ala Ala Ser Pro Gly Glu Lys
                 20                  25                  30
Val Thr Ile Thr Cys Ser Ala Ser Ser Val Ser Tyr Met Asn Trp
             35                  40                  45
Tyr Gln Gln Lys Pro Gly Ser Ser Pro Lys Ile Trp Ile Tyr Gly Ile
 50                  55                  60
Ser Asn Leu Ala Ser Gly Val Pro Ala Arg Phe Ser Gly Ser Gly Ser
 65                  70                  75                  80
Gly Thr Ser Phe Ser Phe Thr Ile Asn Ser Met Glu Ala Glu Asp Val
```

```
                    85                  90                  95
Ala Thr Tyr Tyr Cys Gln Gln Arg Ser Ser Tyr Pro Phe Thr Phe Gly
                100                 105                 110

Ser Gly Thr Lys Leu Glu Ile Lys Arg Ala Asp Ala Ala Pro Thr Val
            115                 120                 125

Ser His Leu Pro
            130

<210> SEQ ID NO 29
<211> LENGTH: 123
<212> TYPE: PRT
<213> ORGANISM: Mus musculus

<400> SEQUENCE: 29

Leu Leu Leu Ile Ser Val Thr Val Ile Val Ser Asn Gly Glu Ile Val
1               5                   10                  15

Leu Thr Gln Ser Pro Thr Thr Met Ala Ala Ser Pro Gly Glu Lys Ile
            20                  25                  30

Thr Ile Thr Cys Ser Ala Ser Ser Ile Ser Ser Asn Tyr Leu His
        35                  40                  45

Trp Tyr Gln Gln Lys Pro Gly Phe Ser Pro Lys Leu Leu Ile Tyr Arg
50                  55                  60

Thr Ser Asn Leu Ala Ser Gly Val Pro Ala Arg Phe Ser Gly Ser Gly
65                  70                  75                  80

Ser Gly Thr Ser Tyr Ser Leu Thr Ile Gly Thr Met Glu Ala Glu Asp
                85                  90                  95

Val Ala Thr Tyr Tyr Cys Gln Gln Gly Ser Ser Ile Pro Arg Thr Phe
                100                 105                 110

Gly Ser Gly Thr Lys Leu Glu Ile Lys Arg Ala
            115                 120

<210> SEQ ID NO 30
<211> LENGTH: 157
<212> TYPE: PRT
<213> ORGANISM: Homo sapiens

<400> SEQUENCE: 30

Met Glu Phe Gly Leu Ser Trp Val Phe Leu Val Ala Ile Leu Lys Gly
1               5                   10                  15

Val Gln Cys Glu Met Gln Leu Val Glu Ser Gly Gly Gly Leu Val Gln
            20                  25                  30

Pro Gly Glu Ser Leu Lys Leu Ser Cys Ala Ala Ser Gly Phe Ser Phe
        35                  40                  45

Ser Gly Ser Thr Ile His Trp Val Arg Gln Ala Ser Gly Arg Gly Leu
    50                  55                  60

Glu Trp Val Gly Arg Ser Arg Ser Lys Ala Asp Asn Phe Met Thr Ser
65                  70                  75                  80

Tyr Ala Pro Ser Ile Lys Gly Lys Phe Ile Ile Ser Arg Asp Asp Ser
                85                  90                  95

Ser Asn Met Leu Tyr Leu Gln Met Asn Asn Leu Lys Thr Glu Asp Thr
                100                 105                 110

Ala Val Tyr Phe Cys Thr Arg Asn Phe Thr Ser Leu Asp Ser Thr Gly
            115                 120                 125

Asn Ser Phe Gly Pro Trp Gly Gln Gly Thr Leu Val Thr Val Ser Ser
        130                 135                 140

Gly Ser Ala Ser Ala Pro Thr Leu Phe Pro Leu Val Ser
```

145              150              155

<210> SEQ ID NO 31
<211> LENGTH: 157
<212> TYPE: PRT
<213> ORGANISM: Homo sapiens

<400> SEQUENCE: 31

Met Glu Phe Gly Leu Ser Trp Val Phe Leu Val Ala Ile Leu Lys Gly
1               5                   10                  15

Val Gln Cys Glu Met Gln Leu Val Glu Ser Gly Gly Gly Leu Val Gln
            20                  25                  30

Pro Gly Glu Ser Phe Lys Leu Ser Cys Ala Ala Ser Gly Phe Ser Phe
        35                  40                  45

Ser Gly Ser Thr Ile His Trp Val Arg Gln Ala Ser Gly Arg Gly Leu
    50                  55                  60

Glu Trp Val Gly Arg Ser Arg Ser Lys Ala Asp Asn Phe Met Thr Ser
65                  70                  75                  80

Tyr Ala Pro Ser Ile Lys Gly Lys Phe Ile Ile Ser Arg Asp Asp Ser
                85                  90                  95

Ser Asn Met Met Tyr Leu Gln Met Asn Asn Leu Lys Asn Glu Asp Thr
            100                 105                 110

Ala Val Tyr Phe Cys Thr Arg Asn Phe Thr Ser Leu Asp Ser Thr Gly
        115                 120                 125

Asn Ser Phe Gly Pro Trp Gly Gln Gly Thr Leu Val Thr Val Ser Ser
    130                 135                 140

Gly Ser Ala Ser Ala Pro Thr Leu Phe Pro Leu Val Ser
145                 150                 155

<210> SEQ ID NO 32
<211> LENGTH: 146
<212> TYPE: PRT
<213> ORGANISM: Homo sapiens

<400> SEQUENCE: 32

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Val
        35                  40                  45

Ser Ser Asn Tyr Met Ser Trp Val Arg Gln Ala Pro Gly Lys Gly Leu
    50                  55                  60

Glu Trp Val Ser Val Ile Tyr Ser Gly Gly Ser Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg His Thr Val Arg Gly Gly His Cys Ala Pro Arg His
        115                 120                 125

Lys Pro Ser Leu Gln Glu Arg Trp Gly Asn Gln Arg Gln Gly Ala Leu
    130                 135                 140

Arg Ser
145

-continued

<210> SEQ ID NO 33
<211> LENGTH: 134
<212> TYPE: PRT
<213> ORGANISM: Homo sapiens

<400> SEQUENCE: 33

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Gly Ser Ala Met His Trp Val Arg Gln Ala Ser Gly Lys Gly Leu
    50                  55                  60

Glu Trp Val Gly His Ile Arg Asp Lys Ala Asn Ser Tyr Ala Thr Thr
65                  70                  75                  80

Tyr Ala Ala Ser Val Lys Gly Arg Phe Thr Ile Ser Arg Asp Asp Ser
                85                  90                  95

Lys Asn Thr Ala Tyr Leu Gln Met Asn Ser Leu Lys Ile Glu Asp Thr
            100                 105                 110

Ala Val Tyr Phe Cys Thr Arg Asn Phe Thr Ser Leu Asp Ser Thr Gly
        115                 120                 125

Asn Ser Phe Gly Pro Trp
    130

<210> SEQ ID NO 34
<211> LENGTH: 108
<212> TYPE: PRT
<213> ORGANISM: Homo sapiens

<400> SEQUENCE: 34

Ser Glu Leu Thr Gln Asp Pro Val Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn Leu Pro
                85                  90                  95

Leu Phe Gly Gly Gly Thr Lys Leu Thr Val Leu Gly
            100                 105

<210> SEQ ID NO 35
<211> LENGTH: 114
<212> TYPE: PRT
<213> ORGANISM: Homo sapiens

<400> SEQUENCE: 35

Asp Ile Gln Met Thr Gln Ser Pro Asp Ser Leu Thr Val Ser Leu Gly
1               5                   10                  15

Glu Arg Ala Thr Ile Asn Cys Lys Ser Ser Gln Ser Ile Leu Tyr Ser
            20                  25                  30

Ser Asn Asp Lys Asn Tyr Leu Ala Trp Tyr Gln Gln Lys Ala Gly Gln
        35                  40                  45

```
Pro Pro Lys Leu Leu Ile Tyr Trp Ala Ser Thr Arg Glu Ser Gly Val
 50                  55                  60

Pro Asp Arg Phe Ser Gly Ser Gly Ser Ala Thr Asp Phe Thr Leu Thr
 65                  70                  75                  80

Ile Ser Ser Leu Gln Ala Glu Asp Val Ala Ile Tyr Tyr Cys Gln Gln
                 85                  90                  95

Tyr Tyr Ser Thr Pro Leu Thr Phe Gly Gly Gly Thr Lys Val Glu Ile
                100                 105                 110

Lys Arg

<210> SEQ ID NO 36
<211> LENGTH: 108
<212> TYPE: PRT
<213> ORGANISM: Homo sapiens

<400> SEQUENCE: 36

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Thr Trp
                 20                  25                  30

Leu Ala Trp Tyr Gln Gln Lys Pro Gly Lys Ala Pro Lys Leu Leu Ile
             35                  40                  45

Tyr Glu Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Val Thr Tyr Tyr Cys Gln Gln Tyr Asn Thr Phe Ser Ser
                 85                  90                  95

Tyr Thr Phe Gly Gln Gly Thr Lys Val Glu Ile Lys
                100                 105

<210> SEQ ID NO 37
<211> LENGTH: 529
<212> TYPE: PRT
<213> ORGANISM: Listeria monocytogenes

<400> SEQUENCE: 37

Met Lys Lys Ile Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Lys
                 20                  25                  30

Glu Asn Ser Ile Ser Ser Met Ala Pro Pro Ala Ser Pro Pro Ala Ser
             35                  40                  45

Pro Lys Thr Pro Ile Glu Lys Lys His Ala Asp Glu Ile Asp Lys Tyr
 50                  55                  60

Ile Gln Gly Leu Asp Tyr Asn Lys Asn Asn Val Leu Val Tyr His Gly
 65                  70                  75                  80

Asp Ala Val Thr Asn Val Pro Pro Arg Lys Gly Tyr Lys Asp Gly Asn
                 85                  90                  95

Glu Tyr Ile Val Val Glu Lys Lys Lys Lys Ser Ile Asn Gln Asn Asn
                100                 105                 110

Ala Asp Ile Gln Val Val Asn Ala Ile Ser Ser Leu Thr Tyr Pro Gly
             115                 120                 125

Ala Leu Val Lys Ala Asn Ser Glu Leu Val Glu Asn Gln Pro Asp Val
130                 135                 140
```

```
Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
            165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
            195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
            245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
            325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Gly Asn Glu Ile Val
            435                 440                 445

Gln His Lys Asn Trp Ser Glu Asn Asn Lys Ser Lys Leu Ala His Phe
450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
            485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
            515                 520                 525

Glu

<210> SEQ ID NO 38
<211> LENGTH: 22
<212> TYPE: DNA
<213> ORGANISM: Artificial Sequence
```

```
<220> FEATURE:
<223> OTHER INFORMATION: Primer

<400> SEQUENCE: 38
ggctcgagca tggagataca cc                                            22

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
ggggactagt ttatggtttc tgagaaca                                      28

<210> SEQ ID NO 40
<211> LENGTH: 31
<212> TYPE: DNA
<213> ORGANISM: Artificial Sequence
<220> FEATURE:
<223> OTHER INFORMATION: Primer

<400> SEQUENCE: 40
gggggctagc cctcctttga ttagtatatt c                                  31

<210> SEQ ID NO 41
<211> LENGTH: 28
<212> TYPE: DNA
<213> ORGANISM: Artificial Sequence
<220> FEATURE:
<223> OTHER INFORMATION: Primer

<400> SEQUENCE: 41
ctccctcgag atcataattt acttcatc                                      28

<210> SEQ ID NO 42
<211> LENGTH: 55
<212> TYPE: DNA
<213> ORGANISM: Artificial Sequence
<220> FEATURE:
<223> OTHER INFORMATION: Primer

<400> SEQUENCE: 42
gactacaagg acgatgaccg acaagtgata acccgggatc taaataaatc cgttt        55

<210> SEQ ID NO 43
<211> LENGTH: 27
<212> TYPE: DNA
<213> ORGANISM: Artificial Sequence
<220> FEATURE:
<223> OTHER INFORMATION: Primer

<400> SEQUENCE: 43
cccgtcgacc agctcttctt ggtgaag                                       27

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
gcggatccca tggagataca cctac                                         25
```

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
gctctagatt atggtttctg ag                                    22

<210> SEQ ID NO 46
<211> LENGTH: 529
<212> TYPE: PRT
<213> ORGANISM: Listeria monocytogenes

<400> SEQUENCE: 46

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

```
Ala Ala Val Ser Gly Lys Ser Val Ser Gly Asp Val Glu Leu Thr Asn
            325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
            435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
            485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
            515                 520                 525

Glu

<210> SEQ ID NO 47
<211> LENGTH: 535
<212> TYPE: PRT
<213> ORGANISM: Listeria monocytogenes

<400> SEQUENCE: 47

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
            85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160
```

```
Met Thr Asn Gln Asp Asn Lys Ile Val Val Lys Asn Ala Thr Lys Ser
            165                 170                 175

Asn Val Asn Asn Ala Val Asn Thr Leu Val Glu Arg Trp Asn Glu Lys
        180                 185                 190

Tyr Ala Gln Ala Tyr Ser Asn Val Ser Ala Lys Ile Asp Tyr Asp Asp
    195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu His His His His His His
    530                 535

<210> SEQ ID NO 48
<211> LENGTH: 1551
<212> TYPE: DNA
<213> ORGANISM: Listeria monocytogenes
```

<400> SEQUENCE: 48

```
catatgaagg atgcatctgc attcaataaa gaaaattcaa tttcatccgt ggcaccacca      60
gcatctccgc ctgcaagtcc taagacgcca atcgaaaaga aacacgcgga tgaaatcgat     120
aagtatatac aaggattgga ttacaataaa acaatgtat tagtatacca cggagatgca      180
gtgacaaatg tgccgccaag aaaaggttac aaagatggaa atgaatatat tgttgtggag     240
aaaaagaaga aatccatcaa tcaaaataat gcagacattc aagttgtgaa tgcaatttcg     300
agcctaacct atccaggtgc tctcgtaaaa gcgaattcgg aattagtaga aaatcaacca     360
gatgttctcc ctgtaaaacg tgattcatta acactcagca ttgatttgcc aggtatgact     420
aatcaagaca ataaaatagt tgtaaaaaat gccactaaat caaacgttaa caacgcagta     480
aatacattag tggaaagatg gaatgaaaaa tatgctcaag cttattcaaa tgtaagtgca     540
aaaattgatt atgatgacga aatggcttac agtgaatcac aattaattgc gaaatttggt     600
acagcattta agctgtaaaa taatagcttg aatgtaaact tcggcgcaat cagtgaaggg     660
aaaatgcaag aagaagtcat tagttttaaa caaatttact ataacgtgaa tgttaatgaa     720
cctacaagac cttccagatt tttcggcaaa gctgttacta agagcagtt gcaagcgctt      780
ggagtgaatg cagaaaatcc tcctgcatat atctcaagtg tggcgtatgg ccgtcaagtt     840
tatttgaaat tatcaactaa ttcccatagt actaaagtaa aagctgcttt tgatgctgcc     900
gtaagcggaa aatctgtctc aggtgatgta gaactaacaa atatcatcaa aaattcttcc     960
ttcaaagccg taatttacgg aggttccgca aaagatgaag ttcaaatcat cgacggcaac    1020
ctcggagact tacgcgatat tttgaaaaaa ggcgctactt ttaatcgaga acaccagga     1080
gttcccattg cttatacaac aaacttccta aaagacaatg aattagctgt tattaaaaac    1140
aactcagaat atattgaaac aacttcaaaa gcttatacag atggaaaaat taacatcgat    1200
cactctggag gatacgttgc tcaattcaac atttcttggg atgaagtaaa ttatgatcct    1260
gaaggtaacg aaattgttca acataaaaac tggagcgaaa acaataaaag caagctagct    1320
catttcacat cgtccatcta tttgcctggt aacgcgagaa atattaatgt ttacgctaaa    1380
gaatgcactg gtttagcttg ggaatggtgg agaacggtaa ttgatgaccg gaacttacca    1440
cttgtgaaaa atagaaatat ctccatctgg ggcaccacgc tttatccgaa atatagtaat    1500
aaagtagata atccaatcga acaccaccac caccaccact aataaggatc c             1551
```

<210> SEQ ID NO 49
<211> LENGTH: 20
<212> TYPE: DNA
<213> ORGANISM: Artificial
<220> FEATURE:
<223> OTHER INFORMATION: Primer

<400> SEQUENCE: 49

```
gctagctcat ttcacatcgt                                                  20
```

<210> SEQ ID NO 50
<211> LENGTH: 54
<212> TYPE: DNA
<213> ORGANISM: Artificial
<220> FEATURE:
<223> OTHER INFORMATION: Primer

<400> SEQUENCE: 50

```
tcttgcagct tcccaagcta aaccagtcgc ttctttagcg taaacattaa tatt            54
```

```
<210> SEQ ID NO 51
<211> LENGTH: 54
<212> TYPE: DNA
<213> ORGANISM: Artificial
<220> FEATURE:
<223> OTHER INFORMATION: Primer

<400> SEQUENCE: 51
gaagcgactg gtttagcttg ggaagctgca agaacggtaa ttgatgaccg gaac          54

<210> SEQ ID NO 52
<211> LENGTH: 39
<212> TYPE: DNA
<213> ORGANISM: Artificial
<220> FEATURE:
<223> OTHER INFORMATION: Primer

<400> SEQUENCE: 52
ggatccttat tagtggtggt ggtggtggtg ttcgattgg                           39

<210> SEQ ID NO 53
<211> LENGTH: 11
<212> TYPE: PRT
<213> ORGANISM: Listeria monocytogenes

<400> SEQUENCE: 53

Glu Ala Thr Gly Leu Ala Trp Glu Ala Ala Arg
 1               5                  10

<210> SEQ ID NO 54
<211> LENGTH: 238
<212> TYPE: PRT
<213> ORGANISM: Listeria monocytogenes

<400> SEQUENCE: 54

Gly Cys Thr Ala Gly Cys Thr Cys Ala Thr Thr Thr Cys Ala Cys Ala
 1               5                  10                  15

Thr Cys Gly Thr Cys Cys Ala Thr Cys Thr Ala Thr Thr Thr Gly Cys
                20                  25                  30

Cys Thr Gly Gly Thr Ala Ala Cys Gly Cys Gly Ala Gly Ala Ala Ala
            35                  40                  45

Thr Ala Thr Thr Ala Ala Thr Gly Thr Thr Thr Ala Cys Gly Cys Thr
        50                  55                  60

Ala Ala Ala Gly Ala Ala Gly Cys Gly Ala Cys Thr Gly Gly Thr Thr
 65                  70                  75                  80

Thr Ala Gly Cys Thr Thr Gly Gly Gly Ala Ala Gly Cys Thr Gly Cys
                85                  90                  95

Ala Ala Gly Ala Ala Cys Gly Gly Thr Ala Ala Thr Thr Gly Ala Thr
                100                 105                 110

Gly Ala Cys Cys Gly Gly Ala Ala Cys Thr Thr Ala Cys Cys Ala Cys
            115                 120                 125

Thr Thr Gly Thr Gly Ala Ala Ala Ala Thr Ala Gly Ala Ala Ala
        130                 135                 140

Thr Ala Thr Cys Thr Cys Cys Ala Cys Thr Gly Gly Gly Gly Cys
145                 150                 155                 160

Ala Cys Cys Ala Cys Gly Cys Thr Thr Ala Thr Cys Cys Gly Ala
                165                 170                 175

Ala Ala Thr Ala Thr Ala Gly Thr Ala Ala Thr Ala Ala Ala Gly Thr
            180                 185                 190

Ala Gly Ala Thr Ala Ala Thr Cys Cys Ala Ala Thr Cys Gly Ala Ala
```

```
            195                 200                 205
Cys Ala Cys Cys Ala Cys Cys Ala Cys Cys Ala Cys Cys
        210                 215                 220

Ala Cys Thr Ala Ala Thr Ala Ala Gly Gly Ala Thr Cys Cys
225                 230                 235
```

<210> SEQ ID NO 55
<211> LENGTH: 11
<212> TYPE: PRT
<213> ORGANISM: Listeria monocytogenes

<400> SEQUENCE: 55

```
Glu Ser Leu Leu Met Trp Ile Thr Gln Cys Arg
1               5                   10
```

<210> SEQ ID NO 56
<211> LENGTH: 20
<212> TYPE: PRT
<213> ORGANISM: Artificial
<220> FEATURE:
<223> OTHER INFORMATION: Primer

<400> SEQUENCE: 56

```
Gly Cys Thr Ala Gly Cys Thr Cys Ala Thr Thr Cys Ala Cys Ala
1               5                   10                  15

Thr Cys Gly Thr
            20
```

<210> SEQ ID NO 57
<211> LENGTH: 54
<212> TYPE: PRT
<213> ORGANISM: Artificial
<220> FEATURE:
<223> OTHER INFORMATION: Primer

<400> SEQUENCE: 57

```
Thr Cys Thr Gly Cys Ala Cys Thr Gly Gly Thr Gly Ala Thr Cys
1               5                   10                  15

Cys Ala Cys Ala Thr Cys Ala Gly Cys Ala Gly Gly Cys Thr Thr Thr
                20                  25                  30

Cys Thr Thr Thr Ala Gly Cys Gly Thr Ala Ala Cys Ala Thr Thr
            35                  40                  45

Ala Ala Thr Ala Thr Thr
        50
```

<210> SEQ ID NO 58
<211> LENGTH: 54
<212> TYPE: PRT
<213> ORGANISM: Artificial
<220> FEATURE:
<223> OTHER INFORMATION: Primer

<400> SEQUENCE: 58

```
Gly Ala Ala Gly Cys Cys Thr Gly Cys Thr Gly Ala Thr Gly Thr
1               5                   10                  15

Gly Gly Ala Thr Cys Ala Cys Cys Ala Gly Thr Gly Cys Ala Gly
                20                  25                  30

Ala Ala Cys Gly Gly Thr Ala Ala Thr Thr Gly Ala Thr Gly Ala Cys
        35                  40                  45

Cys Gly Gly Ala Ala Cys
    50
```

<210> SEQ ID NO 59
<211> LENGTH: 39
<212> TYPE: PRT
<213> ORGANISM: Artificial
<220> FEATURE:
<223> OTHER INFORMATION: Primer

<400> SEQUENCE: 59

Gly Gly Ala Thr Cys Cys Thr Thr Ala Thr Ala Gly Thr Gly Gly
1               5                   10                  15

Thr Gly Gly Thr Gly Gly Thr Gly Gly Thr Gly Gly Thr Gly Thr Thr
            20                  25                  30

Cys Gly Ala Thr Thr Gly Gly
        35

<210> SEQ ID NO 60
<211> LENGTH: 238
<212> TYPE: PRT
<213> ORGANISM: Listeria monocytogenes

<400> SEQUENCE: 60

Gly Cys Thr Ala Gly Cys Thr Cys Ala Thr Thr Thr Cys Ala Cys Ala
1               5                   10                  15

Thr Cys Gly Thr Cys Cys Ala Thr Cys Thr Ala Thr Thr Thr Gly Cys
            20                  25                  30

Cys Thr Gly Gly Thr Ala Ala Cys Gly Cys Gly Ala Gly Ala Ala Ala
        35                  40                  45

Thr Ala Thr Thr Ala Ala Thr Gly Thr Thr Thr Ala Cys Gly Cys Thr
    50                  55                  60

Ala Ala Ala Gly Ala Ala Ala Gly Cys Cys Thr Gly Cys Thr Gly Ala
65                  70                  75                  80

Thr Gly Thr Gly Gly Ala Thr Cys Ala Cys Cys Cys Ala Gly Thr Gly
                85                  90                  95

Cys Ala Gly Ala Ala Cys Gly Gly Thr Ala Ala Thr Thr Gly Ala Thr
            100                 105                 110

Gly Ala Cys Cys Gly Gly Ala Ala Cys Thr Thr Ala Cys Cys Ala Cys
        115                 120                 125

Thr Thr Gly Thr Gly Ala Ala Ala Ala Ala Thr Ala Gly Ala Ala Ala
    130                 135                 140

Thr Ala Thr Cys Thr Cys Cys Ala Thr Cys Thr Gly Gly Gly Gly Cys
145                 150                 155                 160

Ala Cys Cys Ala Cys Gly Cys Thr Thr Ala Thr Cys Cys Gly Ala Ala
                165                 170                 175

Ala Ala Thr Ala Thr Ala Gly Thr Ala Ala Thr Ala Ala Ala Gly Thr
            180                 185                 190

Ala Gly Ala Thr Ala Ala Thr Cys Cys Ala Thr Cys Gly Ala Ala Ala
        195                 200                 205

Cys Ala Cys Cys Ala Cys Cys Ala Cys Cys Ala Cys Cys Ala Cys Cys
    210                 215                 220

Ala Cys Thr Ala Ala Thr Ala Ala Gly Gly Ala Thr Cys Cys
225                 230                 235

<210> SEQ ID NO 61
<211> LENGTH: 810
<212> TYPE: PRT
<213> ORGANISM: Homo sapiens

<400> SEQUENCE: 61

```
Gly Cys Cys Cys Ala Gly Cys Cys Gly Cys Cys Ala Thr Gly Cys Cys
1               5                   10                  15

Ala Gly Gly Thr Gly Ala Ala Gly Cys Thr Gly Cys Ala Gly Gly Ala
            20                  25                  30

Gly Thr Cys Ala Gly Gly Ala Gly Gly Ala Gly Gly Cys Thr Thr Gly
        35                  40                  45

Gly Thr Cys Cys Ala Gly Cys Cys Thr Gly Gly Gly Gly Gly Thr Thr
    50                  55                  60

Cys Thr Cys Thr Gly Ala Gly Thr Cys Thr Cys Thr Cys Cys Thr Gly
65                  70                  75                  80

Thr Gly Cys Ala Gly Cys Thr Thr Cys Thr Gly Gly Ala Thr Thr Cys
                85                  90                  95

Ala Cys Cys Thr Thr Cys Ala Cys Thr Gly Ala Thr Thr Ala Cys Thr
            100                 105                 110

Ala Cys Ala Thr Gly Ala Gly Cys Thr Gly Gly Gly Thr Cys Cys Gly
        115                 120                 125

Cys Cys Ala Gly Cys Cys Thr Cys Cys Ala Gly Gly Gly Ala Ala Gly
    130                 135                 140

Gly Cys Ala Cys Thr Thr Gly Ala Gly Thr Gly Gly Thr Thr Gly Gly
145                 150                 155                 160
Cys Thr Thr Thr Gly Ala Thr Thr Ala Gly Ala Ala Ala Cys Ala Ala
                165                 170                 175

Ala Gly Cys Thr Ala Ala Thr Gly Gly Thr Thr Ala Cys Ala Cys Ala
            180                 185                 190

Gly Ala Gly Thr Ala Cys Ala Gly Thr Gly Cys Ala Thr Cys Thr Gly
        195                 200                 205

Thr Gly Ala Ala Gly Gly Gly Thr Cys Gly Gly Thr Thr Cys Ala Cys
    210                 215                 220

Cys Ala Thr Cys Thr Cys Cys Ala Gly Ala Gly Ala Thr Ala Ala Thr
225                 230                 235                 240

Thr Cys Cys Cys Ala Ala Ala Gly Cys Ala Thr Cys Cys Thr Cys Thr
                245                 250                 255

Ala Thr Cys Thr Thr Cys Ala Ala Ala Thr Gly Ala Ala Thr Gly Cys
            260                 265                 270

Cys Cys Thr Gly Ala Gly Ala Gly Cys Thr Gly Ala Gly Gly Ala Cys
        275                 280                 285

Ala Gly Thr Gly Cys Cys Ala Cys Thr Thr Ala Thr Thr Ala Cys Thr
    290                 295                 300

Gly Thr Gly Cys Ala Ala Gly Ala Gly Ala Thr Cys Cys Cys Ala Ala
305                 310                 315                 320

Thr Thr Ala Cys Thr Ala Cys Gly Ala Thr Gly Gly Thr Ala Gly Cys
                325                 330                 335

Thr Ala Cys Gly Ala Ala Gly Gly Gly Thr Ala Cys Thr Thr Thr Gly
            340                 345                 350

Ala Cys Thr Ala Cys Thr Gly Gly Gly Gly Cys Cys Ala Ala Gly Gly
        355                 360                 365

Gly Ala Cys Cys Ala Cys Gly Gly Thr Cys Ala Cys Cys Gly Thr Cys
    370                 375                 380

Thr Cys Cys Thr Cys Ala Gly Gly Cys Gly Gly Ala Gly Gly Cys Gly
385                 390                 395                 400

Gly Thr Thr Cys Ala Gly Gly Cys Gly Gly Ala Gly Gly Thr Gly Gly
                405                 410                 415
```

```
Cys Thr Cys Thr Gly Gly Cys Gly Gly Thr Gly Gly Cys Gly Gly Ala
                420                 425                 430
Thr Cys Gly Gly Ala Cys Ala Thr Thr Gly Ala Gly Cys Thr Cys Ala
            435                 440                 445
Cys Cys Cys Ala Gly Thr Cys Thr Cys Ala Thr Cys Cys Thr Cys
        450                 455                 460
Ala Cys Thr Gly Thr Cys Thr Gly Cys Ala Thr Cys Thr Cys Thr Gly
465                 470                 475                 480
Gly Gly Ala Gly Gly Cys Ala Ala Gly Thr Cys Ala Cys Cys Ala
                485                 490                 495
Thr Cys Ala Cys Thr Thr Gly Cys Ala Ala Gly Gly Cys Ala Ala Gly
            500                 505                 510
Cys Cys Ala Ala Gly Ala Cys Ala Thr Thr Ala Ala Cys Ala Ala Gly
        515                 520                 525
Thr Ala Thr Ala Thr Ala Gly Cys Thr Thr Gly Gly Thr Ala Cys Cys
        530                 535                 540
Ala Ala Cys Ala Cys Ala Ala Gly Cys Cys Thr Gly Gly Ala Ala Ala
545                 550                 555                 560
Ala Gly Gly Thr Cys Cys Thr Ala Gly Gly Cys Thr Gly Cys Thr Cys
                565                 570                 575
Ala Thr Ala Cys Ala Thr Thr Ala Cys Ala Cys Ala Thr Cys Thr Ala
            580                 585                 590
Cys Ala Thr Thr Ala Cys Ala Gly Cys Ala Gly Gly Cys Ala Thr
        595                 600                 605
Cys Cys Cys Ala Thr Cys Ala Ala Gly Gly Thr Thr Cys Ala Gly Thr
        610                 615                 620
Gly Gly Ala Ala Gly Thr Gly Gly Gly Thr Cys Thr Gly Gly Gly Ala
625                 630                 635                 640
Gly Ala Gly Ala Thr Thr Ala Thr Thr Cys Cys Thr Cys Ala Gly
                645                 650                 655
Cys Ala Thr Cys Ala Gly Cys Ala Ala Cys Cys Thr Gly Gly Ala Gly
            660                 665                 670
Cys Cys Thr Gly Ala Ala Gly Ala Thr Ala Thr Thr Gly Cys Ala Ala
        675                 680                 685
Cys Thr Thr Ala Thr Thr Ala Thr Thr Gly Cys Thr Ala Cys Ala Ala
        690                 695                 700
Gly Thr Ala Thr Gly Ala Thr Ala Ala Thr Cys Thr Gly Thr Ala Cys
705                 710                 715                 720
Ala Cys Gly Thr Thr Cys Gly Gly Cys Thr Cys Gly Gly Gly Gly Ala
                725                 730                 735
Cys Cys Ala Ala Gly Cys Thr Gly Gly Ala Ala Ala Thr Ala Ala Ala
            740                 745                 750
Ala Cys Gly Gly Gly Cys Gly Gly Cys Cys Gly Cys Ala Gly Ala Ala
        755                 760                 765
Cys Ala Ala Ala Ala Ala Cys Thr Cys Ala Thr Cys Thr Cys Ala Gly
        770                 775                 780
Ala Ala Gly Ala Gly Gly Ala Thr Cys Thr Gly Ala Ala Thr Thr Ala
785                 790                 795                 800
Ala Thr Ala Ala Gly Ala Ala Thr Thr Cys
                805                 810

<210> SEQ ID NO 62
<211> LENGTH: 285
<212> TYPE: PRT
```

<213> ORGANISM: Homo sapiens

<400> SEQUENCE: 62

```
Met Lys Tyr Leu Leu Pro Thr Ala Ala Ala Gly Leu Leu Leu Leu Ala
 1               5                  10                  15

Ala Gln Pro Ala Gln Pro Pro Cys Gln Val Lys Leu Gln Glu Ser Gly
                20                  25                  30

Gly Gly Leu Val Gln Pro Gly Gly Ser Leu Ser Leu Ser Cys Ala Ala
            35                  40                  45

Ser Gly Phe Thr Phe Thr Asp Tyr Tyr Met Ser Trp Val Arg Gln Pro
        50                  55                  60

Pro Gly Lys Ala Leu Glu Trp Leu Ala Leu Ile Arg Asn Lys Ala Asn
 65                  70                  75                  80

Gly Tyr Thr Glu Tyr Ser Ala Ser Val Lys Gly Arg Phe Thr Ile Ser
                85                  90                  95

Arg Asp Asn Ser Gln Ser Ile Leu Tyr Leu Gln Met Asn Ala Leu Arg
            100                 105                 110

Ala Glu Asp Ser Ala Thr Tyr Tyr Cys Ala Arg Asp Pro Asn Tyr Tyr
        115                 120                 125

Asp Gly Ser Tyr Glu Gly Tyr Phe Asp Tyr Trp Gly Gln Gly Thr Thr
    130                 135                 140

Val Thr Val Ser Ser Gly Gly Gly Gly Ser Gly Gly Gly Gly Ser Gly
145                 150                 155                 160

Gly Gly Gly Ser Asp Ile Glu Leu Thr Gln Ser Pro Ser Ser Leu Ser
                165                 170                 175

Ala Ser Leu Gly Gly Lys Val Thr Ile Thr Cys Lys Ala Ser Gln Asp
            180                 185                 190

Ile Asn Lys Tyr Ile Ala Trp Tyr Gln His Lys Pro Gly Lys Gly Pro
        195                 200                 205

Arg Leu Leu Ile His Tyr Thr Ser Thr Leu Gln Pro Gly Ile Pro Ser
    210                 215                 220

Arg Phe Ser Gly Ser Gly Ser Gly Arg Asp Tyr Ser Phe Ser Ile Ser
225                 230                 235                 240

Asn Leu Glu Pro Glu Asp Ile Ala Thr Tyr Tyr Cys Leu Gln Tyr Asp
                245                 250                 255

Asn Leu Tyr Thr Phe Gly Ser Gly Thr Lys Leu Glu Ile Lys Arg Ala
            260                 265                 270

Ala Ala Glu Gln Lys Leu Ile Ser Glu Glu Asp Leu Asn
        275                 280                 285

<210> SEQ ID NO 63
<211> LENGTH: 32
<212> TYPE: PRT
<213> ORGANISM: Listeria monocytogenes

<400> SEQUENCE: 63

Lys Glu Asn Ser Ile Ser Ser Met Ala Pro Pro Ala Ser Pro Pro Ala
 1               5                  10                  15

Ser Pro Lys Thr Pro Ile Glu Lys Lys His Ala Asp Glu Ile Asp Lys
                20                  25                  30
```

NON-HEMOLYTIC LLO FUSION PROTEINS AND METHODS OF UTILIZING SAME

GOVERNMENT INTEREST STATEMENT

This invention was made in whole or in part with government support under Grant Number R43 CA108129-01 (SBIR), awarded by the National Institutes of Health. The government may have certain rights in the invention.

FIELD OF INVENTION

The present invention provides recombinant proteins or peptides comprising a mutated listeriolysin O (LLO) protein or fragment thereof, comprising a substitution or internal deletion of the cholesterol-binding domain or a portion thereof, fusion proteins or peptides comprising same, nucleotide molecules encoding same, and vaccine vectors comprising or encoding same. The present invention also provides methods of utilizing recombinant proteins, peptides, nucleotide molecules, and vaccine vectors of the present invention to induce an immune response to a peptide of interest.

BACKGROUND OF THE INVENTION

Stimulation of an immune response is dependent upon the presence of antigens recognized as foreign by the host immune system. Bacterial antigens such as *Salmonella enterica* and *Mycobacterium bovis* BCG remain in the phagosome and stimulate CD4$^+$ T-cells via antigen presentation through major histocompatibility class II molecules. In contrast, bacterial antigens such as *Listeria monocytogenes* exit the phagosome into the cytoplasm. The phagolysosomal escape of *L. monocytogenes* is a unique mechanism, which facilitates major histocompatibility class I antigen presentation of Listerial antigens. This escape is dependent upon the pore-forming sulfhydryl-activated cytolysin, listeriolysin O (LLO).

There exists a long-felt need to develop compositions and methods to enhance the immunogenicity of antigens, especially antigens useful in the prevention and treatment of tumors and intracellular pathogens.

SUMMARY OF THE INVENTION

The present invention provides a recombinant protein comprising a mutated listeriolysin O (LLO) protein or fragment thereof, containing a mutation in or a substitution or internal deletion of the cholesterol-binding domain, fusion proteins or peptides comprising same, nucleotide molecules encoding same, and vaccine vectors comprising or encoding same. The present invention also provides methods of utilizing recombinant proteins, peptides, nucleotide molecules, and vaccine vectors of the present invention to induce an immune response to a peptide of interest.

The present invention provides a recombinant protein comprising a listeriolysin O (LLO) protein or N-terminal fragment thereof, wherein said LLO protein or N-terminal fragment comprises a mutation in a cholesterol-binding domain (CBD), wherein said mutation comprises a substitution of a 1-50 amino acid peptide comprising a CBD as set forth in SEQ ID NO: 18 for a 1-50 amino acid non-LLO peptide, wherein said recombinant protein exhibits a greater than 100-fold reduction in hemolytic activity relative to wild-type LLO.

In another embodiment, the present invention provides a recombinant protein comprising a listeriolysin O (LLO) protein or N-terminal fragment thereof, wherein said LLO protein or N-terminal fragment comprises a mutation in a cholesterol-binding domain (CBD), wherein said mutation comprises a substitution of residue C484, W491, W492, of SEQ ID NO: 37 or a combination thereof, wherein said recombinant protein exhibits a greater than 100-fold reduction in hemolytic activity relative to wild-type LLO.

In another embodiment, the present invention provides a recombinant protein comprising (a) a listeriolysin O (LLO) protein or N-terminal fragment thereof, wherein said LLO protein or N-terminal fragment thereof comprises a 1-50 amino acid internal deletion in the cholesterol-binding domain of the LLO protein as set forth in SEQ ID NO: 18; and (b) a heterologous peptide of interest, wherein said recombinant protein exhibits a greater than 100-fold reduction in hemolytic activity relative to wild-type LLO.

In one embodiment, the mutated LLO protein or mutated N-terminal LLO protein fragment comprises a deletion of the signal peptide sequence thereof. In another embodiment, the mutated LLO protein or mutated N-terminal LLO fragment comprises the signal peptide sequence thereof. In another embodiment, the recombinant protein comprises a heterologous peptide of interest. In another embodiment, the recombinant protein comprises a non-LLO peptide, which in one embodiment, comprises said heterologous peptide of interest. In another embodiment, the heterologous peptide of interest is a full-length protein, which in one embodiment, comprises an antigenic peptide. In one embodiment, the protein is an NY-ESO-1 protein. In another embodiment, the protein is a Human Papilloma Virus (HPV) E7 protein. In another embodiment, the protein is a B-cell receptor (BCR) protein. In another embodiment, the heterologous peptide of interest is an antigenic peptide. In another embodiment, the antigenic peptide is an NY-ESO-1 peptide. In another embodiment, the antigenic peptide is a Human Papilloma Virus (HPV) E7 peptide. In another embodiment, the antigenic peptide is a B-cell receptor (BCR) peptide. In another embodiment, the antigenic peptide is a wherein said antigenic peptide is a Human Papilloma Virus (HPV)-16-E6, HPV-16-E7, HPV-18-E6, HPV-18-E7, a Her/2-neu antigen, a Prostate Specific Antigen (PSA), Prostate Stem Cell Antigen (PSCA), a Stratum Corneum Chymotryptic Enzyme (SCCE) antigen, Wilms tumor antigen 1 (WT-1), human telomerase reverse transcriptase (hTERT), Proteinase 3, Tyrosinase Related Protein 2 (TRP2), High Molecular Weight Melanoma Associated Antigen (HMW-MAA), synovial sarcoma, X (SSX)-2, carcinoembryonic antigen (CEA), MAGE-A, interleukin-13 Receptor alpha (IL13-R alpha), Carbonic anhydrase IX (CAIX), survivin, GP100, or Testisin peptide.

In another embodiment, the present invention provides a vaccine comprising the recombinant protein and an adjuvant. In another embodiment, the adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide. In another embodiment, the present invention provides a composition comprising the recombinant protein and a heterologous peptide of interest, wherein said recombinant protein is not covalently bound to said heterologous peptide of interest. In another embodiment, the present invention provides a vaccine comprising such a composition and an adjuvant. In another embodiment, the present invention provides a recombinant vaccine vector encoding the recombinant protein. In another embodiment, the present invention provides a nucleotide molecule encoding the recombinant protein.

In another embodiment, the present invention provides a vaccine comprising the nucleotide molecule. In another embodiment, the present invention provides a recombinant *Listeria* strain comprising the recombinant protein or peptide. In another embodiment, the present invention provides a method for inducing an immune response in a subject, comprising administering to said subject the recombinant protein or peptide. In another embodiment, the present invention provides a method for inducing an immune response in a subject, comprising administering to said subject the composition. In another embodiment, the present invention provides a method for inducing an immune response in a subject, comprising administering to said subject the recombinant vaccine vector wherein said non-LLO protein or peptide of said recombinant protein or peptide comprises an antigenic peptide of interest, thereby inducing an immune response against said antigenic peptide of interest. In another embodiment, the present invention provides a method for inducing an immune response in a subject, comprising administering to said subject the recombinant vaccine vector that further comprises a heterologous peptide of interest, thereby inducing an immune response against said heterologous peptide of interest. In another embodiment, the present invention provides a method for inducing an immune response in a subject, comprising administering to said subject a recombinant *Listeria* strain wherein said non-LLO protein or peptide of said recombinant protein comprises an antigenic peptide of interest, thereby inducing an immune response against said antigenic peptide of interest. In another embodiment, the present invention provides a method for inducing an immune response in a subject, comprising administering to said subject the recombinant *Listeria* strain and a vector encoding a heterologous peptide of interest thereby inducing an immune response against said heterologous peptide of interest.

In another embodiment, the present invention provides a method for inducing an immune response in a subject against an NY-ESO-1-expressing cancer cell selected from an ovarian melanoma cell and a lung cancer cell, the method comprising the step of administering to said subject a recombinant protein of the present invention. In another embodiment, the present invention provides a method for treating, inhibiting, or suppressing an NY-ESO-1-expressing tumor selected from an ovarian melanoma tumor and a lung cancer tumor in a subject, the method comprising the step of administering to said subject the recombinant protein of the present invention.

In another embodiment, the present invention provides a method for inducing an immune response in a subject against an HPV E7-expressing cancer cell selected from a cervical cancer cell and a head-and-neck cancer cell, the method comprising the step of administering to said subject the recombinant protein of the present invention. In another embodiment, the present invention provides a method for treating, inhibiting, or suppressing an HPV E7-expressing tumor selected from a cervical cancer tumor and a head-and-neck cancer tumor in a subject, the method comprising the step of administering to said subject the recombinant protein of the present invention. In another embodiment, the present invention provides a method for inducing an immune response in a subject against a B-cell receptor (BCR)-expressing lymphoma, the method comprising the step of administering to said subject the recombinant protein of the present invention. In another embodiment, the present invention provides a method for treating, inhibiting, or suppressing a B-cell receptor (BCR)-expressing lymphoma in a subject, the method comprising the step of administering to said subject the recombinant protein of the present invention.

DETAILED DESCRIPTION OF THE INVENTION

Figure 1:
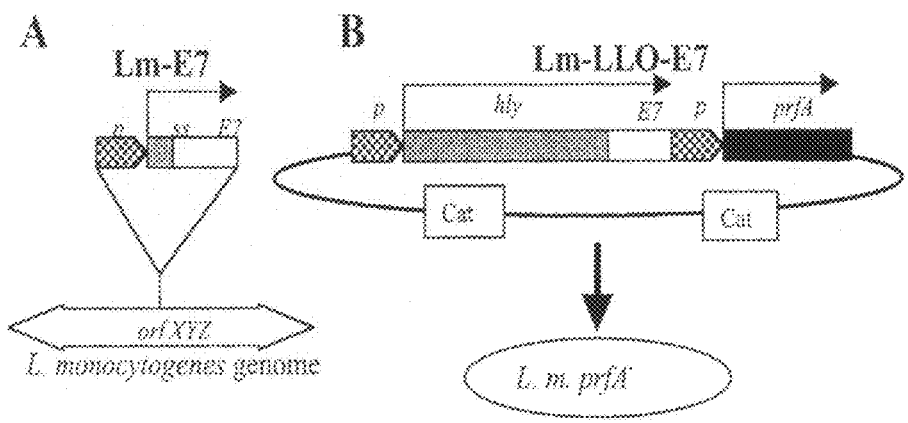
FIG. 1. Lm-E7 and Lm-LLO-E7 use different expression systems to express and secrete E7. Lm-E7 was generated by introducing a gene cassette into the orfZ domain of the *L. monocytogenes* genome (A). The hly promoter drives expression of the hly signal sequence and the first five amino acids (AA) of LLO followed by HPV-16 E7. B), Lm-LLO-E7 was generated by transforming the prfA-strain XFL-7 with the plasmid pGG-55. pGG-55 has the hly promoter driving expression of a nonhemolytic fusion of LLO-E7. pGG-55 also contains the prfA gene to select for retention of the plasmid by XFL-7 in vivo.

The present invention provides recombinant proteins and peptides comprising a mutated listeriolysin O (LLO) protein or fragment thereof, comprising a substitution or internal deletion that includes the cholesterol-binding domain, fusion peptides comprising same, nucleotide molecules encoding same, and vaccine vectors comprising or encoding same. The present invention also provides methods of utilizing recombinant peptides, nucleotide molecules, and vaccine vectors of the present invention to induce an immune response.

In one embodiment, the present invention provides a recombinant protein or polypeptide comprising a listeriolysin O (LLO) protein, wherein said LLO protein comprises a mutation of residues C484, W491, W492, or a combination thereof of the cholesterol-binding domain (CBD) of said LLO protein. In one embodiment, said C484, W491, and W492 residues are residues C484, W491, and W492 of SEQ ID NO: 37, while in another embodiment, they are corresponding residues as can be deduced using sequence alignments, as is known to one of skill in the art. In one embodiment, residues C484, W491, and W492 are mutated. In one embodiment, a mutation is a substitution, in another embodiment, a deletion. In one embodiment, the entire CBD is mutated, while in another embodiment, portions of the CBD are mutated, while in another embodiment, only specific residues within the CBD are mutated.

In another embodiment, the LLO fragment is an N-terminal LLO fragment. In another embodiment, the LLO fragment is at least 492 amino acids (AA) long. In another embodiment, the LLO fragment is 492-528 AA long. In another embodiment, the non-LLO peptide is 1-50 amino acids long. In another embodiment, the mutated region is 1-50 amino acids long. In another embodiment, the non-LLO peptide is the same length as the mutated region. In another embodiment, the non-LLO peptide is shorter, or in another embodiment, longer, than the mutated region. In another embodiment, the substitution is an inactivating mutation with respect to hemolytic activity. In another embodiment, the recombinant peptide exhibits a reduction in hemolytic activity relative to wild-type LLO. In another embodiment, the recombinant peptide is non-hemolytic. Each possibility represents a separate embodiment of the present invention.

In one embodiment, the present invention provides a recombinant protein or polypeptide comprising a mutated LLO protein or fragment thereof, wherein the mutated LLO protein or fragment thereof contains a substitution of a non-LLO peptide for a mutated region of the mutated LLO protein or fragment thereof, the mutated region comprising a residue selected from C484, W491, and W492. In another embodiment, the LLO fragment is an N-terminal LLO fragment. In another embodiment, the LLO fragment is at least 492 amino acids (AA) long. In another embodiment, the LLO fragment is 492-528 AA long. In another embodiment, the non-LLO peptide is 1-50 amino acids long. In another embodiment, the mutated region is 1-50 amino acids long. In another embodiment, the non-LLO peptide is the same length as the mutated region. In another embodiment, the non-LLO peptide has a length different from the mutated region. In another embodiment, the substitution is an inactivating mutation with respect to hemolytic activity. In another embodiment, the recombinant protein or polypeptide exhibits a reduction in hemolytic activity relative to wild-type LLO. In another embodiment, the recombinant protein or polypeptide is non-hemolytic. Each possibility represents a separate embodiment of the present invention.

As provided herein, a mutant LLO protein was created wherein residues C484, W491, and W492 of LLO were substituted with alanine residues (Example 5). The mutated LLO protein, mutLLO, could be expressed and purified in an E. coli expression system (Example 7) and exhibited substantially reduced hemolytic activity relative to wild-type LLO (Example 8).

In another embodiment, the present invention provides a recombinant protein or polypeptide comprising a mutated LLO protein or fragment thereof, wherein the mutated LLO protein or fragment thereof contains a substitution of a non-LLO peptide for a mutated region of the mutated LLO protein or fragment thereof, the mutated region comprising the cholesterol-binding domain (CBD) of the mutated LLO protein or fragment thereof. In another embodiment, the LLO fragment is an N-terminal LLO fragment. In another embodiment, the LLO fragment is at least 492 AA long. In another embodiment, the LLO fragment is 492-528 AA long. In another embodiment, the non-LLO peptide is 1-50 amino acids long. In another embodiment, the mutated region is 11-50 amino acids long. In another embodiment, the non-LLO peptide is the same length as the mutated region. In another embodiment, the non-LLO peptide has a length different from the mutated region. In another embodiment, the substitution is an inactivating mutation with respect to hemolytic activity. In another embodiment, the recombinant protein or polypeptide exhibits a reduction in hemolytic activity relative to wild-type LLO. In another embodiment, the recombinant protein or polypeptide is non-hemolytic. Each possibility represents a separate embodiment of the present invention.

In another embodiment, the present invention provides a recombinant protein or polypeptide comprising a mutated LLO protein or fragment thereof, wherein the mutated LLO protein or fragment thereof contains a substitution of a non-LLO peptide for a mutated region of the mutated LLO protein or fragment thereof, wherein the mutated region is a fragment of the CBD of the mutated LLO protein or fragment thereof. In another embodiment, the LLO fragment is an N-terminal LLO fragment. In another embodiment, the LLO fragment is at least 492 AA long. In another embodiment, the LLO fragment is 492-528 AA long. In another embodiment, the non-LLO peptide is 1-50 amino acids long. In another embodiment, the mutated region is 1-11 amino acids long. In another embodiment, the non-LLO peptide is the same length as the mutated region. In another embodiment, the non-LLO peptide has a length different from the mutated region. In another embodiment, the substitution is an inactivating mutation with respect to hemolytic activity. In another embodiment, the recombinant protein or polypeptide exhibits a reduction in hemolytic activity relative to wild-type LLO. In another embodiment, the recombinant protein or polypeptide is non-hemolytic. Each possibility represents a separate embodiment of the present invention.

In another embodiment, the present invention provides a recombinant protein or polypeptide comprising a mutated LLO protein or fragment thereof, wherein the mutated LLO protein or fragment thereof contains a substitution of a 1-50 amino acid non-LLO peptide for a 1-50 amino acid mutated region of the mutated LLO protein or fragment thereof, wherein the mutated region overlaps the CBD of the mutated LLO protein or fragment thereof. In another embodiment, the LLO fragment is an N-terminal LLO fragment. In another embodiment, the LLO fragment is at least 492 AA long. In another embodiment, the LLO fragment is 492-528 AA long. In another embodiment, the substitution is an inactivating mutation with respect to hemolytic activity. In another embodiment, the recombinant protein or polypeptide exhibits a reduction in hemolytic activity relative to wild-type LLO. In another embodiment, the recombinant protein or polypeptide is non-hemolytic. Each possibility represents a separate embodiment of the present invention.

In another embodiment, the present invention provides a recombinant protein or polypeptide comprising (a) a mutated LLO protein, wherein the mutated LLO protein contains an internal deletion, the internal deletion comprising the cholesterol-binding domain of the mutated LLO protein; and (b) a heterologous peptide of interest. In another embodiment, the sequence of the cholesterol-binding domain is set forth in SEQ ID NO: 18. In another embodiment, the internal deletion is an 11-50 amino acid internal deletion. In another embodiment, the internal deletion is inactivating with regard to the hemolytic activity of the recombinant protein or polypeptide. In another embodiment, the recombinant protein or polypeptide exhibits a reduction in hemolytic activity relative to wild-type LLO. Each possibility represents another embodiment of the present invention.

In another embodiment, the present invention provides a recombinant protein or polypeptide comprising (a) a mutated LLO protein, wherein the mutated LLO protein contains an internal deletion, the internal deletion comprising comprises a residue selected from C484, W491, and W492 of the mutated LLO protein; and (b) a heterologous peptide of interest. In another embodiment, the internal deletion is a 1-50 amino acid internal deletion. In another embodiment, the internal deletion is inactivating with regard to the hemolytic activity of the recombinant protein or polypeptide. In another embodiment, the recombinant protein or polypeptide exhibits a reduction in hemolytic activity relative to wild-type LLO. Each possibility represents another embodiment of the present invention.

In another embodiment, the present invention provides a recombinant protein or polypeptide comprising (a) a mutated LLO protein, wherein the mutated LLO protein contains an internal deletion, the internal deletion comprising a fragment of the cholesterol-binding domain of the mutated LLO protein; and (b) a heterologous peptide of interest. In another embodiment, the internal deletion is a 1-11 amino acid internal deletion. In another embodiment, the sequence of the cholesterol-binding domain is set forth in SEQ ID NO: 18. In another embodiment, the internal deletion is inactivating with regard to the hemolytic activity of the recombinant protein or polypeptide. In another embodiment, the recombinant protein or polypeptide exhibits a reduction in hemolytic activity relative to wild-type LLO. Each possibility represents another embodiment of the present invention.

In another embodiment, the present invention provides a vaccine comprising an adjuvant, a recombinant protein or polypeptide of the present invention, and a heterologous peptide of interest. In another embodiment, the present invention provides a composition comprising an adjuvant, a recombinant protein or polypeptide of the present invention, and a heterologous antigenic peptide of interest. In another embodiment, the recombinant protein or polypeptide is not covalently bound to the heterologous peptide of interest. Each possibility represents a separate embodiment of the present invention.

The mutated region of methods and compositions of the present invention comprises, in another embodiment, residue C484 of SEQ ID NO: 37. In another embodiment, the mutated region comprises a corresponding cysteine residue of a homologous LLO protein. In another embodiment, the mutated region comprises residue W491 of SEQ ID NO: 37. In another embodiment, the mutated region comprises a corresponding tryptophan residue of a homologous LLO protein. In another embodiment, the mutated region comprises residue W492 of SEQ ID NO: 37. In another embodiment, the mutated region comprises a corresponding tryptophan residue of a homologous LLO protein. Methods for identifying corresponding residues of a homologous protein are well known in the art, and include, for example, sequence alignment. Each possibility represents a separate embodiment of the present invention.

In another embodiment, the mutated region comprises residues C484 and W491. In another embodiment, the mutated region comprises residues C484 and W492. In another embodiment, the mutated region comprises residues W491 and W492. In another embodiment, the mutated region comprises residues C484, W491, and W492. Each possibility represents a separate embodiment of the present invention.

In another embodiment, the mutated region of methods and compositions of the present invention comprises the cholesterol-binding domain of the mutated LLO protein or fragment thereof. For example, a mutated region consisting of residues 470-500, 470-510, or 480-500 of SEQ ID NO: 37 comprises the CBD thereof (residues 483-493). In another embodiment, the mutated region is a fragment of the CBD of the mutated LLO protein or fragment thereof. For example, as provided herein, residues C484, W491, and W492, each of which is a fragment of the CBD, were mutated to alanine residues (Example 5). Further, as provided herein, a fragment of the CBD, residues 484-492, was replaced with a heterologous sequence from NY-ESO-1 (Example 6). In another embodiment, the mutated region overlaps the CBD of the mutated LLO protein or fragment thereof. For example, a mutated region consisting of residues 470-490, 480-488, 490-500, or 486-510 of SEQ ID NO: 37 comprises the CBD thereof. In another embodiment, a single peptide may have a deletion in the signal sequence and a mutation or substitution in the CBD. Each possibility represents a separate embodiment of the present invention.

The length of the mutated region is, in another embodiment, 1-50 AA. In another embodiment, the length is 1-11 AA. In another embodiment, the length is 2-11 AA. In another embodiment, the length is 3-11 AA. In another embodiment, the length is 4-11 AA. In another embodiment, the length is 5-11 AA. In another embodiment, the length is 6-11 AA. In another embodiment, the length is 7-11 AA. In another embodiment, the length is 8-11 AA. In another embodiment, the length is 9-1 AA. In another embodiment, the length is 10-11 AA. In another embodiment, the length is 1-2 AA. In another embodiment, the length is 1-3 AA. In another embodiment, the length is 1-4 AA. In another embodiment, the length is 1-5 AA. In another embodiment, the length is 1-6 AA. In another embodiment, the length is 1-7 AA. In another embodiment, the length is 1-8 AA. In another embodiment, the length is 1-9 AA. In another embodiment, the length is 1-10 AA. In another embodiment, the length is 2-3 AA. In another embodiment, the length is 2-4 AA. In another embodiment, the length is 2-5 AA. In another embodiment, the length is 2-6 AA. In another embodiment, the length is 2-7 AA. In another embodiment, the length is 2-8 AA. In another embodiment, the length is 2-9 AA. In another embodiment, the length is 2-10 AA. In another embodiment, the length is 3-4 AA. In another embodiment, the length is 3-5 AA. In another embodiment, the length is 3-6 AA. In another embodiment, the length is 3-7 AA. In another embodiment, the length is 3-8 AA. In another embodiment, the length is 3-9 AA. In another embodiment, the length is 3-10 AA. In another embodiment, the length is 11-50 AA. In another embodiment, the length is 12-50 AA. In another embodiment, the length is 11-15 AA. In another embodiment, the length is 11-20 AA. In another embodiment, the length is 11-25 AA. In another embodiment, the length is 11-30 AA. In another embodiment, the length is 11-35 AA. In another embodiment, the length is 11-40 AA. In another embodiment, the length is 11-60 AA. In another embodiment, the length is 11-70 AA. In another embodiment, the length is 11-80 AA. In another embodiment, the length is 11-90 AA. In another embodiment, the length is 11-100 AA. In another embodiment, the length is 11-150 AA. In another embodiment, the length is 15-20 AA. In another embodiment, the length is 15-25 AA. In another embodiment, the length is 15-30 AA. In another embodiment, the length is 15-35 AA. In another embodiment, the length is 15-40 AA. In another embodiment, the length is 15-60 AA. In another embodiment, the length is 15-70 AA. In another embodiment, the length is 15-80 AA. In another embodiment, the length is 15-90 AA. In another embodiment, the length is 15-100 AA. In another embodiment, the length is 15-150 AA. In another embodiment, the length is 20-25 AA. In another embodiment, the length is 20-30 AA. In another embodiment, the length is 20-35 AA. In another embodiment, the length is 20-40 AA. In another embodiment, the length is 20-60 AA. In another embodiment, the length is 20-70 AA. In another embodiment, the length is 20-80 AA. In another embodiment, the length is 20-90 AA. In another embodiment, the length is 20-100 AA. In another embodiment, the length is 20-150 AA. In another embodiment, the length is 30-35 AA. In another embodiment, the length is 30-40 AA. In another embodiment, the length is 30-60 AA. In another embodiment, the length is 30-70 AA. In another embodiment, the length is 30-80 AA. In another embodiment, the length is 30-90 AA. In another embodiment, the length is 30-100 AA. In another embodiment, the length is 30-150 AA. Each possibility represents another embodiment of the present invention.

The substitution mutation of methods and compositions of the present invention is, in another embodiment, a mutation wherein the mutated region of the LLO protein or fragment thereof is replaced by an equal number of heterologous AA. In another embodiment, a larger number of heterologous AA than the size of the mutated region is introduced. In another embodiment, a smaller number of heterologous AA than the size of the mutated region is introduced. Each possibility represents another embodiment of the present invention.

In another embodiment, the substitution mutation is a point mutation of a single residue. In another embodiment, the substitution mutation is a point mutation of 2 residues. In another embodiment, the substitution mutation is a point mutation of 3 residues. In another embodiment, the substitution mutation is a point mutation of more than 3 residues. In another embodiment, the substitution mutation is a point mutation of several residues. In another embodiment, the multiple residues included in the point mutation are contiguous. In another embodiment, the multiple residues are not contiguous. Each possibility represents another embodiment of the present invention.

The length of the non-LLO peptide that replaces the mutated region of recombinant protein or polypeptides of the present invention is, in another embodiment, 1-50 AA. In another embodiment, the length is 1-11 AA. In another embodiment, the length is 2-11 AA. In another embodiment, the length is 3-11 AA. In another embodiment, the length is 4-11 AA. In another embodiment, the length is 5-11 AA. In another embodiment, the length is 6-11 AA. In another embodiment, the length is 7-11 AA. In another embodiment, the length is 8-11 AA. In another embodiment, the length is 9-11 AA. In another embodiment, the length is 10-11 AA. In another embodiment, the length is 1-2 AA. In another embodiment, the length is 1-3 AA. In another embodiment, the length is 1-4 AA. In another embodiment, the length is 1-5 AA. In another embodiment, the length is 1-6 AA. In another embodiment, the length is 1-7 AA. In another embodiment, the length is 1-8 AA. In another embodiment, the length is 1-9 AA. In another embodiment, the length is 1-10 AA. In another embodiment, the length is 2-3 AA. In another embodiment, the length is 2-4 AA. In another embodiment, the length is 2-5 AA. In another embodiment, the length is 2-6 AA. In another embodiment, the length is 2-7 AA. In another embodiment, the length is 2-8 AA. In another embodiment, the length is 2-9 AA. In another embodiment, the length is 2-10 AA. In another embodiment, the length is 3-4 AA. In another embodiment, the length is 3-5 AA. In another embodiment, the length is 3-6 AA. In another embodiment, the length is 3-7 AA. In another embodiment, the length is 3-8 AA. In another embodiment, the length is 3-9 AA. In another embodiment, the length is 3-10 AA. In another embodiment, the length is 11-50 AA. In another embodiment, the length is 12-50 AA. In another embodiment, the length is 11-15 AA. In another embodiment, the length is 11-20 AA. In another embodiment, the length is 11-25 AA. In another embodiment, the length is 11-30 AA. In another embodiment, the length is 11-35 AA. In another embodiment, the length is 11-40 AA. In another embodiment, the length is 11-60 AA. In another embodiment, the length is 11-70 AA. In another embodiment, the length is 11-80 AA. In another embodiment, the length is 11-90 AA. In another embodiment, the length is 11-100 AA. In another embodiment, the length is 11-150 AA. In another embodiment, the length is 15-20 AA. In another embodiment, the length is 15-25 AA. In another embodiment, the length is 15-30 AA. In another embodiment, the length is 15-35 AA. In another embodiment, the length is 15-40 AA. In another embodiment, the length is 15-60 AA. In another embodiment, the length is 15-70 AA. In another embodiment, the length is 15-80 AA. In another embodiment, the length is 15-90 AA. In another embodiment, the length is 15-100 AA. In another embodiment, the length is 15-150 AA. In another embodiment, the length is 20-25 AA. In another embodiment, the length is 20-30 AA. In another embodiment, the length is 20-35 AA. In another embodiment, the length is 20-40 AA. In another embodiment, the length is 20-60 AA. In another embodiment, the length is 20-70 AA. In another embodiment, the length is 20-80 AA. In another embodiment, the length is 20-90 AA. In another embodiment, the length is 20-100 AA. In another embodiment, the length is 20-150 AA. In another embodiment, the length is 30-35 AA. In another embodiment, the length is 30-40 AA. In another embodiment, the length is 30-60 AA. In another embodiment, the length is 30-70 AA. In another embodiment, the length is 30-80 AA. In another embodiment, the length is 30-90 AA. In another embodiment, the length is 30-100 AA. In another embodiment, the length is 30-150 AA. Each possibility represents another embodiment of the present invention.

In another embodiment, the length of the LLO fragment of methods and compositions of the present invention is at least 484 AA. In another embodiment, the length is over 484 AA. In another embodiment, the length is at least 489 AA. In another embodiment, the length is over 489. In another embodiment, the length is at least 493 AA. In another embodiment, the length is over 493. In another embodiment, the length is at least 500 AA. In another embodiment, the length is over 500. In another embodiment, the length is at least 505 AA. In another embodiment, the length is over 505. In another embodiment, the length is at least 510 AA. In another embodiment, the length is over 510. In another embodiment, the length is at least 515 AA. In another embodiment, the length is over 515. In another embodiment, the length is at least 520 AA. In another embodiment, the length is over 520. In another embodiment, the length is at least 525 AA. In another embodiment, the length is over 520. When referring to the length of an LLO fragment herein, the signal sequence is included. Thus, the numbering of the first cysteine in the CBD is 484, and the total number of AA residues is 529. Each possibility represents another embodiment of the present invention.

In another embodiment, the present invention provides a recombinant protein or polypeptide comprising (a) a mutated LLO protein, wherein the mutated LLO protein contains an internal deletion, the internal deletion comprising the cholesterol-binding domain of the mutated LLO protein; and (b) a heterologous peptide of interest. In another embodiment, the sequence of the cholesterol-binding domain is set forth in SEQ ID NO: 18. In another embodiment, the internal deletion is an 11-50 amino acid internal deletion. In another embodiment, the internal deletion is inactivating with regard to the hemolytic activity of the recombinant protein or polypeptide. In another embodiment, the recombinant protein or polypeptide exhibits a reduction in hemolytic activity relative to wild-type LLO. Each possibility represents another embodiment of the present invention.

In another embodiment, the present invention provides a recombinant protein or polypeptide comprising (a) a mutated LLO protein, wherein the mutated LLO protein contains an internal deletion, the internal deletion comprising comprises a residue selected from C484, W491, and W492 of the mutated LLO protein; and (b) a heterologous peptide of interest. In another embodiment, the internal deletion is a 1-50 amino acid internal deletion. In another embodiment, the sequence of the cholesterol-binding domain is set forth in SEQ ID NO: 18. In another embodiment, the internal deletion is inactivating with regard to the hemolytic activity of the recombinant protein or polypeptide. In another embodiment, the recombinant protein or polypeptide exhibits a reduction in hemolytic activity relative to wild-type LLO. Each possibility represents another embodiment of the present invention.

In another embodiment, the present invention provides a recombinant protein or polypeptide comprising (a) a mutated LLO protein, wherein the mutated LLO protein contains an internal deletion, the internal deletion comprising a fragment of the cholesterol-binding domain of the mutated LLO protein; and (b) a heterologous peptide of interest. In another embodiment, the internal deletion is a 1-11 amino acid internal deletion. In another embodiment, the sequence of the cholesterol-binding domain is set forth in SEQ ID NO: 18. In another embodiment, the internal deletion is inactivating with regard to the hemolytic activity of the recombinant protein or polypeptide. In another embodiment, the recombinant protein or polypeptide exhibits a reduction in hemolytic activity relative to wild-type LLO. Each possibility represents another embodiment of the present invention.

In another embodiment, a peptide of the present invention is a fusion peptide. In another embodiment, "fusion peptide" refers to a peptide or polypeptide comprising two or more proteins linked together by peptide bonds or other chemical bonds. In another embodiment, the proteins are linked together directly by a peptide or other chemical bond. In another embodiment, the proteins are linked together with one or more AA (e.g. a "spacer") between the two or more proteins. Each possibility represents a separate embodiment of the present invention.

As provided herein, a mutant LLO protein was created wherein residues C484, W491, and W492 of LLO were substituted with a CTL epitope from the antigen NY-ESO-1 (Example 6). The mutated LLO protein, mutLLO, could be expressed and purified in an E. coli expression system (Example 7) and exhibited substantially reduced hemolytic activity relative to wild-type LLO (Example 8).

The length of the internal deletion of methods and compositions of the present invention is, in another embodiment, 1-50 AA. In another embodiment, the length is 1-11 AA. In another embodiment, the length is 2-11 AA. In another embodiment, the length is 3-11 AA. In another embodiment, the length is 4-11 AA. In another embodiment, the length is 5-11 AA. In another embodiment, the length is 6-11 AA. In another embodiment, the length is 7-11 AA. In another embodiment, the length is 8-11 AA. In another embodiment, the length is 9-11 AA. In another embodiment, the length is 10-11 AA. In another embodiment, the length is 1-2 AA. In another embodiment, the length is 1-3 AA. In another embodiment, the length is 1-4 AA. In another embodiment, the length is 1-5 AA. In another embodiment, the length is 1-6 AA. In another embodiment, the length is 1-7 AA. In another embodiment, the length is 1-8 AA. In another embodiment, the length is 1-9 AA. In another embodiment, the length is 1-10 AA. In another embodiment, the length is 2-3 AA. In another embodiment, the length is 2-4 AA. In another embodiment, the length is 2-5 AA. In another embodiment, the length is 2-6 AA. In another embodiment, the length is 2-7 AA. In another embodiment, the length is 2-8 AA. In another embodiment, the length is 2-9 AA. In another embodiment, the length is 2-10 AA. In another embodiment, the length is 3-4 AA. In another embodiment, the length is 3-5 AA. In another embodiment, the length is 3-6 AA. In another embodiment, the length is 3-7 AA. In another embodiment, the length is 3-8 AA. In another embodiment, the length is 3-9 AA. In another embodiment, the length is 3-10 AA. In another embodiment, the length is 11-50 AA. In another embodiment, the length is 12-50 AA. In another embodiment, the length is 11-15 AA. In another embodiment, the length is 11-20 AA. In another embodiment, the length is 11-25 AA. In another embodiment, the length is 11-30 AA. In another embodiment, the length is 11-35 AA. In another embodiment, the length is 11-40 AA. In another embodiment, the length is 11-60 AA. In another embodiment, the length is 11-70 AA. In another embodiment, the length is 11-80 AA. In another embodiment, the length is 11-90 AA. In another embodiment, the length is 11-100 AA. In another embodiment, the length is 11-150 AA. In another embodiment, the length is 15-20 AA. In another embodiment, the length is 15-25 AA. In another embodiment, the length is 15-30 AA. In another embodiment, the length is 15-35 AA. In another embodiment, the length is 15-40 AA. In another embodiment, the length is 15-60 AA. In another embodiment, the length is 15-70 AA. In another embodiment, the length is 15-80 AA. In another embodiment, the length is 15-90 AA. In another embodiment, the length is 15-100 AA. In another embodiment, the length is 15-150 AA. In another embodiment, the length is 20-25 AA. In another embodiment, the length is 20-30 AA. In another embodiment, the length is 20-35 AA. In another embodiment, the length is 20-40 AA. In another embodiment, the length is 20-60 AA. In another embodiment, the length is 20-70 AA. In another embodiment, the length is 20-80 AA. In another embodiment, the length is 20-90 AA. In another embodiment, the length is 20-100 AA. In another embodiment, the length is 20-150 AA. In another embodiment, the length is 30-35 AA. In another embodiment, the length is 30-40 AA. In another embodiment, the length is 30-60 AA. In another embodiment, the length is 30-70 AA. In another embodiment, the length is 30-80 AA. In another embodiment, the length is 30-90 AA. In another embodiment, the length is 30-100 AA. In another embodiment, the length is 30-150 AA. Each possibility represents another embodiment of the present invention.

In another embodiment, the mutated LLO protein of the present invention that comprises an internal deletion is full length except for the internal deletion. In another embodiment, the mutated LLO protein comprises an additional internal deletion. In another embodiment, the mutated LLO protein comprises more than one additional internal deletion. In another embodiment, the mutated LLO protein is truncated from the C-terminal end. In another embodiment, the mutated LLO protein is truncated from the N-terminal end. Each possibility represents another embodiment of the present invention.

The internal deletion of methods and compositions of the present invention comprises, in another embodiment, residue C484 of SEQ ID NO: 37. In another embodiment, the internal deletion comprises a corresponding cysteine residue of a homologous LLO protein. In another embodiment, the internal deletion comprises residue W491 of SEQ ID NO: 37. In another embodiment, the internal deletion comprises a corresponding tryptophan residue of a homologous LLO protein. In another embodiment, the internal deletion comprises residue W492 of SEQ ID NO: 37. In another embodiment, the internal deletion comprises a corresponding tryptophan residue of a homologous LLO protein. Methods for identifying corresponding residues of a homologous protein are well known in the art, and include, for example, sequence alignment. Each possibility represents a separate embodiment of the present invention.

In another embodiment, the internal deletion comprises residues C484 and W491. In another embodiment, the internal deletion comprises residues C484 and W492. In another embodiment, the internal deletion comprises residues W491 and W492. In another embodiment, the internal deletion comprises residues C484, W491, and W492. Each possibility represents a separate embodiment of the present invention.

In another embodiment, the internal deletion of methods and compositions of the present invention comprises the CBD of the mutated LLO protein or fragment thereof. For example, an internal deletion consisting of residues 470-500, 470-510, or 480-500 of SEQ ID NO: 37 comprises the CBD thereof (residues 483-493). In another embodiment, the internal deletion is a fragment of the CBD of the mutated LLO protein or fragment thereof. For example, residues 484-492, 485-490, and 486-488 are all fragments of the CBD of SEQ ID NO: 37. In another embodiment, the internal deletion overlaps the CBD of the mutated LLO protein or fragment thereof. For example, an internal deletion consisting of residues 470-490, 480-488, 490-500, or 486-510 of SEQ ID NO: 37 comprises the CBD thereof. Each possibility represents a separate embodiment of the present invention.

"Hemolytic" refers, in another embodiment, to ability to lyse a eukaryotic cell. In another embodiment, the eukaryotic cell is a red blood cell. In another embodiment, the eukaryotic cell is any other type of eukaryotic cell known in the art. In another embodiment, hemolytic activity is measured at an acidic pH. In another embodiment, hemolytic activity is measured at physiologic pH. In another embodiment, hemolytic activity is measured at pH 5.5. In another embodiment, hemolytic activity is measured at pH 7.4. In another embodiment, hemolytic activity is measured at any other pH known in the art.

In another embodiment, a recombinant protein or polypeptide of methods and compositions of the present invention exhibits a greater than 100-fold reduction in hemolytic activity relative to wild-type LLO. In another embodiment, the recombinant protein or polypeptide exhibits a greater than 50-fold reduction in hemolytic activity. In another embodiment, the reduction is greater than 30-fold. In another embodiment, the reduction is greater than 40-fold. In another embodiment, the reduction is greater than 60-fold. In another embodiment, the reduction is greater than 70-fold. In another embodiment, the reduction is greater than 80-fold. In another embodiment, the reduction is greater than 90-fold. In another embodiment, the reduction is greater than 120-fold. In another embodiment, the reduction is greater than 150-fold. In another embodiment, the reduction is greater than 200-fold. In another embodiment, the reduction is greater than 250-fold. In another embodiment, the reduction is greater than 300-fold. In another embodiment, the reduction is greater than 400-fold. In another embodiment, the reduction is greater than 500-fold. In another embodiment, the reduction is greater than 600-fold. In another embodiment, the reduction is greater than 800-fold. In another embodiment, the reduction is greater than 1000-fold. In another embodiment, the reduction is greater than 1200-fold. In another embodiment, the reduction is greater than 1500-fold. In another embodiment, the reduction is greater than 2000-fold. In another embodiment, the reduction is greater than 3000-fold. In another embodiment, the reduction is greater than 5000-fold.

In another embodiment, the reduction is at least 100-fold. In another embodiment, the reduction is at least 50-fold. In another embodiment, the reduction is at least 30-fold. In another embodiment, the reduction is at least 40-fold. In another embodiment, the reduction is at least 60-fold. In another embodiment, the reduction is at least 70-fold. In another embodiment, the reduction is at least 80-fold. In another embodiment, the reduction is at least 90-fold. In another embodiment, the reduction is at least 120-fold. In another embodiment, the reduction is at least 150-fold. In another embodiment, the reduction is at least 200-fold. In another embodiment, the reduction is at least 250-fold. In another embodiment, the reduction is at least 300-fold. In another embodiment, the reduction is at least 400-fold. In another embodiment, the reduction is at least 500-fold. In another embodiment, the reduction is at least 600-fold. In another embodiment, the reduction is at least 800-fold. In another embodiment, the reduction is at least 1000-fold. In another embodiment, the reduction is at least 1200-fold. In another embodiment, the reduction is at least 1500-fold. In another embodiment, the reduction is at least 2000-fold. In another embodiment, the reduction is at least 3000-fold. In another embodiment, the reduction is at least 5000-fold.

Methods of determining hemolytic activity are well known in the art, and are described, for example, in the Examples herein, and in Portnoy D A et al, (J Exp Med Vol 167:1459-1471, 1988) and Dancz C E et al (J Bacteriol. 184: 5935-5945, 2002).

"Inactivating mutation" with respect to hemolytic activity refers, in another embodiment, to a mutation that abolishes detectable hemolytic activity. In another embodiment, the term refers to a mutation that abolishes hemolytic activity at pH 5.5. In another embodiment, the term refers to a mutation that abolishes hemolytic activity at pH 7.4. In another embodiment, the term refers to a mutation that significantly reduces hemolytic activity at pH 5.5. In another embodiment, the term refers to a mutation that significantly reduces hemolytic activity at pH 7.4. In another embodiment, the term refers to a mutation that significantly reduces hemolytic activity at pH 5.5. In another embodiment, the term refers to any other type of inactivating mutation with respect to hemolytic activity. Each possibility represents another embodiment of the present invention.

In another embodiment, the sequence of the cholesterol-binding domain of methods and compositions of the present invention is set forth in SEQ ID NO: 18. In another embodiment, the CBD is any other LLO CBD known in the art. Each possibility represents another embodiment of the present invention.

The non-LLO sequence of methods and compositions of the present invention is, in another embodiment, a heterologous sequence. In another embodiment, the non-LLO sequence is a synthetic sequence. In another embodiment, the non-LLO sequence is a non-naturally occurring sequence. In another embodiment, the non-LLO sequence is a non-*Listeria* sequence. In another embodiment, the non-LLO sequence is a non-*Listeria monocytogenes* sequence. In one embodiment, the compositions of the present invention comprise a mutated LLO in which there is a substitution of an amino acid peptide comprising a CBD for an amino acid comprising a non-LLO peptide and further comprising a heterologous antigen fused to said mutated LLO. Each possibility represents a separate embodiment of the present invention.

In another embodiment, the mutated LLO protein or fragment thereof of methods and compositions of the present invention comprises the signal peptide thereof. In another embodiment, the mutated LLO protein or fragment thereof comprises a signal peptide of a wild-type LLO protein. In another embodiment, the signal peptide is a short (3-60 amino acid long) peptide chain that directs the post-translational transport of a protein. In another embodiment, signal peptides are also targeting signals, signal sequences, transit peptides, or localization signals. In another embodiment, the amino acid sequences of signal peptides direct proteins to certain organelles such as the nucleus, mitochondrial matrix, endoplasmic reticulum, chloroplast, apoplast or peroxisome. In another embodiment, the mutated LLO protein contains a signal sequence of a wild-type LLO protein. In another embodiment, the mutated LLO protein lacks a signal peptide. In another embodiment, the mutated LLO protein lacks a signal sequence. In another embodiment, the signal peptide is unaltered with respect to the wild-type LLO protein from which the mutated LLO protein or fragment thereof was derived. In another embodiment, the signal peptide is on N-terminal end of recombinant protein or polypeptide. Each possibility represents a separate embodiment of the present invention.

In another embodiment, the mutated LLO protein or fragment thereof of methods and compositions of the present invention comprises a PEST-like peptide sequence. In another embodiment, the PEST-like peptide sequence is an LLO PEST-like peptide sequence. In another embodiment, the amino acid sequence of the PEST-like peptide sequence is forth in SEQ ID NO: 63. Each possibility represents a separate embodiment of the present invention.

In one embodiment, PEST sequences are sequences that are rich in prolines (P), glutamic acids (E), serines (S) and threonines (T), generally, but not always, flanked by clusters containing several positively charged amino acids, have rapid intracellular half-lives (Rogers et al., 1986, Science 234:364-369). In another embodiment, PEST sequences target the protein to the ubiquitin-proteosome pathway for degradation (Rechsteiner and Rogers TIBS 1996 21:267-271), which in one embodiment, is a pathway also used by eukaryotic cells to generate immunogenic peptides that bind to MHC class I. PEST sequences are abundant among eukaryotic proteins that give rise to immunogenic peptides (Realini et al. FEBS Lett. 1994 348:109-113). Although PEST sequences are usually found in eurkaryotic proteins, a PEST-like sequence rich in the amino acids proline (P), glutamic acid (E), serine (S) and threonine (T) was identified at the amino terminus of the prokaryotic *Listeria* LLO protein and demonstrated to be essential for *L. monocytogenes* pathogenicity (Decatur, A. L. and Portnoy, D. A. Science 2000 290:992-995). In one embodiment, the presence of this PEST-like sequence in LLO targets the protein for destruction by proteolytic machinery of the host cell so that once the LLO has served its function and facilitated the escape of *L. monocytogenes* from the phagolysosomal vacuole, it is destroyed before it damages the cells.

In another embodiment, the immune response to an antigen can be enhanced by fusion of the antigen to a non-hemolytic truncated form of listeriolysin O (ΔLLO). In one embodiment, the observed enhanced cell mediated immunity and anti-tumor immunity of the fusion protein results from the PEST-like sequence present in LLO which targets the antigen for processing.

In another embodiment, the non-LLO peptide that replaces the mutated region of the recombinant protein or polypeptide comprises an antigenic peptide of interest. In another embodiment, the antigenic peptide is a cytotoxic T lymphocyte (CTL) epitope. In another embodiment, the antigenic peptide is a CD4$^+$ T cell epitope. In another embodiment, the antigenic peptide is any other type of peptide known in the art. Each possibility represents a separate embodiment of the present invention.

In another embodiment, the present invention provides a vaccine comprising an adjuvant and a recombinant protein or polypeptide of the present invention, wherein an antigenic peptide of interest replaces the mutated region. In another embodiment, the present invention provides an immunogenic composition comprising the recombinant protein or polypeptide. Each possibility represents a separate embodiment of the present invention.

In another embodiment, the present invention provides a nucleotide molecule encoding a recombinant protein or polypeptide of the present invention, wherein an antigenic peptide of interest replaces the mutated region.

In another embodiment, a recombinant protein or polypeptide of methods and compositions of the present invention further comprises a heterologous peptide of interest. In another embodiment, the heterologous peptide of interest is fused to the mutated LLO or fragment thereof. In another embodiment, the heterologous peptide of interest is fused to the C-terminal end of the mutated LLO or fragment thereof. In another embodiment, the heterologous peptide of interest is embedded within the mutated LLO or fragment thereof, e.g. at a location other than the mutated region comprising or overlapping the CBD. In another embodiment, the heterologous peptide of interest is inserted into the sequence of the mutated LLO or fragment thereof, e.g. at a location other than the mutated region comprising or overlapping the CBD. In another embodiment, the heterologous peptide of interest is substituted for sequence of the mutated LLO or fragment thereof, e.g. at a location other than the mutated region comprising or overlapping the CBD. Thus, in one embodiment, the recombinant protein or polypeptide of the present invention comprises a mutated LLO or fragment thereof fused or conjugated to an antigenic peptide or protein.

In another embodiment, the present invention provides a vaccine comprising an adjuvant and a recombinant protein or polypeptide of the present invention, wherein the recombinant protein or polypeptide further comprises a heterologous peptide of interest. In another embodiment, the present invention provides an immunogenic composition comprising the recombinant protein or polypeptide. Each possibility represents a separate embodiment of the present invention.

In another embodiment, the present invention provides a nucleotide molecule encoding a recombinant protein or polypeptide of the present invention, wherein the recombinant protein or polypeptide further comprises a heterologous peptide of interest.

In another embodiment, the LLO protein or fragment thereof of methods and compositions of the present invention is on the N-terminal end of a recombinant protein or polypeptide of the present invention. In another embodiment, the LLO protein or fragment thereof is in any other position in the recombinant protein or polypeptide. Each possibility represents a separate embodiment of the present invention.

In another embodiment, the present invention provides a composition comprising a recombinant protein or polypeptide of the present invention and a heterologous peptide of interest. In another embodiment, the present invention provides a composition comprising a recombinant protein or polypeptide of the present invention and a heterologous antigenic peptide of interest. In another embodiment, the recombinant protein or polypeptide is not covalently bound to the heterologous peptide of interest. Each possibility represents a separate embodiment of the present invention.

In another embodiment, the present invention provides a vaccine comprising an adjuvant, a recombinant protein or polypeptide of the present invention, and a heterologous peptide of interest. In another embodiment, the present invention provides a composition comprising an adjuvant, a recombinant protein or polypeptide of the present invention, and a heterologous antigenic peptide of interest. In another embodiment, the recombinant protein or polypeptide is not covalently bound to the heterologous peptide of interest. Each possibility represents a separate embodiment of the present invention.

In another embodiment, the present invention provides a vaccine comprising an adjuvant and a recombinant protein or polypeptide of the present invention. In another embodiment, the present invention provides an immunogenic composition comprising the recombinant protein or polypeptide. Each possibility represents a separate embodiment of the present invention.

In another embodiment, the present invention provides a nucleotide molecule encoding a recombinant protein or polypeptide of the present invention.

In another embodiment, the present invention provides a vaccine comprising a nucleotide molecule of the present invention and an adjuvant.

In another embodiment, the present invention provides a recombinant vaccine vector comprising a nucleotide molecule of the present invention.

In another embodiment, the present invention provides a recombinant vaccine vector encoding a recombinant protein or polypeptide of the present invention.

In another embodiment, the present invention provides a recombinant *Listeria* strain comprising a recombinant protein or polypeptide of the present invention. In another embodiment, the present invention provides a recombinant *Listeria* strain expressing a recombinant protein or polypeptide of the present invention. In another embodiment, the present invention provides a recombinant *Listeria* strain encoding a recombinant protein or polypeptide of the present invention. In another embodiment, the present invention provides a recombinant *Listeria* strain comprising a recombinant nucleotide encoding a recombinant polypeptide of the present invention. In another embodiment, the *Listeria* vaccine strain is the species *Listeria monocytogenes* (LM). Each possibility represents a separate embodiment of the present invention.

In another embodiment, the present invention provides a cell comprising a vector of the present invention. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the present invention provides a vaccine comprising a nucleotide molecule of the present invention. In another embodiment, the present invention provides an immunogenic composition comprising the nucleotide molecule. Each possibility represents a separate embodiment of the present invention.

The adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

In another embodiment, the present invention provides a method for inducing an immune response in a subject, comprising administering to the subject a recombinant protein or polypeptide of the present invention, wherein the recombinant protein or polypeptide contains an antigenic peptide of interest, thereby inducing an immune response against an antigenic peptide of interest.

In another embodiment, the present invention provides a method for inducing an immune response in a subject, comprising administering to the subject a recombinant protein or polypeptide of the present invention, wherein the recombinant protein or polypeptide contains a heterologous peptide of interest, thereby inducing an immune response against a heterologous peptide of interest.

In another embodiment, the present invention provides a method for inducing an immune response in a subject, comprising administering to the subject a recombinant vaccine vector of the present invention, wherein the recombinant vaccine vector comprises or encodes a recombinant protein or polypeptide that comprises a heterologous antigenic peptide of interest, thereby inducing an immune response against the antigenic peptide of interest.

In another embodiment, the present invention provides a method for inducing an immune response in a subject, comprising administering to the subject a recombinant vaccine vector of the present invention, wherein the recombinant vaccine vector comprises or encodes a recombinant protein or polypeptide that comprises a heterologous peptide of interest, thereby inducing an immune response against the heterologous peptide of interest.

In another embodiment, the present invention provides a method for inducing an immune response in a subject, comprising administering to the subject a recombinant *Listeria* strain of the present invention, wherein the recombinant *Listeria* strain comprises or encodes a recombinant protein or polypeptide that comprises a heterologous peptide of interest, thereby inducing an immune response against the heterologous peptide of interest.

In another embodiment, the present invention provides a method for inducing an immune response in a subject, comprising administering to the subject a recombinant *Listeria* strain of the present invention, wherein the recombinant *Listeria* strain comprises or encodes a recombinant protein or polypeptide that comprises a heterologous antigenic peptide of interest, thereby inducing an immune response against the heterologous peptide of interest.

In another embodiment of methods and compositions of the present invention, a peptide or nucleotide molecule of the present invention is administered to a subject having a lymphoma, cancer cell, or infectious disease expressing a target antigen of the present invention. In another embodiment, the peptide or nucleotide molecule is administered ex vivo to cells of a subject. In another embodiment, the peptide is administered to a lymphocyte donor; lymphocytes from the donor are then administered, in another embodiment, to a subject. In another embodiment, the peptide is administered to an antibody or lymphocyte donor; antiserum or lymphocytes from the donor is then administered, in another embodiment, to a subject. Each possibility represents a separate embodiment of the present invention.

In another embodiment, the heterologous peptide of interest is a full-length protein, which in one embodiment, comprises an antigenic peptide. In one embodiment, the protein is an NY-ESO-1 protein. In another embodiment, the protein is a Human Papilloma Virus (HPV) E7 protein. In another embodiment, the protein is a B-cell receptor (BCR) protein. In another embodiment, the heterologous peptide of interest is an antigenic peptide.

The antigenic peptide of interest of methods and compositions of the present invention is, in another embodiment, an NY-ESO-1 peptide.

In another embodiment, the present invention provides a recombinant nucleotide molecule encoding an NY-ESO-1-containing peptide of the present invention.

In another embodiment, the present invention provides a composition comprising a mutant-LLO containing recombinant protein or polypeptide of the present invention and an NY-ESO-1 peptide.

In another embodiment, the present invention provides a recombinant vaccine vector encoding an NY-ESO-1-containing peptide of the present invention.

In another embodiment, the present invention provides a recombinant *Listeria* strain encoding an NY-ESO-1-containing peptide of the present invention.

In one embodiment, NY-ESO-1 is a "cancer-testis" antigen expressed in epithelial ovarian cancer (EOC). In another embodiment, NY-ESO-1 is expressed in metastatic melanoma, breast cancer, lung cancer, esophageal cancer, which in one embodiment, is esophageal squamous cell carcinoma, or a combination thereof. Therefore, in one embodiment, the compositions and methods of the present invention comprising NY-ESO-1 are particularly useful in the prevention or treatment of the above-mentioned cancers.

In another embodiment, the present invention provides a method of producing a recombinant protein or polypeptide of the present invention comprising the step of chemically conjugating a peptide comprising said mutated LLO protein or mutated N-terminal LLO fragment to a peptide comprising said heterologous peptide of interest. In another embodiment, the present invention provides a method of producing a recombinant protein or polypeptide of the present invention comprising the step of translating said recombinant protein or polypeptide from a nucleotide molecule encoding same. In another embodiment, the present invention provides a product made by one or more of the processes described herein.

In another embodiment, the present invention provides a method for inducing an immune response in a subject against an NY-ESO-1-expressing cancer cell, the method comprising the step of administering to the subject an NY-ESO-1 antigen-containing recombinant peptide, protein or polypeptide of the present invention, thereby inducing an immune response against an NY-ESO-1-expressing cancer cell. In another embodiment, the cancer cell is an ovarian melanoma cell. In another embodiment, the cancer cell is a lung cancer cell. In another embodiment, the cancer cell is any other NY-ESO-1-expressing cancer cell known in the art. Each possibility represents a separate embodiment of the present invention.

In another embodiment, the present invention provides a method for treating an NY-ESO-1-expressing tumor in a subject, the method comprising the step of administering to the subject an NY-ESO-1 antigen-containing recombinant peptide, protein or polypeptide of the present invention, thereby treating an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inhibiting an NY-ESO-1-expressing tumor in a subject, the method comprising the step of administering to the subject an NY-ESO-1 antigen-containing recombinant peptide, protein or polypeptide of the present invention, thereby inhibiting an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for suppressing an NY-ESO-1-expressing tumor in a subject, the method comprising the step of administering to the subject an NY-ESO-1 antigen-containing recombinant peptide, protein or polypeptide of the present invention, thereby suppressing an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inducing regression of an NY-ESO-1-expressing tumor in a subject, the method comprising the step of administering to the subject an NY-ESO-1 antigen-containing recombinant peptide, protein or polypeptide of the present invention, thereby inducing regression of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for reducing an incidence of an NY-ESO-1-expressing tumor in a subject, the method comprising the step of administering to the subject an NY-ESO-1 antigen-containing recombinant peptide, protein or polypeptide of the present invention, thereby reducing an incidence of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for protecting a subject against an NY-ESO-1-expressing tumor, the method comprising the step of administering to the subject an NY-ESO-1 antigen-containing recombinant peptide, protein or polypeptide of the present invention, thereby protecting a subject against an NY-ESO-1-expressing tumor. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inducing an immune response in a subject against an NY-ESO-1-expressing cancer cell, the method comprising the step of administering to the subject an NY-ESO-1 antigen-expressing vaccine vector of the present invention, thereby inducing an immune response against an NY-ESO-1-expressing cancer cell. In another embodiment, the cancer cell is an ovarian melanoma cell. In another embodiment, the cancer cell is a lung cancer cell. In another embodiment, the cancer cell is any other NY-ESO-1-expressing cancer cell known in the art. Each possibility represents a separate embodiment of the present invention.

In another embodiment, the present invention provides a method for treating or reducing an incidence of an NY-ESO-1-expressing tumor in a subject, the method comprising the step of administering to the subject an NY-ESO-1 antigen-expressing vaccine vector of the present invention, thereby treating or reducing an incidence of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inducing regression of an NY-ESO-1-expressing tumor in a subject, the method comprising the step of administering to the subject an NY-ESO-1 antigen-expressing vaccine vector of the present invention, thereby inducing regression of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for protecting a subject against an NY-ESO-1-expressing tumor, the method comprising the step of administering to the subject an NY-ESO-1 antigen-expressing vaccine vector of the present invention, thereby protecting a subject against an NY-ESO-1-expressing tumor. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inducing an immune response in a subject against an NY-ESO-1-expressing cancer cell, the method comprising the step of administering to the subject an NY-ESO-1 antigen-encoding nucleotide molecule of the present invention, thereby inducing an immune response against an NY-ESO-1-expressing cancer cell. In another embodiment, the cancer cell is an ovarian melanoma cell. In another embodiment, the cancer cell is a lung cancer cell. In another embodiment, the cancer cell is any other NY-ESO-1-expressing cancer cell known in the art. Each possibility represents a separate embodiment of the present invention.

In another embodiment, the present invention provides a method for treating or reducing an incidence of an NY-ESO-1-expressing tumor in a subject, the method comprising the step of administering to the subject an NY-ESO-1 antigen-encoding nucleotide molecule of the present invention, thereby treating or reducing an incidence of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inhibiting an NY-ESO-1-expressing tumor in a subject, the method comprising the step of administering to the subject an NY-ESO-1 antigen-encoding nucleotide molecule of the present invention, thereby inhibiting an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for suppressing an NY-ESO-1-expressing tumor in a subject, the method comprising the step of administering to the subject an NY-ESO-1 antigen-encoding nucleotide molecule of the present invention, thereby inhibiting an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inducing regression of an NY-ESO-1-expressing tumor in a subject, the method comprising the step of administering to the subject an NY-ESO-1 antigen-encoding nucleotide molecule of the present invention, thereby inducing regression of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for protecting a subject against an NY-ESO-1-expressing tumor, the method comprising the step of administering to the subject an NY-ESO-1-antigen-encoding nucleotide molecule of the present invention, thereby protecting a subject against an NY-ESO-1-expressing tumor. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inducing an immune response in a subject against an NY-ESO-1-expressing cancer cell, the method comprising the step of administering to the subject an NY-ESO-1 antigen-expressing recombinant *Listeria* strain of the present invention, thereby inducing an immune response against an NY-ESO-1-expressing cancer cell. In another embodiment, the cancer cell is an ovarian melanoma cell. In another embodiment, the cancer cell is a lung cancer cell. In another embodiment, the cancer cell is any other NY-ESO-1-expressing cancer cell known in the art. Each possibility represents a separate embodiment of the present invention.

In another embodiment, the present invention provides a method for treating or reducing an incidence of an NY-ESO-1-expressing tumor in a subject, the method comprising the step of administering to the subject an NY-ESO-1 antigen-expressing recombinant *Listeria* strain of the present invention, thereby treating or reducing an incidence of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inhibiting an NY-ESO-1-expressing tumor in a subject, the method comprising the step of administering to the subject an NY-ESO-1 antigen-expressing recombinant *Listeria* strain of the present invention, thereby treating or reducing an incidence of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for suppressing an NY-ESO-1-expressing tumor in a subject, the method comprising the step of administering to the subject an NY-ESO-1 antigen-expressing recombinant *Listeria* strain of the present invention, thereby treating or reducing an incidence of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inducing regression of an NY-ESO-1-expressing tumor in a subject, the method comprising the step of administering to the subject an NY-ESO-1 antigen-expressing recombinant *Listeria* strain of the present invention, thereby inducing regression of an NY-ESO-1-expressing tumor in a subject. In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for protecting a subject against an NY-ESO-1-expressing tumor, the method comprising the step of administering to the subject an NY-ESO-1 antigen-expressing recombinant *Listeria* strain of the present invention, thereby protecting a subject against an NY-ESO-1-expressing tumor.

In another embodiment, the tumor is an ovarian melanoma tumor. In another embodiment, the tumor is a lung cancer tumor. In another embodiment, the tumor is any other NY-ESO-1-expressing tumor known in the art. Each possibility represents a separate embodiment of the present invention.

In another embodiment, the present invention provides a method for inducing an immune response against an NY-ESO-1 epitope, comprising the step of administering to the subject an NY-ESO-1 antigen-containing recombinant peptide, protein or polypeptide of the present invention, thereby inducing an immune response against an NY-ESO-1 epitope.

In another embodiment, the present invention provides a method for inducing an immune response against an NY-ESO-1 antigen, comprising the step of administering to the subject a recombinant peptide, protein or polypeptide of the present invention containing said NY-ESO-1 antigen, thereby inducing an immune response against an NY-ESO-1 epitope.

In one embodiment, a NY-ESO-1 epitope for use in the compositions and methods of the present invention is ASGPGGGAPR: 53-62 (A31), ARGPESRLL: 80-88 (Cw6), LAMPFATPM: 92-100 (Cw3), MPFATPMEA: 94-102 (B35, B51), TVSGNILTR: 127-136 (A68), TVSGNILT: 127-135 (Cw15), SLLMWITQC: 157-165 (A2; Example 6), or another NY-ESO-1 epitope known in the art.

In another embodiment, the present invention provides a method for inducing an immune response against an NY-ESO-1-expressing target cell, comprising the step of administering to the subject an NY-ESO-1 antigen-containing recombinant peptide, protein or polypeptide of the present invention, thereby inducing an immune response against an NY-ESO-1-expressing target cell. In another embodiment, the target cell is an ovarian melanoma cell. In another embodiment, the target cell is a lung cancer cell. In another embodiment, the target cell is any other NY-ESO-1-expressing cell known in the art. Each possibility represents a separate embodiment of the present invention.

In another embodiment, the target NY-ESO-1-expressing cancer cell or tumor of methods and compositions of the present invention is a non-small cell lung cancer (NSCLC) cell or tumor. In another embodiment, the NY-ESO-1-expressing cancer cell is a lung adenocarcinoma cell or tumor. In another embodiment, the NY-ESO-1-expressing cancer cell is a bronchioloalveolar carcinoma (BAC) cell or tumor. In another embodiment, the NY-ESO-1-expressing cancer cell is a cell or tumor from an adenocarcinoma with bronchioloalveolar features (AdenoBAC). In another embodiment, the NY-ESO-1-expressing cancer cell or tumor is from a squamous cell carcinoma of the lung. Each possibility represents a separate embodiment of the present invention.

The NY-ESO-1 peptide of methods and compositions of the present invention is, in another embodiment, a peptide from an NY-ESO-1 protein, wherein the sequence of the protein is:

MQAEGRGTGGSTGDADGPGGPGIPDGPG-
GNAGGPGEAGATGGRGPRGAGAARASGPGGGAP
RGPHGGAASGLNGCCRCGARGPESRLLE-
FYLAMPFATPMEAELARRSLAQDAP-
PLPVPGVLLKEFTV SGNILTIRLTAADHRQLQLSISS-
CLQQLSLLMWITQCFLPVFLAQPPSGQRR (SEQ ID NO: 1; GenBank Accession No. NM_001327). In another embodiment, the NY-ESO-1 protein is a homologue of SEQ ID NO: 1. In another embodiment, the NY-ESO-1 protein is a variant of SEQ ID NO: 1. In another embodiment, the NY-ESO-1 protein is an isomer of SEQ ID NO: 1. In another embodiment, the NY-ESO-1 protein is a fragment of SEQ ID NO: 1. In another embodiment, the NY-ESO-1 protein is a fragment of a homologue of SEQ ID NO: 1. In another embodiment, the NY-ESO-1 protein is a fragment of a variant of SEQ ID NO: 1. In another embodiment, the NY-ESO-1 protein is a fragment of an isomer of SEQ ID NO: 1. Each possibility represents a separate embodiment of the present invention.

In another embodiment, the NY-ESO-1 peptide of methods and compositions of the present invention is derived from any other NY-ESO-1 protein known in the art. Each possibility represents another embodiment of the present invention. In another embodiment, the NY-ESO-1 antigen is a peptide having the sequence: SLLMWITQC (SEQ ID NO: 2). In another embodiment, the sequence is SLLMWITQCFL (SEQ ID NO: 3). In another embodiment, the sequence is SLLMWITQCFLP (SEQ ID NO: 4). In another embodiment, the sequence is SLLMWITQCFLPV (SEQ ID NO: 5). In another embodiment, the sequence is SLLMWITQCFLPVF (SEQ ID NO: 6). In another embodiment, the sequence is SLLMWITQCFLPVFL (SEQ ID NO: 7). In another embodiment, the sequence is WITQCFLPVFLAQPPSGQRR (SEQ ID NO: 8). In another embodiment, the sequence is YLAMPFATPMEAELARRSLA (SEQ ID NO: 9). In another embodiment, the sequence is ASGPGGGAPR (SEQ ID NO: 10). In another embodiment, the sequence is MPFATPMEA (SEQ ID NO: 11). In another embodiment, the sequence is LAMPFATPM (SEQ ID NO: 12). In another embodiment, the sequence is ARGPESRLL (SEQ ID NO: 13). In another embodiment, the sequence is LLMWITQCF (SEQ ID NO: 14). In another embodiment, the sequence is SLLMWITQV (SEQ ID NO: 15). In one embodiment, the NY-ESO-1 antigen is a peptide comprising positions 157-165 of the wild-type the NY-ESO-1 peptide. In another embodiment, the NY-ESO-1 antigen is a peptide comprising positions 53-62 of the wild-type the NY-ESO-1 peptide. In another embodiment, the NY-ESO-1 antigen is a peptide comprising positions 94-102 of the wild-type the NY-ESO-1 peptide. In another embodiment, the NY-ESO-1 antigen is a peptide comprising positions 92-100 of the wild-type the NY-ESO-1 peptide. In another embodiment, the NY-ESO-1 antigen is a peptide comprising positions 80-88 of the wild-type the NY-ESO-1 peptide. In another embodiment, the NY-ESO-1 antigen is a peptide comprising positions 158-166 of the wild-type the NY-ESO-1 peptide. In another embodiment, the NY-ESO-1 antigen is a variant of a wild-type NY-ESO-1 peptide. An example of a variant is SLLMWITQV (SEQ ID NO: 16). Each possibility represents another embodiment of the present invention.

In another embodiment, the antigenic peptide of interest of methods and compositions of the present invention is a Human Papilloma Virus (HPV) E7 peptide. In another embodiment, the antigenic peptide is a whole E7 protein. In another embodiment, the antigenic peptide is a fragment of an E7 protein. Each possibility represents a separate embodiment of the present invention.

In another embodiment, the present invention provides a recombinant nucleotide molecule encoding an E7-containing peptide of the present invention.

In another embodiment, the present invention provides a composition comprising a mutant-LLO containing recombinant peptide, protein or polypeptide of the present invention and an E7 peptide.

In another embodiment, the present invention provides a recombinant vaccine vector encoding an E7-containing peptide of the present invention.

In another embodiment, the present invention provides a recombinant Listeria strain encoding an E7-containing peptide of the present invention.

In another embodiment, the present invention provides a method for inducing an immune response in a subject against an HPV E7 epitope, the method comprising the step of administering to the subject the recombinant peptide, protein or polypeptide of the present invention, thereby inducing an immune response against an HPV E7 epitope.

In one embodiment, an HPV E7 epitope for use in the compositions and methods of the present invention is TLHEYMLDL: 7-15 (B8), YMLDLQPETT: 11-20 (A2), LLMGTLGIV: 82-90 (A2), TLGIVCPI: 86-93 (A2), or another HPV E7 epitope known in the art.

In another embodiment, the present invention provides a method for inducing an immune response in a subject against an HPV E7 antigen, the method comprising the step of administering to the subject an HPV-E7 containing recombinant peptide, protein or polypeptide of the present invention, thereby inducing an immune response against an HPV E7 antigen.

In another embodiment, the present invention provides a method for inducing an immune response in a subject against an HPV E7-expressing target cell, the method comprising the step of administering to the subject an HPV-E7 containing recombinant peptide, protein or polypeptide of the present invention, thereby inducing an immune response against an HPV E7-expressing target cell. In another embodiment, the target cell is a cervical cancer cell. In another embodiment, the target cell is a head-and-neck cancer cell. In another embodiment, the target cell is any other type of HPV E7-expressing cell known in the art. Each possibility represents a separate embodiment of the present invention.

In another embodiment, the present invention provides a method for treating an HPV E7-expressing tumor in a subject, the method comprising the step of administering to the subject an HPV-E7 containing recombinant peptide, protein or polypeptide of the present invention, thereby treating an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inhibiting or suppressing an HPV E7-expressing tumor in a subject, the method comprising the step of administering to the subject an HPV-E7 containing recombinant peptide, protein or polypeptide of the present invention, thereby inhibiting or suppressing an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inducing regression of an HPV E7-expressing tumor in a subject, the method comprising the step of administering to the subject an HPV-E7 containing recombinant peptide, protein or polypeptide of the present invention, thereby inducing regression of an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for reducing an incidence of an HPV E7-expressing tumor in a subject, the method comprising the step of administering to the subject an HPV-E7 containing recombinant peptide, protein or polypeptide of the present invention, thereby reducing an incidence of an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for protecting a subject against an HPV E7-expressing tumor in a subject, the method comprising the step of administering to the subject an HPV-E7 containing recombinant peptide, protein or polypeptide of the present invention, thereby protecting a subject against an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inducing an immune response in a subject against an HPV E7-expressing target cell, the method comprising the step of administering to the subject a vaccine vector encoding an HPV E7-containing recombinant peptide, protein or polypeptide of the present invention, thereby inducing an immune response against an HPV E7-expressing target cell. In another embodiment, the target cell is a cervical cancer cell. In another embodiment, the target cell is a head-and-neck cancer cell. In another embodiment, the target cell is any other type of HPV E7-expressing cell known in the art. Each possibility represents a separate embodiment of the present invention.

In another embodiment, the present invention provides a method for treating or reducing an incidence of an HPV E7-expressing tumor in a subject, the method comprising the step of administering to the subject an HPV-E7 encoding vaccine vector of the present invention, thereby treating or reducing an incidence of an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inhibiting or suppressing an HPV E7-expressing tumor in a subject, the method comprising the step of administering to the subject an HPV-E7 encoding vaccine vector of the present invention, thereby inhibiting or suppressing an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inducing regression of an HPV E7-expressing tumor in a subject, the method comprising the step of administering to the subject an HPV-E7 encoding vaccine vector of the present invention, thereby inducing regression of an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for protecting a subject against an HPV E7-expressing tumor in a subject, the method comprising the step of administering to the subject an HPV-E7 encoding vaccine vector of the present invention, thereby protecting a subject against an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inducing an immune response in a subject against an HPV E7-expressing target cell, the method comprising the step of administering to the subject an HPV-E7 encoding nucleotide molecule of the present invention, thereby inducing an immune response against an HPV E7-expressing target cell. In another embodiment, the target cell is a cervical cancer cell. In another embodiment, the target cell is a head-and-neck cancer cell. In another embodiment, the target cell is any other type of HPV E7-expressing cell known in the art. Each possibility represents a separate embodiment of the present invention.

In another embodiment, the present invention provides a method for treating or reducing an incidence of an HPV E7-expressing tumor in a subject, the method comprising the step of administering to the subject an HPV-E7 encoding nucleotide molecule of the present invention, thereby treating or reducing an incidence of an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inhibiting or suppressing an HPV E7-expressing tumor in a subject, the method comprising the step of administering to the subject an HPV-E7 encoding nucleotide molecule of the present invention, thereby inhibiting or suppressing an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inducing regression of an HPV E7-expressing tumor in a subject, the method comprising the step of administering to the subject an HPV-E7 encoding nucleotide molecule of the present invention, thereby inducing regression of an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for protecting a subject against an HPV E7-expressing tumor in a subject, the method comprising the step of administering to the subject an HPV-E7 encoding nucleotide molecule of the present invention, thereby protecting a subject against an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inducing an immune response in a subject against an HPV E7-expressing target cell, the method comprising the step of administering to the subject an a *Listeria* strain encoding an HPV-E7-containing peptide of the present invention, thereby inducing an immune response against an HPV E7-expressing target cell. In another embodiment, the target cell is a cervical cancer cell. In another embodiment, the target cell is a head-and-neck cancer cell. In another embodiment, the target cell is any other type of HPV E7-expressing cell known in the art. Each possibility represents a separate embodiment of the present invention.

In another embodiment, the present invention provides a method for treating or reducing an incidence of an HPV E7-expressing tumor in a subject, the method comprising the step of administering to the subject an HPV-E7 encoding *Listeria* strain of the present invention, thereby treating or reducing an incidence of an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inhibiting or suppressing an HPV E7-expressing tumor in a subject, the method comprising the step of administering to the subject an HPV-E7 encoding *Listeria* strain of the present invention, thereby inhibiting or suppressing an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for inducing regression of an HPV E7-expressing tumor in a subject, the method comprising the step of administering to the subject an HPV-E7 encoding *Listeria* strain of the present invention, thereby inducing regression of an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

In another embodiment, the present invention provides a method for protecting a subject against an HPV E7-expressing tumor in a subject, the method comprising the step of administering to the subject an HPV-E7 encoding *Listeria* strain of the present invention, thereby protecting a subject against an HPV E7-expressing tumor in a subject. In another embodiment, the tumor is a cervical tumor. In another embodiment, the tumor is a head-and-neck tumor. In another embodiment, the tumor is any other type of HPV E7-expressing tumor known in the art. Each possibility represents a separate embodiment of the present invention.

The cervical tumor targeted by methods of the present invention is, in another embodiment, a squamous cell carcinoma. In another embodiment, the cervical tumor is an adenocarcinoma. In another embodiment, the cervical tumor is an adenosquamous carcinoma. In another embodiment, the cervical tumor is a small cell carcinoma. In another embodiment, the cervical tumor is any other type of cervical tumor known in the art. Each possibility represents a separate embodiment of the present invention.

In one embodiment, the tumor targeted by methods of the present invention is a head and neck carcinoma. In another embodiment, the tumor is an anal carcinoma. In another embodiment, the tumor is a vulvar carcinoma. In another embodiment, the tumor is a vaginal carcinoma. Each possibility represents a separate embodiment of the present invention.

In one embodiment, the methods provided herein may be used in conjunction with other methods of treating, inhibiting, or suppressing cervical cancer, including, inter alia, surgery, radiation therapy, chemotherapy, surveillance, adjuvant (additional), or a combination of these treatments.

In another embodiment, the methods provided herein may be used in conjunction with other methods of treating, inhibiting, or suppressing head and neck carcinoma, including, inter alia, surgery, radiation therapy, chemotherapy, surveillance, adjuvant (additional), or a combination of these treatments.

In another embodiment, the methods provided herein may be used in conjunction with other methods of treating, inhibiting, or suppressing anal carcinoma, including, inter alia, surgery, radiation therapy, chemotherapy, surveillance, adjuvant (additional), or a combination of these treatments.

In another embodiment, the methods provided herein may be used in conjunction with other methods of treating, inhibiting, or suppressing vulvar carcinoma, including, inter alia, surgery, radiation therapy, chemotherapy, surveillance, adjuvant (additional), or a combination of these treatments.

In another embodiment, the methods provided herein may be used in conjunction with other methods of treating, inhibiting, or suppressing vaginal carcinoma, including, inter alia, surgery, radiation therapy, chemotherapy, surveillance, adjuvant (additional), or a combination of these treatments.

The E7 protein that is utilized (either whole or as the source of the fragments) has, in another embodiment, the sequence MHGDTPTLHEYMLDLQPETTDLY-CYEQLNDSSEEEDEIDGPAGQAEP-DRAHYNIVTFCCKCDS TLRLCVQSTHVDIRTLEDLL-MGTLGIVCPICSQKP (SEQ ID NO: 17). In another embodiment, the E7 protein is a homologue of SEQ ID NO: 17. In another embodiment, the E7 protein is a variant of SEQ ID NO: 17. In another embodiment, the E7 protein is an isomer of SEQ ID NO: 17. In another embodiment, the E7 protein is a fragment of SEQ ID NO: 17. In another embodiment, the E7 protein is a fragment of a homologue of SEQ ID NO: 17. In another embodiment, the E7 protein is a fragment of a variant of SEQ ID NO: 17. In another embodiment, the E7 protein is a fragment of an isomer of SEQ ID NO: 17. Each possibility represents a separate embodiment of the present invention.

In one embodiment, the cholesterol binding domain of LLO (ECTGLAWEWWR; SEQ ID NO: 18) is substituted with an E7 epitope (RAHYNIVTF; SEQ ID NO: 19).

In another embodiment, the sequence of the E7 protein is: MHGPKATLQDIVLHLEPQ-NEIPVDLLCHEQLSDSEEENDEIDGVN-HQHLPARRAEPQRHTMLC MCCKCEARIELVVES-SADDLRAFQQLFLNTLSFVCPWCASQQ (SEQ ID NO: 20). In another embodiment, the E7 protein is a homologue of SEQ ID NO: 20. In another embodiment, the E7 protein is a variant of SEQ ID NO: 20. In another embodiment, the E7 protein is an isomer of SEQ ID NO: 20. In another embodiment, the E7 protein is a fragment of SEQ ID NO: 20. In another embodiment, the E7 protein is a fragment of a homologue of SEQ ID NO: 20. In another embodiment, the E7 protein is a fragment of a variant of SEQ ID NO: 20. In another embodiment, the E7 protein is a fragment of an isomer of SEQ ID NO: 20. Each possibility represents a separate embodiment of the present invention.

In another embodiment, the E7 protein has a sequence set forth in one of the following GenBank entries: M24215, NC_004500, V01116, X62843, or M14119. In another embodiment, the E7 protein is a homologue of a sequence from one of the above GenBank entries. In another embodiment, the E7 protein is a variant of a sequence from one of the above GenBank entries. In another embodiment, the E7 protein is an isomer of a sequence from one of the above GenBank entries. In another embodiment, the E7 protein is a fragment of a sequence from one of the above GenBank entries. In another embodiment, the E7 protein is a fragment of a homologue of a sequence from one of the above GenBank entries. In another embodiment, the E7 protein is a fragment of a variant of a sequence from one of the above GenBank entries. In another embodiment, the E7 protein is a fragment of an isomer of a sequence from one of the above GenBank entries. Each possibility represents a separate embodiment of the present invention.

In one embodiment, the HPV16 E7 antigen is a peptide having the sequence: TLGIVCPI (SEQ ID NO: 21). In another embodiment, the HPV16 E7 antigen is a peptide having the sequence: LLMGTLGIV (SEQ ID NO: 22). In another embodiment, the HPV16 E7 antigen is a peptide having the sequence: YMLDLQPETT (SEQ ID NO: 23). In one embodiment, the HPV16 E7 antigen is a peptide comprising positions 86-93 of the wild-type HPV16 E7 antigen. In one embodiment, the HPV16 E7 antigen is a peptide comprising positions 82-90 of the wild-type HPV16 E7 antigen. In one embodiment, the HPV16 E7 antigen is a peptide comprising positions 11-20 of the wild-type HPV16 E7 antigen. In another embodiment, the HPV16 E7 antigen is a peptide consisting of positions 86-93, 82-90, or 11-20 of the wild-type HPV16 E7 antigen. In another embodiment, the HPV16 E7 antigen is a variant of a wild-type HPV16 E7 peptide. In another embodiment, the HPV16 E7 antigen is any HPV16 E7 antigen described in Ressing at al., J Immunol 1995 154 (11):5934-43, which is incorporated herein by reference in its entirety.

Each possibility represents another embodiment of the present invention.

In another embodiment, the antigenic peptide of interest of methods and compositions of the present invention is an HPV E6 peptide. In another embodiment, the antigenic peptide is a whole E6 protein. In another embodiment, the antigenic peptide is a fragment of an E6 protein. Each possibility represents a separate embodiment of the present invention.

The E6 protein that is utilized (either whole or as the source of the fragments) has, in another embodiment, the sequence MHQKRTAMFQDPQERPRKLPQLCTELQT- TIHDIILECVYCKQQLLRREVYDFAFRDLCIVYRD GNPYAVCDKCLKFYSKISEYRHYCYS- LYGTTLEQQYNKPLCDLLIRCINCQK- PLCPEEKQRHLDKKQR FHNIRGRWTGRCMSCCRSS- RTRRETQL (SEQ ID NO: 24). In another embodiment, the E6 protein is a homologue of SEQ ID NO: 24. In another embodiment, the E6 protein is a variant of SEQ ID NO: 24. In another embodiment, the E6 protein is an isomer of SEQ ID NO: 24. In another embodiment, the E6 protein is a fragment of SEQ ID NO: 24. In another embodiment, the E6 protein is a fragment of a homologue of SEQ ID NO: 24. In another embodiment, the E6 protein is a fragment of a variant of SEQ ID NO: 24. In another embodiment, the E6 protein is a fragment of an isomer of SEQ ID NO: 24. Each possibility represents a separate embodiment of the present invention.

In another embodiment, the sequence of the E6 protein is: MARFEDPTRRPYKLP- DLCTELNTSLQDIEITCVYCKTV- LELTEVFEFAFKDLFVVYRDSIPHAA CHKCIDFYSR- IRELRHYSDSVYGDTLEKLTNTGLYNLLIRCLRCQ KPLNPAEKLRHLNEKRRFHNIAG HYRGQCHSCCN- RARQERLQRRRETQV (SEQ ID NO: 25). In another embodiment, In another embodiment, the E6 protein is a homologue of SEQ ID NO: 25. In another embodiment, the E6 protein is a variant of SEQ ID NO: 25. In another embodiment, the E6 protein is an isomer of SEQ ID NO: 25. In another embodiment, the E6 protein is a fragment of SEQ ID NO: 25. In another embodiment, the E6 protein is a fragment of a homologue of SEQ ID NO: 25. In another embodiment, the E6 protein is a fragment of a variant of SEQ ID NO: 25. In another embodiment, the E6 protein is a fragment of an isomer of SEQ ID NO: 25. Each possibility represents a separate embodiment of the present invention.

In another embodiment, the E6 protein has a sequence set forth in one of the following GenBank entries: M24215, M14119, NC_004500, V01116, X62843, or M14119. In another embodiment, the E6 protein is a homologue of a sequence from one of the above GenBank entries. In another embodiment, the E6 protein is a variant of a sequence from one of the above GenBank entries. In another embodiment, the E6 protein is an isomer of a sequence from one of the above GenBank entries. In another embodiment, the E6 protein is a fragment of a sequence from one of the above GenBank entries. In another embodiment, the E6 protein is a fragment of a homologue of a sequence from one of the above GenBank entries. In another embodiment, the E6 protein is a fragment of a variant of a sequence from one of the above GenBank entries. In another embodiment, the E6 protein is a fragment of an isomer of a sequence from one of the above GenBank entries. Each possibility represents a separate embodiment of the present invention.

The HPV that is the source of the heterologous antigen of methods of the present invention is, in another embodiment, an HPV 16. In another embodiment, the HPV is an HPV-18. In another embodiment, the HPV is selected from HPV-16 and HPV-18. In another embodiment, the HPV is an HPV-31. In another embodiment, the HPV is an HPV-35. In another embodiment, the HPV is an HPV-39. In another embodiment, the HPV is an HPV-45. In another embodiment, the HPV is an HPV-51. In another embodiment, the HPV is an HPV-52. In another embodiment, the HPV is an HPV-58. In another embodiment, the HPV is a high-risk HPV type. In another embodiment, the HPV is a mucosal HPV type. Each possibility represents a separate embodiment of the present invention.

In another embodiment, the antigenic peptide of interest of methods and compositions of the present invention is a BCR idiotype.

Cytogenetic studies have shown that some histological and immunological sub-types of NHL have chromosomal abnormalities with reciprocal translocations, frequently involving genes for the B-cell receptor and an oncogene. Lymphomagenesis results in clonal expansion of the transformed B-cell, with each daughter cell expressing the BCR on the cell surface as well as BCR-derived peptides associated with MHC class I and II molecules. The BCR has a unique conformation formed by the hypervariable regions of the heavy and light chain, this is referred to as the "idiotype," is the same for every daughter cell within the tumor, and is not present on significant numbers of normal cells. Therefore, the idiotype is a specific tumor antigen and a target for lymphoma therapy.

As provided herein, the present invention has produced a conformationally intact fusion protein comprising an LLO protein and a BCR idiotype (Experimental Details section herein).

In another embodiment, the present invention provides a method for inducing an immune response against a lymphoma in a subject, comprising the step of administering to the subject a BCR idiotype-containing recombinant peptide, protein or polypeptide of the present invention, thereby inducing an immune response against a lymphoma.

In another embodiment, the present invention provides a method for inducing an immune response against a lymphoma in a subject, comprising the step of administering to the subject a BCR idiotype-encoding nucleotide molecule of the present invention, thereby inducing an immune response against a lymphoma.

In another embodiment, the present invention provides a method for inducing an immune response against a lymphoma in a subject, comprising the step of administering to the subject a BCR idiotype-expressing recombinant vaccine vector of the present invention, thereby inducing an immune response against a lymphoma.

In another embodiment, the present invention provides a method for inducing an immune response against a lymphoma in a subject, comprising the step of administering to the subject a BCR idiotype-expressing *Listeria* strain of the present invention, thereby inducing an immune response against a lymphoma.

In another embodiment, the present invention provides a method for treating, inhibiting, or suppressing a lymphoma in a subject, comprising the step of administering to the subject a BCR idiotype-containing peptide of the present invention, thereby treating a lymphoma.

In another embodiment, the present invention provides a method for treating, inhibiting, or suppressing a lymphoma in a subject, comprising the step of administering to the subject a BCR idiotype-encoding nucleotide molecule of the present invention, thereby treating a lymphoma.

In another embodiment, the present invention provides a method for treating, inhibiting, or suppressing a lymphoma in a subject, comprising the step of administering to the subject a BCR idiotype-expressing recombinant vaccine vector of the present invention, thereby treating a lymphoma in a subject.

In another embodiment, the present invention provides a method for treating, inhibiting, or suppressing a lymphoma in a subject, comprising the step of administering to the subject a BCR idiotype-expressing *Listeria* strain of the present invention, thereby treating a lymphoma in a subject.

In another embodiment, the present invention provides a method for inducing a regression of a lymphoma in a subject, comprising the step of administering to the subject a BCR idiotype-containing peptide of the present invention, thereby inducing a regression of a lymphoma.

In another embodiment, the present invention provides a method for inducing a regression of a lymphoma in a subject, comprising the step of administering to the subject a BCR idiotype-encoding nucleotide molecule of the present invention, thereby inducing a regression of a lymphoma.

In another embodiment, the present invention provides a method for inducing a regression of a lymphoma in a subject, comprising the step of administering to the subject a BCR idiotype-expressing recombinant vaccine vector of the present invention, thereby inducing a regression of a lymphoma in a subject.

In another embodiment, the present invention provides a method for inducing a regression of a lymphoma in a subject, comprising the step of administering to the subject a BCR idiotype-expressing *Listeria* strain of the present invention, thereby inducing a regression of a lymphoma in a subject.

As provided in the Experimental Details section herein, fusion of LLO to an antigen increases its immunogenicity. In addition, administration of fusion proteins of the present invention results in protection against tumor challenge.

Moreover, as provided herein, the present invention has produced a conformationally intact fusion protein comprising an LLO protein and a BCR idiotype, has demonstrated accurate and effective methodologies for testing anti-lymphoma vaccines in mouse and animal models, and has shown the efficacy of vaccines of the present invention in protecting against lymphoma and their superiority over currently accepted anti-lymphoma vaccines (Experimental Details section).

In one embodiment, a vaccine of the present invention is a composition that upon administration stimulates antibody production or cellular immunity against an antigen.

In one embodiment, vaccines are administered as killed or attenuated micro-organisms, while in another embodiment, vaccines comprise natural or genetically engineered antigens. In one embodiment, effective vaccines stimulate the immune system to promote the development of antibodies that can quickly and effectively attack cells, microorganisms or viruses that produce the antigen against which the subject was vaccination, when they are produced in the subject, thereby preventing disease development.

In one embodiment, a vaccine of the present invention is prophylactic, while in another embodiment, a vaccine of the present invention is therapeutic. In one embodiment, a prophylactic vaccine is administered to a population that is susceptible to developing or contracting a particular disease or condition, whether via environmental exposure or genetic predisposition. Such susceptibility factors are disease-dependent and are well-known to those of skill in the art. For example, the population comprising smokers (in one embodiment, cigarette, cigar, pipe, etc) is known in the art to be susceptible to developing lung cancer. The population comprising a mutation in BRCA-1 and BRCA-2 is known in the art to be susceptible to breast and/or ovarian cancer. The population comprising particular single nucleotide polymorphisms (SNPs) in chromosome 15 inside a region that contains genes for the nicotinic acetylcholine receptor alpha subunits 3 and 5 is known in the art to be susceptible to lung cancer. Other similar susceptibility factors are known in the art, and such susceptible populations are envisioned in one embodiment, to be a population for which a prophylactic vaccine of the instant invention would be most useful.

Thus, vaccines of the present invention are efficacious in inducing an immune response to, preventing, treating, and inducing remission of lymphoma. In another embodiment, the present invention provides a method for overcoming an immune tolerance to a lymphoma in a subject, comprising the step of administering to the subject a peptide of the present invention, thereby overcoming an immune tolerance to a lymphoma.

In another embodiment, the present invention provides a method for overcoming an immune tolerance to a lymphoma in a subject, comprising the step of administering to the subject a nucleotide molecule of the present invention, thereby overcoming an immune tolerance to a lymphoma.

"Tolerance" refers, in another embodiment, to a lack of responsiveness of the host to an antigen. In another embodiment, the term refers to a lack of detectable responsiveness of the host to an antigen. In another embodiment, the term refers to a lack of immunogenicity of an antigen in a host. In another embodiment, tolerance is measured by lack of responsiveness in an in vitro CTL killing assay. In another embodiment, tolerance is measured by lack of responsiveness in a delayed-type hypersensitivity assay. In another embodiment, tolerance is measured by lack of responsiveness in any other suitable assay known in the art. In another embodiment, tolerance is determined or measured as depicted in the Examples herein. Each possibility represents another embodiment of the present invention.

"Overcome" refers, in another embodiment, to a reversal of tolerance by a vaccine. In another embodiment, the term refers to conferment of detectable immune response by a vaccine. In another embodiment, overcoming of immune tolerance is determined or measured as depicted in the Examples herein. Each possibility represents another embodiment of the present invention.

In another embodiment, the present invention provides a method for reducing an incidence of relapse of a lymphoma in a subject in remission from the lymphoma, comprising the step of administering to the subject a peptide of the present invention, thereby reducing an incidence of relapse of a lymphoma in a subject in remission from the lymphoma.

In another embodiment, the present invention provides a method for reducing an incidence of relapse of a lymphoma in a subject in remission from the lymphoma, comprising administering to the subject a nucleotide molecule of the present invention, thereby reducing an incidence of relapse of a lymphoma in a subject in remission from the lymphoma.

In another embodiment, the present invention provides a method for suppressing a formation of a lymphoma, comprising the step of administering a recombinant peptide, protein or polypeptide of the present invention thereby suppressing a formation of a lymphoma.

In another embodiment, the present invention provides a method for suppressing a formation of a lymphoma, comprising the step of administering a nucleotide molecule of the present invention, thereby suppressing a formation of a lymphoma.

In another embodiment, the present invention provides a method of inducing a remission of a residual B cell lymphoma disease, comprising administering a peptide of the present invention, thereby inducing a remission of a residual B cell lymphoma disease.

In another embodiment, the present invention provides a method of inducing a remission of a residual B cell lymphoma disease, comprising administering a nucleotide molecule of the present invention, thereby inducing a remission of a residual B cell lymphoma disease.

In another embodiment, the present invention provides a method of eliminating minimal residual B cell lymphoma disease, comprising administering a peptide of the present invention, thereby eliminating minimal residual B cell lymphoma disease.

In another embodiment, the present invention provides a method of eliminating minimal residual B cell lymphoma disease, comprising administering a nucleotide molecule of the present invention, thereby eliminating minimal residual B cell lymphoma disease.

In another embodiment, the present invention provides a method of reducing a size of a B cell lymphoma, comprising administering a peptide of the present invention, thereby reducing a size of a B cell lymphoma.

In another embodiment, the present invention provides a method of reducing a size of a B cell lymphoma, comprising administering a nucleotide molecule of the present invention, thereby reducing a size of a B cell lymphoma.

In another embodiment, the present invention provides a method of reducing a volume of a B cell lymphoma, comprising administering a peptide of the present invention, thereby reducing a volume of a B cell lymphoma.

In another embodiment, the present invention provides a method of reducing a volume of a B cell lymphoma, comprising administering a nucleotide molecule of the present invention, thereby reducing a volume of a B cell lymphoma.

In another embodiment, the lymphoma that is a target of a method of present invention is, in another embodiment, a Non-Hodgkin's Lymphoma. In another embodiment, a lymphoma is a B cell lymphoma. In another embodiment, a lymphoma is a low-grade lymphoma. In another embodiment, a lymphoma is a low-grade NHL. In another embodiment, a lymphoma is residual disease from one of the above types of lymphoma. In another embodiment, the lymphoma is any other type of lymphoma known in the art. In another embodiment, the lymphoma is a Burkitt's Lymphoma. In another embodiment, the lymphoma is follicular lymphoma. In another embodiment, the lymphoma is marginal zone lymphoma. In another embodiment, the lymphoma is splenic marginal zone lymphoma. In another embodiment, the lymphoma is a mantle cell lymphoma. In another embodiment, the lymphoma is an indolent mantle cell lymphoma. In another embodiment, the lymphoma is any other known type of lymphoma that expresses a BCR. Each type of lymphoma represents a separate embodiment of the present invention.

In another embodiment, cells of the tumor that is targeted by methods and compositions of the present invention express a BCR. In another embodiment, the tumor is associated with a BCR. In another embodiment, the BCR has an idiotype that is characteristic of the tumor. In another embodiment, the BCR expressed by a tumor cell is the target of the immune responses induced by methods and compositions of the present invention.

In another embodiment, the BCR expressed by the target cell is required for a tumor phenotype. In another embodiment, the BCR is necessary for transformation of a tumor cell. In another embodiment, tumor cells that lose expression of the BCR lose their uncontrolled growth, invasiveness, or another feature of malignancy. Each possibility represents a separate embodiment of the present invention.

Methods and compositions of the present invention apply equally to any BCR of a non-Hodgkin's lymphoma and any idiotype thereof. Sequences of BCR are well known in the art, and are readily obtained from lymphoma samples.

An exemplary sequence of a BCR immunoglobulin (Ig) heavy chain precursor is:

MKLWLNWIFLVTLLNGIQCEVKLVESGGGLVQPGGSLSLSCAASGFTFTD

YYMSWVRQPPGKALEWLALIRNKANGYTTEYSASVKGRFTISRDNSQSIL

YLQMNALRAEDSATYYCARDPNYYDGSYEGYFDYWAQGTTLTVSS
(SEQ ID NO: 26; GenBank Accession No. X14096).

An exemplary sequence of a BCR Ig light chain precursor is:

LLLISVTVIVSNGEIVLTQSPTTMAASPGEKITITCSASSSISSNYLHWYQQKPGFSPKLLIYRTSN (SEQ ID NO: 27;

LASGVPARFSGSGSGTSYSLTIGTMEAEDVATYYCQQGSSIPRGVTFGSGTKLEIKR    GenBank Accession No. X14097).

Another exemplary sequence of a BCR Ig light chain precursor is:

GFLLISVTVILTNGEIFLTQSPAIIAASPGEKVTITCSASSSVSYMNWYQQKPGSSPKIWIYGISNL (SEQ ID NO: 28;
ASGVPARFSGSGSGTSFSFTINSMEAEDVATYYCQQRSSYPFTFGSGTKLEIKRADAAPTVSHLP   GenBank Accession No. X14098).

Another exemplary sequence of a BCR Ig light chain precursor is:

LLLISVTVIVSNGEIVLTQSPTTMAASPGEKITITCSASSSISSNYLHWYQQKPGFSPKLLIYRTSN (SEQ ID NO: 29;
LASGVPARFSGSGSGTSYSLTIGTMEAEDVATYYCQQGSSIPRTFGSGTKLEIKRA            GenBank Accession No. X14099).

Another exemplary sequence of a BCR Ig heavy chain is:

MEFGLSWVFLVAILKGVQCEMQLVESGGGLVQPGESLKLSCAASGFSFSGSTIHWVRQASGRGLEWV   (SEQ ID NO: 30;
GRSRSKADNFMTSYAPSIKGKFIISRDDSSNMLYLQMNNLKTEDTAVYFCTRNFTSLDSTGNSFGPWG  human follicular lymphoma IgM
QGTLVTVSSGSASAPTLFPLVS                                                heavy chain; GenBank Accession
                                                                      No. X70200).

Another exemplary sequence of a BCR Ig heavy chain is:

MEFGLSWVFLVAILKGVQCEMQLVESGGGLVQPGESFKLSCAASGFSFSGSTIHWVRQASGRGLEWV   (SEQ ID NO: 31;
GRSRSKADNFMTSYAPSIKGKFIISRDDSSNMMYLQMNNLKNEDTAVYFCTRNFTSLDSTGNSFGPW   human follicular lymphoma IgM
GQGTLVTVSSGSASAPTLFPLVS                                               heavy chain; GenBank Accession
                                                                      No. X70199).

Another exemplary sequence of a BCR Ig heavy chain is:

MEFGLSWVFLVAILKGVQCEVQLVESGGGLVQPGGSLRLSCAASGFTVSSNYMSWVRQAPGKGLEW    (SEQ ID NO: 32;
VSVIYSGGSTYYADSVKGRFTISRDNSKNTLYLQMNSLRAEDTAVYYCARHTVRGGHCAPRHKPSL    human follicular lymphoma IgM
QERWGNQRQGALRS                                                        heavy chain; GenBank Accession
                                                                      No. X70208).

Another exemplary sequence of a BCR Ig heavy chain is:

MEFGLSWVFLVAILKGVQCEVQLVESGGGLVQPGGSLKLSCAASGFTFSGSAMHWVRQASGKGLEWV   (SEQ ID NO: 33;
GHIRDKANSYATTYAASVKGRFTISRDDSKNTAYLQMNSLKWDTAVYFCTRNFTSLDSTGNSFGPW    human follicular lymphoma IgM
                                                                      heavy chain; GenBank Accession
                                                                      No. X70207).

Another exemplary sequence of a BCR Ig light chain is:

SELTQDPVVSVALGQTVRITCQGDSLRSYYASWYQQKPGQAPVLVIYGKNNRPSGIPDRFSGS   (SEQ ID NO: 34;
SSGNTASLTTTGAQAEDEADYYCNSRDSSGNLPLFGGGTKLTVLG                    human lymphoplasmacytic/
                                                                 lymphoplasmacytoid
                                                                 immunocytoma light
                                                                 chain; GenBank Accession
                                                                 No. AAD14088).

Another exemplary sequence of a BCR Ig light chain is:

DIQMTQSPDSLTVSLGERATINCKSSQSILYSSNDKNYLAWYQQKAGQPPKLLIYWASTRESG   (SEQ ID NO: 35;
VPDRFSGSGSATDFTLTISSLQAEDVAIYYCQQYYSTPLTFGGGTKVEIKR               human follicular lymphoma
                                                                  light chain; GenBank Accession
                                                                  No. Y09250).

Another exemplary sequence of a BCR Ig light chain is:

DIQMTQSPSTLSASVGDRVTITCRASQSISTWLAWYQQKPGKAPKLLIYEASSLESGVPSRFSGS   (SEQ ID NO: 36;
GSGTEFTLTISSLQPDDFVTYYCQQYNTFSSYTFGQGTKVEIK                         human splenic marginal zone
                                                                    lymphoma light chain;
                                                                    GenBank Accession No.
                                                                    AAX93805).

Sequences of other exemplary BCR Ig light chains are found in GenBank Accession Nos. AAX93769-93802, CAA25477, AAB31509, CAE52829-CAE52832, AAF79132-79143, and other sequences found in GenBank. Each sequence represents a separate embodiment of the present invention. CAA73059

Sequences of other exemplary BCR Ig heavy chains are found in GenBank Accession Nos. CAA73044-73059, AAX93809-AAX93842, AAQ74129, CAC39369, AAB52590-AAB52597, and other sequences found in GenBank. Each sequence represents a separate embodiment of the present invention.

Methods for determining complementarity-determining regions (cdr) of a BCR are well known in the art. For example, the CDR1 of SEQ ID NO: 26 consists of residues 50-54; the CDR2 consists of residues 66-87; the D segment consists of residues 120-130; and the J segment consists of residues 131-145. The CDR1 of SEQ ID NO: 30 consists of residues 148-162; the FR2 consists of residues 163-204; the CDR2 consists of residues 205-261; the FR3 consists of residues 262-357; the CDR3 consists of residues 358-432; and the CH1 consists of residues 433-473. In another embodiment, the framework regions (non-cdr regions) are determined by homology with known framework regions of other immunoglobulin molecules from the same species. Each possibility represents a separate embodiment of the present invention.

In another embodiment, an idiotype is identified by determining the cdr of a BCR of methods and compositions of the present invention.

In another embodiment, a complete BCR is contained or utilized in methods and compositions of the present invention. In another embodiment, a fragment of a BCR is contained or utilized. In another embodiment, the BCR fragment contains the idiotype thereof. In another embodiment, the BCR fragment contains a T cell epitope. In another embodiment, the BCR fragment contains an antibody epitope. In another embodiment, "antigen" is used herein to refer to the BCR or fragment thereof that is the target of immune responses induced by methods and compositions of the present invention.

In another embodiment, the fragment of a BCR contained in peptides of the present invention is a single chain fragment of the variable regions (scFV) of the BCR. In another embodiment, the BCR fragment is conformationally intact. In another embodiment, the BCR fragment contains the idiotype of the BCR. In another embodiment, the BCR idiotype is conformationally intact. Each possibility represents a separate embodiment of the present invention.

"Idiotype" refers, in another embodiment, to the structure formed by the complementarity-determining region (cdr) of a BCR. In another embodiment, the term refers to the unique region of a BCR. In another embodiment, the term refers to the antigen-binding site of the BCR. Each possibility represents a separate embodiment of the present invention.

"Conformationally intact" refers, in another embodiment, to a conformation that is not significantly altered relative to the native conformation. In another embodiment, the term refers to an antibody reactivity that is not significantly altered relative to the native protein. In another embodiment, the term refers to an antibody reactivity that overlaps substantially with the native protein. Each possibility represents a separate embodiment of the present invention.

In another embodiment, a peptide utilized in methods of the present invention comprises an idiotype that is homologous to an idiotype expressed by cells of the lymphoma. In another embodiment, the peptide comprises an idiotype that is identical to an idiotype expressed by cells of the lymphoma. Each possibility represents a separate embodiment of the present invention.

In another embodiment, a nucleotide molecule utilized in methods of the present invention encodes an idiotype that is homologous to an idiotype expressed by cells of the lymphoma. In another embodiment, the nucleotide molecule encodes an idiotype that is identical to an idiotype expressed by cells of the lymphoma. In another embodiment, the antigen is highly homologous to the antigen expressed by the tumor cell. "Highly homologous" refers, in another embodiment, to a homology of greater than 90%. In another embodiment, the term refers to a homology of greater than 92%. In another embodiment, the term refers to a homology of greater than 93%. In another embodiment, the term refers to a homology of greater than 94%. In another embodiment, the term refers to a homology of greater than 95%. In another embodiment, the term refers to a homology of greater than 96%. In another embodiment, the term refers to a homology of greater than 97%. In another embodiment, the term refers to a homology of greater than 98%. In another embodiment, the term refers to a homology of greater than 99%. In another embodiment, the term refers to a homology of 100%. Each possibility represents a separate embodiment of the present invention.

In another embodiment, the residual B cell lymphoma disease or minimal residual B cell lymphoma disease treated by a method of the present invention is that remaining after de-bulking therapy. Methods for performing de-bulking therapy are well known in the art, and are described, for example, in Winter J N et al (Low-grade lymphoma. Hematology (Am Soc Hematol Educ Program). 2004; 203-20) and Buske C et al (Current status and perspective of antibody therapy in follicular lymphoma. Haematologica. 2006 January; 91(1):104-12). Each possibility represents a separate embodiment of the present invention.

The heterologous antigenic peptide of methods and compositions of the present invention is, in another embodiment, an antigenic protein. In another embodiment, the antigenic peptide is a fragment of an antigenic protein. In another embodiment, the antigenic peptide is an immunogenic peptide derived from tumor. In another embodiment, the antigenic peptide is an immunogenic peptide derived from metastasis. In another embodiment, the antigenic peptide is an immunogenic peptide derived from cancerous cells. In another embodiment, the antigenic peptide is a pro-angiogenesis immunogenic peptide.

In another embodiment, the antigenic polypeptide is Human Papilloma Virus-E7 (HPV-E7) antigen, which in one embodiment, is from HPV16 (in one embodiment, GenBank Accession No. AAD33253) and in another embodiment, from HPV18 (in one embodiment, GenBank Accession No. P06788). In another embodiment, the antigenic polypeptide is HPV-E6, which in one embodiment, is from HPV16 (in one embodiment, GenBank Accession No. AAD33252, AAM51854, AAM51853, or AAB67615) and in another embodiment, from HPV18 (in one embodiment, GenBank Accession No. P06463). In another embodiment, the antigenic polypeptide is a Her/2-neu antigen. In another embodiment, the antigenic polypeptide is Prostate Specific Antigen (PSA) (in one embodiment, GenBank Accession No. CAD30844, CAD54617, AAA58802, or NP_001639). In another embodiment, the antigenic polypeptide is Stratum Corneum Chymotryptic Enzyme (SCCE) antigen (in one embodiment, GenBank Accession No. AAK69652, AAK69624, AAG33360, AAF01139, or AAC37551). In another embodiment, the antigenic polypeptide is Wilms tumor antigen 1, which in another embodiment is WT-1

Telomerase (GenBank Accession. No. P49952, P22561, NP_659032, CAC39220.2, or EAW68222.1). In another embodiment, the antigenic polypeptide is hTERT or Telomerase (GenBank Accession. No. NM003219 (variant 1), NM198255 (variant 2), NM 198253 (variant 3), or NM 198254 (variant 4). In another embodiment, the antigenic polypeptide is Proteinase 3 (in one embodiment, GenBank Accession No. M29142, M75154, M96839, X55668, NM 00277, M96628 or X56606). In another embodiment, the antigenic polypeptide is Tyrosinase Related Protein 2 (TRP2) (in one embodiment, GenBank Accession No. NP_001913, ABI73976, AAP33051, or Q95119). In another embodiment, the antigenic polypeptide is High Molecular Weight Melanoma Associated Antigen (HMW-MAA) (in one embodiment, GenBank Accession No. NP_001888, AAI28111, or AAQ62842). In another embodiment, the antigenic polypeptide is Testisin (in one embodiment, GenBank Accession No. AAF79020, AAF79019, AAG02255, AAK29360, AAD41588, or NP_659206). In another embodiment, the antigenic polypeptide is NY-ESO-1 antigen (in one embodiment, GenBank Accession No. CAA05908, P78358, AAB49693, or NP_640343). In another embodiment, the antigenic polypeptide is PSCA (in one embodiment, GenBank Accession No. AAH65183, NP_005663, NP_082492, O43653, or CAB97347). In another embodiment, the antigenic polypeptide is Interleukin (IL) 13 Receptor alpha (in one embodiment, GenBank Accession No. NP_000631, NP_001551, NP_032382, NP_598751, NP_001003075, or NP_999506). In another embodiment, the antigenic polypeptide is Carbonic anhydrase IX (CAIX) (in one embodiment, GenBank Accession No. CAI13455, CAI10985, EAW58359, NP_001207, NP_647466, or NP_001101426). In another embodiment, the antigenic polypeptide is carcinoembryonic antigen (CEA) (in one embodiment, GenBank Accession No. AAA66186, CAA79884, CAA66955, AAA51966, AAD15250, or AAA51970.). In another embodiment, the antigenic polypeptide is MAGE-A (in one embodiment, GenBank Accession No. NP_786885, NP_786884, NP_005352, NP_004979, NP_005358, or NP_005353). In another embodiment, the antigenic polypeptide is survivin (in one embodiment, GenBank Accession No. AAC51660, AAY15202, ABF60110, NP_001003019, or NP_001082350). In another embodiment, the antigenic polypeptide is GP100 (in one embodiment, GenBank Accession No. AAC60634, YP_655861, or AAB31176). In another embodiment, the antigenic polypeptide is any other antigenic polypeptide known in the art. In another embodiment, the antigenic peptide of the compositions and methods of the present invention comprise an immunogenic portion of the antigenic polypeptide. Each possibility represents a separate embodiment of the present invention.

In other embodiments, the antigen is derived from a fungal pathogen, bacteria, parasite, helminth, or viruses. In other embodiments, the antigen is selected from tetanus toxoid, hemagglutinin molecules from influenza virus, diphtheria toxoid, HIV gp120, HIV gag protein, HIV env protein, IgA protease, insulin peptide B, *Spongospora subterranea* antigen, vibriose antigens, *Salmonella* antigens, pneumococcus antigens, respiratory syncytial virus antigens, *Haemophilus influenza* outer membrane proteins, *Helicobacter pylori* urease, *Neisseria meningitidis* pilins, *N. gonorrhoeae* pilins, human papilloma virus antigens E1 and E2 from type HPV-16, -18, -31, -33, -35 or -45 human papilloma viruses, the tumor antigens CEA, the ras protein, mutated or otherwise, the p53 protein, mutated or otherwise.

In various embodiments, the antigen of methods and compositions of the present invention includes but is not limited to antigens from the following infectious diseases, measles, mumps, rubella, poliomyelitis, hepatitis A, B (e.g., GenBank Accession No. E02707), and C (e.g., GenBank Accession No. E06890), as well as other hepatitis viruses, type A influenza, other types of influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and HIV (e.g., GenBank Accession No. U18552). Bacterial and parasitic antigens will be derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae, Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leishmaniasis, giardiasis (e.g., GenBank Accession No. M33641), amoebiasis, filariasis (e.g., GenBank Accession No. J03266), borreliosis, and trichinosis.

In other embodiments, the antigen is one of the following tumor antigens: any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, TRP-2, gp-100, tyrosinase, MART-1, HSP-70, and beta-HCG; a tyrosinase; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUC1 antigen associated with breast carcinoma (e.g., GenBank Accession No. J0365 1), CEA (carcinoembryonic antigen) associated with colorectal cancer (e.g., GenBank Accession No. X983 11), gp100 (e.g., GenBank Accession No. S73003) or MART1 antigens associated with melanoma, and the prostate-specific antigen (KLK3) associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Tumor antigens encompassed by the present invention further include, but are not limited to, Her-2/Neu (e.g. GenBank Accession Nos. M16789.1, M16790.1, M16791.1, M16792.1), NY-ESO-1 (e.g. GenBank Accession No. U87459), WT-1 (e.g. GenBank Accession Nos. NM000378 (variant A), NM024424 (variant B), NM 024425 (variant C), and NM024426 (variant D)), LAGE-1 (e.g. GenBank Accession No. CAA11044), synovial sarcoma, X (SSX)-2; (e.g. GenBank Accession No. NP_003138, NP_783629, NP_783729, NP_066295), and stratum corneum chymotryptic enzyme (SCCE; GenBank Accession No. NM_005046 and NM_139277)). Thus, the present invention can be used as immunotherapeutics for cancers including, but not limited to, cervical, breast, colorectal, prostate, lung cancers, and for melanomas.

Each antigen represents a separate embodiment of the present invention.

In one embodiment, methods of evaluating the production of an immune response by a subject to an antigen are known in the art, and in one embodiment, are described hereinbelow in the Examples section.

The LLO protein utilized to construct vaccines of the present invention (in another embodiment, used as the source of the LLO fragment incorporated in the vaccines) has, in another embodiment, the sequence: MKKIMLVFITLILVS-LPIAQQTEAKDASAFNKENSISSMAP-PASPPASPKTPIEKKHADEIDKYIQGLDY NKNNVLVY-HGDAVTNVPPRKGYKDGNEYIVVEKKKKSINQN NADIQVVNAISSLTYPGALVKANSEL VENQPDV-LPVKRDSLTLSIDLPGMTNQDNKIV-VKNATKSNVNNAVNTLVERWNEKYAQAYPNVSAK IDYDDEMAYSESQLIAKFG-TAFKAVNNSLNVNFGAISEGKMQEEVIS-FKQIYYNVNVNEPTRPSRFFG KAVTKEQLQALGV-NAENPPAYISSVAYGRQVYLKLSTNSHSTKVKAA FDAAVSGKSVSGDVELTNII KNSS-FKAVIYGGSAKDEVQIIDGNLGDLRDIL-KKGATFNRETPGVPIAYTTNFLKDNELAVIKNNSEYI ETTSKAYTDGKINIDHSGGYVA-QFNISWDEVNYDPEGNEIVQHKNWSENN-KSKLAHFTSSIYLPGNAR NINVYAKECTGLAWEW-WRTVIDDRNLPLVKNRNISIWGTTLYPKYSNKVDNPIE (GenBank Accession No. P13128; SEQ ID NO: 37; nucleic acid sequence is set forth in GenBank Accession No. X15127). The first 25 AA of the proprotein corresponding to this sequence are the signal sequence and are cleaved from LLO when it is secreted by the bacterium. Thus, in this embodiment, the full-length active LLO protein is 504 residues long. In another embodiment, the LLO protein is a homologue of SEQ ID NO: 37. In another embodiment, the LLO protein is a variant of SEQ ID NO: 37. In another embodiment, the LLO protein is an isomer of SEQ ID NO: 37. In another embodiment, the LLO protein is a fragment of SEQ ID NO: 37. In another embodiment, the LLO protein is a fragment of a homologue of SEQ ID NO: 37. In another embodiment, the LLO protein is a fragment of a variant of SEQ ID NO: 37. In another embodiment, the LLO protein is a fragment of an isomer of SEQ ID NO: 37. Each possibility represents a separate embodiment of the present invention.

In another embodiment, the LLO protein utilized to construct vaccines of methods and compositions the present invention has the sequence as set forth in SEQ ID NO: 46 (Example 5 hereinbelow). In another embodiment, the LLO protein is a variant of SEQ ID NO: 46. In another embodiment, the LLO protein is an isomer of SEQ ID NO: 46. In another embodiment, the LLO protein is a fragment of SEQ ID NO: 46. In another embodiment, the LLO protein is a fragment of a homologue of SEQ ID NO: 46. In another embodiment, the LLO protein is a fragment of a variant of SEQ ID NO: 46. In another embodiment, the LLO protein is a fragment of an isomer of SEQ ID NO: 46.

In another embodiment, the LLO protein utilized to construct vaccines of methods and compositions as provided herein is a detoxified LLO (DTLLO). In another embodiment, the DTLLO is a fragment of the full protein thereof. In another embodiment, LLO is detoxified by replacing the cholesterol binding region with an antigen peptide or epitope thereof. In another embodiment, LLO detoxified by replacing the cholesterol binding region with the E7 epitope. In another embodiment, LLO is detoxified by deleting the cholesterol binding region/domain. In another embodiment, LLO is detoxified by deleting the signal sequence portion of LLO. In another embodiment, LLO is detoxified by deleting the signal sequence and the cholesterol binding region/domain. In another embodiment, DTLLO is used in genetic or chemical fusions to target antigens to increase antigen immunogenicity. In another embodiment, detoxLLO is fused to an antigen. In another embodiment, DTLLO is fused to an antigenic peptide of the methods and compositions described herein.

In one embodiment, the cholesterol binding region or cholesterol binding domain is known as for LLO or may be deduced using methods known in the Art (reviewed in Alouf, Int J Med. Microbiol. 2000 October; 290(4-5):351-6, incorporated herein by reference), including site-directed mutagenesis followed by a cholesterol binding assay or sequence conservation of proteins with similar cholesterol-binding functions.

In another embodiment, the LLO protein is a ctLLO. In another embodiment ctLLO is full length LLO in which the CBD has been replaced by an antigen peptide or epitope thereof. In another embodiment "replaced" in can mean via a substitution, or deletion mutation. In another embodiment, the LLO protein is a mutLLO. In another embodiment, a mutLLO is one in which the CBD has been mutated. In another embodiment, the mutLLO is one in which the amino acids in the CBD have been mutated. In another embodiment the mutation is a point mutation, a deletion, an inversion, a substitution, or a combination thereof. In another embodiment the mutation is any mutation known in the art. In another embodiment, the mutated LLO protein comprises any combination of deletions, substitutions, or point mutations in the CBD and/or deletions of the signal sequence of LLO. In another embodiment, mutating the CBD reduces the hemolytic activity of LLO. In another embodiment, the CBD is replaced by known HLA class I restricted epitopes to be used as a vaccine. In another embodiment, the mutated LLO is expressed and purified from *E. coli* expression systems.

In another embodiment, "LLO fragment" or "ΔLLO" refers to a fragment of LLO that comprises the PEST-like domain thereof. In another embodiment, the terms refer to an LLO fragment that comprises a PEST sequence. Each possibility represents another embodiment of the present invention.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein.

In another embodiment, the LLO fragment is any other LLO fragment known in the art. Each possibility represents a separate embodiment of the present invention.

In another embodiment, a whole LLO protein is utilized in methods and compositions of the present invention. In another embodiment, the whole LLO protein is a non-hemolytic LLO protein.

In another embodiment, a recombinant peptide, protein or polypeptide of the present invention further comprises a detectable tag polypeptide. In another embodiment, a detectable tag polypeptide is not included. In other embodiments, the tag polypeptide is green fluorescent protein (GFP), myc, myc-pyruvate kinase (myc-PK), $His_6$, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. In another embodiment, the present invention utilizes any nucleic acid sequence encoding a polypeptide which functions in a manner substantially similar to these tag polypeptides. Each possibility represents a separate embodiment of the present invention.

In another embodiment, the recombinant vaccine vector of methods and compositions of the present invention is a plasmid. In another embodiment, the present invention provides a method for the introduction of a nucleotide molecule of the present invention into a cell. Methods for constructing and utilizing recombinant vectors are well known in the art and are described, for example, in Sambrook et al. (2001, Molecular Cloning: A Laboratory Manual, Cold Spring Harbor Laboratory, New York), and in Brent et al. (2003, Current Protocols in Molecular Biology, John Wiley & Sons, New York). In another embodiment, the vector is a bacterial vector. In other embodiments, the vector is selected from *Salmonella* sp., *Shigella* sp., BCG, *L. monocytogenes* and *S. gordonii*. In another embodiment, the fusion proteins are delivered by recombinant bacterial vectors modified to escape phagolysosomal fusion and live in the cytoplasm of the cell. In another embodiment, the vector is a viral vector. In other embodiments, the vector is selected from Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. In another embodiment, the vector is a naked DNA vector. In another embodiment, the vector is any other vector known in the art. Each possibility represents a separate embodiment of the present invention.

In another embodiment, a nucleotide of the present invention is operably linked to a promoter/regulatory sequence that drives expression of the encoded peptide in cells into which the vector is introduced. Promoter/regulatory sequences useful for driving constitutive expression of a gene in a prokaryotic cell are well known in the art and include, for example, the *Listeria* p60 promoter, the in1A (encodes internalin) promoter, the hly promoter, and the ActA promoter is used. In another embodiment, any other gram positive promoter is used. Promoter/regulatory sequences useful for driving constitutive expression of a gene in a eukaryotic cell (e.g. for a DNA vaccine) are well known in the art and include, but are not limited to, for example, the cytomegalovirus immediate early promoter enhancer sequence, the SV40 early promoter, and the Rous sarcoma virus promoter. In another embodiment, inducible and tissue specific expression of the nucleic acid encoding a peptide of the present invention is accomplished by placing the nucleic acid encoding the peptide under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the invention includes the use of any promoter/regulatory sequence, which is either known or unknown, and which is capable of driving expression of the desired protein operably linked thereto.

In another embodiment, a peptide of the present invention activates an APC (e.g. a DC), mediating at least part of its increased immunogenicity. In another embodiment, the inactivated LLO need not be attached to the idiotype-containing protein to enhance its immunogenicity. Each possibility represents a separate embodiment of the present invention.

In another embodiment, the present invention provides a method for enhancing the immunogenicity of an antigen, comprising fusing an LLO protein or fragment thereof to the antigen. As demonstrated by the data disclosed herein, fusing a mutated LLO protein to an antigen enhances the immunogenicity of the antigen.

In another embodiment of methods and compositions of the present invention, a PEST-like AA sequence is contained in an LLO fusion protein of the present invention. As provided herein, enhanced cell mediated immunity was demonstrated for fusion proteins comprising an antigen and LLO containing the PEST-like AA sequence KENSISSMAP-PASPPASPKTPIEKKHADEIDK (SEQ ID NO: 63). In another embodiment, fusion of an antigen to a non-hemolytic LLO including the PEST-like AA sequence, SEQ ID NO: 1, can enhance cell mediated and anti-tumor immunity of the antigen.

In another embodiment, the non-hemolytic LLO protein or fragment thereof of the present invention need not be that which is set forth exactly in the sequences set forth herein, but rather that other alterations, modifications, or changes can be made that retain the functional characteristics of an LLO fused to an antigen as set forth elsewhere herein. In another embodiment, the present invention utilizes an analog of an LLO protein or fragment thereof of the present invention. Analogs differ, in another embodiment, from naturally occurring proteins or peptides by conservative AA sequence differences or by modifications that do not affect sequence, or by both.

In one embodiment, the present invention provides a composition or method in which cytokine expression is increased (see for e.g., Example 19). In one embodiment, the cytokine is TNF-alpha, while in another embodiment, the cytokine is IL-12, while in another embodiment, the cytokine is ISG15, while in another embodiment, the cytokine is a different cytokine known in the art. In one embodiment, the increase may be in cytokine mRNA expression, while in another embodiment, it may be in cytokine secretion, while in another embodiment, the increase may be in both mRNA expression and secretion of cytokines. In another embodiment, compositions and methods of the present invention may increase dendritic cell maturation markers, which in one embodiment, is CD86, in another embodiment, CD40, and in another embodiment MHCII, in another embodiment, another dendritic cell maturation marker known in the art, or, in another embodiment, a combination thereof (see for e.g., Example 20). In another embodiment, compositions and method of the present invention may cause nuclear translocation of transcription factors, which in one embodiment, is NF-kappa-B (see for e.g. Example 22), or in another embodiment, is a different transcription factor known in the art. In another embodiment, compositions and method of the present invention may cause upregulation of cell surface markers, which in one embodiment, may be CD11b, which in one embodiment is Integrin-alpha M (ITGAM); cluster of differentiation molecule 11B; complement receptor 3A (CR3A); or macrophage 1 antigen (MAC-1)A. In another embodiment, a different cell surface marker expressed by immune cells, may be upregulated as would be understood by a skilled artisan.

In one embodiment, "homology" refers to identity to an LLO sequence (e.g. to any of SEQ ID NO: 37, 46, or 48) of greater than 70%. In another embodiment, "homology" refers to identity to any of SEQ ID NO: 37, 46, or 48 of greater than 72%. In another embodiment, "homology" refers to identity to any of SEQ ID NO: 37, 46, or 48 of greater than 75%. In another embodiment, "homology" refers to identity to any of SEQ ID NO: 37, 46, or 48 of greater than 78%. In another embodiment, "homology" refers to identity to any of SEQ ID NO: 37, 46, or 48 of greater than 80%. In another embodiment, "homology" refers to identity to any of SEQ ID NO: 37, 46, or 48 of greater than 82%. In another embodiment, "homology" refers to identity to any of SEQ ID NO: 37, 46, or 48 of greater than 83%. In another embodiment, "homology" refers to identity to any of SEQ ID NO: 37, 46, or 48 of greater than 85%. In another embodiment, "homology" refers to identity to any of SEQ ID NO: 37, 46, or 48 of greater than 87%. In another embodiment, "homology" refers to identity to any of SEQ ID NO: 37, 46, or 48 of greater than 88%. In another embodiment, "homology" refers to identity to any of SEQ ID NO: 37, 46, or 48 of greater than 90%. In another embodiment, "homology" refers to identity to any of SEQ ID NO: 37, 46, or 48 of greater than 92%. In another embodiment, "homology" refers to identity to any of SEQ ID NO: 37, 46, or 48 of greater than 93%. In another embodiment, "homology" refers to identity to any of SEQ ID NO: 37, 46, or 48 of greater than 95%. In another embodiment, "homology" refers to identity to any of SEQ ID NO: 37, 46, or 48 of greater than 96%. In another embodiment, "homology" refers to identity to any of SEQ ID NO: 37, 46, or 48 of greater than 97%. In another embodiment, "homology" refers to identity to any of SEQ ID NO: 37, 46, or 48 of greater than 98%. In another embodiment, "homology" refers to identity to any of SEQ ID NO: 37, 46, or 48 of greater than 99%. In another embodiment, "homology" refers to identity to any of SEQ ID NO: 37, 46, or 48 of 100%. Each possibility represents a separate embodiment of the present invention.

In another embodiment, "homology" refers to identity to a cholesterol-binding domain (e.g. to any of SEQ ID NO: 18, 53, or 55) of greater than 70%. In another embodiment, "homology" refers to identity to any of SEQ ID NO: 18, 53, or 55 of greater than 72%. In another embodiment, "homology" refers to identity to any of SEQ ID NO: 18, 53, or 55 of greater than 75%. In another embodiment, "homology" refers to identity to any of SEQ ID NO: 18, 53, or 55 of greater than 78%. In another embodiment, "homology" refers to identity to any of SEQ ID NO: 18, 53, or 55 of greater than 80%. In another embodiment, "homology" refers to identity to any of SEQ ID NO: 18, 53, or 55 of greater than 82%. In another embodiment, "homology" refers to identity to any of SEQ ID NO: 18, 53, or 55 of greater than 83%. In another embodiment, "homology" refers to identity to any of SEQ ID NO: 18, 53, or 55 of greater than 85%. In another embodiment, "homology" refers to identity to any of SEQ ID NO: 18, 53, or 55 of greater than 87%. In another embodiment, "homology" refers to identity to any of SEQ ID NO: 18, 53, or 55 of greater than 88%. In another embodiment, "homology" refers to identity to any of SEQ ID NO: 18, 53, or 55 of greater than 90%. In another embodiment, "homology" refers to identity to any of SEQ ID NO: 18, 53, or 55 of greater than 92%. In another embodiment, "homology" refers to identity to any of SEQ ID NO: 18, 53, or 55 of greater than 93%. In another embodiment, "homology" refers to identity to any of SEQ ID NO: 18, 53, or 55 of greater than 95%. In another embodiment, "homology" refers to identity to any of SEQ ID NO: 18, 53, or 55 of greater than 96%. In another embodiment, "homology" refers to identity to any of SEQ ID NO: 18, 53, or 55 of greater than 97%. In another embodiment, "homology" refers to identity to any of SEQ ID NO: 18, 53, or 55 of greater than 98%. In another embodiment, "homology" refers to identity to any of SEQ ID NO: 18, 53, or 55 of greater than 99%. In another embodiment, "homology" refers to identity to any of SEQ ID NO: 18, 53, or 55 of 100%. Each possibility represents a separate embodiment of the present invention.

In another embodiment, "homology" refers to identity to an NY-ESO-1 sequence (e.g. to any of SEQ ID NO: 1-15) of greater than 70%. In another embodiment, "homology" refers to identity to any of SEQ ID NO: 1-15 of greater than 72%. In another embodiment, "homology" refers to identity to any of SEQ ID NO: 1-15 of greater than 75%. In another embodiment, "homology" refers to identity to any of SEQ ID NO: 1-15 of greater than 78%. In another embodiment, "homology" refers to identity to any of SEQ ID NO: 1-15 of greater than 80%. In another embodiment, "homology" refers to identity to any of SEQ ID NO: 1-15 of greater than 82%. In another embodiment, "homology" refers to identity to any of SEQ ID NO: 1-15 of greater than 83%. In another embodiment, "homology" refers to identity to any of SEQ ID NO: 1-15 of greater than 85%. In another embodiment, "homology" refers to identity to any of SEQ ID NO: 1-15 of greater than 87%. In another embodiment, "homology" refers to identity to any of SEQ ID NO: 1-15 of greater than 88%. In another embodiment, "homology" refers to identity to any of SEQ ID NO: 1-15 of greater than 90%. In another embodiment, "homology" refers to identity to any of SEQ ID NO: 1-15 of greater than 92%. In another embodiment, "homology" refers to identity to any of SEQ ID NO: 1-15 of greater than 93%. In another embodiment, "homology" refers to identity to any of SEQ ID NO: 1-15 of greater than 95%. In another embodiment, "homology" refers to identity to any of SEQ ID NO: 1-15 of greater than 96%. In another embodiment, "homology" refers to identity to any of SEQ ID NO: 1-15 of greater than 97%. In another embodiment, "homology" refers to identity to any of SEQ ID NO: 1-15 of greater than 98%. In another embodiment, "homology" refers to identity to any of SEQ ID NO: 1-15 of greater than 99%. In another embodiment, "homology" refers to identity to any of SEQ ID NO: 1-15 of 100%. Each possibility represents a separate embodiment of the present invention.

In another embodiment, "homology" refers to identity to an E7 sequence (e.g. to any of any of SEQ ID NO: 17, 19-23) of greater than 70%. In another embodiment, "homology" refers to identity to any of SEQ ID NO: 17, 19-23 of greater than 72%. In another embodiment, "homology" refers to identity to any of SEQ ID NO: 17, 19-23 of greater than 75%. In another embodiment, "homology" refers to identity to any of SEQ ID NO: 17, 19-23 of greater than 78%. In another embodiment, "homology" refers to identity to any of SEQ ID NO: 17, 19-23 of greater than 80%. In another embodiment, "homology" refers to identity to any of SEQ ID NO: 17, 19-23 of greater than 82%. In another embodiment, "homology" refers to identity to any of SEQ ID NO: 17, 19-23 of greater than 83%. In another embodiment, "homology" refers to identity to any of SEQ ID NO: 17, 19-23 of greater than 85%. In another embodiment, "homology" refers to identity to any of SEQ ID NO: 17, 19-23 of greater than 87%. In another embodiment, "homology" refers to identity to any of SEQ ID NO: 17, 19-23 of greater than 88%. In another embodiment, "homology" refers to identity to any of SEQ ID NO: 17, 19-23 of greater than 90%. In another embodiment, "homology" refers to identity to any of SEQ ID NO: 17, 19-23 of greater than 92%. In another embodiment, "homology" refers to identity to any of SEQ ID NO: 17, 19-23 of greater than 93%. In another embodiment, "homology" refers to identity to any of SEQ ID NO: 17, 19-23 of greater than 95%. In another embodiment, "homology" refers to identity to any of SEQ ID NO: 17, 19-23 of greater than 96%. In another embodiment, "homology" refers to identity to any of SEQ ID NO: 17, 19-23 of greater than 97%. In another embodiment, "homology" refers to identity to any of SEQ ID NO: 17, 19-23 of greater than 98%. In another embodiment, "homology" refers to identity to any of SEQ ID NO: 17, 19-23 of greater than 99%. In another embodiment, "homology" refers to identity to any of SEQ ID NO: 17, 19-23 of 100%. Each possibility represents a separate embodiment of the present invention.

In another embodiment, "homology" refers to identity to a BCR sequence (e.g. to any of any one of SEQ ID NO: 26-36) of greater than 70%. In another embodiment, "homology" refers to identity to any one of SEQ ID NO: 26-36 of greater than 72%. In another embodiment, "homology" refers to identity to any one of SEQ ID NO: 26-36 of greater than 75%. In another embodiment, "homology" refers to identity to any one of SEQ ID NO: 26-36 of greater than 78%. In another embodiment, "homology" refers to identity to any one of SEQ ID NO: 26-36 of greater than 80%. In another embodiment, "homology" refers to identity to any one of SEQ ID NO: 26-36 of greater than 82%. In another embodiment, "homology" refers to identity to any one of SEQ ID NO: 26-36 of greater than 83%. In another embodiment, "homology" refers to identity to any one of SEQ ID NO: 26-36 of greater than 85%. In another embodiment, "homology" refers to identity to any one of SEQ ID NO: 26-36 of greater than 87%. In another embodiment, "homology" refers to identity to any one of SEQ ID NO: 26-36 of greater than 88%. In another embodiment, "homology" refers to identity to any one of SEQ ID NO: 26-36 of greater than 90%. In another embodiment, "homology" refers to identity to any one of SEQ ID NO: 26-36 of greater than 92%. In another embodiment, "homology" refers to identity to any one of SEQ ID NO: 26-36 of greater than 93%. In another embodiment, "homology" refers to identity to any one of SEQ ID NO: 26-36 of greater than 95%. In another embodiment, "homology" refers to identity to any one of SEQ ID NO: 26-36 of greater than 96%. In another embodiment, "homology" refers to identity to any one of SEQ ID NO: 26-36 of greater than 97%. In another embodiment, "homology" refers to identity to any one of SEQ ID NO: 26-36 of greater than 98%. In another embodiment, "homology" refers to identity to any one of SEQ ID NO: 26-36 of greater than 99%. In another embodiment, "homology" refers to identity to any one of SEQ ID NO: 26-36 of 100%. Each possibility represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). In other embodiments, DNA can be in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any AA sequence listed herein is determined, in one embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and employ, in other embodiments, the use of the Smith and Waterman algorithms, and/or global/local or BLOCKS alignments for analysis, for example. Each method of determining homology represents a separate embodiment of the present invention.

In another embodiment, a recombinant peptide, protein or polypeptide of the present invention is made by a process that comprises the step of chemically conjugating a peptide comprising the LLO protein or fragment thereof to a peptide comprising the antigen. In another embodiment, an LLO protein or fragment thereof is chemically conjugated to a peptide comprising the antigen. In another embodiment, a peptide comprising the LLO protein or fragment thereof is chemically conjugated to the antigen. In another embodiment, the LLO protein or fragment thereof is chemically conjugated to the antigen. Each possibility represents a separate embodiment of the present invention.

"Peptide" refers, in another embodiment, to a chain of AA connected with peptide bonds. In one embodiment, a peptide is a short chain of AAs. In another embodiment, the term refers to a variant peptide molecule, containing any modification disclosed or enumerated herein. In another embodiment, the term refers to a molecule containing one or more moieties introduced by a chemical cross-linker. In another embodiment, the term refers to a peptide mimetic molecule. In another embodiment, the term refers to any other type of variant of a peptide molecule known in the art. Each possibility represents a separate embodiment of the present invention.

In one embodiment, the term "protein" or "polypeptide" is an amino acid chain comprising multiple peptide subunits, including a full-length protein, oligopeptides, and fragments thereof, wherein the amino acid residues are linked by covalent peptide bonds. In one embodiment, a protein described in the present invention may alternatively be a polypeptide of the present invention.

As used herein in the specification and in the examples section which follows the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH$_2$—), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |

TABLE 2-continued

| Non-conventional amino acid | Code | Non-conventional amino acid | Code |
|---|---|---|---|
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanin | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

In another embodiment, the method used for conjugating the non-hemolytic LLO protein or fragment thereof to the antigen is that described in Example 11. In another embodiment, another method known in the art is utilized. Methods for chemical conjugation of peptides to one another are well known in the art, and are described for, example, in (Biragyn, A and Kwak, L W (2001) Mouse models for lymphoma in "Current Protocols in Immunology" 20.6.1-20.6.30) and (Collawn, J. F. and Paterson, Y. (1989) Preparation of Anti-peptide antibodies. In Current Protocols in Molecular Biology. Supplement 6. Ed. F. M. Ausubel et. al. Greene Publishing/Wiley 11.14.1-11.15.3).

In another embodiment, the non-hemolytic LLO protein or fragment thereof or N-terminal LLO fragment is attached to the antigen or fragment thereof by chemical conjugation. In another embodiment, the non-hemolytic LLO protein or fragment thereof or N-terminal LLO fragment is attached to the heterologous peptide by chemical conjugation. In another embodiment, glutaraldehyde is used for the conjugation. In another embodiment, the conjugation is performed using any suitable method known in the art. Each possibility represents another embodiment of the present invention.

In another embodiment, a fusion peptide of the present invention is synthesized using standard chemical peptide synthesis techniques. In another embodiment, the chimeric molecule is synthesized as a single contiguous polypeptide. In another embodiment, the LLO protein, ActA protein, or fragment thereof; and the BCR or fragment thereof are synthesized separately, then fused by condensation of the amino terminus of one molecule with the carboxyl terminus of the other molecule, thereby forming a peptide bond. In another embodiment, the ActA protein or LLO protein and antigen are each condensed with one end of a peptide spacer molecule, thereby forming a contiguous fusion protein.

In another embodiment, fusion proteins of the present invention are prepared by any suitable method, including, for example, cloning and restriction of appropriate sequences or direct chemical synthesis by methods discussed below. In another embodiment, subsequences are cloned and the appropriate subsequences cleaved using appropriate restriction enzymes. The fragments are then ligated, in another embodiment, to produce the desired DNA sequence. In another embodiment, DNA encoding the fusion protein is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The insert is then ligated into a plasmid.

In another embodiment, a recombinant peptide, protein or polypeptide of the present invention is synthesized using standard chemical peptide synthesis techniques. In another embodiment, the chimeric molecule is synthesized as a single contiguous polypeptide. In another embodiment, the non-hemolytic LLO protein or fragment thereof; and the antigen are synthesized separately, then fused by condensation of the amino terminus of one molecule with the carboxyl terminus of the other molecule, thereby forming a peptide bond. In another embodiment, the LLO protein and antigen are each condensed with one end of a peptide spacer molecule, thereby forming a contiguous fusion protein.

In another embodiment, the peptides and proteins of the present invention are prepared by solid-phase peptide synthesis (SPPS) as described by Stewart et al. in Solid Phase Peptide Synthesis, 2nd Edition, 1984, Pierce Chemical Company, Rockford, Ill.; or as described by Bodanszky and Bodanszky (The Practice of Peptide Synthesis, 1984, Springer-Verlag, New York). In another embodiment, a suitably protected AA residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial AA, and couple thereto of the carboxyl end of the next AA in the sequence of the desired peptide. This AA is also suitably protected. The carboxyl of the incoming AA can be activated to react with the N-terminus of the support-bound AA by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the alpha-amino protecting group, and the FMOC method which utilizes 9-fluorenylmethyloxcarbonyl to protect the alpha-amino of the AA residues, both methods of which are well-known by those of skill in the art.

In another embodiment, incorporation of N- and/or C-blocking groups is achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin coupled peptide can be treated with 20% acetic anhydride in acetonitrile. The N-blocked peptide product can then be cleaved from the resin, deprotected and subsequently isolated.

In another embodiment, analysis of the peptide composition is conducted to verify the identity of the produced peptide. In another embodiment, AA composition analysis is conducted using high-resolution mass spectrometry to determine the molecular weight of the peptide. Alternatively, or additionally, the AA content of the peptide is confirmed by hydrolyzing the peptide in aqueous acid, and separating, identifying and quantifying the components of the mixture using HPLC, or an AA analyzer. Protein sequencers, which sequentially degrade the peptide and identify the AA in order, can also be used to determine definitely the sequence of the peptide.

In another embodiment, prior to its use, the peptide is purified to remove contaminants. In another embodiment, the peptide is purified so as to meet the standards set out by the appropriate regulatory agencies and guidelines. Any one of a number of a conventional purification procedures can be used to attain the required level of purity, including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Solid phase synthesis in which the C-terminal AA of the sequence is attached to an insoluble support followed by sequential addition of the remaining AA in the sequence is used, in another embodiment, for the chemical synthesis of the peptides of this invention. Techniques for solid phase synthesis are described by Barany and Merrifield in Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984).

In another embodiment, fusion proteins of the present invention are synthesized using recombinant DNA methodology. In another embodiment, DNA encoding the fusion protein of the present invention is prepared by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 1859-1862); and the solid support method of U.S. Pat. No. 4,458,066.

In another embodiment, peptides of the present invention incorporate AA residues that are modified without affecting activity. In another embodiment, the termini are derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

In another embodiment, blocking groups include protecting groups conventionally used in the art of peptide chemistry that will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino AA analogs are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkyl amino groups such as methyl amino, ethylamino, dimethylamino, diethylamino, methylethylamino and the like are examples of C-terminal blocking groups. Descarboxylated AA analogues such as agmatine are also useful C-terminal blocking groups and can be either coupled to the peptide's C-terminal residue or used in place of it. In another embodiment, the free amino and carboxyl groups at the termini are removed altogether from the peptide to yield desamino and descarboxylated forms thereof without affect on peptide activity.

In another embodiment, other modifications are incorporated without adversely affecting the activity. In another embodiment, such modifications include, but are not limited to, substitution of one or more of the AA in the natural L-isomeric form with D-isomeric AA. In another embodiment, the peptide includes one or more D-amino acid resides, or comprises AA that are all in the D-form. Retro-inverso forms of peptides in accordance with the present invention are also contemplated, for example, inverted peptides in which all amino acids are substituted with D-amino acid forms.

In another embodiment, acid addition salts peptides of the present invention are utilized as functional equivalents thereof. In another embodiment, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

In another embodiment, modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated AA residues, e.g., phosphotyrosine, phosphoserine, or phosphothreonine.

In another embodiment, polypeptides are modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In another embodiment, the present invention provides a kit comprising an non-hemolytic LLO protein or fragment thereof fused to an antigen, an applicator, and instructional material that describes use of the methods of the invention.

Although model kits are described below, the contents of other useful kits will be apparent to the skilled artisan in light of the present disclosure. Each of these kits is contemplated within the present invention.

In another embodiment, the *Listeria* strain of methods and compositions of the present invention is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art. Each possibility represents a separate embodiment of the present invention.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding a recombinant peptide, protein or polypeptide of the present invention. In another embodiment, the *Listeria* strain carries a plasmid comprising the gene encoding a recombinant peptide, protein or polypeptide of the present invention. Methods for passaging a recombinant *Listeria* strain through an animal host are well known in the art, and are described, for example, in United States Patent Application No. 2006/0233835, which is incorporated herein by reference. In another embodiment, the passaging is performed by any other method known in the art. Each possibility represents a separate embodiment of the present invention.

In another embodiment, the recombinant *Listeria* strain utilized in methods of the present invention has been stored in a frozen cell bank. In another embodiment, the recombinant *Listeria* strain has been stored in a lyophilized cell bank. Each possibility represents a separate embodiment of the present invention.

In another embodiment, the cell bank of methods and compositions of the present invention is a master cell bank. In another embodiment, the cell bank is a working cell bank. In another embodiment, the cell bank is Good Manufacturing Practice (GMP) cell bank. In another embodiment, the cell bank is intended for production of clinical-grade material. In another embodiment, the cell bank conforms to regulatory practices for human use. In another embodiment, the cell bank is any other type of cell bank known in the art. Each possibility represents a separate embodiment of the present invention.

"Good Manufacturing Practices" are defined, in another embodiment, by (21 CFR 210-211) of the United States Code of Federal Regulations. In another embodiment, "Good Manufacturing Practices" are defined by other standards for production of clinical-grade material or for human consumption; e.g. standards of a country other than the United States. Each possibility represents a separate embodiment of the present invention.

In another embodiment, a recombinant *Listeria* strain utilized in methods of the present invention is from a batch of vaccine doses.

In another embodiment, a recombinant *Listeria* strain utilized in methods of the present invention is from a frozen stock produced by a method disclosed herein.

In another embodiment, a recombinant *Listeria* strain utilized in methods of the present invention is from a lyophilized stock produced by a method disclosed herein. Methods for lyophilizing recombinant *Listeria* strains are well known in the art, and are described, for example, in PCT International Patent Application Publication No. WO 2007/061848. Each method represents a separate embodiment of the present invention.

In another embodiment, a cell bank, frozen stock, or batch of vaccine doses of the present invention is cryopreserved by a method that comprises growing a culture of the *Listeria* strain in a nutrient media, freezing the culture in a solution comprising glycerol, and storing the *Listeria* strain at below −20 degrees Celsius. In another embodiment, the temperature is about −70 degrees Celsius. In another embodiment, the temperature is about −70-−80 degrees Celsius.

In another embodiment, a cell bank, frozen stock, or batch of vaccine doses of the present invention is cryopreserved by a method that comprises growing a culture of the *Listeria* strain in a defined media of the present invention (as described below), freezing the culture in a solution comprising glycerol, and storing the *Listeria* strain at below −20 degrees Celsius. In another embodiment, the temperature is about −70 degrees Celsius. In another embodiment, the temperature is about −70-−80 degrees Celsius. Methods for cryopreservation of recombinant *Listeria* strains are well known in the art, and are described, for example, in PCT International Patent Application Publication No. WO 2007/061848. Each method represents a separate embodiment of the present invention.

In another embodiment, any defined microbiological media of the present invention may be used in this method. Each defined microbiological media represents a separate embodiment of the present invention.

In another embodiment of methods and compositions of the present invention, the culture (e.g. the culture of a *Listeria* vaccine strain that is used to produce a batch of *Listeria* vaccine doses) is inoculated from a cell bank. In another embodiment, the culture is inoculated from a frozen stock. In another embodiment, the culture is inoculated from a starter culture. In another embodiment, the culture is inoculated from a colony. In another embodiment, the culture is inoculated at mid-log growth phase. In another embodiment, the culture is inoculated at approximately mid-log growth phase. In another embodiment, the culture is inoculated at another growth phase. Each possibility represents a separate embodiment of the present invention.

In another embodiment, the solution used for freezing contains another colligative additive or additive with anti-freeze properties, in place of glycerol. In another embodiment, the solution used for freezing contains another colligative additive or additive with anti-freeze properties, in addition to glycerol. In another embodiment, the additive is mannitol. In another embodiment, the additive is DMSO. In another embodiment, the additive is sucrose. In another embodiment, the additive is any other colligative additive or additive with anti-freeze properties that is known in the art. Each possibility represents a separate embodiment of the present invention.

In another embodiment, the nutrient media utilized for growing a culture of a *Listeria* strain is LB. In another embodiment, the nutrient media is TB. In another embodiment, the nutrient media is a modified, animal-product free Terrific Broth. In another embodiment, the nutrient media is a defined media. In another embodiment, the nutrient media is a defined media of the present invention. In another embodiment, the nutrient media is any other type of nutrient media known in the art. Each possibility represents a separate embodiment of the present invention.

In another embodiment of methods and compositions of the present invention, the step of growing is performed with a shake flask. In another embodiment, the flask is a baffled shake flask. In another embodiment, the growing is performed with a batch fermenter. In another embodiment, the growing is performed with a stirred tank or flask. In another embodiment, the growing is performed with an airflit fermenter. In another embodiment, the growing is performed with a fed batch. In another embodiment, the growing is performed with a continuous cell reactor. In another embodiment, the growing is performed with an immobilized cell reactor. In another embodiment, the growing is performed with any other means of growing bacteria that is known in the art. Each possibility represents a separate embodiment of the present invention.

In another embodiment, a constant pH is maintained during growth of the culture (e.g. in a batch fermenter). In another embodiment, the pH is maintained at about 7.0. In another embodiment, the pH is about 6. In another embodiment, the pH is about 6.5. In another embodiment, the pH is about 7.5. In another embodiment, the pH is about 8. In another embodiment, the pH is 6.5-7.5. In another embodiment, the pH is 6-8. In another embodiment, the pH is 6-7. In another embodiment, the pH is 7-8. Each possibility represents a separate embodiment of the present invention.

In another embodiment, a constant temperature is maintained during growth of the culture. In another embodiment, the temperature is maintained at about 37° C. In another embodiment, the temperature is 37° C. In another embodiment, the temperature is 25° C. In another embodiment, the temperature is 27° C. In another embodiment, the temperature is 28° C. In another embodiment, the temperature is 30° C. In another embodiment, the temperature is 32° C. In another embodiment, the temperature is 34° C. In another embodiment, the temperature is 35° C. In another embodiment, the temperature is 36° C. In another embodiment, the temperature is 38° C. In another embodiment, the temperature is 39° C. Each possibility represents a separate embodiment of the present invention.

In another embodiment, a constant dissolved oxygen concentration is maintained during growth of the culture. In another embodiment, the dissolved oxygen concentration is maintained at 20% of saturation. In another embodiment, the concentration is 15% of saturation. In another embodiment, the concentration is 16% of saturation. In another embodiment, the concentration is 18% of saturation. In another embodiment, the concentration is 22% of saturation. In another embodiment, the concentration is 25% of saturation. In another embodiment, the concentration is 30% of saturation. In another embodiment, the concentration is 35% of saturation. In another embodiment, the concentration is 40% of saturation. In another embodiment, the concentration is 45% of saturation. In another embodiment, the concentration is 50% of saturation. In another embodiment, the concentration is 55% of saturation. In another embodiment, the concentration is 60% of saturation. In another embodiment, the concentration is 65% of saturation. In another embodiment, the concentration is 70% of saturation. In another embodiment, the concentration is 75% of saturation. In another embodiment, the concentration is 80% of saturation. In another embodiment, the concentration is 85% of saturation. In another embodiment, the concentration is 90% of saturation. In another embodiment, the concentration is 95% of saturation. In another embodiment, the concentration is 100% of saturation. In another embodiment, the concentration is near 100% of saturation. Each possibility represents a separate embodiment of the present invention.

In another embodiment of methods and compositions of the present invention, the *Listeria* culture is flash-frozen in liquid nitrogen, followed by storage at the final freezing temperature. In another embodiment, the culture is frozen in a more gradual manner; e.g. by placing in a vial of the culture in the final storage temperature. In another embodiment, the culture is frozen by any other method known in the art for freezing a bacterial culture. Each possibility represents a separate embodiment of the present invention.

In another embodiment of methods and compositions of the present invention, the storage temperature of the culture is between $^-20$ and $^-80$ degrees Celsius (° C.). In another embodiment, the temperature is significantly below $^-20°$ C. In another embodiment, the temperature is not warmer than $^-70°$ C. In another embodiment, the temperature is $^-70°$ C. In another embodiment, the temperature is about $^-70°$ C. In another embodiment, the temperature is $^-20°$ C. In another embodiment, the temperature is about $^-20°$ C. In another embodiment, the temperature is $^-30°$ C. In another embodiment, the temperature is $^-40°$ C. In another embodiment, the temperature is $^-50°$ C. In another embodiment, the temperature is $^-60°$ C. In another embodiment, the temperature is $^-80°$ C. In another embodiment, the temperature is $^-30$-$^-70°$ C. In another embodiment, the temperature is $^-40$-$^-70°$ C. In another embodiment, the temperature is $^-50$-$^-70°$ C. In another embodiment, the temperature is $^-60$-$^-70°$ C. In another embodiment, the temperature is $^-30$-$^-80°$ C. In another embodiment, the temperature is $^-40$-$^-80°$ C. In another embodiment, the temperature is $^-50$-$^-80°$ C. In another embodiment, the temperature is $^-60$-$^-80°$ C. In another embodiment, the temperature is $^-70$-$^-80°$ C. In another embodiment, the temperature is colder than $^-70°$ C. In another embodiment, the temperature is colder than $^-80°$ C. Each possibility represents a separate embodiment of the present invention.

Methods for lyophilization and cryopreservation of recombinant *Listeria* strains are well known to those skilled in the art. Each possibility represents a separate embodiment of the present invention.

In one embodiment, "genetically fused" as provided herein is meant to result in a chimeric DNA containing, each in its own discrete embodiment, a promoter and a coding sequence that are not associated in nature.

In one embodiment, the "B-cell Receptors" or "BCR" is the cell-surface receptor of B cells for a specific antigen. In another embodiment, the BCR is composed of a transmembrane immunoglobulin molecule associated with the invariant Igα and Igβ chains in a noncovalent complex. In another embodiment, B-cell receptor (BCR) signaling regulates several B-cell fate decisions throughout development. In another embodiment, continued expression of the signaling subunits of the BCR is required for survival of mature B cells. In another embodiment, alterations in BCR signaling may support lymphomagenesis. In one embodiment, cells have the CD20 protein on the outside of the cell. In another embodiment, cancerous B cells also carry the CD20 protein. In another embodiment, CD20 is highly expressed in at least 95% of B-cell lymphomas. In one embodiment, the BCR is expressed in B-cell lymphomas. In another embodiment, BCR is expressed in Follicular Lymphoma, Small Non-Cleaved Cell Lymphoma, Marginal Zone Lymphoma, Splenic Lymphoma with villous lymphocytes, Mantle Cell Lymphoma, Large Cell Lymphoma Diffuse large Cell Lymphoma, Small Lymphocytic Lymphoma, Endemic Burkitt's lymphoma, Sporadic Burkitt's lymphoma, Non-Burkitt's lymphoma, Mucosa-Associated Lymphoid Tissue MALT/MALToma (extranodal), Monocytoid B-cell, lymphoma (nodal), Diffuse Mixed Cell, Immunoblastic Lymphoma, Primary Mediastinal B-Cell Lymphoma, Angiocentric Lymphoma-Pulmonary B-Cell. In another embodiment, CD20 is expressed in the BCR is expressed in Follicular Lymphoma, Small Non-Cleaved Cell Lymphoma, Marginal Zone Lymphoma, Splenic Lymphoma with villous lymphocytes, Mantle Cell Lymphoma, Large Cell Lymphoma Diffuse large Cell Lymphoma, Small Lymphocytic Lymphoma, Endemic Burkitt's lymphoma, Sporadic Burkitt's lymphoma, Non-Burkitt's lymphoma, Mucosa-Associated Lymphoid Tissue MALT/MALToma (extranodal), Monocytoid B-cell, lymphoma (nodal), Diffuse Mixed Cell, Primary Mediastinal B-Cell Lymphoma, Angiocentric Lymphoma-Pulmonary B-Cell. Therefore, in one embodiment, the compositions and methods of the present invention comprising BCR are particularly useful in the prevention or treatment of the above-mentioned cancers.

In one embodiment, a major etiological factor in the genesis of cervical carcinoma is the infection by human papillomaviruses (HPVs), which, in one embodiment, are small DNA viruses that infect epithelial cells of either the skin or mucosa. In one embodiment, HPV related malignancies include oral, cervical, anogenital, and cervical cancers as well as respiratory papillomatsis. In one embodiment, HPV expresses six or seven non-structural proteins and two structural proteins, each of which may serve as a target in the immunoprophylactic or immunotherapeutic approaches described herein. In one embodiment, the viral capsid proteins L1 and L2 are late structural proteins. In one embodiment, L1 is the major capsid protein, the amino acid sequence of which is highly conserved among different HPV types.

In one embodiment, proteins E6 and E7 are two of seven early non-structural proteins, some of which play a role in virus replication (E1, E2, E4) and/or in virus maturation (E4). In another embodiment, proteins E6 and E7 are oncoproteins that are critical for viral replication, as well as for host cell immortalization and transformation. In one embodiment, E6 and E7 viral proteins are not expressed in normal cervical squamous epithelia. In another embodiment, the expression of the E6 and E7 genes in epithelial stem cells of the mucosa is required to initiate and maintain cervical carcinogenesis. Further and in some embodiments, the progression of pre-neoplastic lesions to invasive cervical cancers is associated with a continuous enhanced expression of the E6 and E7 oncoprotein. Thus, in another embodiment, E6 and E7 are expressed in cervical cancers. In another embodiment, the oncogenic potential of E6 and E7 may arise from their binding properties to host cell proteins. For example and in one embodiment, E6 binds to the tumor-suppressor protein p53 leading to ubiquitin-dependent degradation of the protein, and, in another embodiment, E7 binds and promotes degradation of the tumor-suppressor retinoblastoma protein (pRb). Therefore, in one embodiment, the compositions and methods of the present invention comprising HPV-E7 are particularly useful in the prevention or treatment of the above-mentioned cancers.

NY-ESO-1 is, in one embodiment, a "cancer-testis" antigen expressed in epithelial ovarian cancer (EOC). In another embodiment, NY-ESO-1 is expressed in metastatic melanoma, breast cancer, lung cancer, esophageal cancer, which in one embodiment, is esophageal squamous cell carcinoma, or a combination thereof. In one embodiment, NY-ESO-1 is one of the most immunogenic cancer testis antigens. In another embodiment NY-ESO-1 is able to induce strong humoral (antibody) and cellular (T cell) immune responses in patients with NY-ESO-1 expressing cancers either through natural or spontaneous induction by the patients tumor or following specific vaccination using defined peptide epitopes. In another embodiment, NY-ESO-1 peptide epitopes are presented by MHC class II molecules Therefore, in one embodiment, the compositions and methods of the present invention comprising NY-ESO-1 are particularly useful in the prevention or treatment of the above-mentioned cancers.

EXPERIMENTAL DETAILS SECTION

Example 1

LLO-Antigen Fusions Induce Anti-Tumor Immunity

Materials and Experimental Methods

Examples 1-2

Cell Lines

The C57BL/6 syngeneic TC-1 tumor was immortalized with HPV-16 E6 and E7 and transformed with the c-Ha-ras oncogene. TC-1 expresses low levels of E6 and E7 and is highly tumorigenic. TC-1 was grown in RPMI 1640, 10% FCS, 2 mM L-glutamine, 100 U/ml penicillin, 100 µg/ml streptomycin, 100 µM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

L. monocytogenes Strains and Propagation

Figure 2:
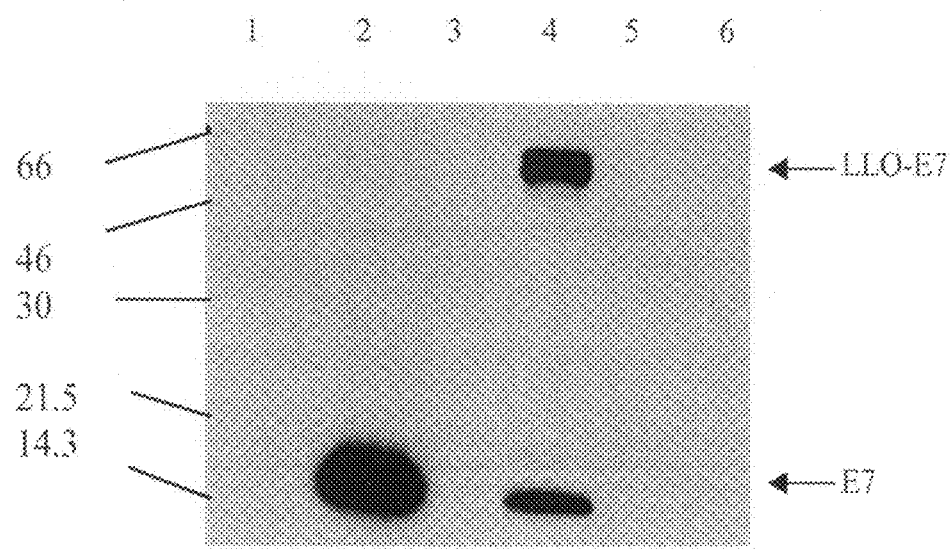
FIG. 2. Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), then developed using ECL detection reagents.

Listeria strains used were Lm-LLO-E7 (hly-E7 fusion gene in an episomal expression system; FIG. 1A), Lm-E7 (single-copy E7 gene cassette integrated into Listeria genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GG CTCGAGCATGGAGATACACC-3' (SEQ ID NO: 38; XhoI site is underlined) and 5'-GGGG ACTAGTTTATGGTTTCTGAGAACA-3' (SEQ ID NO: 39; SpeI site is underlined) and ligated into pCR2.1 (Invitrogen, San Diego, Calif.). E7 was excised from pCR2.1 by XhoI/SpeI digestion and ligated into pGG-55. The hly-E7 fusion gene and the pluripotential transcription factor prfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO," and having the sequence set forth in SEQ ID NO: 17), which is joined by the XhoI site to the E7 gene, yielding a hly-E7 fusion gene that is transcribed and secreted as LLO-E7. Transformation of a prfA negative strain of Listeria, XFL-7 (provided by Dr. Hao Shen, University of Pennsylvania), with pGG-55 selected for the retention of the plasmid in vivo (FIGS. 1A-B). The hly promoter and gene fragment were generated using primers 5'-GGGG GCTAGCCCTCCTTTGATTAGTATATTC-3' (SEQ ID NO: 40; NheI site is underlined) and 5'-CTCC CTCGAGATCATAATTTACTTCATC-3' (SEQ ID NO: 41;

XhoI site is underlined). The prfA gene was PCR amplified using primers 5'-GACTACAAGGACGATGACCGA-CAAGTGATAACCCGGGATCTAAATAAATCCGTTT-3' (SEQ ID NO: 42; XbaI site is underlined) and 5'-CCC GTCGACCAGCTCTTCTTGGTGAAG-3' (SEQ ID NO: 43; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GC GGATCCCATGGAGATACACCTAC-3' (SEQ ID NO: 44; BamHI site is underlined) and 5'-GC TCTAGATTATGGTTTCTGAG-3' (SEQ ID NO: 45; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 µg/ml). Bacteria were frozen in aliquots at −80° C. Expression was verified by Western blotting (FIG. 2)

Western Blotting

*Listeria* strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (Zymed Laboratories, South San Francisco, Calif.), then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Effects of *Listeria* Recombinants on Established Tumor Growth

Six- to 8-wk-old C57BL/6 mice (Charles River) received $2 \times 10^5$ TC-1 cells s.c. on the left flank. One week following tumor inoculation, the tumors had reached a palpable size of 4-5 mm in diameter. Groups of eight mice were then treated with 0.1 $LD_{50}$ i.p. Lm-LLO-E7 ($10^7$ CFU), Lm-E7 ($10^6$ CFU), Lm-LLO-NP ($10^7$ CFU), or Lm-Gag ($5 \times 10^5$ CFU) on days 7 and 14.

$^{51}$Cr Release Assay

C57BL/6 mice, 6-8 wk old, were immunized i.p. with $0.1 LD_{50}$ Lm-LLO-E7, Lm-E7, Lm-LLO-NP, or Lm-Gag.

Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7H-2b peptide (RAHYNIVTF; SEQ ID NO: 19). E:T cell ratios, performed in triplicate, were 80:1, 40:1, 20:1, 10:1, 5:1, and 2.5:1. Following a 4-h incubation at 37° C., cells were pelleted, and 50 µl supernatant was removed from each well. Samples were assayed with a Wallac 1450 scintillation counter (Gaithersburg, Md.). The percent specific lysis was determined as [(experimental counts per minute−spontaneous counts per minute)/(total counts per minute−spontaneous counts per minute)]×100.

TC-1-Specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5 \times 10^5$/well in flat-bottom 96-well plates with $2.5 \times 10^4$, $1.25 \times 10^4$, $6 \times 10^3$, or $3 \times 10^3$ irradiated TC-1 cells/well as a source of E7 Ag, or without TC-1 cells or with 10 µg/ml Con A. Cells were pulsed 45 h later with 0.5 µCi [$^3$H]thymidine/well. Plates were harvested 18 h later using a Tomtec harvester 96 (Orange, Conn.), and proliferation was assessed with a Wallac 1450 scintillation counter. The change in counts per minute was calculated as experimental counts per minute-no Ag counts per minute.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7H-2 Db tetramer was performed using a FACSCalibur® flow cytometer with CellQuest® software (Becton Dickinson, Mountain View, Calif.). Splenocytes harvested 5 days after the boost were stained at room temperature (rt) with H-2 Db tetramers loaded with the E7 peptide (RAHYNIVTF; SEQ ID NO: 19) or a control (HIV-Gag) peptide. Tetramers were used at a 1/200 dilution and were provided by Dr. Larry R. Pease (Mayo Clinic, Rochester, Minn.) and by the National Institute of Allergy and Infectious Diseases Tetramer Core Facility and the National Institutes of Health AIDS Research and Reference Reagent Program. Tetramer$^+$, CD8$^+$, CD62L$^{low}$ cells were analyzed.

Depletion of Specific Immune Components

CD8$^+$ cells, CD4$^+$ cells and IFN were depleted in TC-1-bearing mice by injecting the mice with 0.5 mg per mouse of mAb: 2.43, GK1.5, or xmg1.2, respectively, on days 6, 7, 8, 10, 12, and 14 post-tumor challenge. CD4$^+$ and CD8$^+$ cell populations were reduced by 99% (flow cytometric analysis). CD25$^+$ cells were depleted by i.p. injection of 0.5 mg/mouse anti-CD25 mAb (PC61, provided by Andrew J. Caton) on days 4 and 6. TGF was depleted by i.p. injection of the anti-TGF-mAb (2G7, provided by H. I. Levitsky), into TC-1-bearing mice on days 6, 7, 8, 10, 12, 14, 16, 18, and 20. Mice were treated with $10^7$ Lm-LLO-E7 or Lm-E7 on day 7 following tumor challenge.

Adoptive Transfer

Donor C57BL/6 mice were immunized and boosted 7 days later with 0.1 $LD_{50}$ Lm-E7 or Lm-Gag. The donor splenocytes were harvested and passed over nylon wool columns to enrich for T cells. CD8+ T cells were depleted in vitro by incubating with 0.1 µg 2.43 anti-CD8 mAb for 30 min at rt. The labeled cells were then treated with rabbit complement. The donor splenocytes were >60% CD4+ T cells (flow cytometric analysis). TC-1 tumor-bearing recipient mice were immunized with 0.1 $LD_{50}$ 7 days post-tumor challenge. CD4+-enriched donor splenocytes ($10^7$) were transferred 9 days after tumor challenge to recipient mice by i.v. injection.

B16F0-Ova Experiment

24 C57BL/6 mice were inoculated with $5\times10^5$ B16F0-Ova cells. On days 3, 10 and 17, groups of 8 mice were immunized with 0.1 $LD_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. $p \leq 0.05$ was considered significant.

Results

Figure 3A:
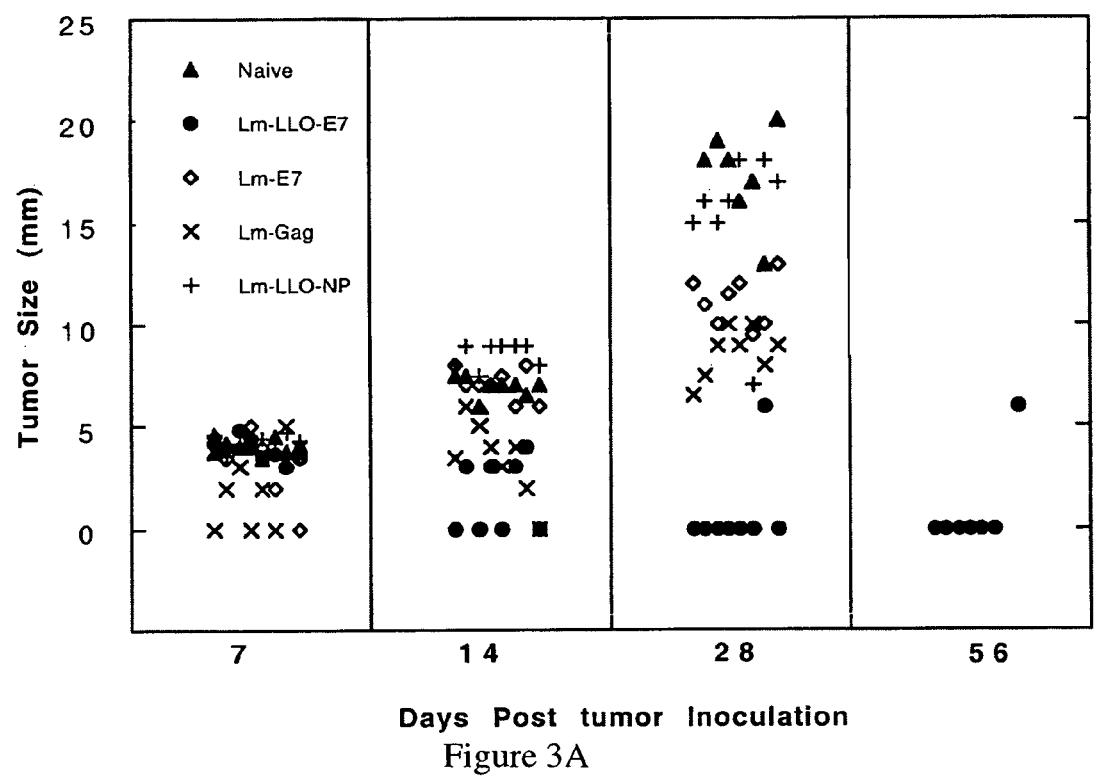
FIG. 3. A. Tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles. B. Tumor immunotherapeutic efficacy of LLO-Ova fusions.

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 $LD_{50}$ Lm-E7, Lm-LLO-E7, or, as controls, Lm-Gag and Lm-LLO-NP. Lm-LLO-E7 induced complete regression of 75% of established TC-1 tumors, while the other 2 mice in the group controlled their tumor growth (FIG. 3A). By contrast, immunization Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with two other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7 remained tumor free until termination of the experiment (day 124 in the case of TC-1 and day 54 for EL-4/E7).

Figure 3B:
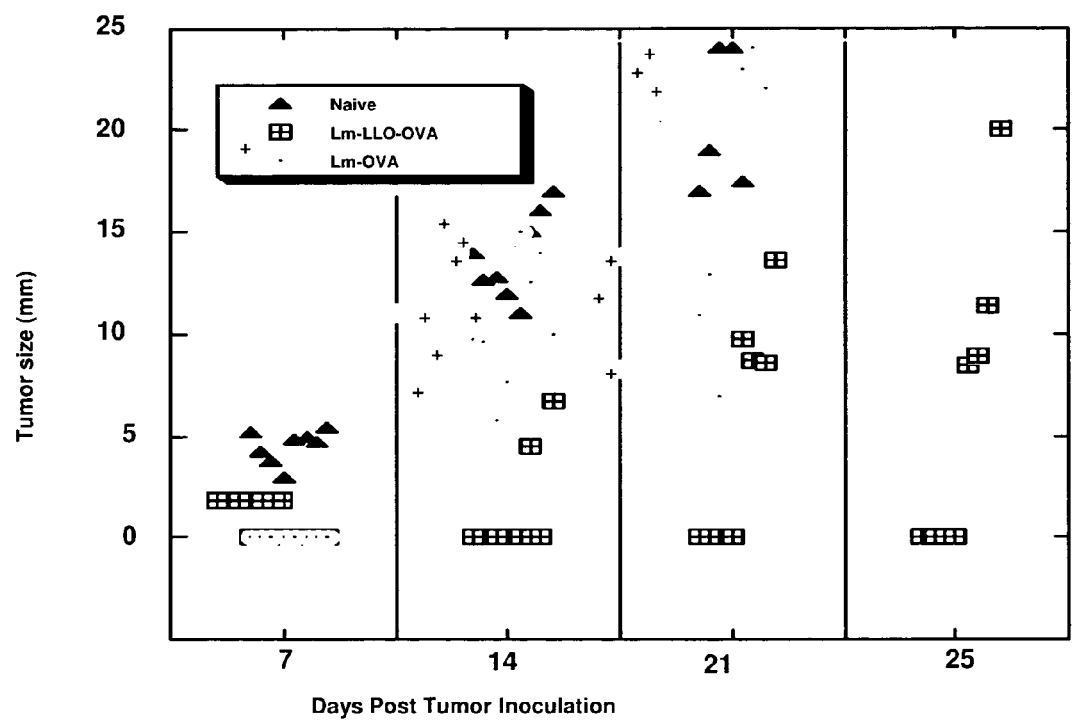

A similar experiment was performed with the chicken ovalbumin antigen (OVA). Mice were immunized with either an Lm-OVA or Lm-LLO-OVA, then challenged with either an EL-4 thymoma engineered to express OVA or the very aggressive murine melanoma cell line B16F0-Ova, which has very low MHC class I expression. In both cases, Lm-LLO-OVA, but not Lm-OVA, induced the regression of established tumors. For example, at the end of the B16F0 experiment (day 25), all the mice in the naive group and the Lm-OVA group had died. All the Lm-LLO-OVA mice were alive, and 50% of them were tumor free. (FIG. 3B).

Thus, expression of an antigen gene as a fusion protein with ΔLLO enhances the immunogenicity of the antigen.

Example 2

LM-LLO-E7 Treatment Elicits TC-1 Specific Splenocyte Proliferation

Figure 4:
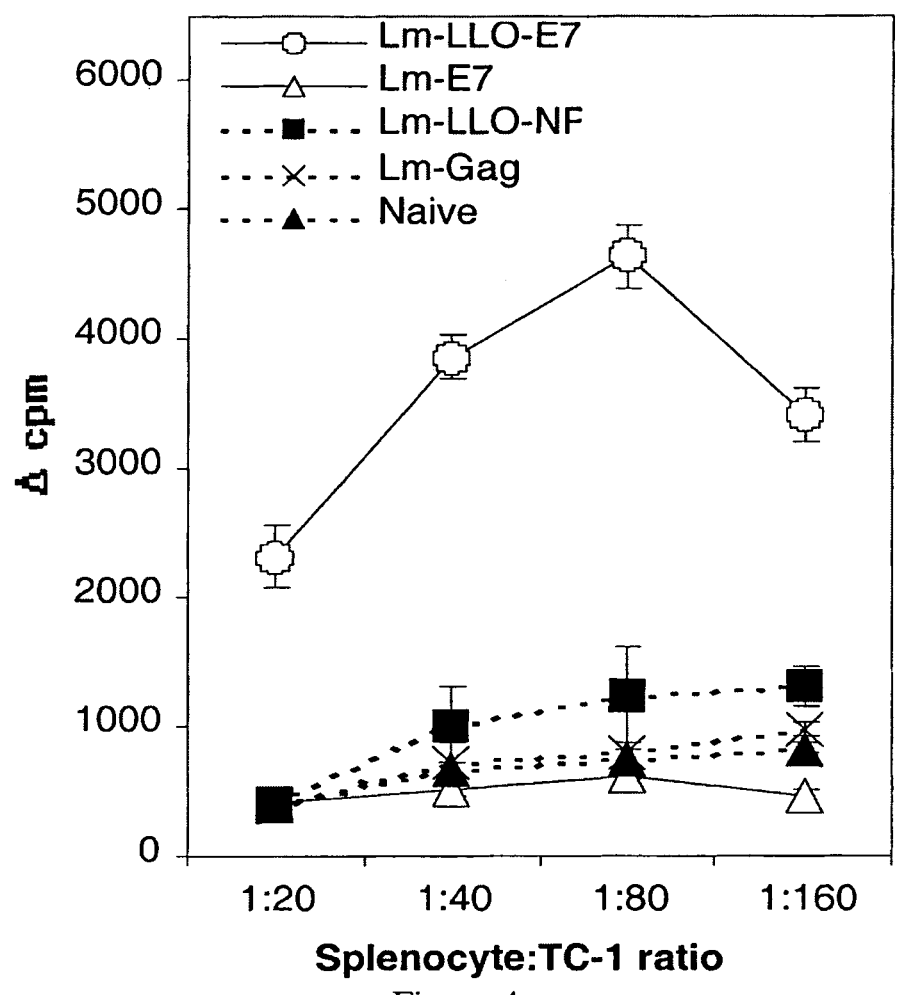
FIG. 4. Splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)–(no-TC-1 control).

To measure induction of T cells by Lm-E7 with Lm-LLO-E7, TC-1-specific proliferative responses of splenocytes from rLm-immunized mice, a measure of antigen-specific immunocompetence, were assessed. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control immunized mice exhibited only background levels of proliferation.

Example 3

Fusion of NP to LLO Enhances its Immunogenicity

Materials and Experimental Methods

Lm-LLO-NP was prepared as depicted in FIG. 1, except that influenza nucleoprotein (NP) replaced E7 as the antigen. 32 BALB/c mice were inoculated with $5\times10^5$ RENCA-NP tumor cells. RENCA-NP is a renal cell carcinoma retrovirally transduced with influenza nucleoprotein NP (described in U.S. Pat. No. 5,830,702, which is incorporated herein by reference). After palpable macroscopic tumors had grown on day 10, eight animals in each group were immunized i.p. with 0.1 $LD_{50}$ of the respective *Listeria* vector. The animals received a second immunization one week later.

Results

Figure 5:
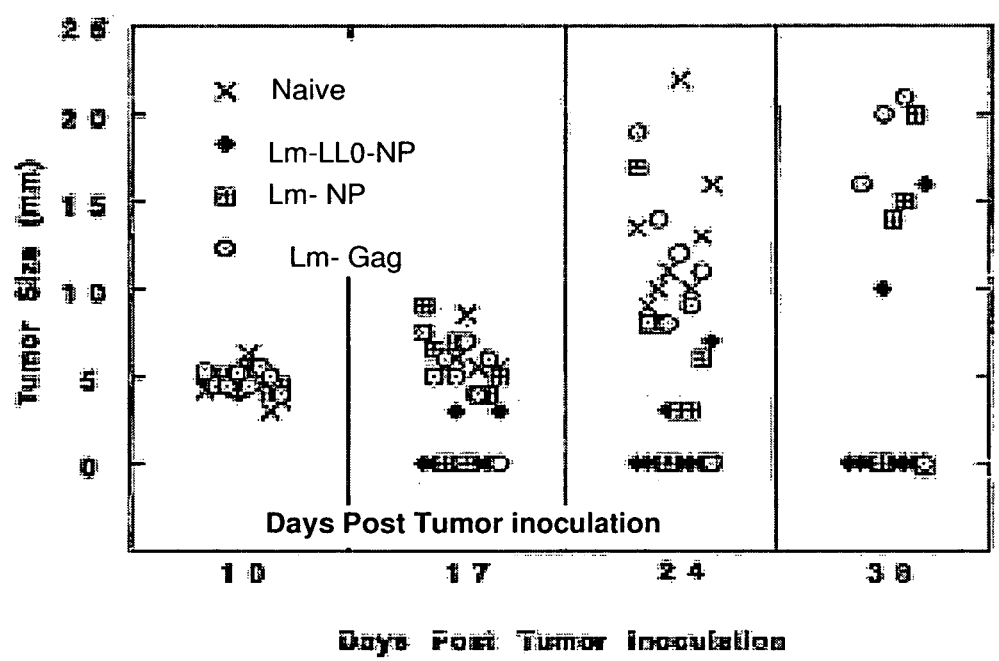
FIG. 5. Tumor immunotherapeutic efficacy of NP antigen expressed in LM. Tumor size in millimeters in mice is shown at 10, 17, 24, and 38 days post tumor-inoculation. Naive mice: X's; mice administered Lm-LLO-NP: filled diamonds; Lm-NP: squares; Lm-Gag: open circles.

In order to confirm the generality of the finding that fusing LLO to an antigen confers enhanced immunity, Lm-LLO-NP and Lm-NP (similar to the Lm-E7 vectors) were constructed, and the vectors were compared for ability to induce tumor regression, with Lm-Gag (isogenic with Lm-NP except for the antigen expressed) as a negative control. As depicted in FIG. 5, 6/8 of the mice that received Lm-LLO-NP were tumor free. By contrast, only 1/8 and 2/8 mice in the Lm-Gag and Lm-NP groups, respectively, were tumor free. All the mice in the naive group had large tumors or had died by day 40. Thus, enhancement of immunogenicity of an antigen by fusion to LLO is not restricted to E7, but rather is a general phenomenon.

Example 4

Figure 6:
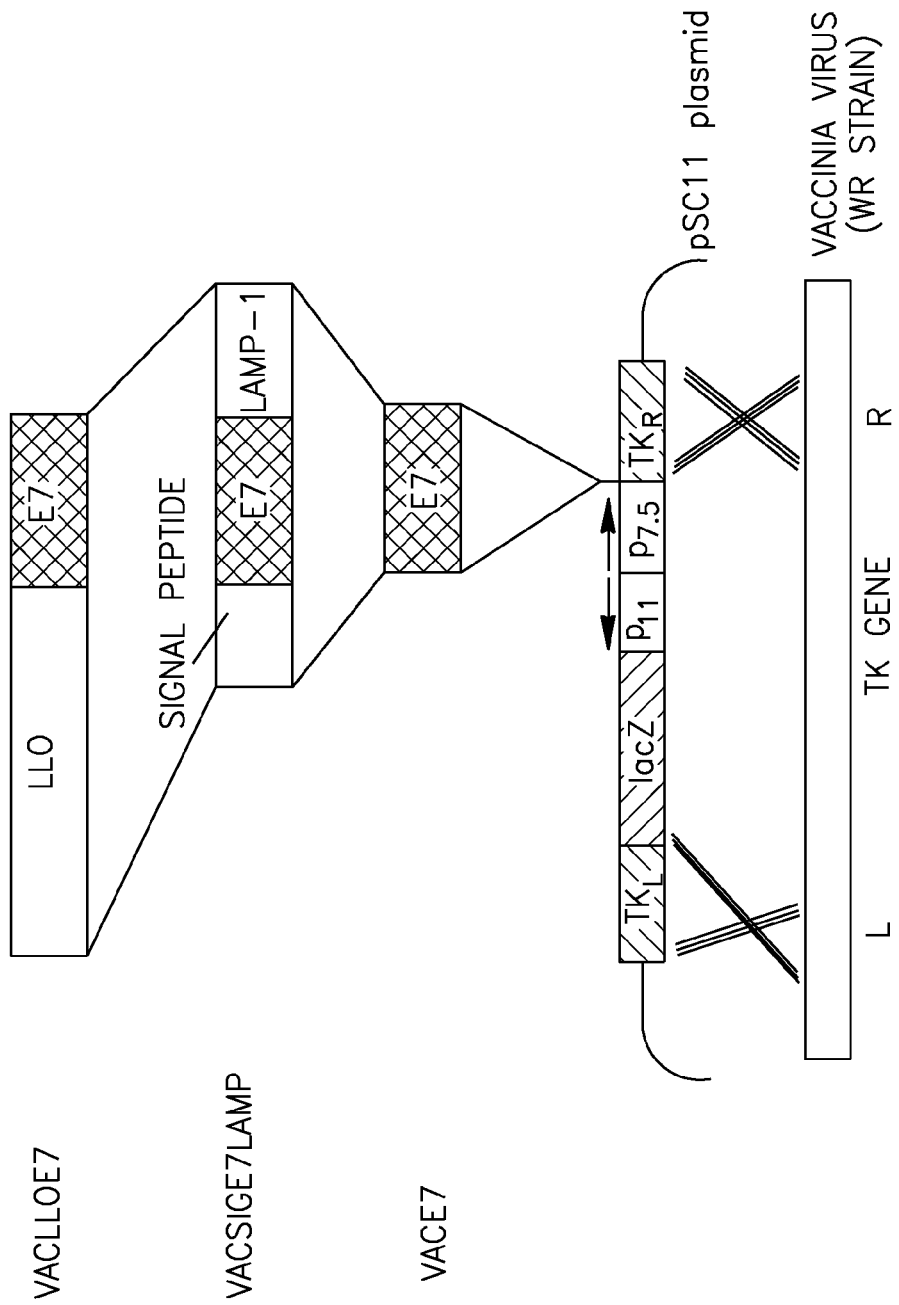
FIG. 6. Depiction of vaccinia virus constructs expressing different forms of HPV16 E7 protein.

Enhancement of Immunogenicity by Fusion of an Antigen to LLO does not Require a *Listeria* Vector Materials and Experimental Methods Construction of Vac-SigE7Lamp The WR strain of vaccinia was used as the recipient and the fusion gene was excised from the Listerial plasmid and inserted into pSC11 under the control of the p75 promoter. This vector was chosen because it is the transfer vector used for the vaccinia constructs Vac-SigE7Lamp and Vac-E7 and would therefore allow direct comparison with Vac-LLO-E7. In this way all three vaccinia recombinants would be expressed under control of the same early/late compound promoter p7.5. In addition, SC11 allows the selection of recombinant viral plaques to TK selection and beta-galactosidase screening. FIG. 6 depicts the various vaccinia constructs used in these experiments. Vac-SigE7Lamp is a recombinant vaccinia virus that expressed the E7 protein fused between lysosomal associated membrane protein (LAMP-1) signal sequence and sequence from the cytoplasmic tail of LAMP-1. It was designed to facilitate the targeting of the antigen to the MHC class II pathway.

The following modifications were made to allow expression of the gene product by vaccinia: (a) the T5XT sequence that prevents early transcription by vaccinia was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resultant pSC1 1-E7 construct was used to transfect the TK-ve cell line CV1 that had been infected with the wild-type vaccinia strain, WR. Cell lysates obtained from this co-infection/transfection step contain vaccinia recombinants that were plaque-purified 3 times. Expression of the LLO-E7 fusion product by plaque purified vaccinia was verified by Western blot using an antibody directed against the LLO protein sequence. In addition, the ability of Vac-LLO-E7 to produce CD8+ T cells specific to LLO and E7 was determined using the LLO (91-99) and E7 (49-57) epitopes of Balb/c and C57/BL6 mice, respectively. Results were confirmed in a chromium release assay.

Results

Figure 7:
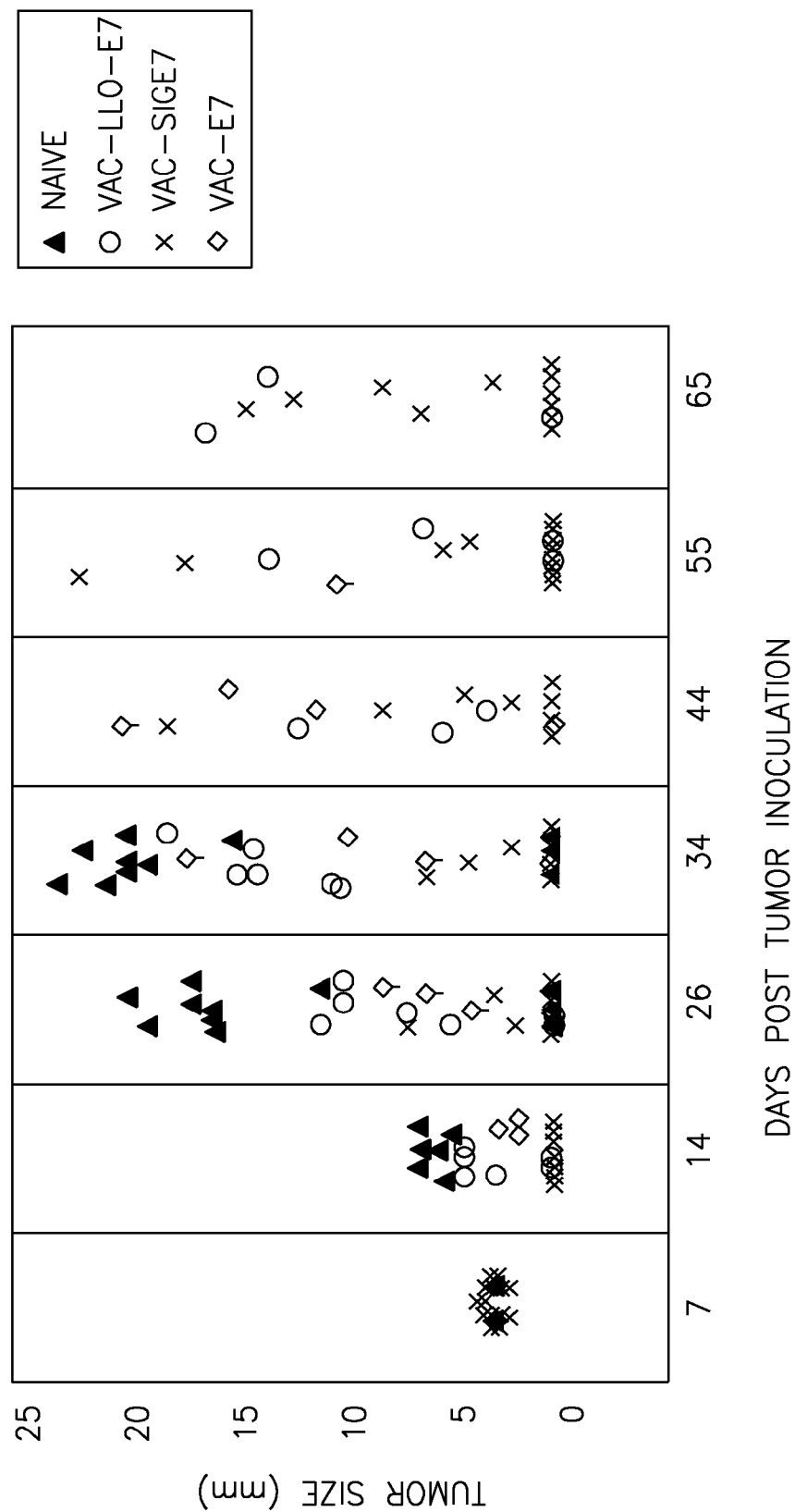
FIG. 7. Vac-LLO-E7 causes long-term regression of tumors established from $2 \times 10^5$ TC-1 cells injected s.c. into C57BL/6 mice. Mice were injected 11 and 18 days after tumor challenge with $10^7$ PFU of Vac-LLO-E7, Vac-SigE7LAMP-1, or VacE7/mouse i.p. or were untreated (naive). 8 mice per treatment group were used, and the cross section for each tumor (average of 2 measurements) is shown for the indicated days after tumor inoculation.

To determine whether enhancement of immunogenicity by fusion of an antigen to LLO requires a *Listeria* vector, a vaccinia vector expressing E7 as a fusion protein with a non-hemolytic truncated form of LLO (ΔLLO) was constructed. Tumor rejection studies were performed with TC-1 following the protocol described for Example 1. Two experiments were performed with differing delays before treatment was started. In one experiment, treatments were initiated when the tumors were about 3 mm in diameter (FIG. 7). As of day 76, 50% of the Vac-LLO-E7 treated mice were tumor free, while only 25% of the Vac-SigE7Lamp mice were tumor free. In other experiments, ΔLLO-antigen fusions were more immunogenic than E7 peptide mixed with SBAS2 or unmethylated CpG oligonucleotides in a side-by-side comparison.

These results show that (a) fusion of ΔLLO-antigen fusions are immunogenic not only in the context of *Listeria*, but also in other contexts; and (b) the immunogenicity of ΔLLO-antigen fusions compares favorably with other accepted vaccine approaches.

Example 5

Site-Directed Mutagenesis of the LLO Cholesterol-Binding Domain

Site-directed mutagenesis was performed on LLO to introduce inactivating point mutations in the CBD, using the following strategy. The resulting protein is termed "mutLLO":
Subcloning of LLO into pET29b
The amino acid sequence of wild-type LLO is:

```
MKKIMLVFITLILVSLPIAQQTEAKDASAFNKENSISSVAPPASPPASPKTPIEKKHADEIKYIQ       (SEQ ID NO: 46)

GLDYNKNNVLVYHGDAVTNVPPRKGYKDGNEYIVVEKKKKSINQNNADIQVVNAISSLTYPGALVK

ANSELVENQPDVLPVKRDSLTLSIDLPGMTNQDNKIVVKNATKSNVNNAVNTLVERWNEKYAQAYS

NVSAKIDYDDEMAYSESQLIAKFGTAFKAVNNSLNVNFGAISEGKMQEEVISFKQIYYNVNVNEPTRP

SRFFGKAVTKEQLQALGVNAENPPAYISSVAYGRQVYLKLSTNSHSTKVKAAFDAAVSGKSVSGDVE

LTNIIKNSSFKAVIYGGSAKDEVQIIDGNLGDLRDILKKGATFNRETPGVPIAYTTTNFLKDNELAVIKNN

SEYIETTSKAYTDGKINIDHSGGYVAQFNISWDEVNYDPEGNEIVQHKNWSENNKSKLAHFTSSIYLP

GNARNINVYAKECTGLAWEWWRTVIDDRNLPLVKNRNISIWGTTLYPKYSNKVDNPIE.

The signal peptide and the cholesterol-binding domain (CBD) are under-
lined, with 3 critical residues in the CBD (C484, W491, and W492) in
bold-italics.
```

A 6×His tag (HHHHHH) was added to the C-terminal region of LLO. The amino acid sequence of His-tagged LLO is:

```
MKKIMLVFITLILVSLPIAQQTEAKDASAFNKENSISSVAPPASPPASPKTPIEKKHADEIDKYIQGLDYN    (SEQ ID NO: 47)

KNNVLVYHGDAVTNVPPRKGYKDGNEYIVVEKKKKSINQNNADIQVVNAISSLTYPGALVKANSEL

VENQPDVLPVKRDSLTLSIDLPGMTNQDNKIVVKNATKSNVNNAVNTLVERWNEKYAQAYSNVSAK

IDYDDEMAYSESQLIAKFGTAFKAVNNSLNVNFGAISEGKMQEEVISFKQIYYNVNVNEPTRPSRFFG

KAVTKEQLQALGVNAENPPAYISSVAYGRQVYLKLSTNSHSTKVKAAFDAAVSGKSVSGDVELTNII

KNSSFKAVIYGGSAKDEVQIIDGNLGDLRDILKKGATFNRETPGVPIAYTTNFLKDNELAVIKNNSEYI

ETTSKAYTDGKINDHSGGYVAQFNISWDEVNYDPEGNEIVQHKNWSENNKSKLAHFTSSIYLPGNAR

NINVYAKECTGLAWEWWRTVIDDRNLPLVKNRNISIWGTTLYPKYSNKVDNPIEHHHHHH.
```

Figure 8A:
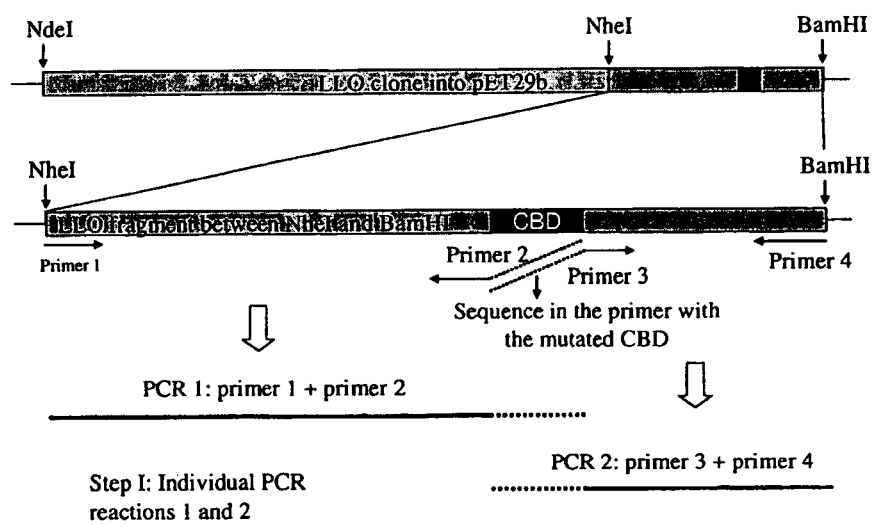
FIG. 8A-B. SOE mutagenesis strategy. Decreasing/lowering the virulence of LLO was achieved by mutating the 4th domain of LLO. This domain contains a cholesterol binding site allowing it to bind to membranes where it oligomerizes to form pores.
Figure 8B:
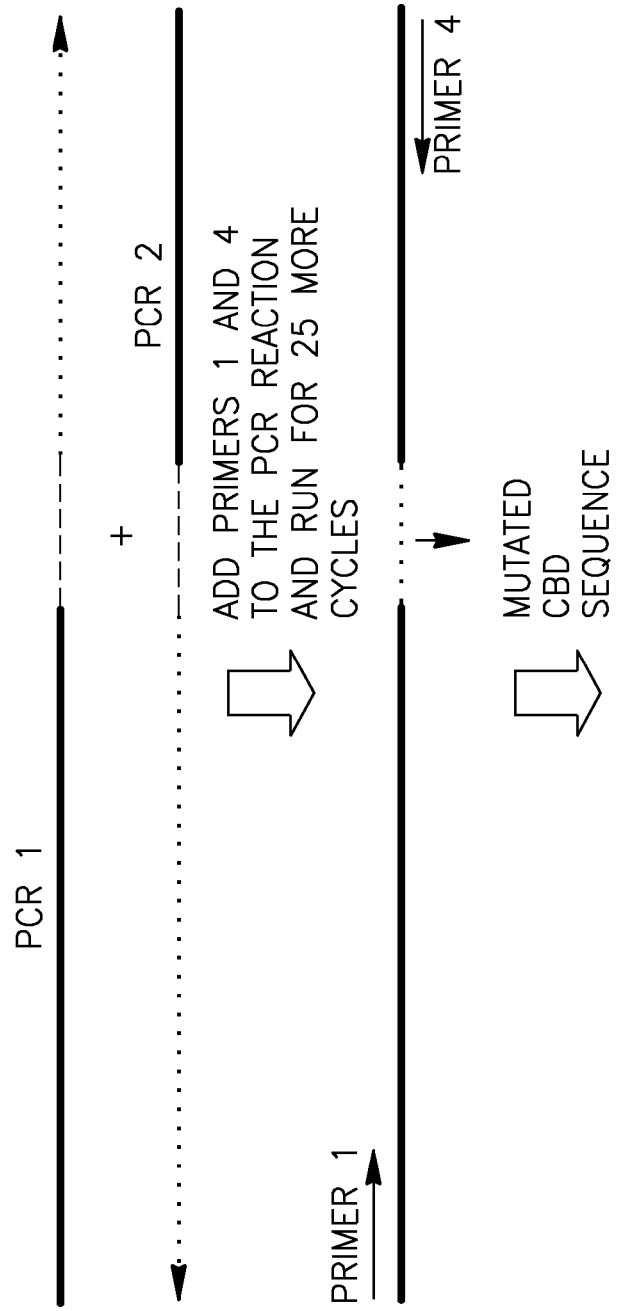
Figure 8C:
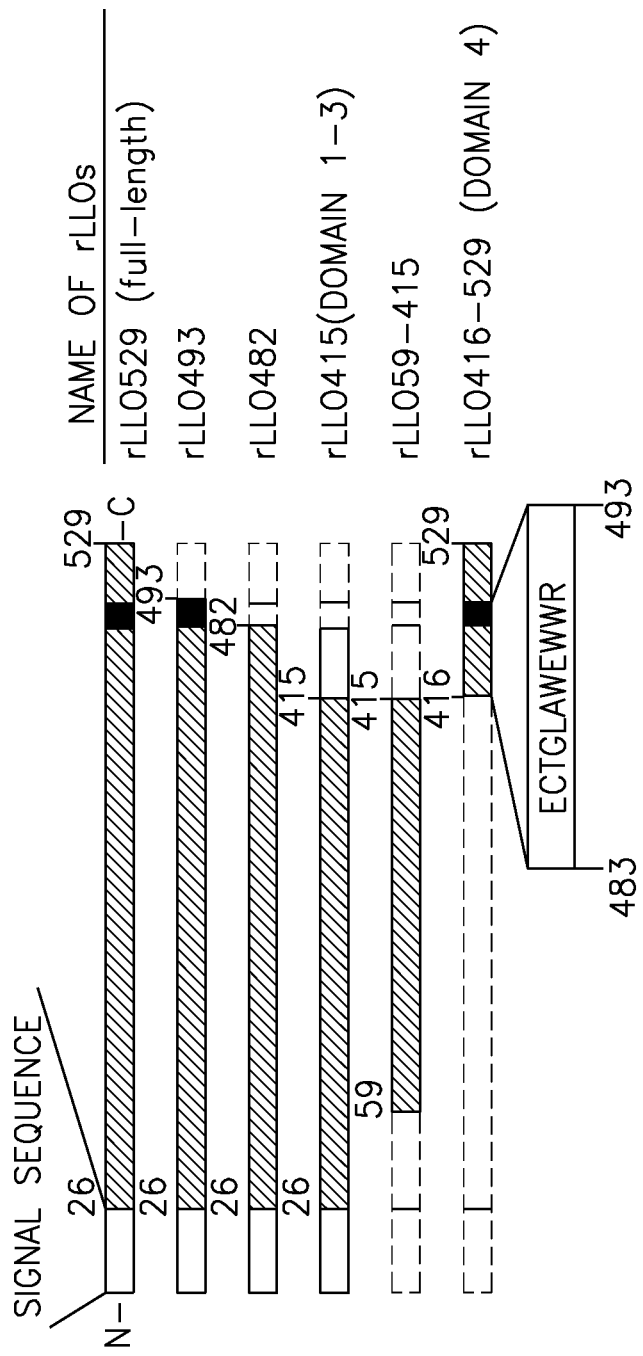
FIG. 8C. Shows fragments of full length LLO (rLLO529). Recombinant LLO, rLLO493, represents a LLO N-terminal fragment spanning from amino acids 1-493 (including the signal sequence). Recombinant LLO, rLLO482, represents an N-terminal LLO fragment (including a deletion of the cholesterol binding domain—amino acids 483-493—) spanning from amino acids 1-482 (including the signal sequence). Recombinant LLO, rLLO415, represents a N-terminal LLO fragment (including a deletion of the cholesterol binding domain—amino acids 483-493—) spanning from amino acids 1-415 (including the signal sequence). Recombinant LLO, rLLO59-415, represents a N-terminal LLO fragment that spans from amino acids 59-415 (excluding the cholesterol binding domain). Recombinant LLO, rLLO416-529, represents a N-terminal LLO fragment that spans from amino acids 416-529 and includes the cholesterol binding domain.

A gene encoding a His-tagged LLO protein was digested with NdeI/BamHI, and the NdeI/BamHI was subcloned into the expression vector pET29b, between the NdeI and BamHI sites. The sequence of the gene encoding the LLO protein is:

region), and PCR was performed with primers #1 and #4 for 25 more cycles (FIG. 8B). PCR reaction cycle: A) 94° C. 2 min 30 sec, B) 94° C. 30 sec, C) 72° C. 1 min, Repeat steps B to C 9 times (10 cycles total), Add primers #1 and #4, D) 94°

(SEQ ID NO: 48)

```
catatgaaggatgcatctgcattcaataaagaaaattcaatttcatccgtggcaccaccagcatctccgcctgcaagtcctaagacgccaatcgaaaagaaac acgcggatgaaatcgataagtatatacaaggattggattacaataaaaacaatgtattagtataccacggagatgcagtgacaaatgtgccgccaagaaaagg ttacaaagatggaaatgaatatattgttgtggagaaaaagaagaaatccatcaatcaaaataatgcagacattcaagttgtgaatgcaatttcgagcctaacc tatccaggtgctctcgtaaaagcgaattcggaattagtagaaaatcaaccagatgttctccctgtaaaacgtgattcattaacactcagcattgatttgccag gtatgactaatcaagacaataaaatagttgtaaaaaatgccactaaatcaaacgttaacaacgcagtaaatacattagtggaaagatggaatgaaaaatatgc tcaagcttattcaaatgtaagtgcaaaaattgattatgatgacgaaatggcttacagtgaatcacaattaattgcgaaatttggtacagcatttaaagctgta aataatagcttgaatgtaaacttcggcgcaatcagtgaagggaaaatgcaagaagaagtcattagttttaaacaaatttactataacgtgaatgttaatgaac ctacaagaccttccagattttcggcaaagctgttactaaagagcagttgcaagcgcttggagtgaatgcagaaaatcctcctgcatatatctcaagtgtggc gtatggccgtcaagtttatttgaaattatcaactaattcccatagtactaaagtaaaagctgcttttgatgctgccgtaagcggaaaatcgtctcaggtgatg tagaactaacaaatatcatcaaaattcttccttcaaagccgtaatttacggaggttccgcaaaagatgaagttcaaatcatcgacggcaacctcggagactta cgcgatattttgaaaaaaggcgctacttttaatcgagaaacaccaggagttcccattgcttatacaacaaacttcctaaaagacaatgaattagctgttatta aaaacaactcagaatatattgaaacaacttcaaaagcttatacagatggaaaaattaacatcgatcactctggaggatacgttgctcaattcaacatttcttg ggatgaagtaaattatgatcctgaaggtaacgaaattgttcaacataaaaactggagcgaaaacaataaaagcaagctagctcatttcacatcgtccatctat ttgcctggtaacgcgagaaatattaatgtttacgctaaagaatgcactggtttagcttgggaatggtggaga acggtaattgatgaccggaacttaccact tgtgaaaaatagaaatatctccatctggggcaccacgctttatccgaaatatagtaataaagtagataatccaatcgaacaccaccaccaccaccactaat aaggatcc.

The underlined sequences are, starting from the beginning of the sequence, the NdeI site, the NheI
site, the CBG-encoding region, the 6x His tag, and the BamHI site. The CBD resides to be mutated in the
next step are in bold-italics.
```

Splicing by Overlap Extension (SOE) PCR

Step 1: PCR reactions #1 and #2 were performed on the pET29b-LLO template. PCR reaction #1, utilizing primers #1 and #2, amplified the fragment between the NheI site and the C. 30 sec, E) 55° C. 30 sec, F) 72° C. 1 min, Repeat steps D to F 24 times (25 cycles total), G) 72° C. 10 min.

Primer sequences:

| | | |
|---|---|---|
| Primer 1: | GCTAGCTCATTTCACATCGT | (SEQ ID NO: 49; NheI sequence is underlined). |
| Primer 2: | **TCT*TGCAGC*TTCCCAAGCTAAACCAGT*CGC*TTC**TTTAGCGTAAACATTAATATT | (SEQ ID NO: 50; CBD-encoding sequence is underlined; mutated codons are in bold-italics). |
| Primer 3: | **GAA*GCG*ACTGGTTTAGCTTGGGA*AGCTGCA*AGA**ACGTAATTGATGACCGGAAC | (SEQ ID NO: 51; CBD-encoding sequence is underlined; mutated codons are in bold-italics). |
| Primer 4: | GGATCCTTATTAGTGGTGGTGGTGGTGTTCGATTGG | (SEQ ID NO: 52; BamHI sequence is underlined). |

CBD, inclusive, introducing a mutation into the CBD. PCR reaction #2, utilizing primers #3 and #4, amplified the fragment between the CBD and the BamHI site, inclusive, introducing the same mutation into the CBD (FIG. 8A).

PCR reaction #1 cycle: A) 94° C. 2 min 30 sec, B) 94° C. 30 sec, C) 55° C. 30 sec, D) 72° C. 1 min, Repeat steps B to D 29 times (30 cycles total), E) 72° C. 10 min.

PCR reaction #2 cycle: A) 94° C. 2 min 30 sec, B) 94° C. 30 sec, C) 60° C. 30 sec, D) 72° C. 1 min, Repeat steps B to D 29 times (30 cycles total), E) 72° C. 10 min.

Step 2: The products of PCR reactions #1 and #2 were mixed, allowed to anneal (at the mutated CBD-encoding The wild-type CBD sequence is ECTGLAWEWWR (SEQ ID NO: 18).

The mutated CBD sequence is EATGLAWEAAR (SEQ ID NO: 53).

The sequence of the mutated NheI-BamHI fragment is (SEQ ID NO: 54)

GCTAGCTCATTTCACATCGTCCATCTATTTGCCTGGTAACGCGAGAAATA

TTAATGTTTACGCTAAA**GAA*GCG*ACTGGTTTAGCTTGGGAA**

```
-continued
GCTGCAAGAAACGGTAATTGATGACCGGAACTTAC-
CACTTGTGAAAAATA

GAAATATCTCCATCTGGGGCACCACGCTTTATCCGAAATATAGTAATAAA

GTAGATAATCCAATCGAACACCACCACCACCACCACTAATAAGGATCC.
```

Example 6

Replacement of Part of the LLO CBD with a CTL Epitope

Site-directed mutagenesis was performed on LLO to replace 9 amino acids (AA) of the CBD with a CTL epitope from the antigen NY-ESO-1. The sequence of the CBD (SEQ ID NO: 18) was replaced with the sequence E SLLMWITQCR (SEQ ID NO: 55; mutated residues underlined), which contains the HLA-A2 restricted epitope 157-165 from NY-ESO-1, termed "ctLLO."

The subcloning strategy used was similar to the previous Example.

The primers used were as follows:

```
Primer 1:   GCTAGCTCATTTCACATCGT                                    (SEQ ID NO: 56;
                                                                    NheI sequence is underlined).

Primer 2:   TCTGCACTGGGTGATCCACATCAGCAGGCTTTCTTTAGCGTAAACAT         (SEQ ID NO: 57;
            TAATATT                                                 CBD-encoding sequence is underlined;
                                                                    mutated (NY-ESO-1) codons are in
                                                                    bold-italics).

Primer 3:   GAAAGCCTGCTGATGTGGATCACCCAGTGCAGAACGGTAATTGATGA         (SEQ ID NO: 58;
            CCGGAAC                                                 CBD-encoding sequence is underlined;
                                                                    mutated (NY-ESO-1) codons are in
                                                                    bold-italics).

Primer 4:   GGATCCTTATTAGTGGTGGTGGTGGTGITCGATTGG                    (SEQ ID NO: 59;
                                                                    BamHI sequence is underlined).
```

The sequence of the resulting NheI/BamHI fragment is as follows:

```
                                                    (SEQ ID NO: 60)
GCTAGCTCATTTCACATCGTCCATCTATTTGCCTGGTAACGCGAGAAATA

TTAATGTTTACGCTAAAGAAAGCCTGCTGATGTGGATCACC

CAGTGCAGAACGGTAATTGATGACCGGAACTTAC-
CACTTGTGAAAAATAGA

AATATCTCCATCTGGGGCACCACGCTTTATCCGAAATATAGTAATAAAGT

AGATAATCCAATCGAACACCACCACCACCACCACTAATAAGGATCC.
```

Figure 9A:
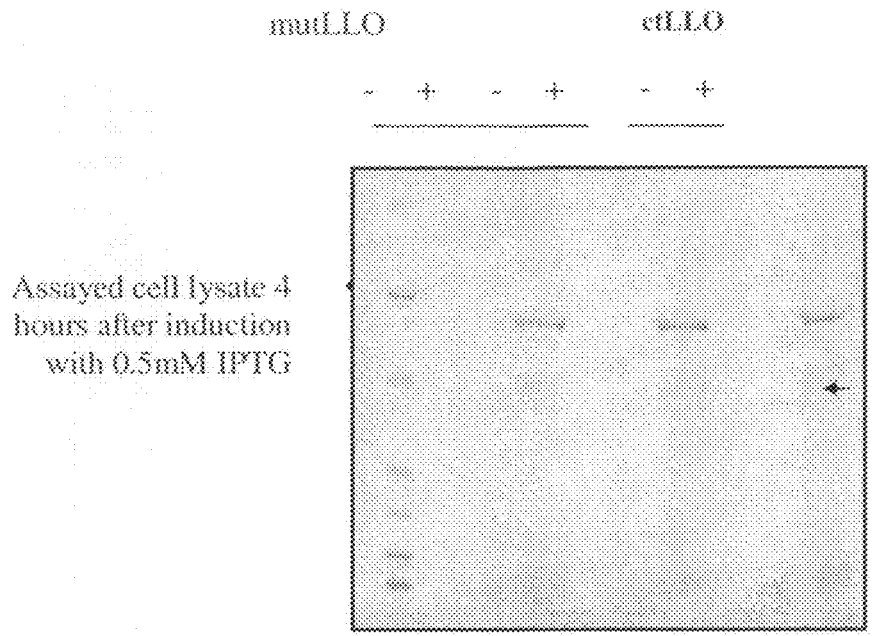
FIG. 9. Expression of mutant LLO proteins by Coomassie staining (A) and Western blot (B).
Figure 9B:
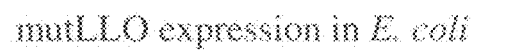
Figure 9B:
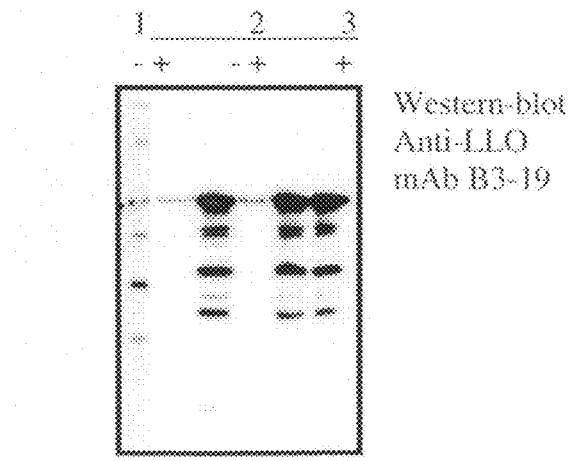

Example 7 mutLLO and ctLLO are Able to be Expressed and Purified in E. coli Expression Systems To show that mutLLO and ctLLO could be expressed in E. coli, E. coli were transformed with pET29b and induced with 0.5 mM IPTG, then cell lysates were harvested 4 hours later and the total proteins were separated in a SDS-PAGE gel and subject to Coomassie staining (FIG. 9A) and anti-LLO Western blot, using monoclonal antibody B3-19 (FIG. 9B). Thus, LLO proteins containing point mutations or substitutions in the CBD can be expressed and purified in E. coli expression systems.

Example 8 mutLLO and ctLLO Exhibit Significant Reduction in Hemolytic Activity

Materials and Experimental Methods

Hemolysis Assay

Figure 10A:
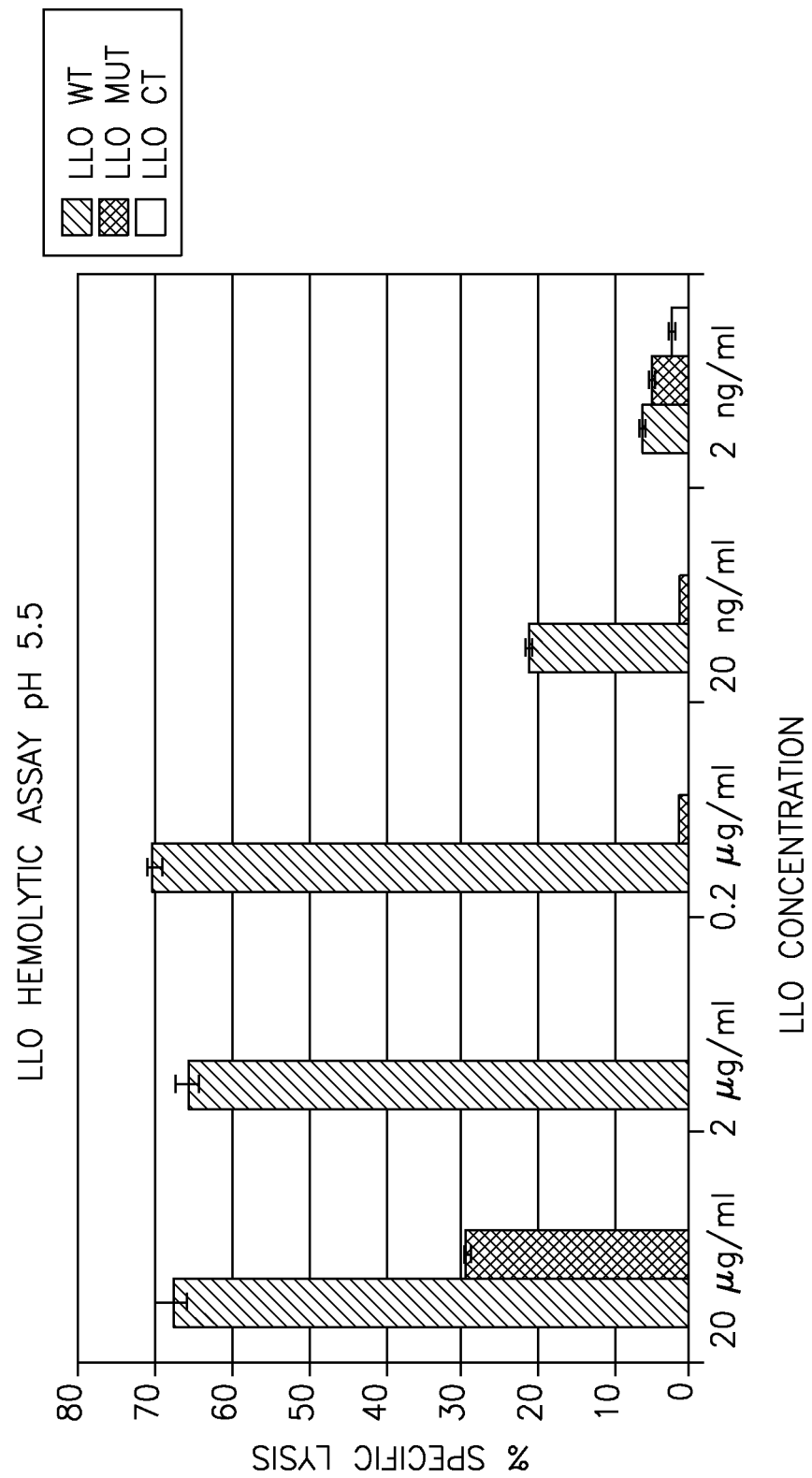
FIG. 10. Hemolytic activity of mutant LLO (mutLLO and ctLLO) proteins at pH 5.5 (A) and 7.4 (B).
Figure 10B:
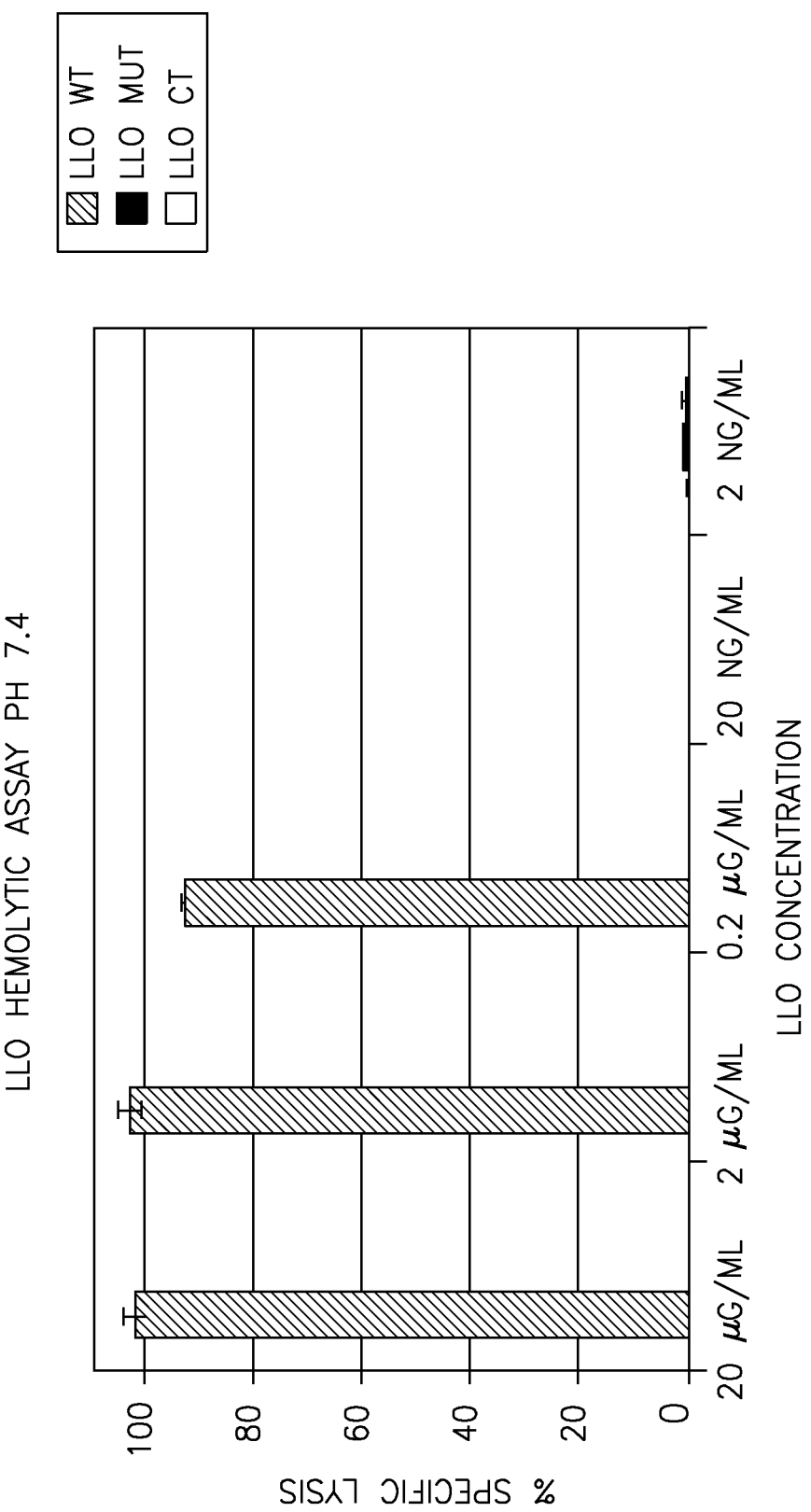

1. Wild-type and mutated LLO were diluted to the dilutions indicated in FIGS. 10A-B in 900 µl of 1× PBS-cysteine (PBS adjusted to pH 5.5 with 0.5 M Cysteine hydrochloride or was adjusted to 7.4). 2. LLO was activated by incubating at 37° C. for 30 minutes. 3. Sheep red blood cells (200 µl/sample) were washed twice in PBS-cysteine and 3 to 5 times in 1×PBS until the supernatant was relatively clear. 4. The final pellet of sheep red blood cells was resuspended in PBS-cysteine and 100 µl of the cell suspension was added to the 900 µl of the LLO solution (10% final solution). 5. 50 µl of sheep red blood cells was added to 950 µl of water+10% Tween 20 (Positive control for lysis, will contain 50% the amount of lysed cells as the total amount of cells add to the other tubes; "50% control.") 6. All tubes were mixed gently and incubated at 37° C. for 45 minutes. 7. Red blood cells were centrifuged in a microcentrifuge for 10 minutes at 1500 rpm. 8. A 200 µl aliquot of the supernatant was transferred to 96-well ELISA plate and read at 570 nm to measure the concentration of released hemoglobin after hemolysis, and samples were titered according to the 50% control.

Results

The hemolytic activity of mutLLO and ctLLO was determined using a sheep red blood cell assay. mutLLO exhibited significantly reduced (between 100-fold and 1000-fold) hemolytic titer at pH 5.5, and undetectable hemolytic activity at pH 7.4. ctLLO exhibited undetectable hemolytic activity at either pH (FIGS. 1A-B).

Thus, point (mutLLO) or substitution (ctLLO) mutation of LLO CBD residues, including C484, W491, and W492, abolishes or severely reduces hemolytic activity. Further, replacement of the CBD with a heterologous antigenic peptide is an effective means of creating an immunogenic carrier of a heterologous epitope, with significantly reduced hemolytic activity relative to wild-type LLO.

Example 9

Expression of the 38C13 BCR as an scFv Protein

A modified pUC119 plasmid was utilized to express the scFv protein in E. coli (Sure® strain, Statagene, La Jolla, Calif.). The plasmid contained the 38C13 scFv DNA (provided by Dr. Ronald Levy, Stanford University), sequences coding for the bacterial leader pelB (facilitates secretion of the protein into the periplasmic space) and the human c-myc peptide tag, which aids detection of protein expression in *E. coli* and purification of the tumor antigen. The 38C13 VH sequence starts with the Gly residue encoded by residues 133-135 and ends with the Val residue encoded by residues 478-480. The 38C13 VK sequence starts with the Glu residue encoded by residues 538-540). The 38C13 VK has a myc tag on the end; the VK ends with a Lys (encoded by residues 848-850).

The relevant fragment of the plasmid had the following sequence:

```
(SEQ ID NO: 61)
gcccagccgccatgccaggtgaagctgcaggagtcaggaggaggcttggt ccagcctggggttctctgagtctctcctgtgcagcttctggattcacct tcactgattactacatgagctgggtccgccagcctccagggaaggcactt gagtggttggctttgattagaaacaaagctaatggttacacagagtacag tgcatctgtgaagggtcggttcaccatctccagagataattcccaaagca tcctctatcttcaaatgaatgccctgagagctgaggacagtgccacttat tactgtgcaagagatcccaattactacgatggtagctacgaagggtactt tgactactggggccaagggaccacggtcaccgtctcctcaggcggaggcg gttcaggcggaggtggctctggcggtggcggatcggacattgagctcacc cagtctccatcctcactgtctgcatctctgggaggcaaagtcaccatcac ttgcaaggcaagccaagacattaacaagtatatagcttggtaccaacaca agcctggaaaaggtcctaggctgctcatacattacacatctacattacag ccaggcatcccatcaaggttcagtggaagtgggtctgggagagattattc cttcagcatcagcaacctggagcctgaagatattgcaacttattattgtc tacagtatgataatctgtacacgttcggctcggggaccaagctggaaata aaacgggcggccgcagaacaaaaactcatctcagaagaggatctgaatta ataagaattc.
```

The encoded protein had the sequence:

```
(SEQ ID NO: 62)
MKYLLPTAAAGLLLLAAQPAQPPCQVKLQESGGGLVQPGGSLSL

SCAASGFTFTDYYMSWVRQPPGKALEWLALIRNKANGYTEYSASVKGRIF

TISRDNSQSILYLQMNALRAEDSATYYCARDPNYYDGSYEGYFDYWGQGT

TVTVSSGGGGSGGGGSGGGGSDIELTQSPSSLSASLGGKVTITCKASQDI

NKYIAWYQHKPGKGPRLLIHYTSTLQPGIPSRFSGSGSGRDYSFSISNLE

PEDIATYYCLQYDNLYTFGSGTKLEIKRAAAEQKLISEEDLN.
```

Initially, the 38C13 plasmid was transformed into the *E. coli* strain BL21*. Following IPTG-induction, the BL21* cells expressed the recombinant protein, with a minor fraction present in the periplasmic space, and the majority present in the *E. coli* inclusion bodies. The inclusion bodies were solubilized (at <80 mcg/ml total protein) in 6M guanidine; the solubilized proteins were refolded in the presence of L-arginine, oxidized glutathione, and EDTA at 10° C. for 3-5 days. The refolded 38scFv protein was then purified from other proteins on an immuno-affinity column containing the S1C5 antibody (anti-38C13 BCR clone) linked to CNBr sepharose using the Amino-link® kit (Pierce Endogen).

Figure 11:
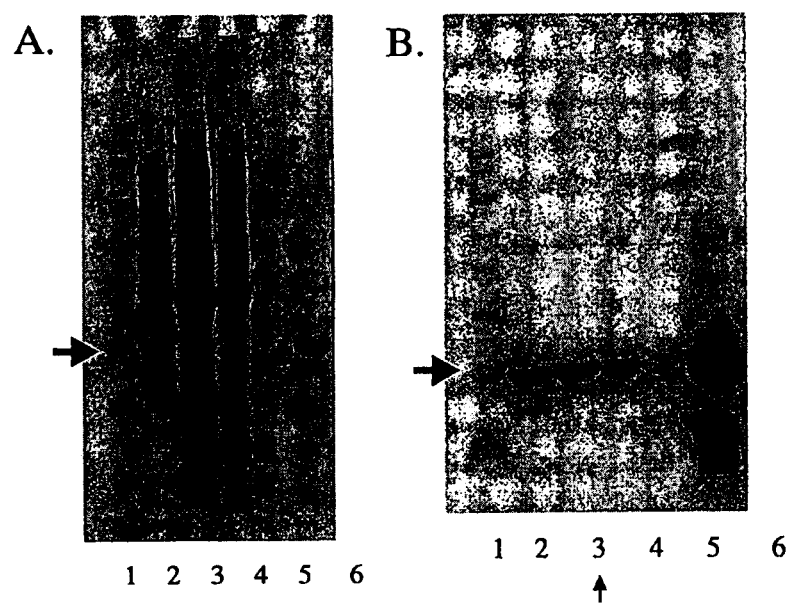
FIG. 11. Expression of 38C13 soluble protein yields 2.34 mg soluble protein from the cell pellet per liter of induction medium. Induction of 38C13scFv protein expression in BL21* was performed using 1 mM IPTG in Superbroth containing 0.5% glycine and 1% triton X-100 at 20° C. for 16 hours. Soluble proteins were extracted from the cell pellet using a protocol including freeze/thaw in nonionic detergent, lysozyme and sonication. 38scFv proteins were purified from the extracted soluble proteins in the anti-idiotype sepharose column. Samples from the affinity chromatography study were electophoresed on SDS-PAGE gels and Coomassie staining (A) or myc tag Western (B). The flow through (ft) and wash fractions contained the 38scFv protein, indicating the Id-Sepharose® column was overloaded with the protein. These fractions were re-loaded onto the Id-Sepharose® slurry and further recombinant protein recovered. Lanes: 1—M Wt; 2—soluble fraction; 3—ft; 4—wash at 1 ml; 5—wash at 100 ml; 6—pooled elution fraction.
Figure 12:
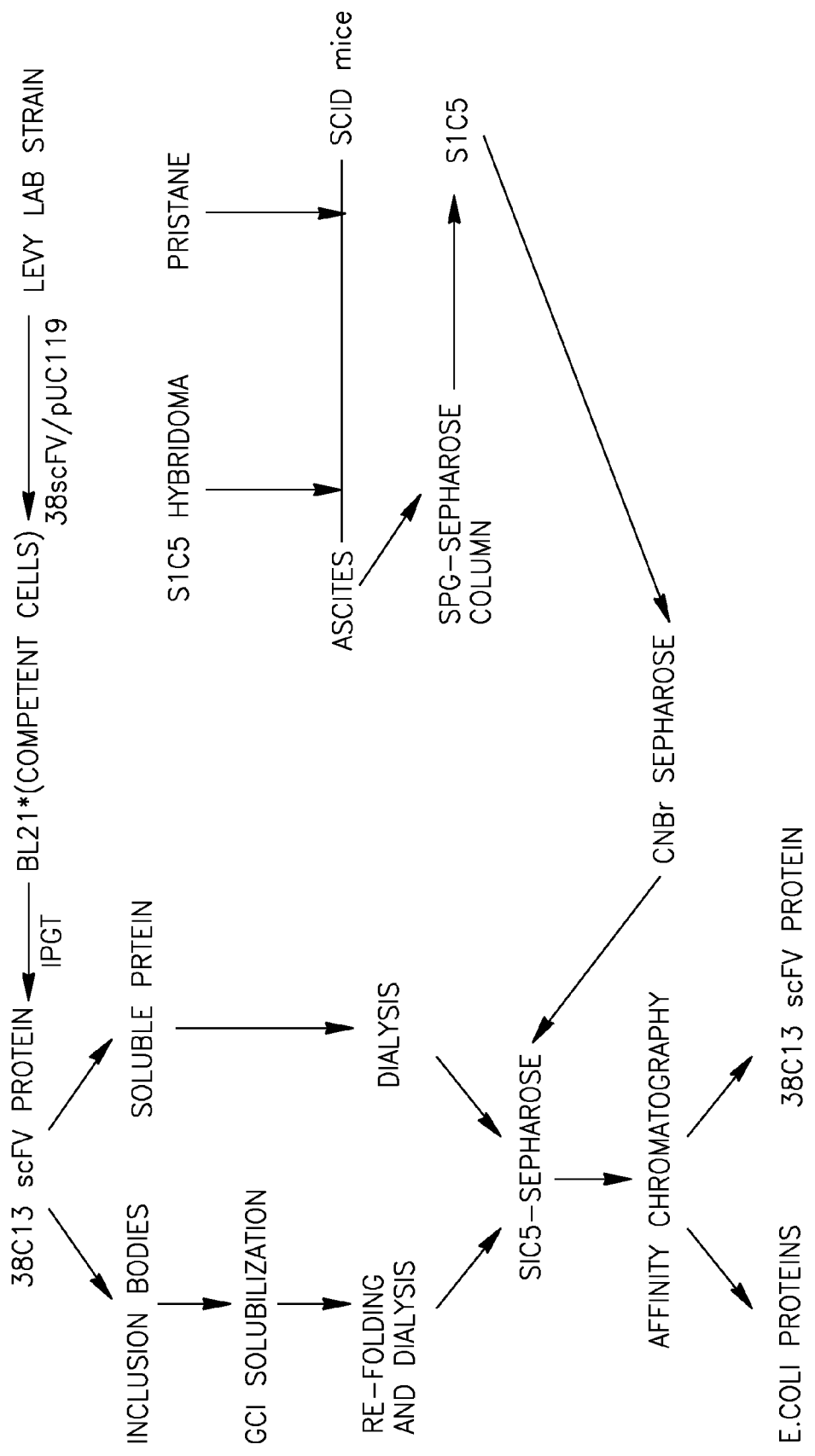
FIG. 12. Strategy for 38scFv protein expression in *E. coli* and subsequent purification by affinity chromatography. Diagram shows the pathway for production of purified 38C13scFv and subsequent purification on an immunoaffinity column with the anti-Id antibody S1C5.

To increase the yield, recombinant protein was recovered from soluble protein extracts. Induction of 38C13scFv expression and recovery of soluble versus insoluble protein at 20° C. and 30° C. were compared. Greater yields of soluble 38C13scFv were recovered by induction at 20° C. Furthermore, maximal yield of soluble protein in the culture supernatant (SN) or from cells was achieved when 0.5% glycine or 1% TX-100 was included in the induction medium. Finally, a 1-liter induction culture performed in medium containing 0.5% glycine and 1% TX-100 yielded 2.34 mg pure soluble 38C13scFv following affinity chromatography (FIG. 11). The overall strategy for production of scFV tumor antigen is summarized in FIG. 12.

Example 10

Verification of 38C13 SCFV Conformational Integrity by ELISA

Figure 13:
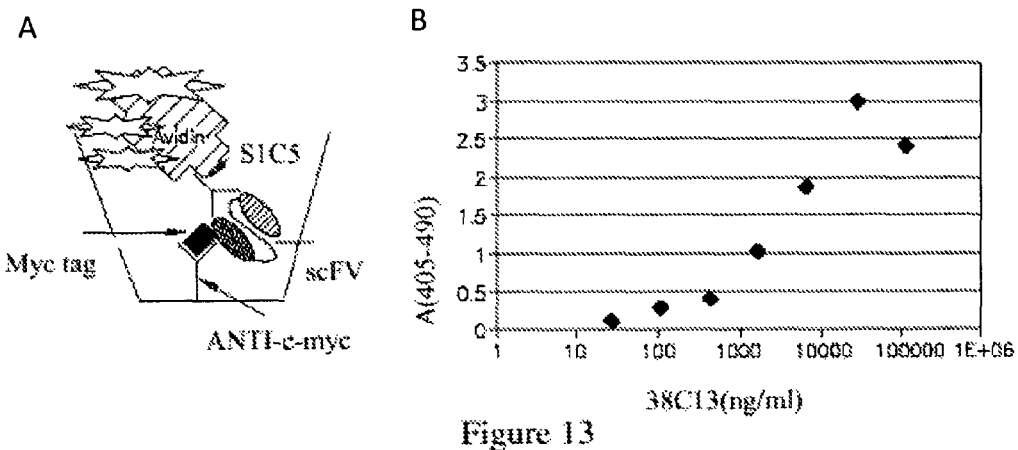
FIG. 13. ELISA assay to quantitate 38C13scFv production in induction cultures, to test correct folding of the protein after conjugation to immunogens, and to monitor the humoral immune response. The principle of the ELISA assay is depicted in (a). A standard curve (b) shows the change in A(405-490) for serial dilutions of purified 38scFv.

To verify that correctly folded 38C13scFv protein was produced by the above method, an ELISA assay was developed. Using serial dilutions of purified 38C13scFv protein, a standard curve was established. This assay showed that correctly folded 38C13scFv protein was produced (FIG. 13). This ELISA assay can also be used to quantitate correctly folded soluble protein in induction media as well as cell protein extracts, for further optimization of conditions for producing 38C13scFv protein.

Production of Non-Hemolytic LLO:

LLO was rendered non-hemolytic by conjugation to 38C13 BCR with aldehyde. The *E. coli* LLO/pET29 plasmid was obtained from Dr. Margaret Gedde (Gedde M M, Higgins D E, Tilney L G, Portnoy D A. Role of listeriolysin O in cell-to-cell spread of *Listeria monocytogenes*. Infect Immun. 2000 February; 68(2):999-1003) which has a $(HIS)_6$ tag at the 3' end The *E. coli* strain BL21* was transformed with LLO/pET29 plasmid by temperature shock and the bacteria plated onto selection medium. Colonies were selected and the BL21*/LLO/pet29 were cultured in LB medium at 37° C. in an incubator shaker until plateau phase. Cell aliquots were then frozen in LB/glycerol at −20° C. When induction expression was to be performed, the frozen BL21*/LLO/pet29 were streaked onto agar selection plates, plates were incubated overnight at 37° C., colonies selected and grown in LB broth with kanamycin and chloramphenicol. The culture was then incubated at 30° C. in an incubator shaker until the $OD_{600}$=0.6-0.7, at this point IPTG (1 mM final concentration) was added to the culture and incubated for a further 8 hours. The LB broth was then spun at 5,000 rpm, the cells were collected and frozen at −20° C. until affinity purification was to be performed. Recombinant LLO (AA sequence 20 to 442 of LLO, excluding the signal sequence) was purified from the bacteria soluble protein fraction according to the protocol provided by QIAGEN. Briefly, frozen cells were thawed on ice, incubated in lysis buffer (50 mM phosphate, pH8, 500 mM NaCl, 20 mM imidazole, 10 mM β-mercaptoethanol) supplemented with lysozyme (Calbiochem) and a cocktail of protease inhibitors (Roche) for 30 minutes at 4° C. The cells were then sonicated three times for 10 second bursts each until all bacterial clumps were removed. The lysed bacteria were then spun at 24,000 g and the supernatant removed (soluble protein fraction). The soluble proteins were then loaded onto a pre-equilibrated $Ni^+$-NTA agarose (QIAGEN) column; weakly bound proteins were removed by washing until the $A_{280}$=<0.05. At this point, the recombinant LLO was removed from the column by addition of elution buffer containing 500 mM imidazole. Elution fractions were collected and pooled, dialyzed against LLO storage buffer overnight (50 mM phosphate/acetate, pH6, 1M NaCl, 5 mM DTT) at 4° C. and then stored in 1 mg/ml aliquots at −80° C. until needed. Conjugation of 38C13 Lymphoma Idiotype Protein to Immunogenic Proteins and Validation 38C13 Id protein was conjugated to either Keyhole Limpet Hemocyanin (KLH, Pierce Endogen) or purified recombinant LLO using glutareldehyde to cross-link primary amines on the proteins. Briefly, 1 mg/l Id protein and 1 mg/ml immunogen were combined in a sterile tube with fresh 0.1% glutaraldehyde (SIGMA), the proteins were then mixed on a rotator for 10-15 minutes at room temperature. The conjugated proteins were then dialyzed against 0.1M PBS at 4° C. overnight; the conjugation of Id protein to immunogens was confirmed complete by SDS-PAGE and Coumassie stain. The conjugate proteins were then depleted of endotoxin using Detoxigel (Pierce Endogen), all vaccines had <1EU/µg protein. Protein conjugates containing recombinant LLO were checked for the absence of residual lytic function using sheep red cells as the target as described for detoxLLO.

Example 11

Construction of the 38C13 BCR-LLO Vaccine

Purification of Idiotype Proteins.

Figure 14:
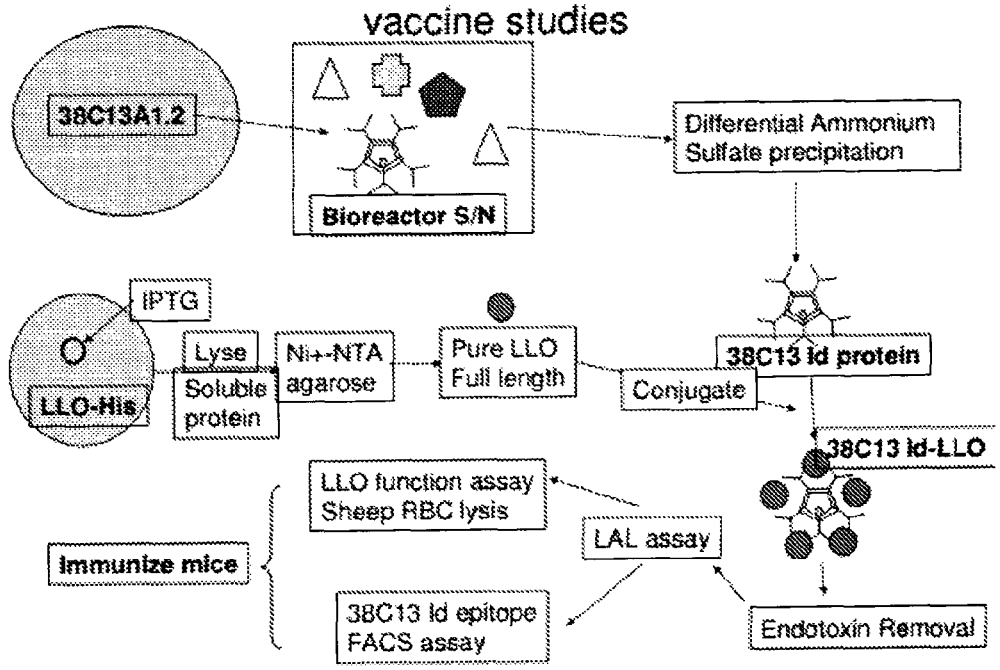
FIG. 14. Production of whole 38Id protein-LLO conjugates for vaccine studies. The 38C13 IgM protein was secreted by the 38C13A1.2 hybridoma into the bioreactor culture supernatant. The 38C13 IgM protein was purified from the culture supernatant using differential ammonium sulfate precipitation. Soluble LLO-His protein was expressed in *E. coli* following induction by IPTG, the soluble protein was then purified on a Ni+-NTA column and purity confirmed by Coumassie and Western blot using the LLO antibody B3-19. The 38C13 Id protein was conjugated to glutaraldehyde, dialyzed against PBS and passed through a Polymixin B column to remove endotoxin; endotoxin removal was confirmed by the LAL assay. The hemolytic activity of the 38Id-LLO conjugate was then tested using sheep red cells and compared to purified LLO, the 38Id-LLO was found to be non-hemolytic.
Figure 15:
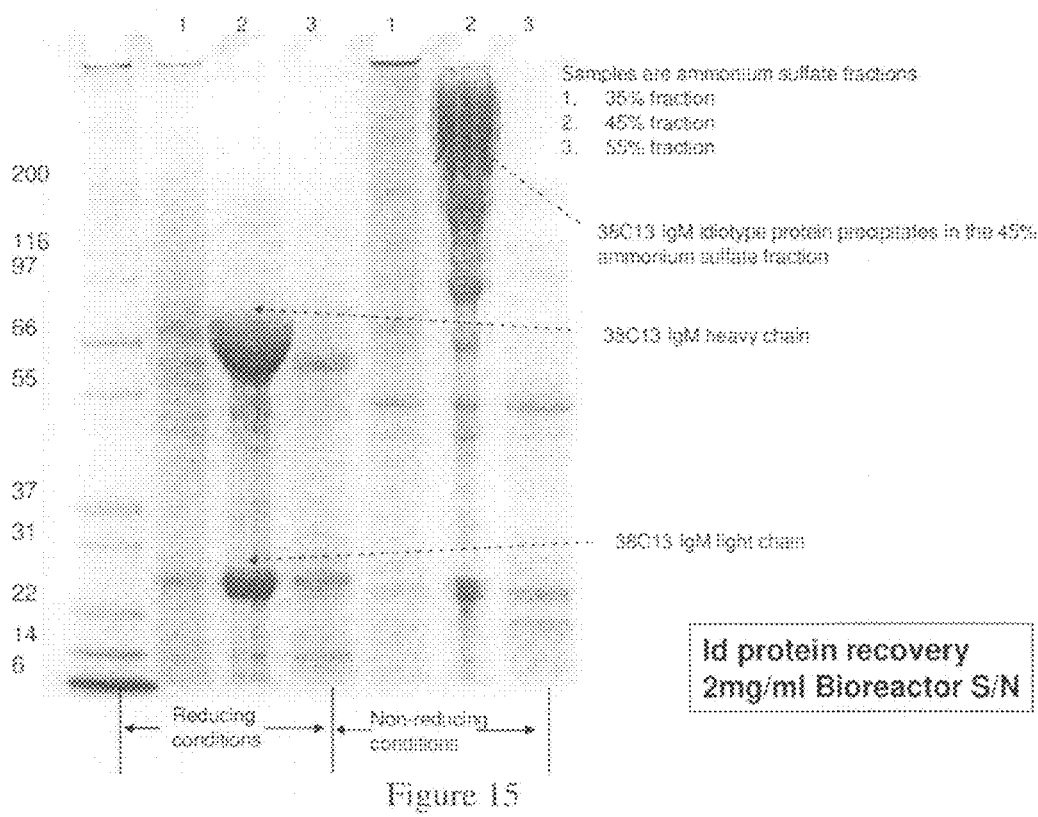
FIG. 15. Samples from differential ammonium sulfate precipitation of bioreactor supernatant following culture of the hybridoma 38C13A1.2 were run by SDS-PAGE gel and stained by Coumassie. The 38C13 idiotype protein was recovered from the 45% fraction and characterized in both reducing and non-reducing conditions.

B-cell lymphoma idiotype proteins were purified from hybridoma supernatant via differential ammonium sulfate precipitation. The process for production of the 38C13 lymphoma idiotype protein is outlined in FIG. 14. The 38C13A1.2 hybridoma secreted the IgM protein into the Bioreactor (BD Celline) supernatant. The IgM protein was recovered from the bioreactor supernatant following differential ammonium sulfate precipitation. Samples from each fraction were run by SDS-PAGE under reducing and non-reducing conditions and characterized by Coumassie stain (see FIG. 15). The 45% fraction from the bioreactor supernatant contained the 38C13 IgM protein; recovery was 2 mg/ml supernatant.

Figure 16:
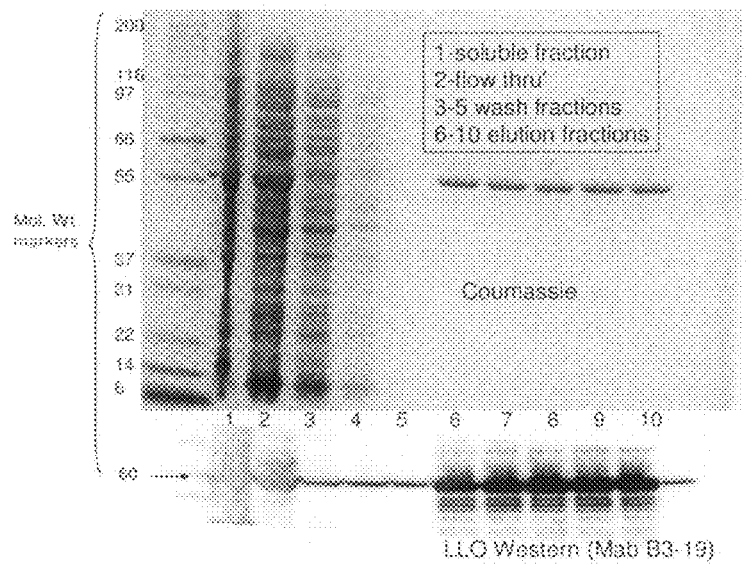
FIG. 16. Soluble proteins were recovered from *E. coli* strain BL21* following an induction expression culture in LB medium and 1 mM IPTG for 18 hours at 30 C. Recombinant LLO-His was then purified on a Ni+-NTA column; the purity of the elution fractions were confirmed by SDS PAGE followed by a Coumassie stain or a Western blot performed using Mab B3-19.

Recombinant LLO was recovered from soluble proteins from BL21* following IPTG-induced expression induction for 18 hours at 30° C. The soluble proteins were incubated in batch form with Ni$^+$-NTA agarose for 30 minutes at room temperature. Non-specifically bound proteins were removed following a washing step in phosphate buffer, pH 8 containing 20 mM imidazole. The recombinant LLO-His was then eluted from the column using phosphate buffer pH 8 plus 500 mM imidazole. The purity of the elution fractions was confirmed by SDS PAGE followed by Coumassie stain or Western blot using the Mab B3-19. Results show (FIG. 16) that a single band of molecular weight 58 kD was eluted from the Ni$^+$-NTA column and its identity as confirmed as LLO by the Mab B3-19.

Figure 17:
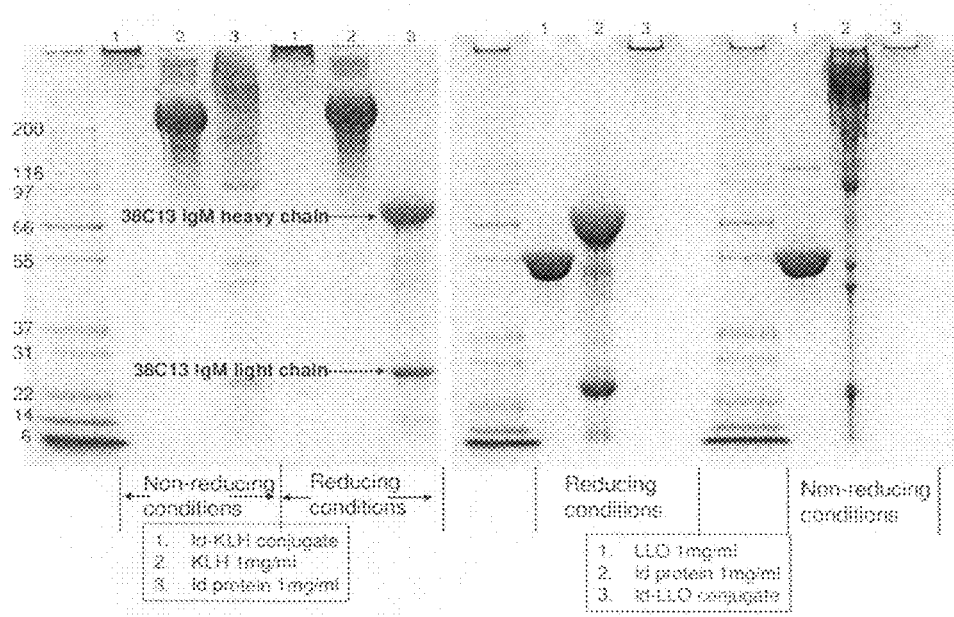
FIG. 17. 38C13 idiotype (Id) protein was conjugated to either KLH (left panel) or LLO (right panel). Conjugation of 38C13 idiotype protein to KLH or LLO is complete, as confirmed by Coumassie stain on SDS-PAGE gel run under reducing and non-reducing conditions; both 38Id-KLH and 38Id-LLO conjugates show no evidence of free 38Id or the immunogenic proteins.
Figure 18:
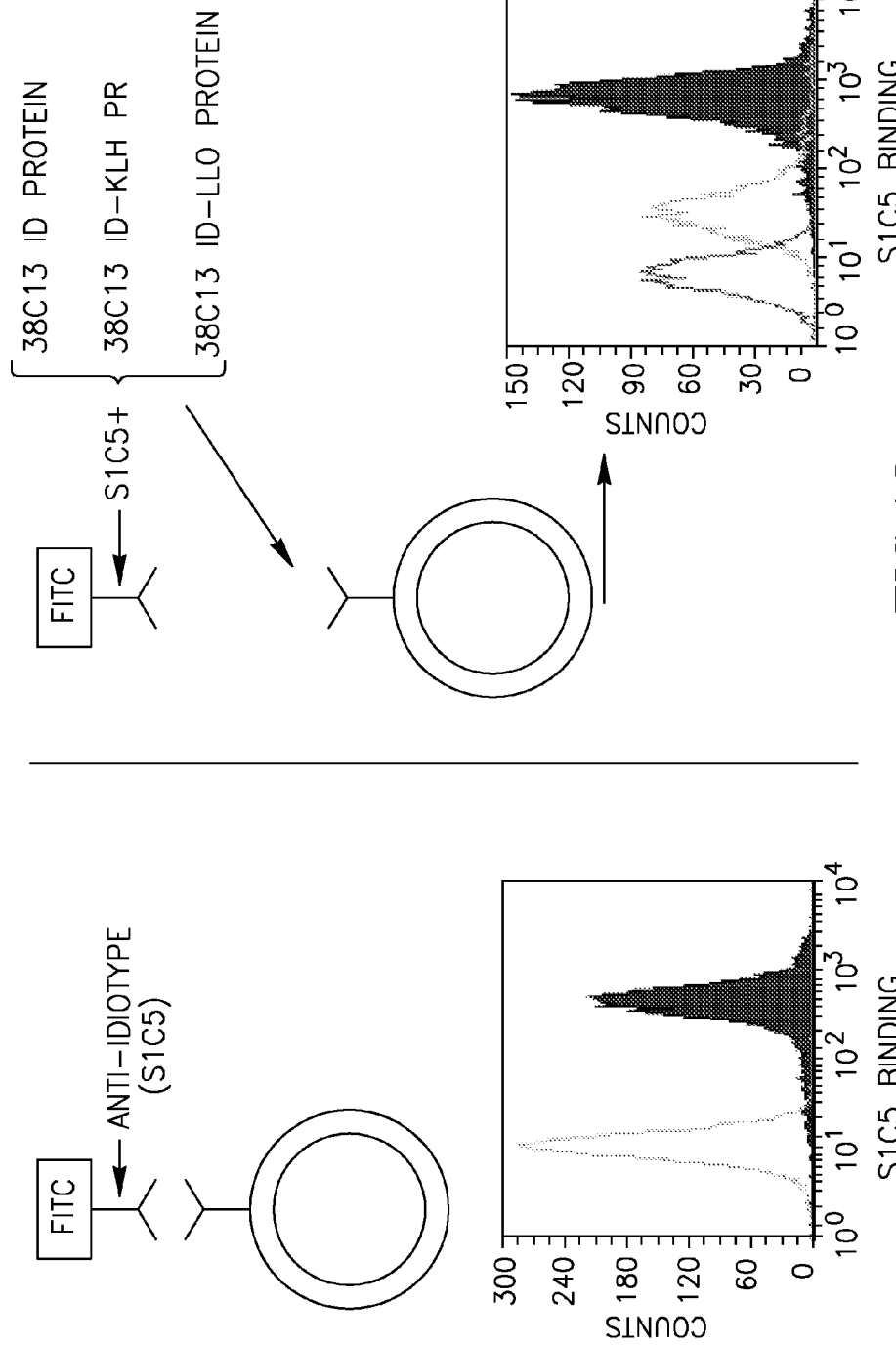
FIG. 18. Principle of the assay system designed to demonstrate the presence of the 38C13 idiotype epitope. The presence of the 38C13 idiotype epitope was confirmed using a blocking assay, in this system the anti-38C13 idiotype antibody S1C5-FITC is incubated with the Id protein or the conjugates 38Id-KLH or 38Id-LLO. Subsequently the binding of the S1C5-FITC to the 38C13 cell line B-cell receptor (BCR) is assessed by flow cytometry. In the presence of 38Id protein, the binding of S1C5-FITC to 38C13 lymphoma is impaired.
Figure 19:
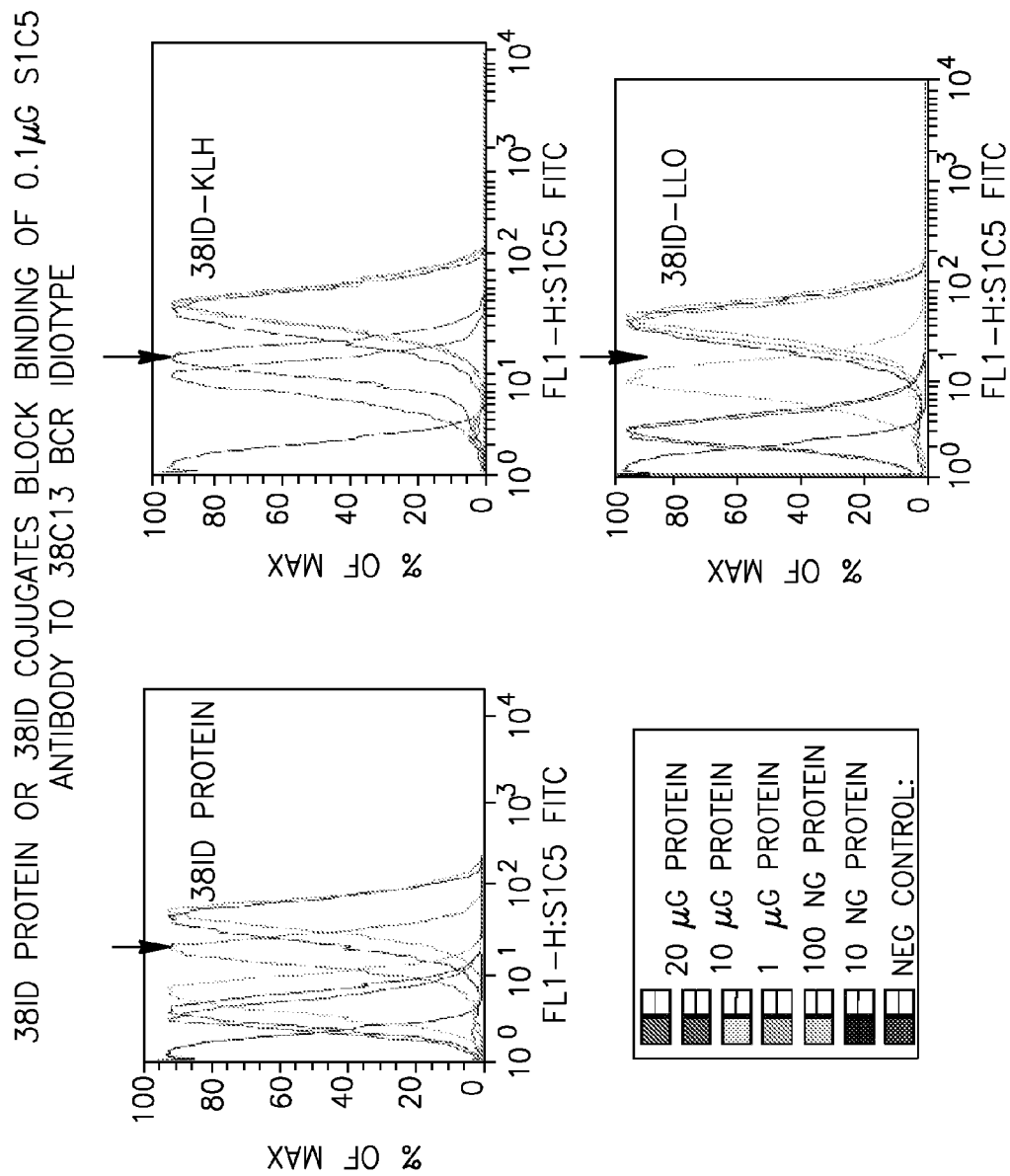
FIG. 19. 38C13 Id protein conjugated to LLO or KLH retains the binding site for the S1C5 MAb and inhibits binding of S1C5-FITC to 38C13 lymphoma cells. Arrow marks approximately 5-fold reduction in fluorescence. For unconjugated protein (top left panel), this corresponded to 100 ng protein. For 38Id-KLH, this corresponded to 10 mcg protein (upper right panel). For 38Id-LLO, this corresponded to between 100 ng-1 mcg protein (lower right panel).

Subsequently, the 38C13 idiotype protein was conjugated to recombinant LLO or KLH using 0.1% glutaraldehyde for 10 minutes at room temperature. The glutaraldehyde was removed following dialysis against 0.1M PBS at 4° C. overnight. The 38Id-LLO and 38Id-KLH conjugates were then characterized by SDS-PAGE under reducing and non-reducing conditions followed by Coumassie stain (FIG. 17). Results showed the conjugation was successful with no free 38Id protein nor immunogenic protein in either conjugate. To ascertain that the 38C13 idiotype epitope was still present following conjugation, a FACS-based competitive binding assay was developed (FIG. 18). This assay detects the ability of the 38Id conjugate to block the specific binding of FITC conjugated S1C5 Mab to the 38C13 lymphoma BCR. The presence of 100 ng 38Id protein was sufficient to block binding of the 0.1 ug S1C5 Mab to 38C13 lymphoma cells (FIG. 19). In contrast, 1 mcg 38Id-LLO or 10 mcg 38Id-KLH were required to block binding of 0.1 mcg S1C5 Mab to 38C13 lymphoma cells.

Example 12

Figure 20A:
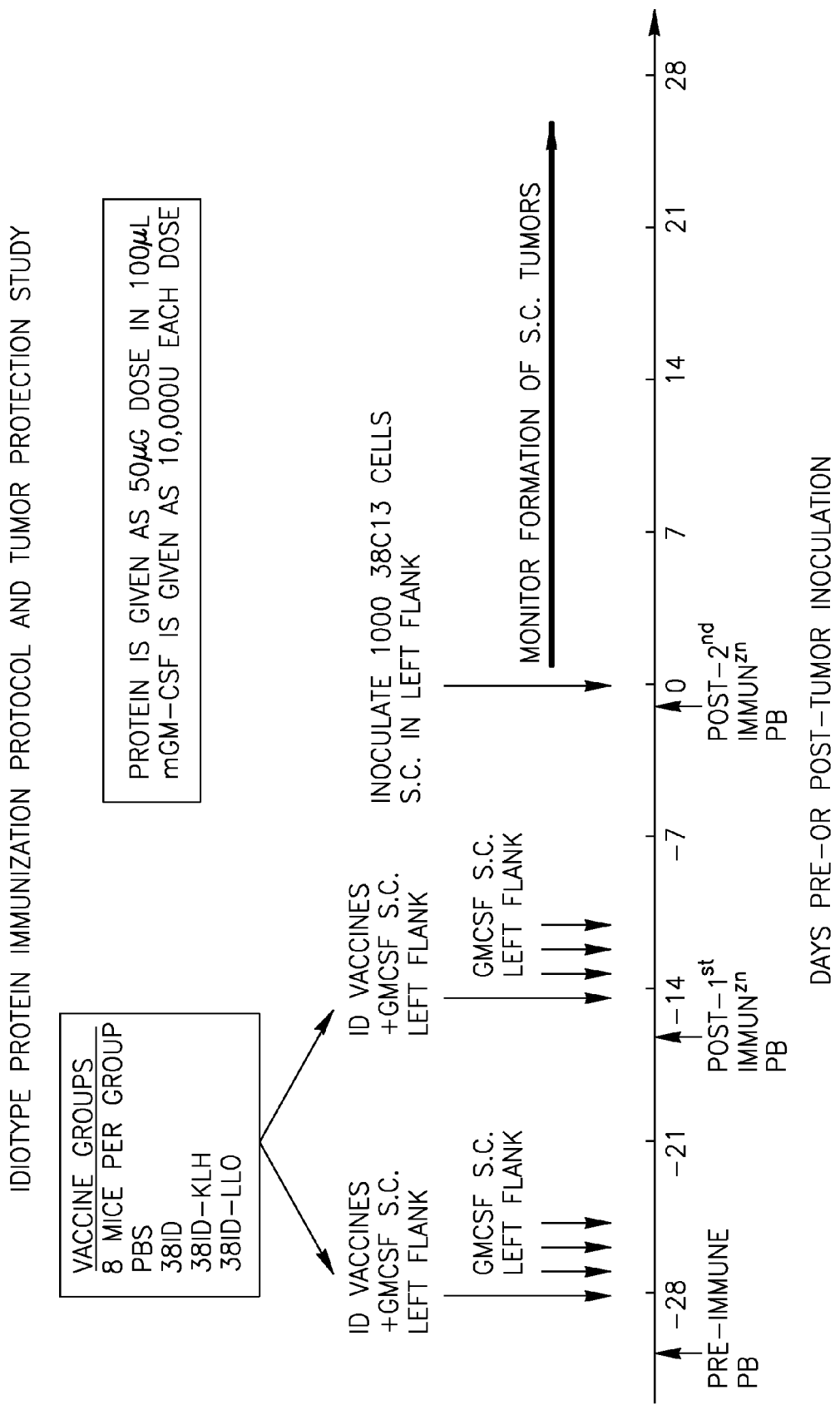
FIG. 20. Id-LLO immunization protects mice from 38C13 lymphoma challenge. Mice were immunized with 38Id or 38Id conjugates and challenged with 38C13 lymphoma (A). The development of s.c. lymphoma was monitored for each mouse over the next 60 days (B), and the results presented as the frequency of each vaccine group tumor free. Statistical analysis was performed (non-parametric Kaplan-Meier, Log Rank Mantel-Cox test) using SPSS software. Asterisk-result is statistically different (p<0.05) from control groups.
Figure 20B:
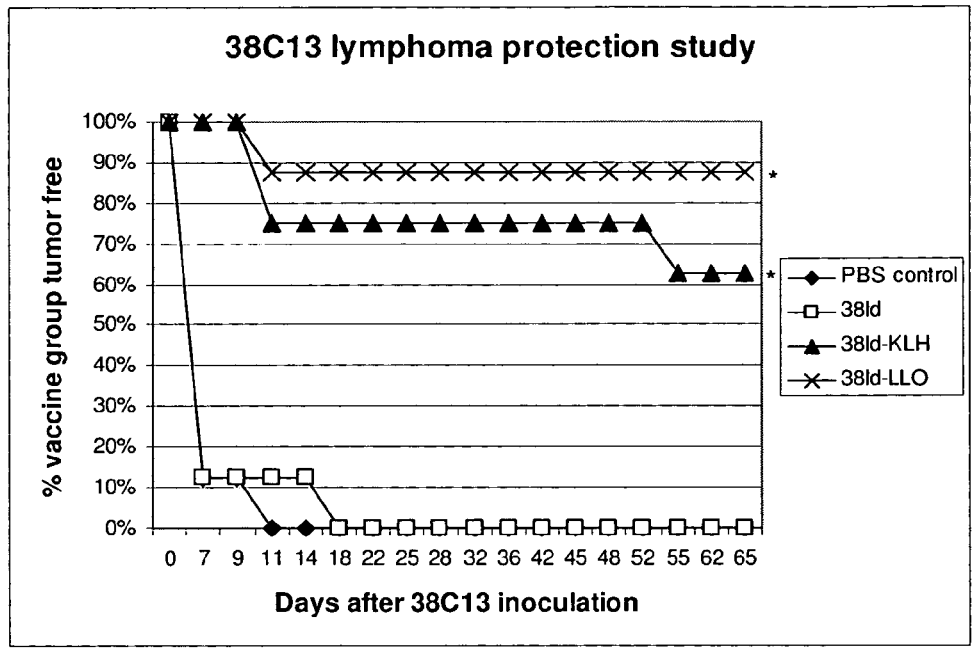

38C13 BCR-LLO Vaccines are Efficacious in a Mouse Non-Hodgkin's Lymphoma Tumor Protection Model C3H/HeN mice (n=8) were vaccinated with (a) 38C13 idiotype protein (38-Id), (b) 38Id coupled to Keyhole Limpet Hemocyanin (38Id-KLH); (c) 38Id-LLO; or (d) PBS (negative control). Vaccines were administered as two 50 mcg s.c. doses on days 0 and 14 days, with 10,000 U murine GMCSF (mGM-CSF). In addition, 10,000 U Mgm-CSF was administered on the same flank for 3 consecutive days. On day 28, mice were challenged with $10^3$ 38C13 lymphoma cells on the flank used for immunization, and tumor formation was monitored for 100 days. The 38Id-LLO vaccine induced tumor protection in 7/8 mice up to 65 days (FIG. 20). Mice vaccinated with 38Id-KLH were shown to have a lower level of resistance to the 38C13 lymphoma (5/8 tumor free at day 65) compared to mice vaccinated with 38Id-LLO (7/8 tumor free), but this did not reach statistical significance (p=0.273). In contrast, mice immunized with 38Id or PBS had poor 38C13 lymphoma resistance, with all mice developing tumors by day 22. When the incidence of tumor formation was examined statistically, the test vaccine group (Id-LLO) was shown to have a significantly lower incidence of tumors versus the 38Id (p=0.0016) or the PBS group (p=0.0001).

Example 13

Figure 21A:
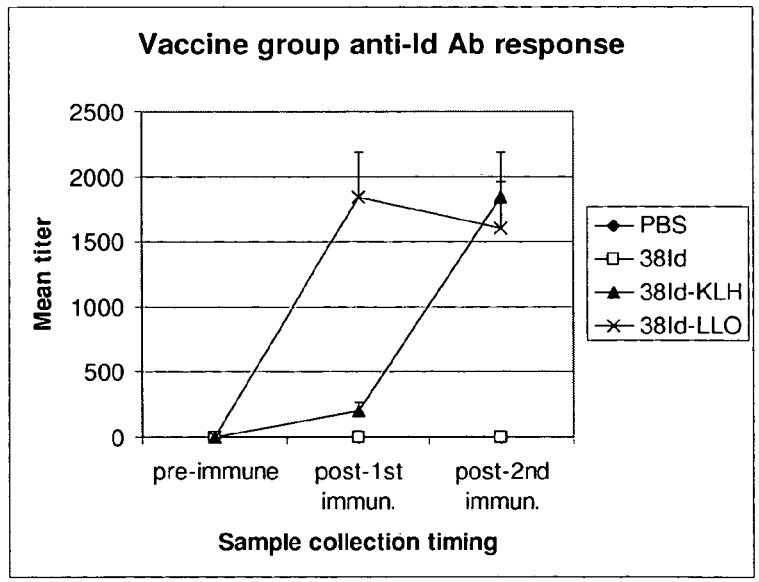
FIG. 21. Id protein vaccine induces anti-idiotype antibodies when the Id protein is conjugated to KLH or LLO. Peripheral blood samples were collected from individual mice prior to and 12 days after each immunization. The serum samples were then tested by ELISA assay for the presence of anti-idiotype antibodies. The results for each vaccine group have been summarized in. Mice from the 38Id-LLO and 38Id-KLH vaccine groups were the only vaccine groups with sera positive for anti-idiotype antibodies (A). An isotyping assay was performed to characterize the anti-idiotype antibodies induced by 38Id-LLO versus 38Id-KLH. Following a single immunization with 38Id-LLO, a high titer polyclonal response was induced with equivalent levels of IgG1 and IgG2a anti-idioype antibodies (B). The level of the 38Id-LLO induced antibodies increased after the second immunization; however the ratio of IgG1:IgG2a (1.0) remained the same. In contrast, the 38Id-KLH vaccine induced a higher level of IgG1 versus IgG2a anti-idiotype antibodies after both immunizations (IgG1:IgG2a ratio was 1.8 and 1.3 respectively (B).
Figure 21B:
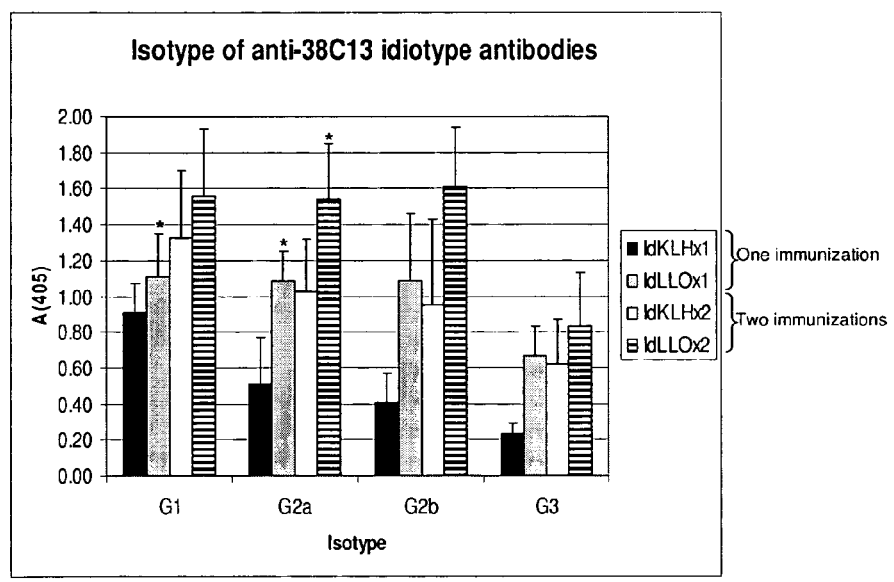

38ID-LLO Induces High Titer Anti-Idiotype Antibodies after One Immunization with a Strong Ig2A Subtype Peripheral blood samples were collected from individual mice prior to and 12 days after each immunization. The serum samples were then tested by ELISA assay for the presence of anti-idiotype antibodies. Mice from the 38Id-LLO and 38Id-KLH vaccine groups were the only vaccine groups with sera positive for anti-idiotype antibodies (FIG. 21A). Compared with control vaccine groups, mice immunized with 38Id-LLO had high titer anti-idiotype antibodies following one immunization; whereas mice immunized with 38Id-KLH required two immunizations to achieve the same titer. An isotyping assay was performed to characterize the anti-idiotype antibodies induced by 38Id-LLO versus 38Id-KLH. Following a single immunization with 38Id-LLO, a high titer polyclonal response was induced with equivalent levels of IgG1 and IgG2a anti-idioype antibodies (FIG. 21B). The level of the 38Id-LLO induced antibodies increased after the second immunization; however the ratio of IgG1:IgG2a (1.0) remained the same. In contrast, the 38Id-KLH vaccine induced a higher level of IgG1 versus IgG2a anti-idiotype antibodies after both immunizations (IgG1:IgG2a ratio was 1.8 and 1.3 respectively; FIG. 21B). Levels of IgG2a anti-Id antibodies were statistically different between Id-LLO and Id-KLH sera after the first (p=0.0001) and second (p=0.002) immunizations. The level of IgG1 anti-idiotype antibody was only statistically different between these two vaccine groups after the first immunization (p=0.03). The anti-Id antibody status correlated well with the days to formation of a tumor for each vaccine group. While the naïve and Id alone vaccine groups had all formed tumors by day 18 and were negative for anti-Id antibodies, all Id-LLO and Id-KLH immunized mice developed anti-Id antibodies, and this correlated with tumor resistance, with 7/8 Id-LLO mice and 5/8 Id-KLH mice tumor free 60 days after 38C13 challenge.

Figure 22:
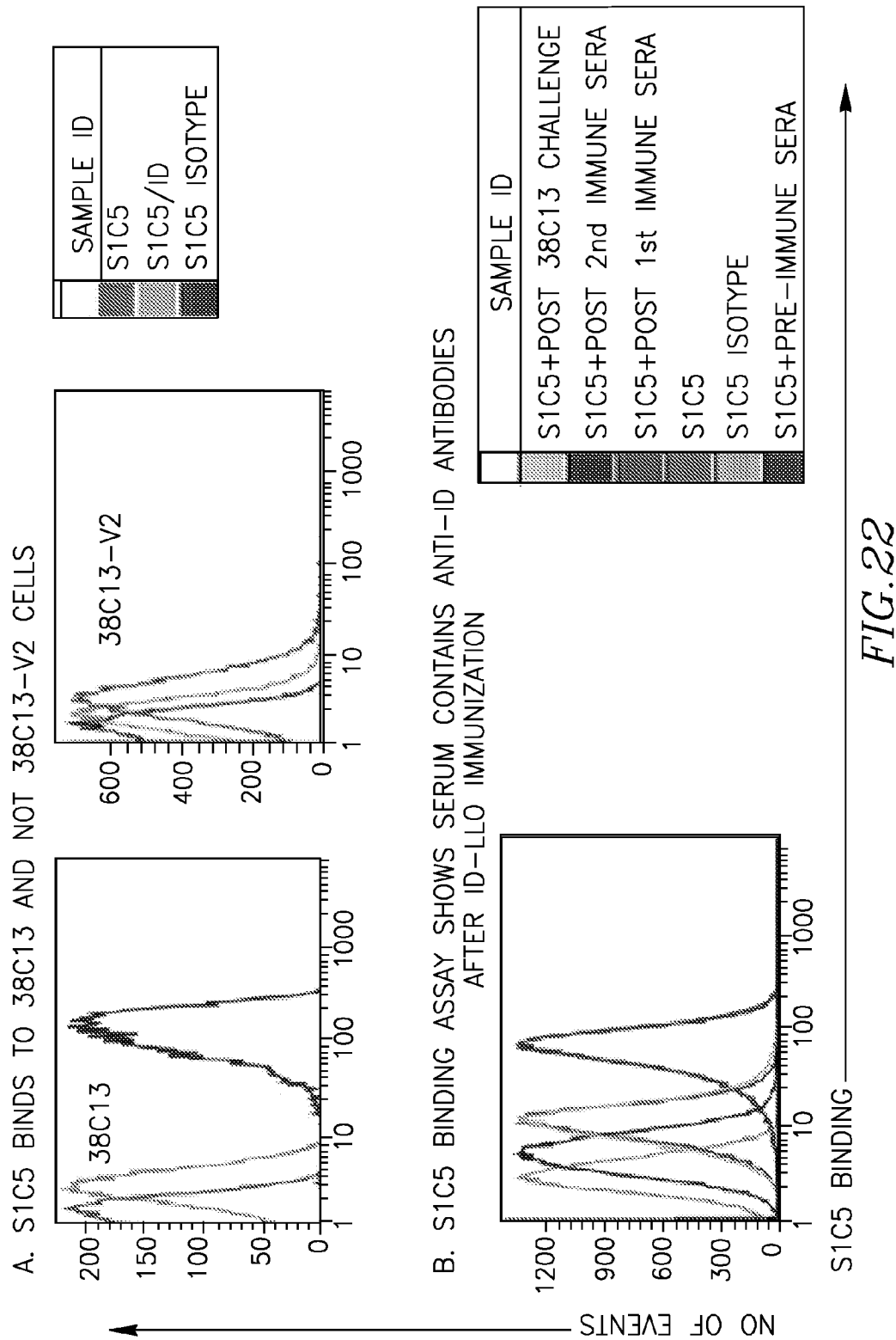
FIG. 22. Anti-idiotype antibodies are present in mouse serum after immunization and tumor challenges. To confirm the above results, the ability of immunized mouse serum to block binding of S1C5-FITC to 38C13 cells was measured, as a decrease in fluorescence by FACS. In the first experiment (A), the binding specificity of S1C5 to the 38C13 lymphoma idiotype was verified. Subsequently, the inhibition of S1C5 binding to 38C13 cells by mouse serum (taken at various stages through Id-LLO immunization and after tumor challenges) was investigated (B).

To confirm the above results, the ability of immunized mouse serum to block binding of S1C5-FITC to 38C13 cells was measured, as a decrease in fluorescence by FACS. In the first experiment (FIG. 22A), the binding specificity of S1C5 to the 38C13 lymphoma idiotype was verified. Subsequently, the inhibition of S1C5 binding to 38C13 cells by mouse serum (taken at various stages through Id-LLO immunization and after tumor challenges) was investigated (FIG. 22B). In this study, mouse serum inhibited binding of S1C5 to the 38C13 cells after the $1^{st}$ and $2^{nd}$ immunizations and after tumor challenges, but not pre-immunization Example 14

38Id-LLO Immunization Induces a Th1 Response in the DLN

Figure 23A:
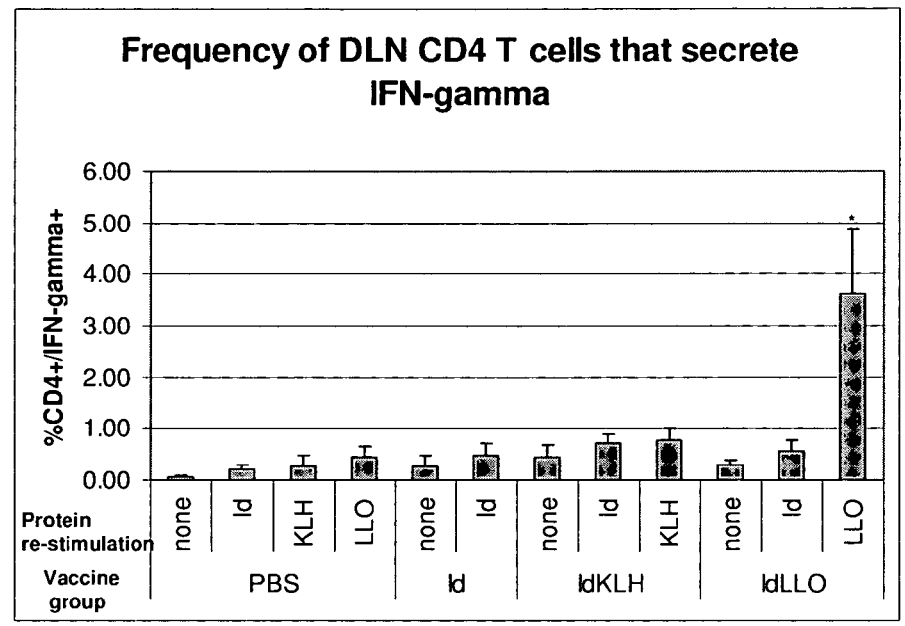
FIG. 23. Id-LLO immunization induces a Th1 response and antigen-specific CD8 T cells. Cells were harvested from DLN 14 days after s.c. immunization. CFSE-stained DLN cells were incubated with purified proteins for 5 days before being re-stimulated with PMA/Ionomycin for 5 hours in the presence of monensin. Cells were stained for surface CD4 and CD8, and then fixed and stained for intracellular cytokine. Percentage (mean±SD) of gated cells secreting cytokines is depicted. (A) CD4 T cell IFN-γ secretion; (B) CD4 T cell IL-4 secretion; (C) CD8 T cell IFN-γ secretion; (D) CD4 proliferation results. Student t-test was used to analyze the data; asterisk indicates a significantly different result with in vitro protein stimulation (p=<0.05) compared to media only in that vaccine group.

To investigate the CD4$^+$ and CD8$^+$ T cell responses to the protein vaccines, DLN were harvested 14 days after the immunization protocol. Cytokine secretion was examined by FACS, CD4$^+$ T cells from the Id-LLO vaccine group secreted IFN-γ in response to in vitro re-stimulation with LLO protein versus the PBS control (p=0.02, FIG. 23A). In no other vaccine groups did significant numbers of CD4$^+$ T cells secrete IFN-γ in response to protein re-stimulation. However, CD4$^+$ T cells from the same vaccine groups did not respond significantly to in vitro re-stimulation with 38Id protein.

Figure 23B:
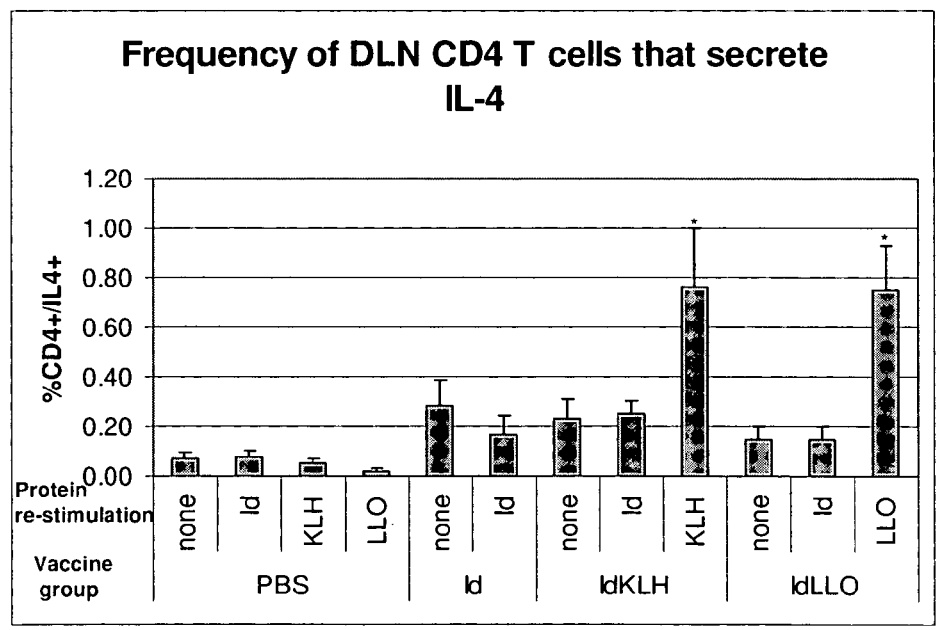
Figure 23C:
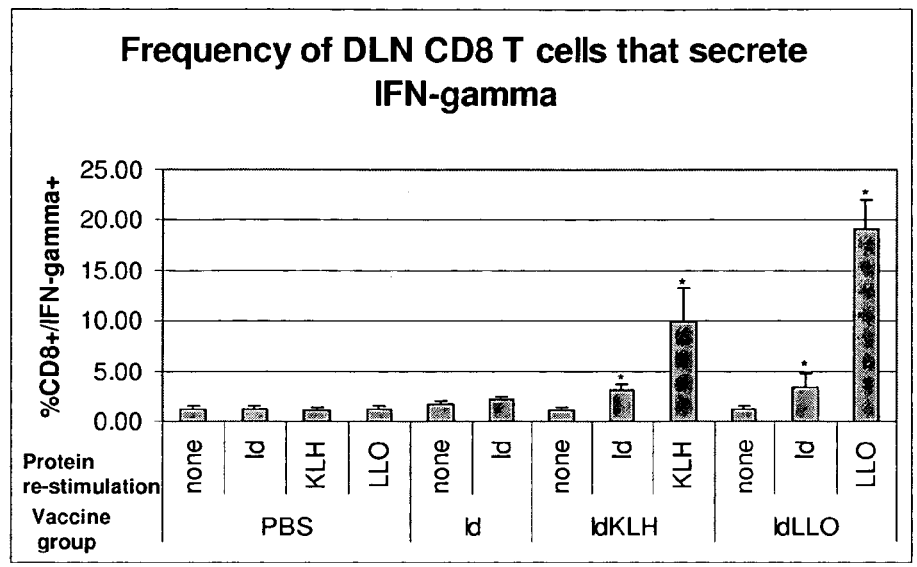

IL-4 secretion in response to in vitro protein re-stimulation was also examined. In mice immunized with Id-KLH, Id-LLO or LLO alone, CD4$^+$ DLN cells responded significantly to in vitro restimulation with the immunogens KLH or LLO (FIG. 23B). The frequency of CD4 T cells (from the Id-LLO vaccine groups) responding to LLO re-stimulation by secreting IL-4 (0.7) % was lower than that observed for CD4 T cells secreting IFN-γ (3.8) %. Simultaneously, DLN CD8 T cell response to protein re-stimulation was examined in immunized mice (FIG. 23C). The level of IFN-γ secretion in response to LLO re-stimulation was 18% in mice immunized with Id-LLO (p=0.0005) significantly higher compared to KLH re-stimulated Id-KLH immunized mice (10%, p=0.009). A significant response to re-stimulation with the idiotype protein was also seen in the DLN CD8 T cells from mice immunized with Id-LLO (p=0.04) and Id-KLH (p=0.02).

Figure 23D:
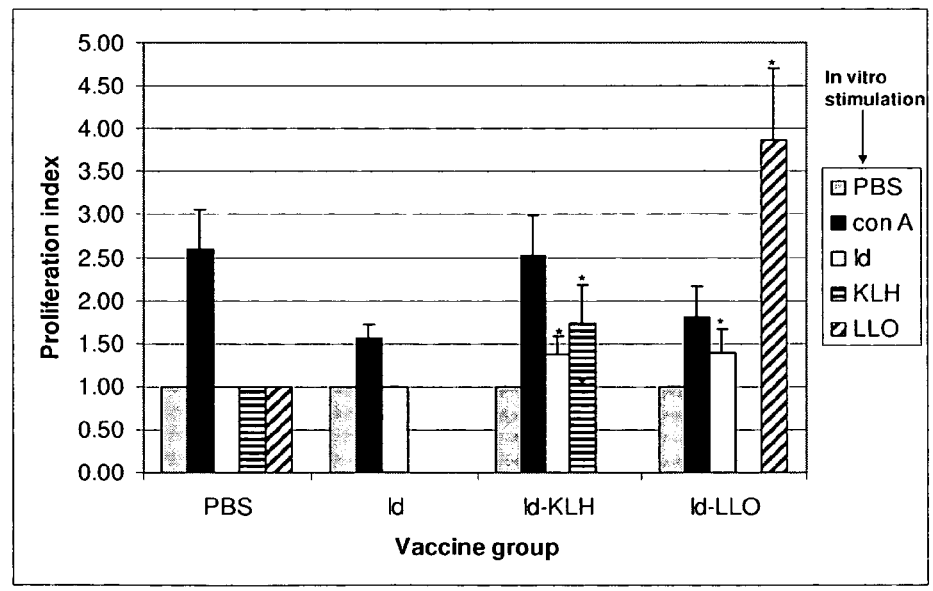
Figure 24:
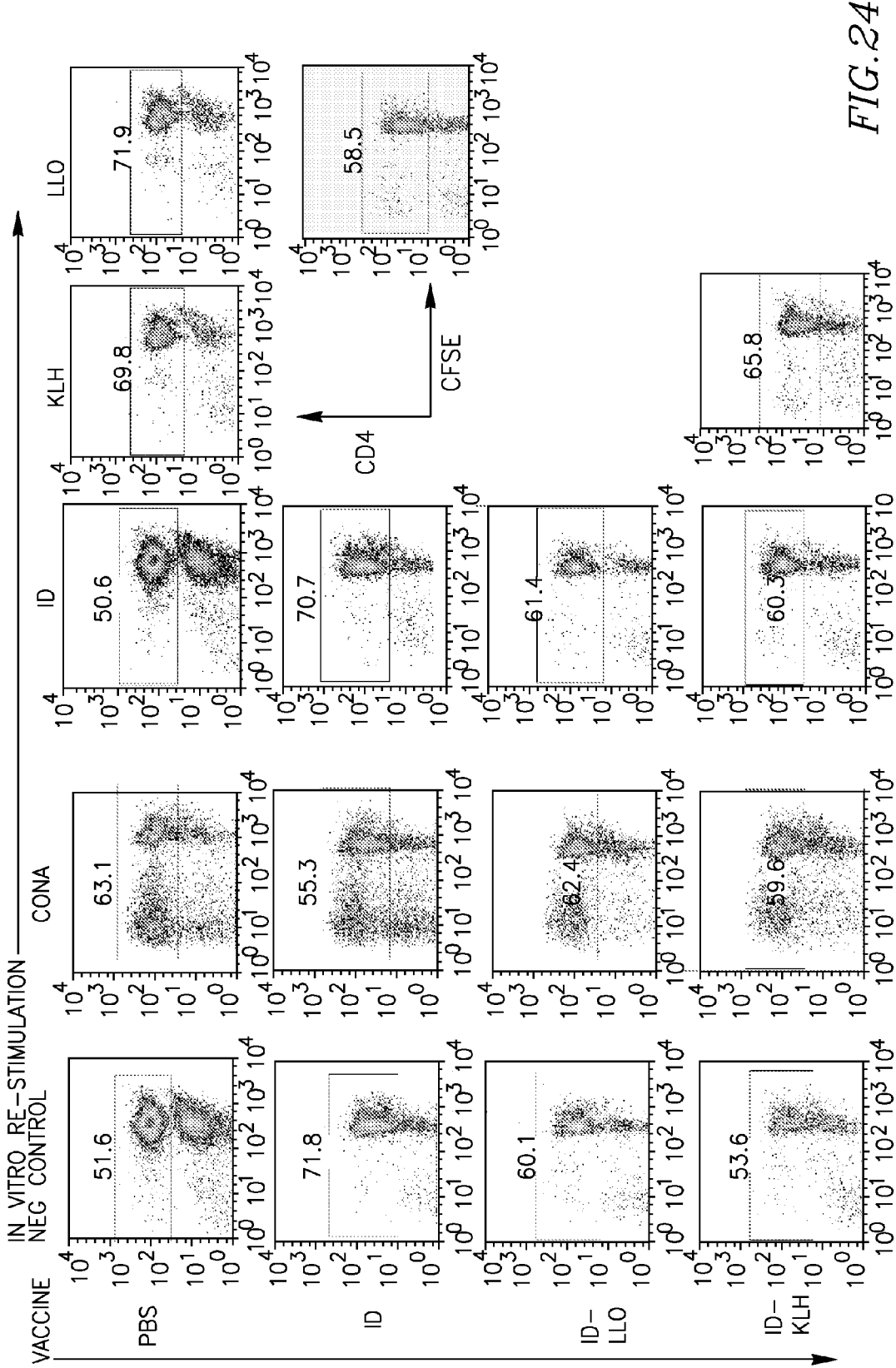
FIG. 24. Representative dot plots of CD4 CFSE proliferation assay. which FIG. 23D data were calculated. DLNs were collected 14 days after s.c. immunization and cells harvested. CFSE-stained DLN cells were then incubated with purified proteins for 5 days before being re-stimulated with PMA/Ionomycin for 5 hours in the presence of monensin. Cells were then stained for surface CD4 and CD8, fixed and stained for intracellular cytokine. Data was acquired on a FACSCalibur and analyzed by FlowJo software. Representative dot-plots for CD4 CFSE proliferation are shown in FIG. 24.
Figure 25A:
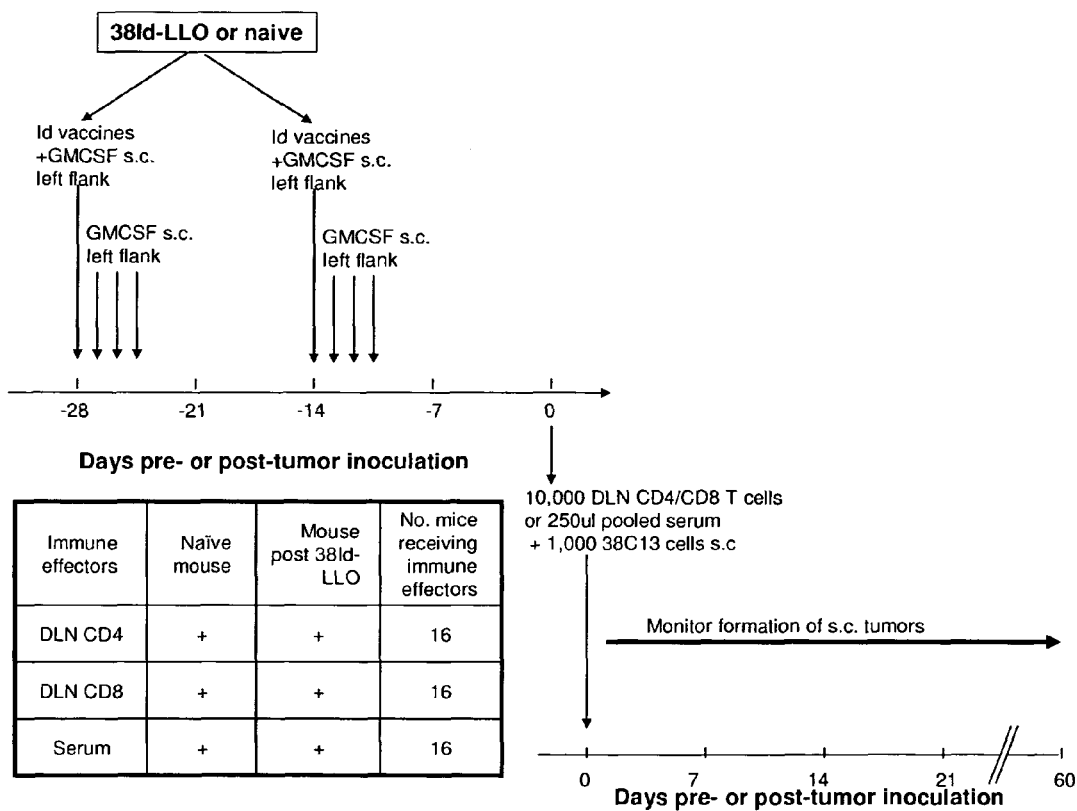
FIG. 25. Co-inoculation of post-Id-LLO serum, CD4 or CD8 T cells inhibits the growth of 38C13 lymphoma cells. Transfer of serum, CD4 or CD8 T cells after Id-LLO immunization protects from in vivo challenge with 38C13 lymphoma. Experimental design is depicted in (A). Mice were immunized with 2 rounds of Id-LLO+mGMCSF; control group was naïve mice. Fourteen days after the second round of immunization, DLNs were collected and purified DLN CD4 or CD8 T cells were prepared as well as a pool of serum. The serum, CD4 or CD8 T cells were then co-inoculated s.c. with 38C13 cells on the left flank into recipient mice (8 per group), and mice were monitored for 60 days to assess lymphoma development. Results for serum transfer are shown in (B), CD4 or CD8 transfer in (C). Statistical analysis was performed (non-parametric Kaplan-Meier, Log Rank Mantel-Cox test) using SPSS software). Asterisk-statistical difference (p<0.05) in anti-tumor efficacy between effectors from immunized and naïve mice.
Figure 25B:
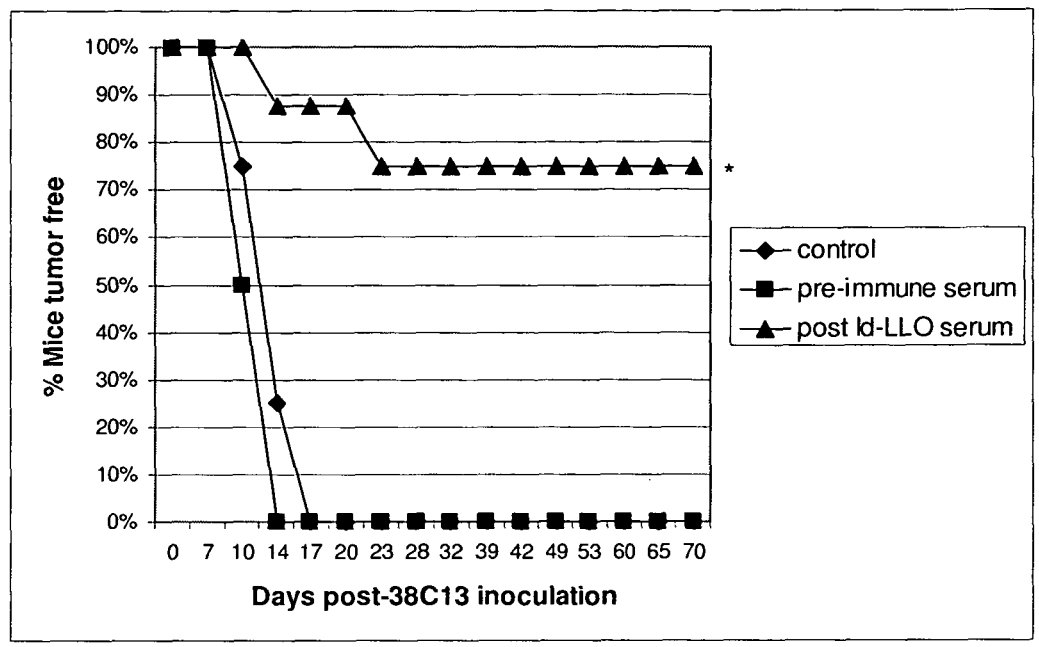
Figure 25C:
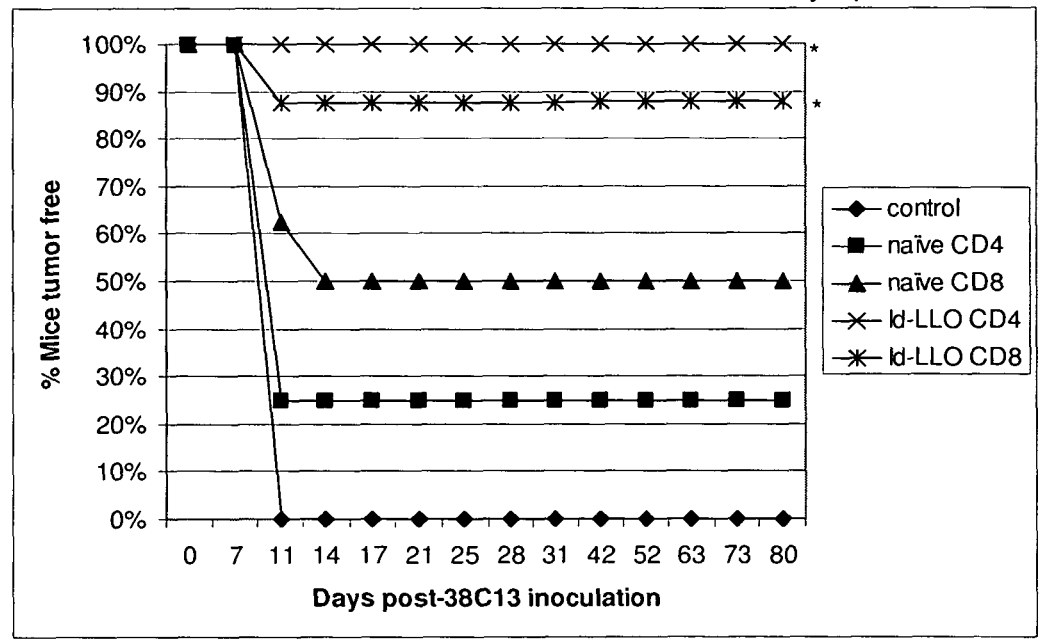
Figure 26:
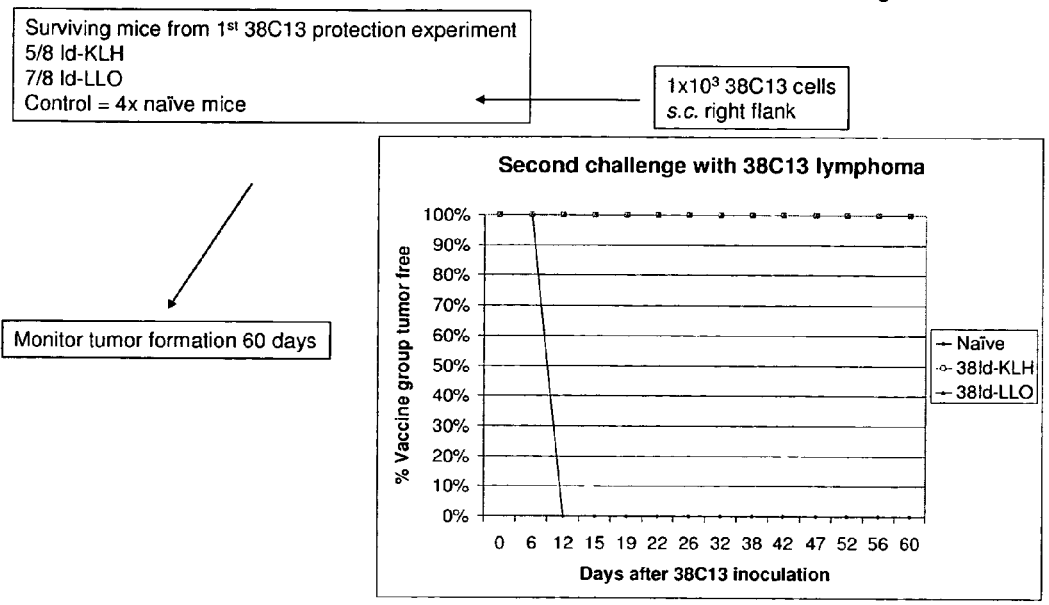
FIG. 26. Mice immunized with 38Id-KLH or 38Id-LLO are protected from 38C13 challenge on the opposite flank to the initial immunization and challenge.

Proliferative responses of DLN CD4 T cells to immunization and in vitro re-stimulation were examined by CFSE fluorescence. In each vaccine group, the conA positive control demonstrated the proliferative potential of the cells (FIG. 24). This proliferative response was characterized by 7 cell divisions by a subset of the initial CD4 T cell population. The average number of cell divisions responding CD4 T cells underwent in response to in vitro re-stimulation (proliferative index) ranged from 1.7-3.0 in the presence of conA (FIGS. 23D and 24). There was no proliferation in the 2 control vaccine groups, PBS and 38Id, in the presence or absence of protein re-stimulation (proliferative index of 1.0), while cells from the 38Id-LLO and 38Id-KLH vaccine groups responded to 38Id protein restimulation with a proliferative index of 1.2 in each vaccine group. Also, the Id-LLO vaccine group cells exhibited a marked proliferative capacity in response to LLO re-stimulation (proliferative index of 3.2). The response of cells from the 38Id-KLH group to KLH re-stimulation had a proliferative index of 1.3.

Thus, 38Id-LLO immunization induces a draining lymph node Th1 response.

Example 15

Construction and Testing of mutLLO-38C13 BCR and ctLLO-38C13 BCR Vaccines mutLLO-38C13 BCR and ctLLO-38C13 BCR vaccines are constructed from mutLLO-, ctLLO-, and 38C13-encoding DNA as described in Example 11. The vaccines are tested as described in Example 12, and are found to exhibit protective anti-lymphoma activity.

Example 16

Construction and Testing of mutLLO-e7 and ctLLO-E7 Vaccines mutLLO-E7 and ctLLO-E7 vaccines are constructed from mutLLO-, ctLLO-, and E7-encoding DNA as described in Example 11. The vaccines are tested as described in Example 12, and exhibit protective anti-tumor activity.

Example 17

The Impact of Immunization with Detox LLO-E7 Compared to Controls on TC-1 Growth Vaccine Preparation Recombinant E7 and Detox LLO comprising mutations or deletions in CBD were purified on a nickel column and LPS was removed on a Norgen Proteospin column according to the manufacturer's directions. E7 was conjugated chemically to LLO by mixing 2 mg of Detox LLO with 500 μg of E7 and adding paraformaldehyde to a final concentration of 1%. The mixture was shaken on a rotator for 40 minutes at room temperature and then dialysed at 4° C. overnight in PBS.

Tumor Regression

1×10$^5$ TC-1 were established on the flank of each mouse, and on days 3 and 10, mice were immunized subcutaneously along the back with 250 μl of PBS containing E7 50 μg, Detox LLO 200 μg mixed with 50 μg of E7, DetoxLLO-E7 conjugate 250 μg or PBS only (naïve).

The Impact of Immunization with Detox LLO Chemically Conjugated to E7 and Detox LLO+E7 on TC-1 Growth Mice were immunized subcutaneously along the back with 250 μl of PBS containing: E7 (50 μg), DetoxLLO (200 μg) mixed with E7 (50 μg), DetoxLLO-E7 conjugate (250 μg), or PBS only (naïve).

Figure 27:
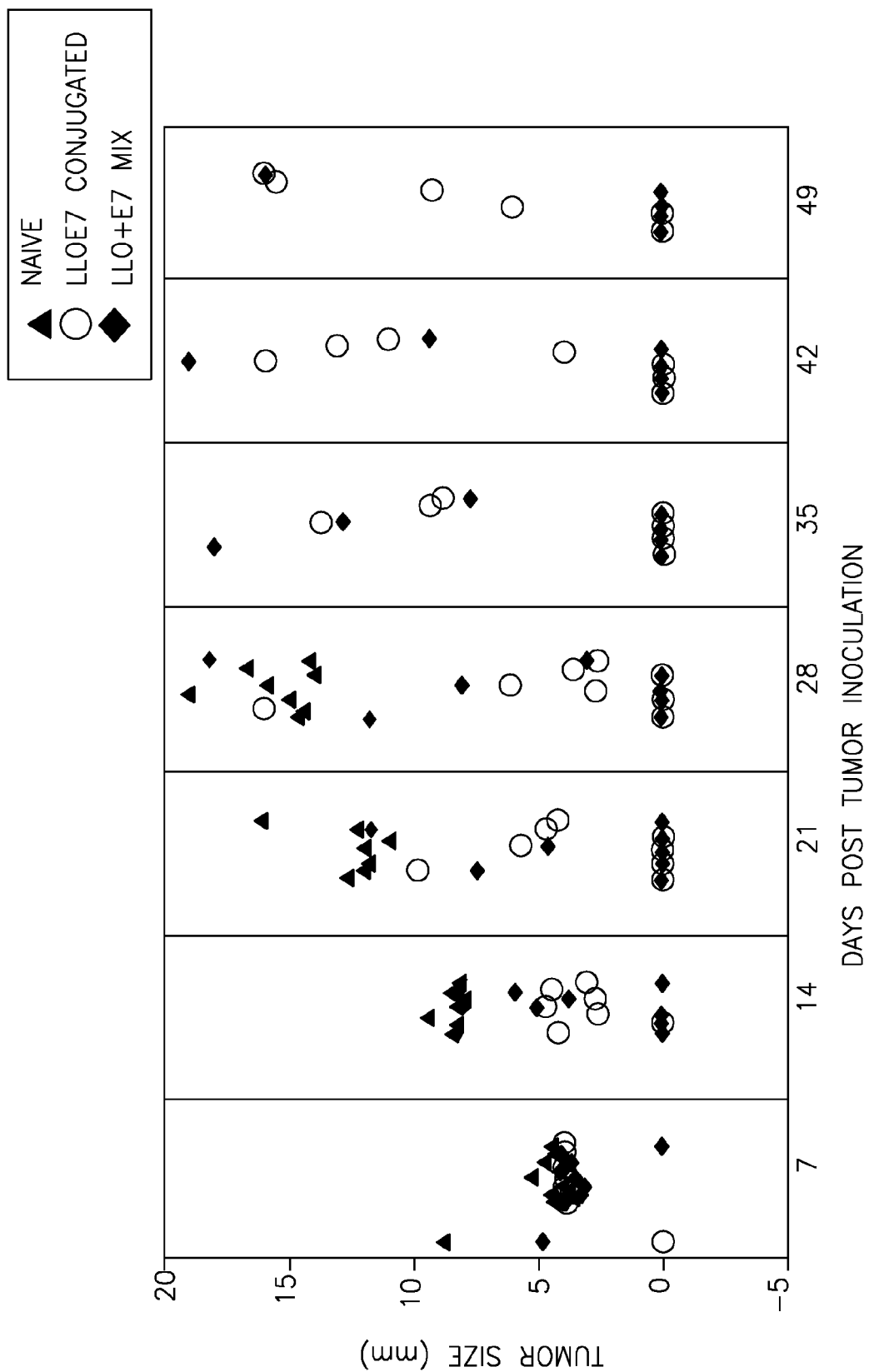
FIG. 27. The ability of rLLO+rE7 chemically conjugated and rLLO+rE7 mixed together to impact on TC-1 growth.

Mice administered conjugated LLO-E7 demonstrated an attenuated increase of tumor size compared to naïve controls. Mice administered LLO+E7 mixed also demonstrated an attenuated increase in tumor size (FIG. 27). While all naïve animals had tumors by day 7, 2/8 mice were tumor free following administration of DetoxLLO-E7 conjugate and 4/8 mice were tumor free following administration of DetoxLLO mixed with E7 on day 49 (FIG. 27, Table 3).

The Impact of Immunization with E7 or LLO Protein on TC-1 Growth

Mice were immunized subcutaneously along the back with 250 μl of PBS containing: E7 (50 μg), LLO (250 μg) or PBS only (naïve).

Figure 28:
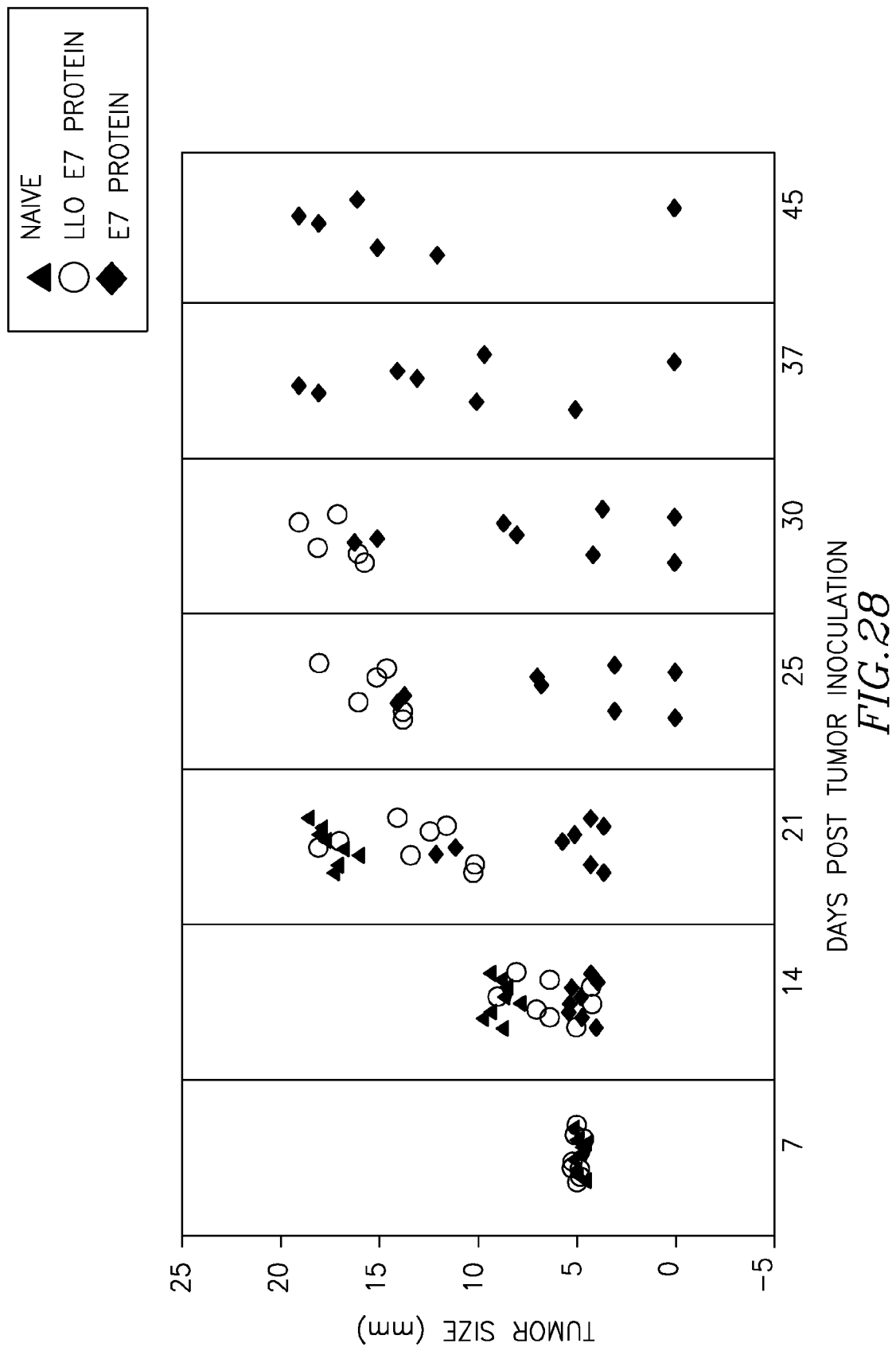
FIG. 28. The ability of rE7 and rLLO protein to impact on TC-1 growth.

Tumor regression was not noted in mice that were immunized with either LLO or E7 alone where in each respective case, 0/8 and 1/8 mice were tumor free on day 45, Immunization with LLO, and to a greater extent with E7 delayed the time to tumor onset (FIG. 28). However, by day 45, only 0/8 and 1/8 mice were tumor free from the LLO and E7 groups, respectively.

The Impact of Immunization with DTLLO Genetically Fused to the Whole E7 Sequence and LLO Detoxified by Replacing the Cholesterol Binding Region with the E7 Epitope on TC-1 Growth Mice were immunized subcutaneously along the back with 250 μl of PBS containing: recombinant DTLLO-E7 whole (whole E7 sequence genetically fused to DTLLO; 250 μg), DTLLO-E7 chimera (LLO detoxified by substitution of CBD with E7 epitope; 250 μg) or PBS only (naïve).

Figure 29:
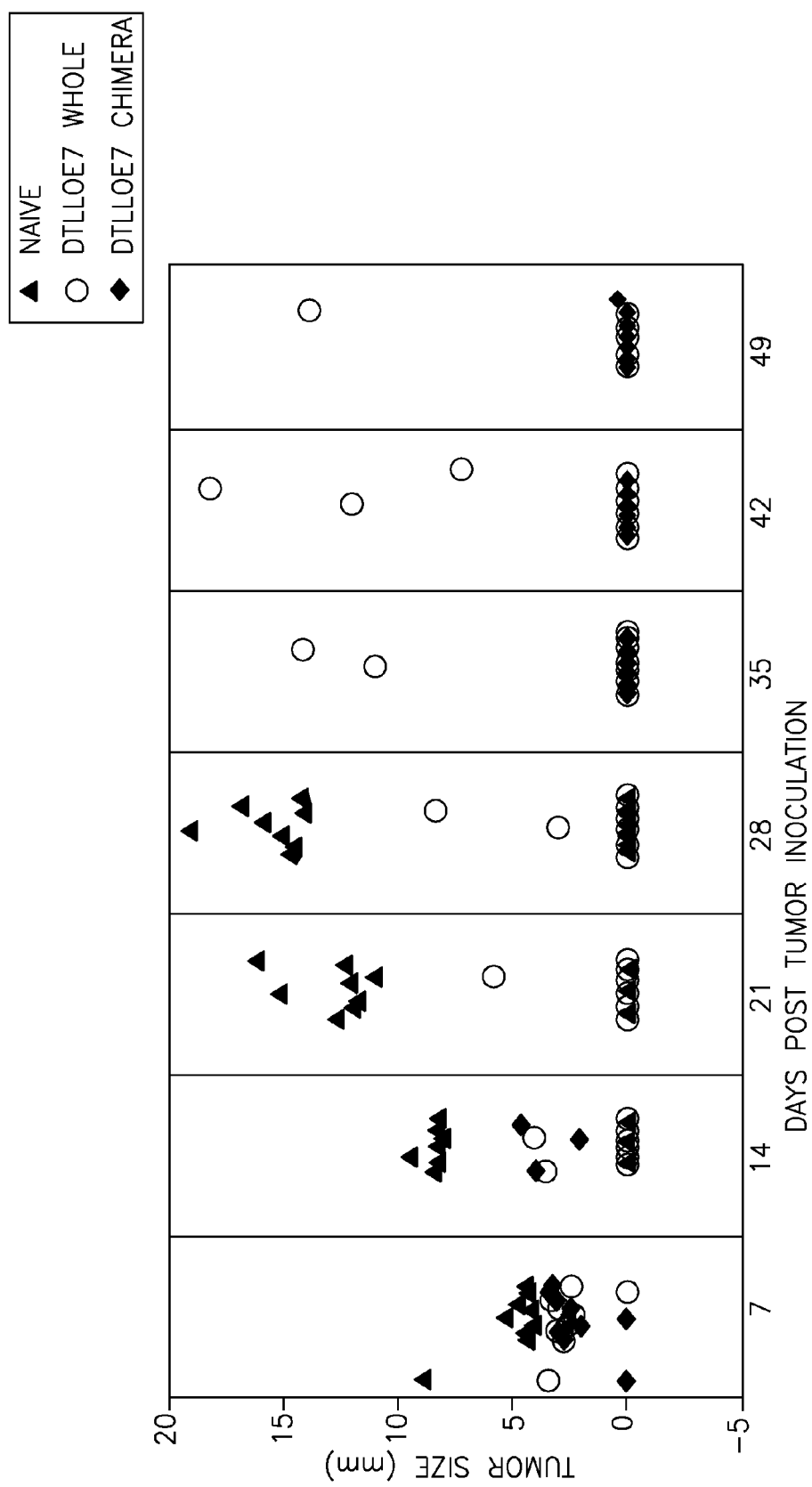
FIG. 29. The ability of recombinant detoxified LLOE7 (rDTLLO-E7; whole sequence) and rDTLLO-E7 (chimera) to impact on TC-1 growth.
Figure 30:
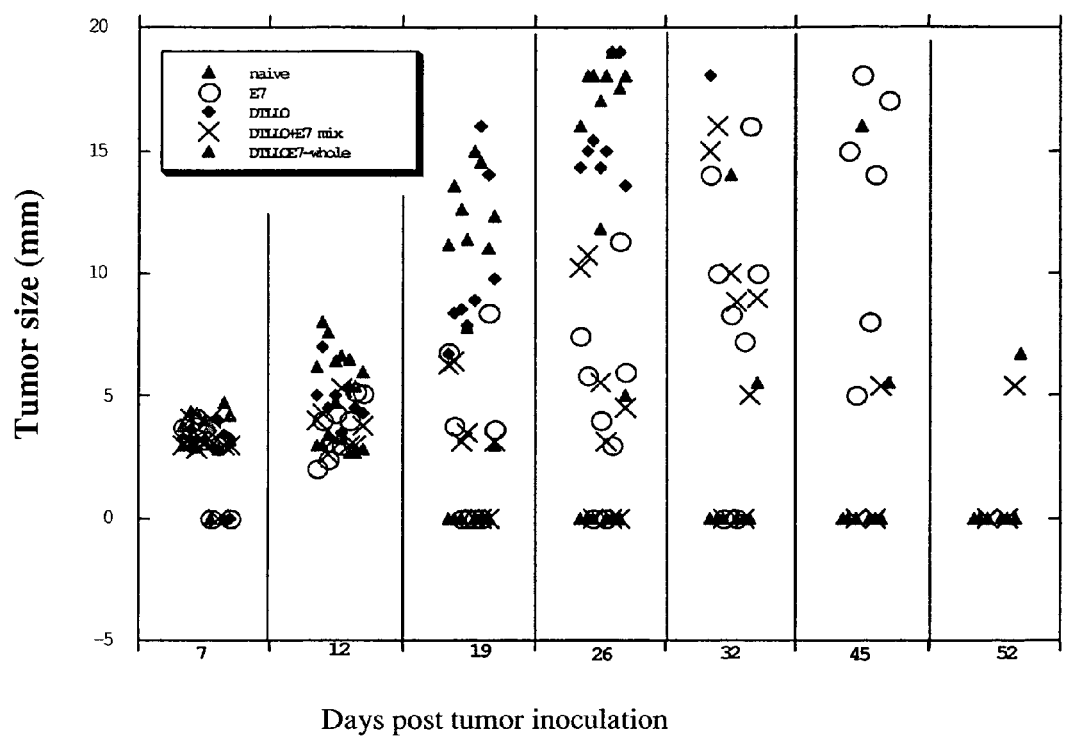
FIG. 30. TC-1 tumor regression after immunization with rE7, rLLO, rLLO+E7 and rDTLLO-E7.
Figure 31:
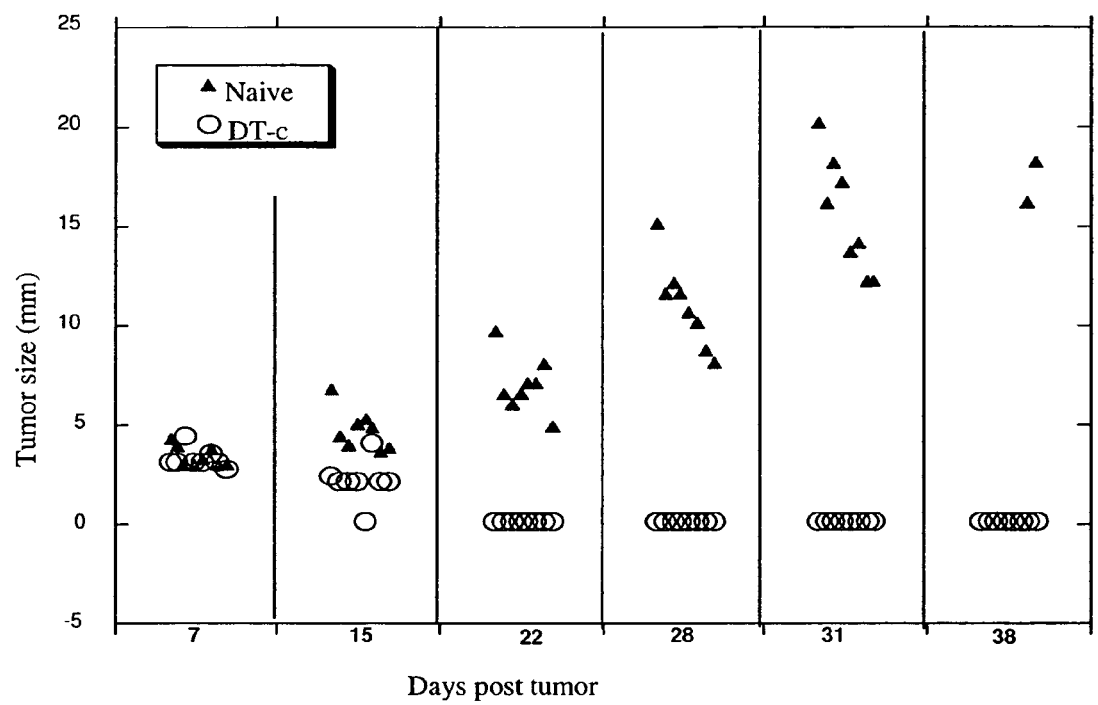
FIG. 31. TC-1 tumor regression after immunization with rDTLLO-chimera.
Figure 32:
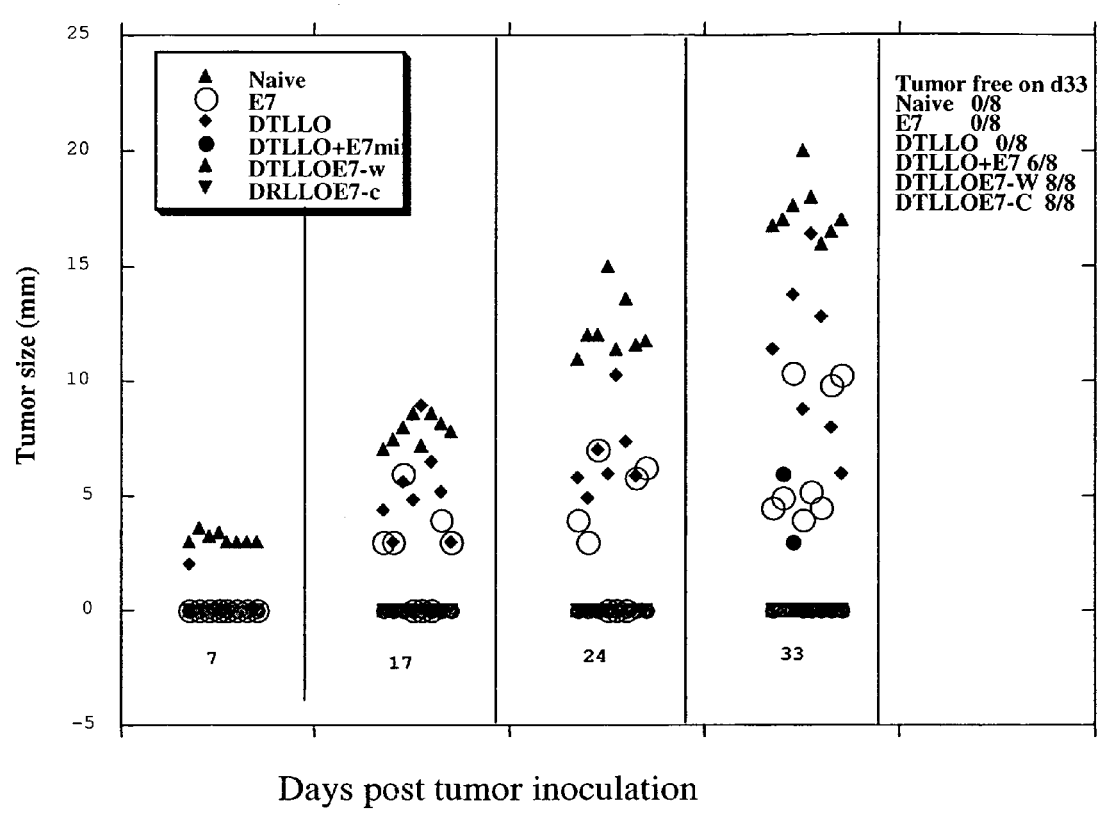
FIG. 32. TC-1 tumor regression after immunization with rE7, rDTLLO, rDTLLO+rE7, rDTLLO-E7 and rDT-LLO-E7-chimera.

DTLLO-E7 whole and DTLLO-E7 chimera delayed the appearance of tumors compared to naïve controls (FIG. 29). DTLLO-E7 chimera demonstrated a stronger inhibition of tumor growth (8/8 tumor free at day 49 post-tumor inoculation) compared to DTLLO-E7 whole (5/8 tumor free at day 49 post tumor inoculation; FIG. 29 and Table 3). Comparable results were obtained in repeated experiments (FIGS. 30-32).

Example 18

TC-1 Tumor Regression after Immunization with ACTA, E7, or ACTA+E7 Mixed or Genetically Fused ACTA-E7

Vaccine Preparation.

Recombinant E7 and Recombinant ActA or ActA-E7 fusion protein were purified on a nickel column and LPS was removed on a Norgen Proteospin column according to the manufacturer's directions.

Tumor Regression $1 \times 10^5$ TC-1 were established on the flank of each mouse, and on days 6 and 13, the mice were immunized subcutaneously along the back with 250 μl of PBS containing E7 (50 μg), ActA (200 μg) mixed with E7 (50 μg), genetically fused ActA-E7 (250 μg), or PBS only (naïve).

Results

Figure 33:
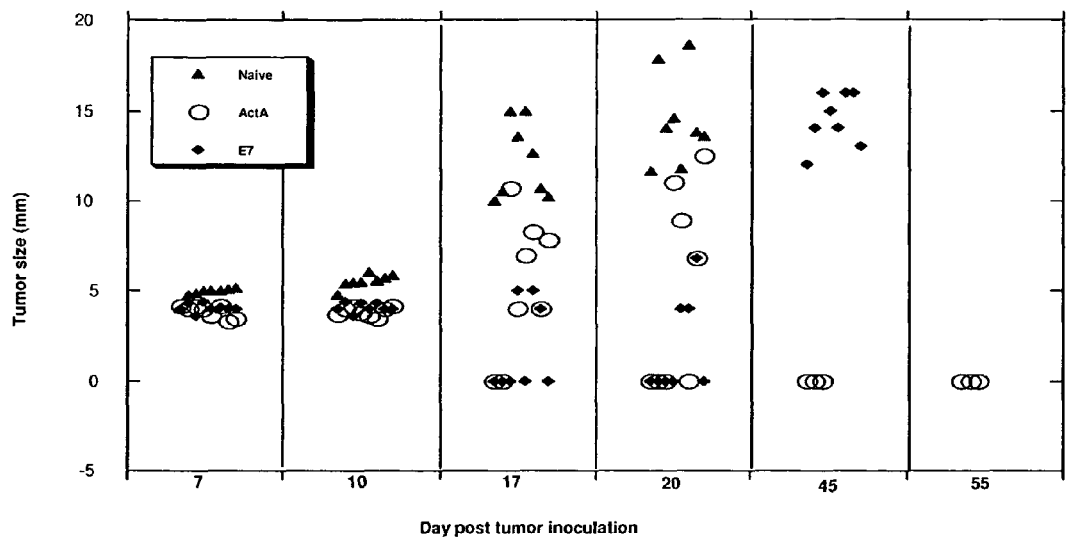
FIG. 33. TC-1 tumor regression immunized with ActA–E7 and E7 protein.
Figure 34:
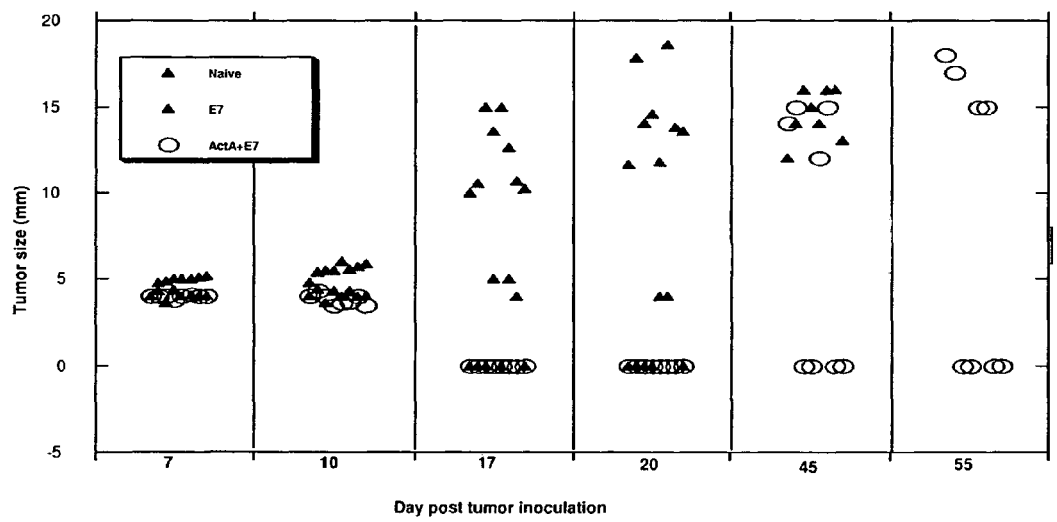
FIG. 34. TC-1 tumor regression immunized with ActA+E7 and E7 protein.
Figure 35:
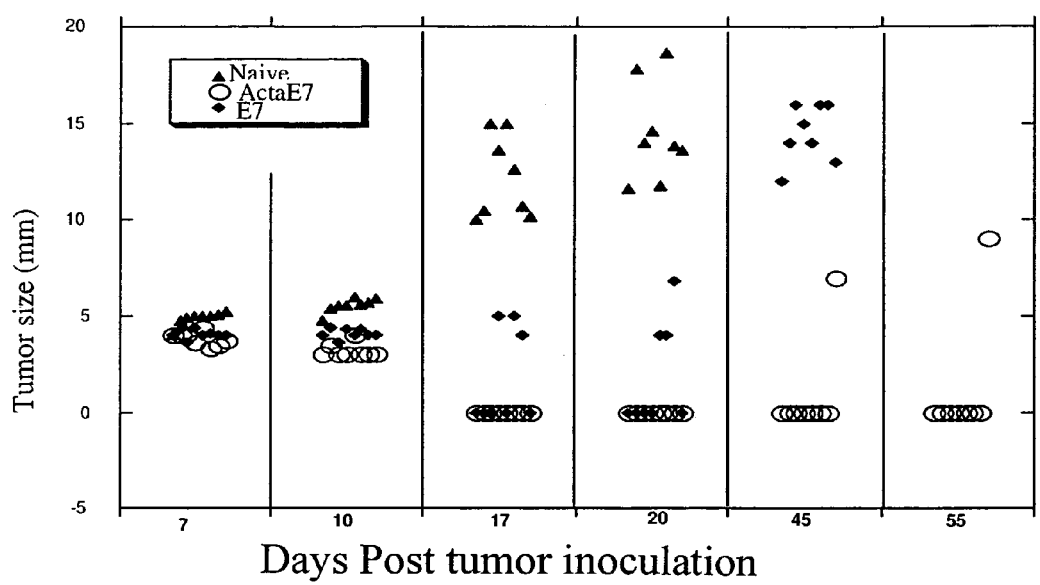
FIG. 35. TC-1 tumor regression immunized with ActA and E7 protein.
Figure 36:
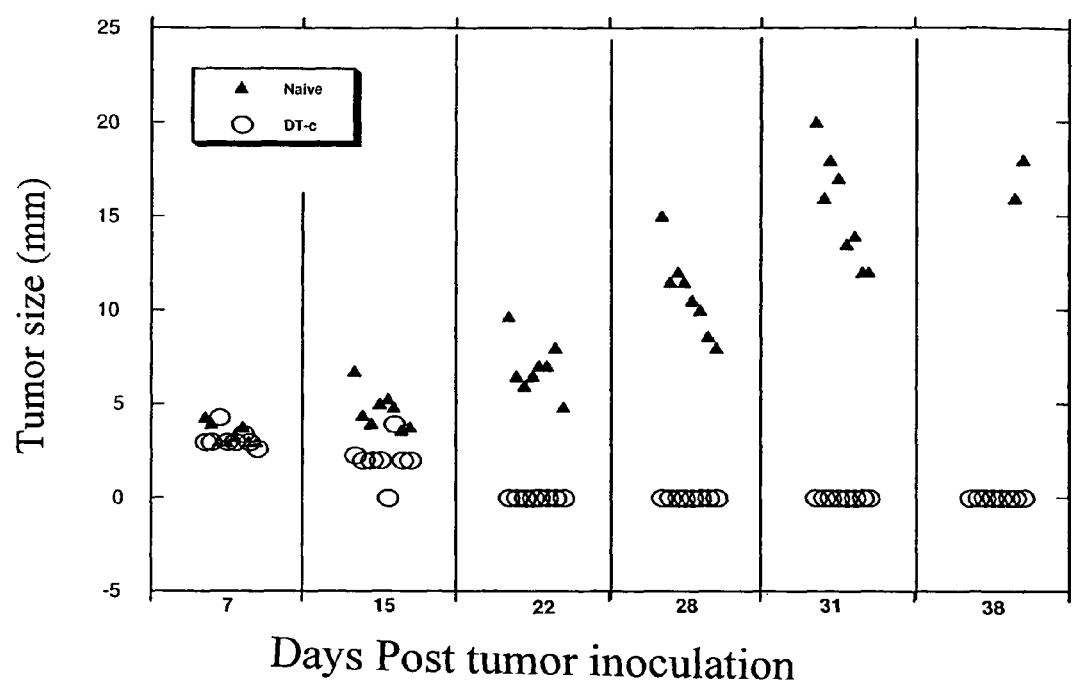
FIG. 36. TC-1 tumor regression after immunization with rDTLLO-chimera

Mice immunized with ActA alone, E7 alone, ActA-E7, or ActA+E7 demonstrated an increased latency to onset of tumors compared to controls (FIGS. 33-35). Mice immunized with ActA-E7 (genetically fused) demonstrated strong tumor regression, with 7/8 mice tumor free on day 55 following immunization (FIG. 33, Table 3). Mice immunized with ActA+E7 demonstrated superior tumor regression compared to E7 and naïve controls, with 7/8 mice tumor free on day 55 following tumor inoculation (FIG. 34, Table 3). Mice immunized with ActA alone demonstrated superior tumor regression compared to mice immunized with E7 or PBS-injected controls (3/8 mice tumor free following immunization compared to none of the mice in the E7 or naïve groups; FIG. 35, Table 3).

TABLE 3

Summary of rates of tumor-free mice: Examples 17-18

| Vaccine | FIG. | # mice tumor free | Comments |
|---|---|---|---|
| LLO-E7 | 27 | 4/8 | Chemically conjugated |
| LLO + E7 | 27 | 2/8 | Mixed |
| E7 | 28 | 1/8 | |
| LLO | 28 | 0/8 | |
| LLO-E7 | 29 | 5/8 | Genetically fused |
| LLO-E7-chimera | 29 | 7/8 | Genetically replaced |
| E7 | 30 | 0/8 | |
| LLO | 30 | 0/8 | |
| LLO-E7 | 30 | 6/8 | Genetically fused |
| LLO + E7 | 30 | 2/8 | Mixed |
| LLO-E7-chimera | 31 | 8/8 | Genetically replaced |
| E7 | 32 | 0/8 | Day 33 |
| LLO | 32 | 0/8 | Day 33 |
| LLO-E7 | 32 | 8/8 | Day 33 |
| LLO + E7 | 32 | 6/8 | Day 33 |
| LLO-E7-chimera | 32 | 8/8 | Day 33 |
| ActA-E7 | 7 | 7/8 | Old expression system |
| ActA + E7 | 7 | 4/8 | |
| E7 | 7 | 0/8 | |
| ActA | 7 | 3/8 | |

Example 19

DETOXLLO Induces Cytokine mRNA Expression and Cytokine Secretion by Bone Marrow (BM) Macrophages 8e5 Day 7 BMDCs were thawed overnight at 37° C. in RF10 media. Next, BMDCs were centrifugated and resuspended in 1 mL of fresh RF10 at 37° C. for 1 hr. BMDCs were treated w/40 mcg/mL of LLOE7 and molar equivalents of E7 and LLO (or with PBS as negative control or 1 mcg/mL LPS as positive control). After 2 and 24 hrs, cells were collected by centrifugation and media saved for ELISA and analyzed for cytokine secretion. RNA was extracted from cells and converted to cDNA. cDNA was then subjected to qPCR analysis with primers for various cytokines, and cytokine mRNA expression levels were assessed.

Results

Figure 37A:
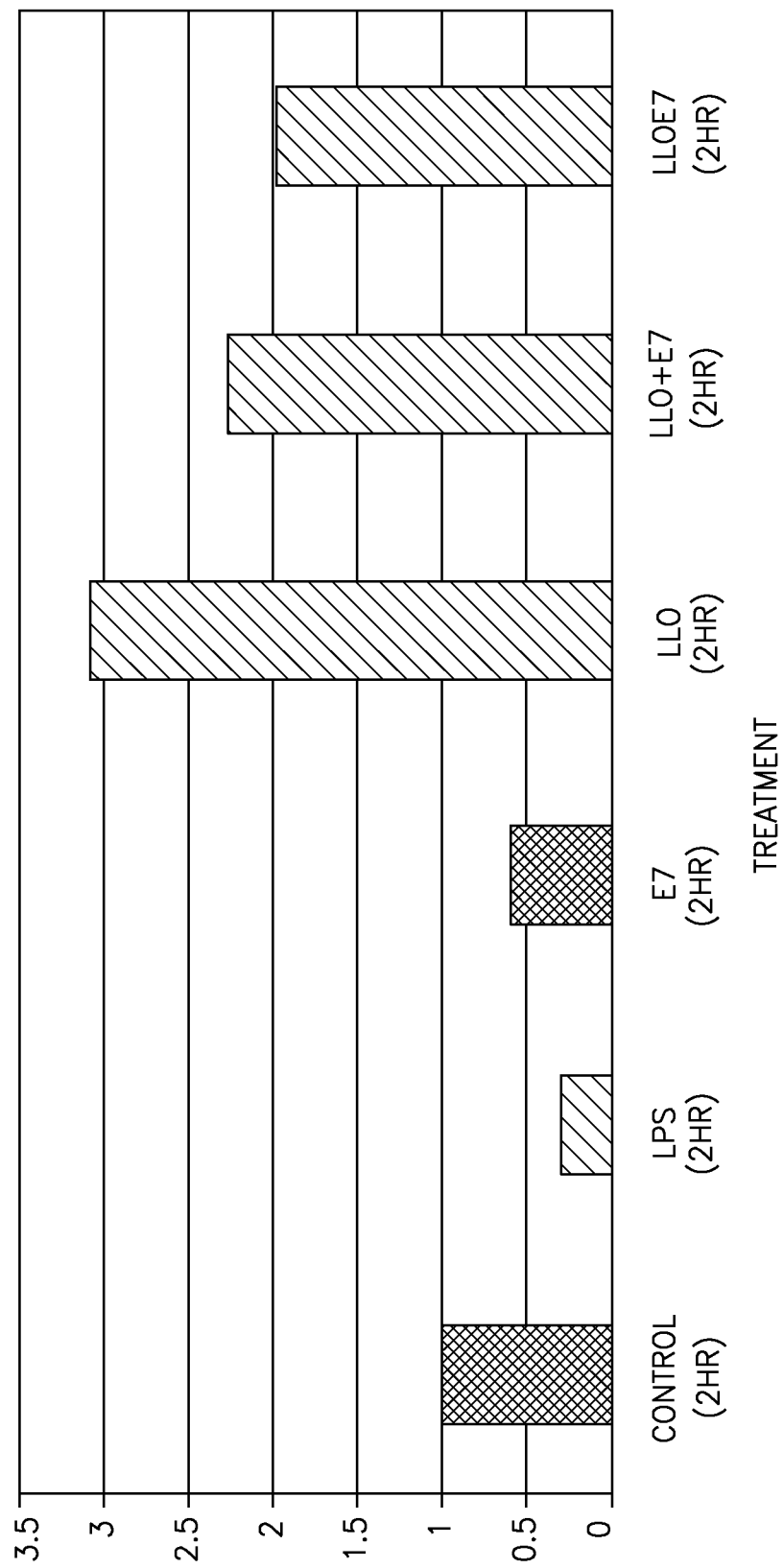
FIG. 37. DetoxLLO Induces Cytokine mRNA expression by Bone Marrow (BM) Macrophages. 8e5 Day 7 BMDCs were thawed overnight at 37° C. in RF10 media. Next, BMDCs were centrifuged and resuspended in 1 mL of fresh RF10 at 37° C. for 1 hr. BMDCs were treated w/40 mcg/mL of LLOE7 and molar equivalents of E7 and LLO (or with PBS as negative control or 1 mcg/mL LPS as positive control). After 2 and 24 hrs, cells were collected by centrifugation and media saved for ELISA. RNA was extracted from cells and converted to cDNA. cDNA was then subjected to qPCR analysis with primers for various cytokines.
Figure 37B:
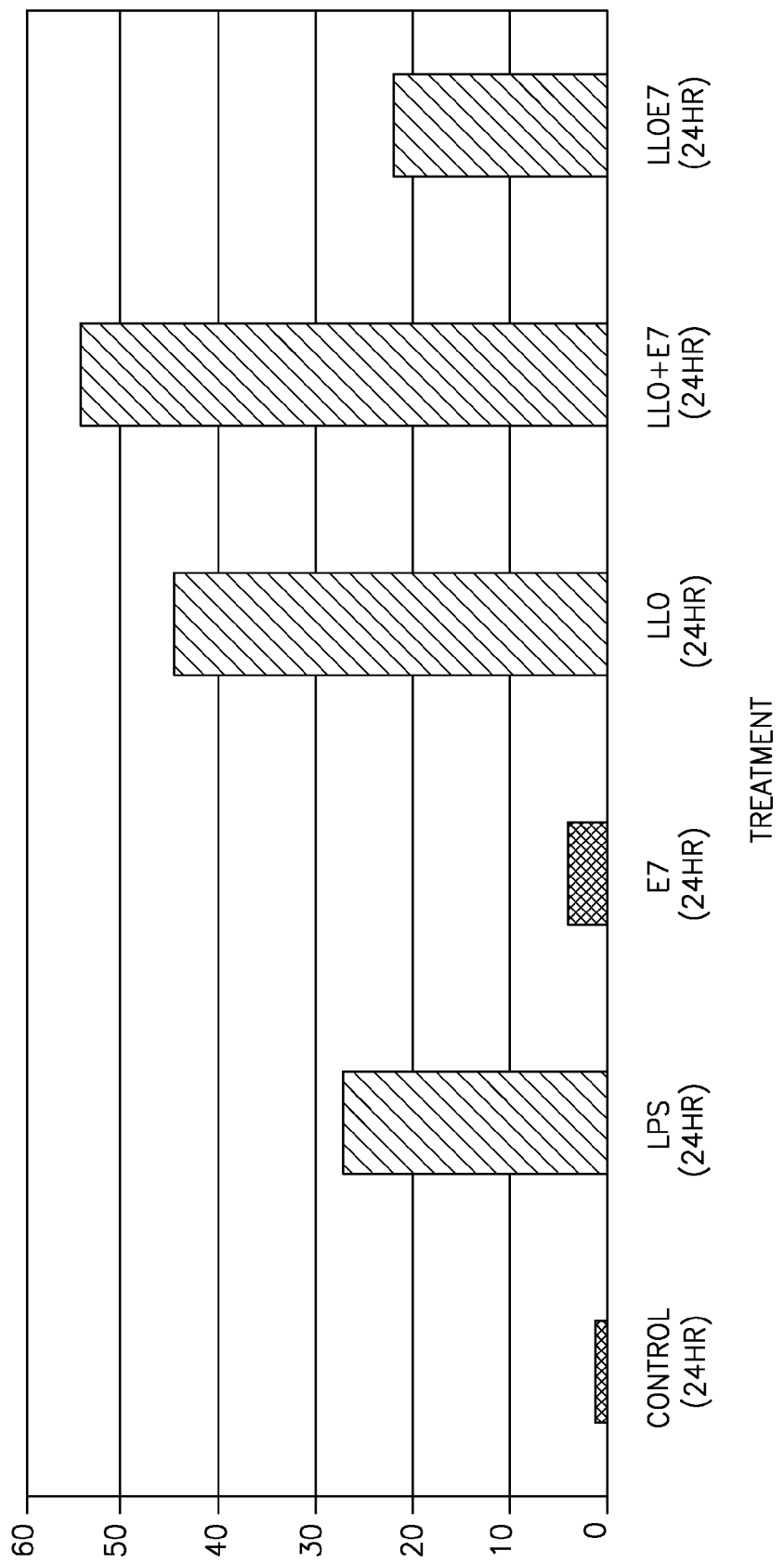
Figure 37C:
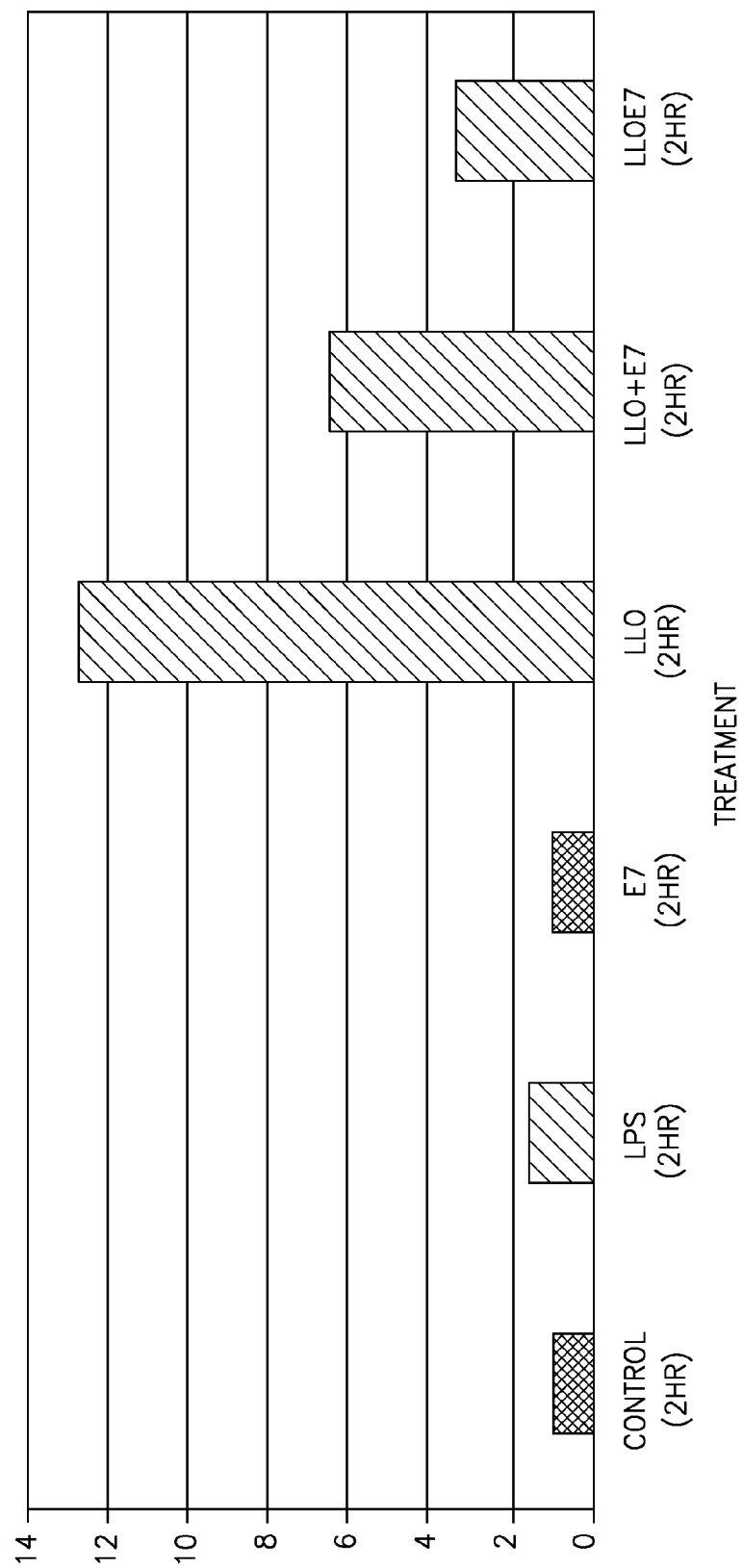
Figure 37D:
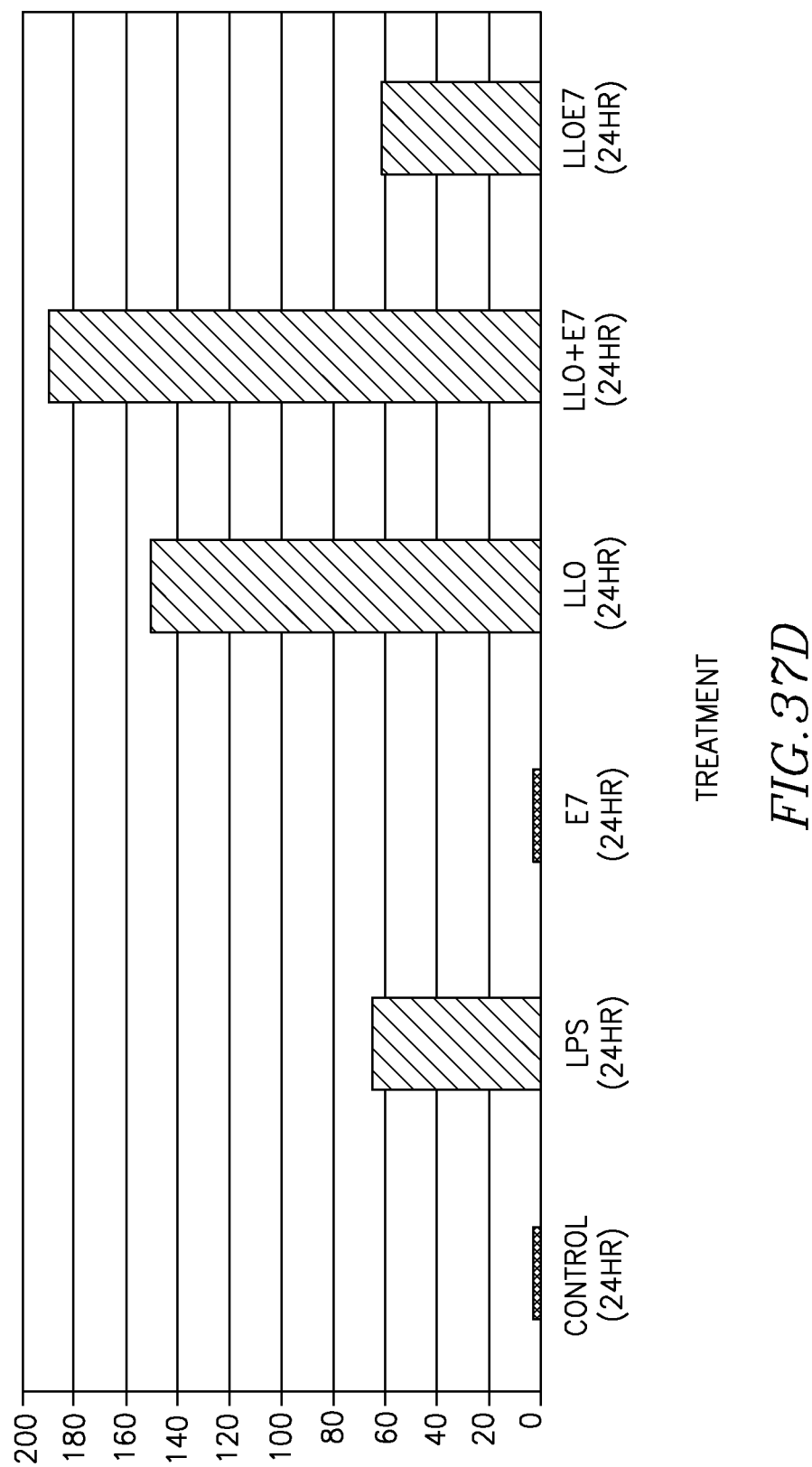
Figure 37E:
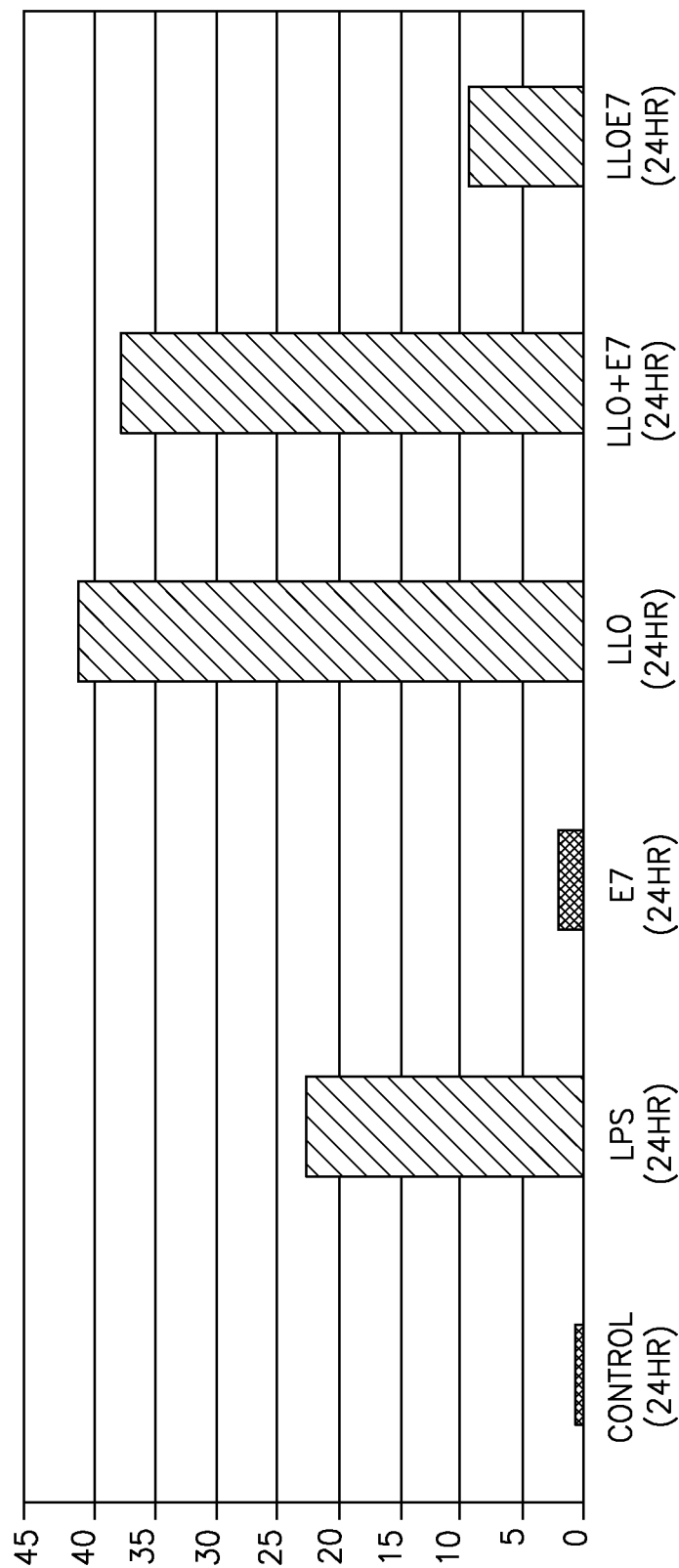
Figure 38A:
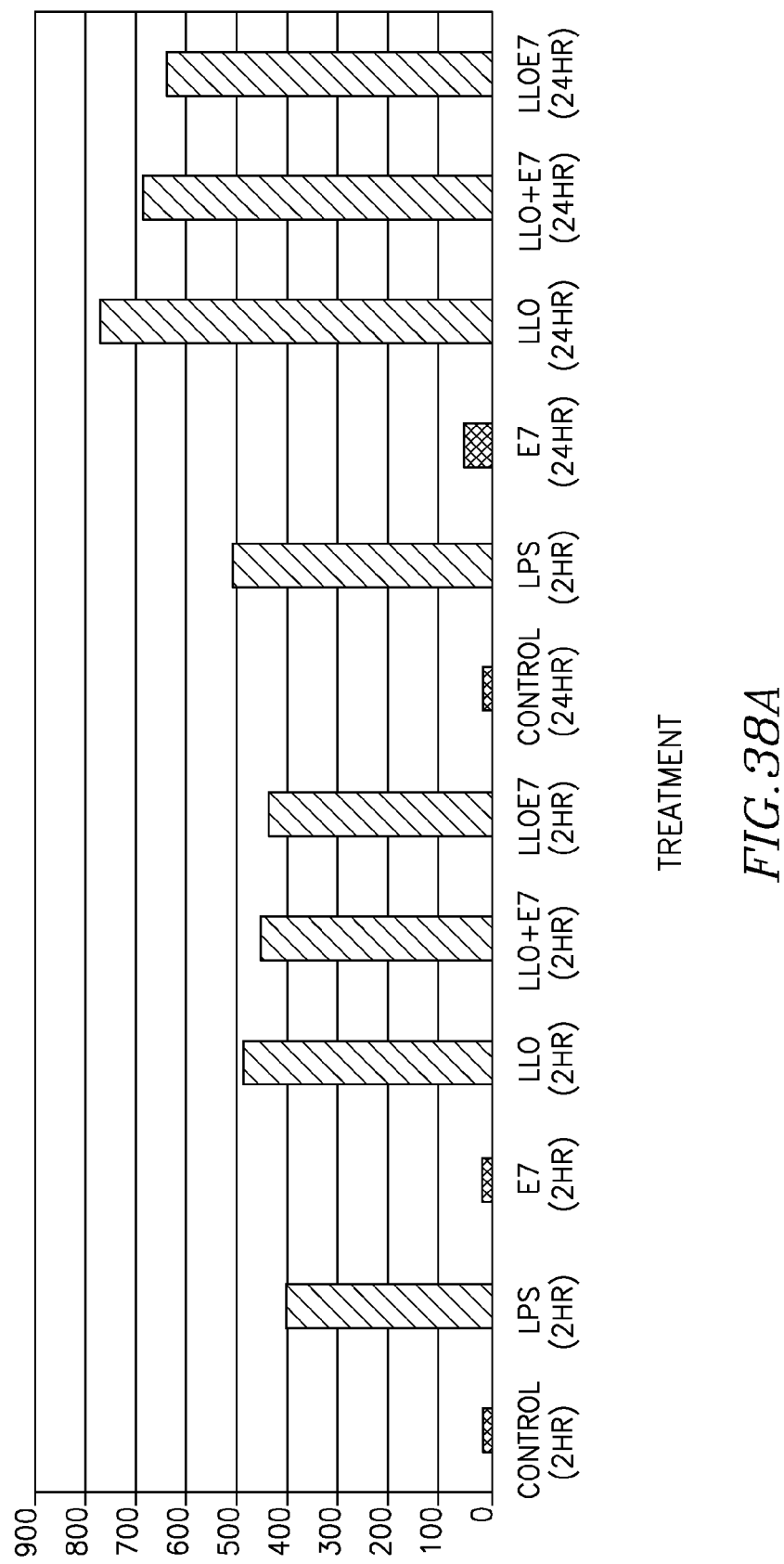
FIG. 38. Detox LLO Induces Cytokine Secretion by BM Macrophages. Same treatment protocol as described for FIG. 36, except media was subjected to ELISA analysis after treatments.
Figure 38B:
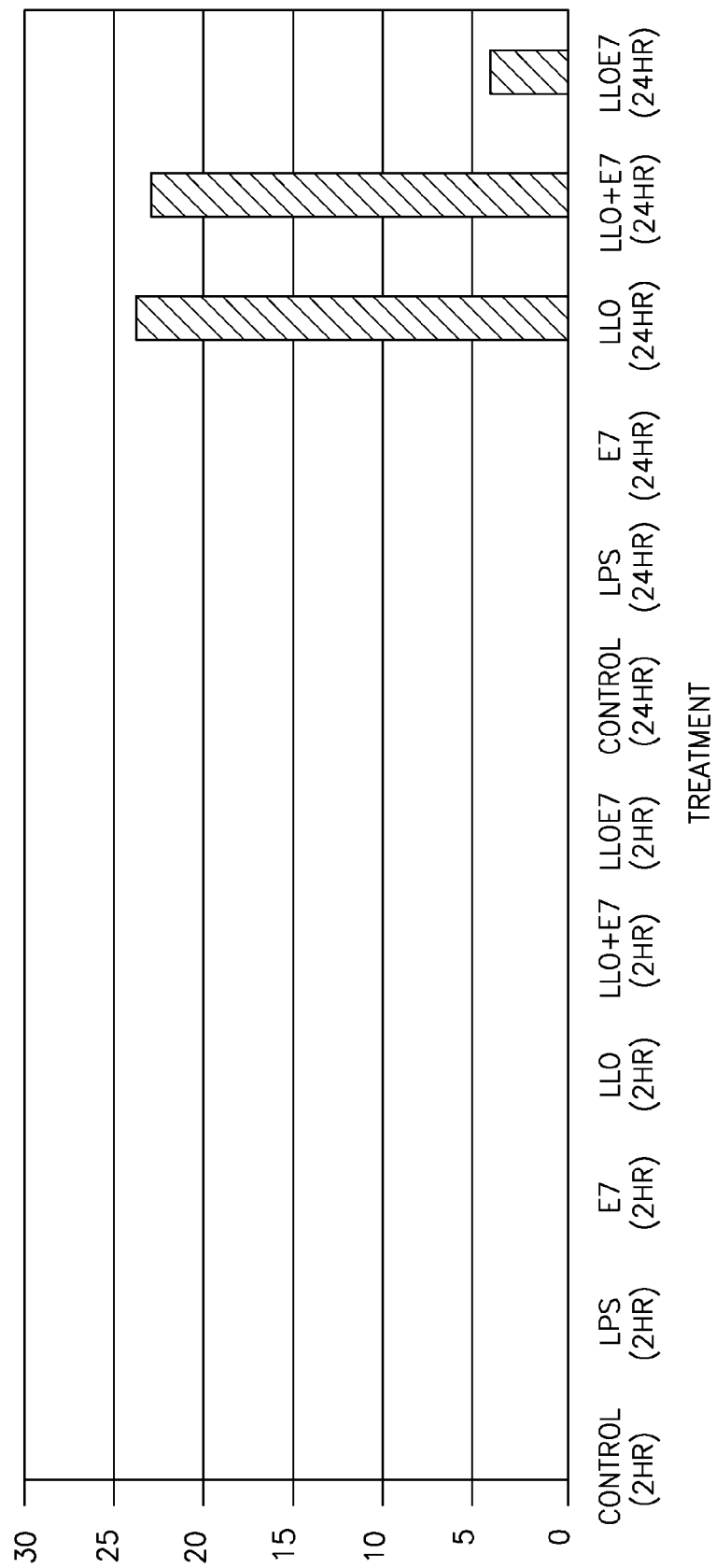

DetoxLLO, administered alone, with E7, or fused to E7, induced TNF-α (FIGS. 37A-B), IL-12 (FIGS. 37C-D), and ISG15 (FIG. 37E) mRNA expression by BM Macrophages after 2 (FIGS. 37A and 37C) and 24 hours (FIGS. 37B, 37D, and 37E) compared to controls. Similarly, detoxLLO induced secretion of TNF-α (FIG. 38A) and EL-12 (FIG. 38B) by BM Macrophages after 2 and 24 hours.

Example 20

Detox LLO Upregulates Dendritic Cell Maturation Markers

Bone marrow was collected from the femurs of C57BL/6 mice at 6-8 wk of age. Bone marrow cells from four mice were pooled, and cells were cultured in RPMI 1640 medium containing 10% FCS and 100 U/ml penicillin/streptomycin in 100×15-mm petri dishes. After 2-h incubation at 37° C. in 10% $CO_2$, nonadherent cells were removed by washing with warm medium. The remaining adherent cells were collected by scraping with a sterile cell scraper. After washing, the cells were adjusted to 0.5×10^6/ml, and were placed in a 24-well plate with 20 ng/ml recombinant murine GM-CSF (R&D Systems, Minneapolis, Minn.). The medium was changed every 2-3 days. After 7 days of culture, nonadherent cells were collected, washed, and used in the experiments.

These bone marrow derived dendritic cells (day 7) were plated at 2×10^6/ml and then pulsed with either E7 (10 mcg/ml), LLO (40 mcg/ml), or LLOE7 (50 mcg/ml) plus LLO (40 mcg/ml) for 16 hr in 37° C., 5% $CO_2$. The phenotype of the DCs obtained using this protocol were analyzed by FACS analysis. DCs were harvested after 16 h as described above. Cells were stained with APC-labeled mAbs specific for mouse CD11c, or FITC-labeled mAb specific for mouse CD86, MHC class II, CD40. Isotype-matched mouse IgG was used as a negative control and subtracted from the background. Cells were incubated with mAbs for 30 min at 4° C. in the dark. Following two washes with PBS, 10 μl of 7AAD (Beckman Coulter, Marseille, France) was added 10 min before cells were analyzed on a FACS flow cytometer.

Results

Figure 39A:
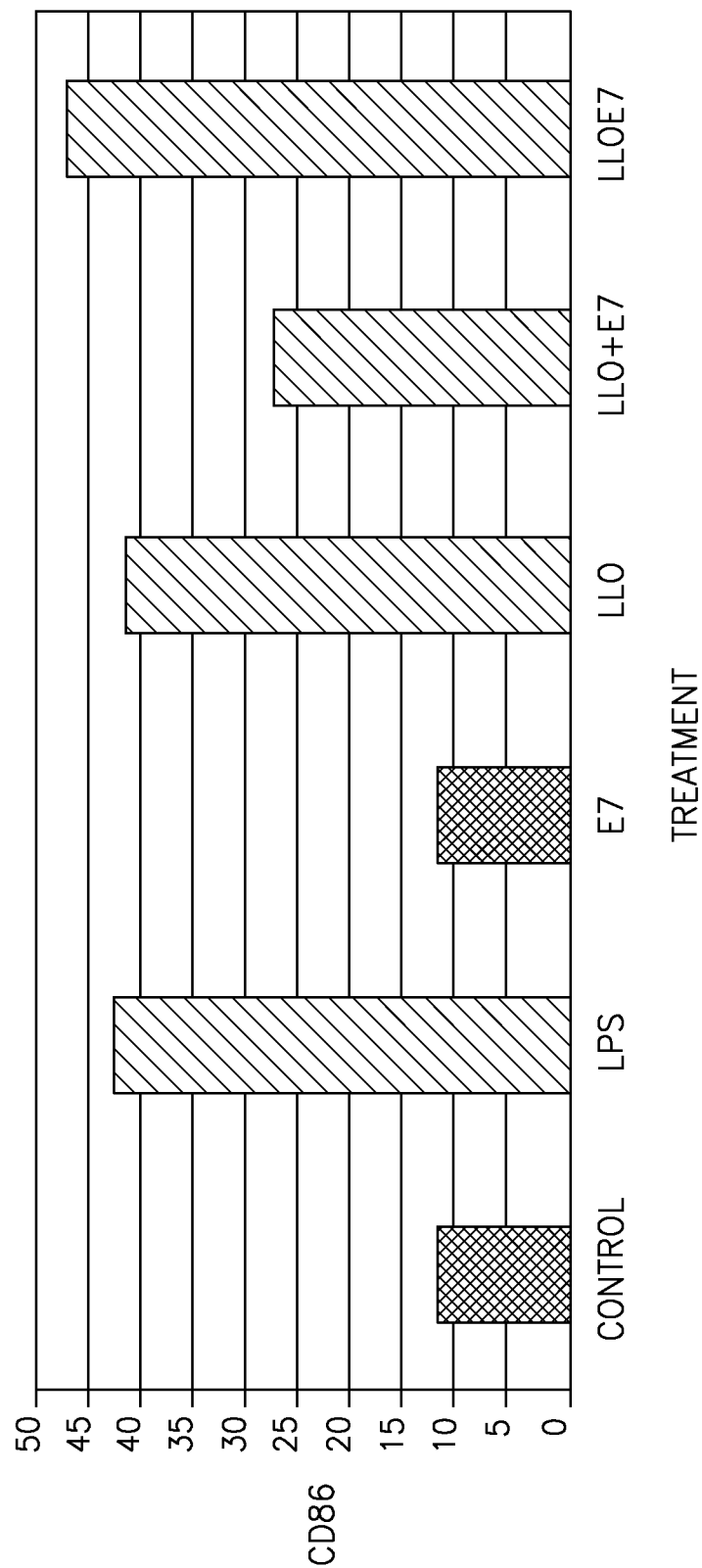
FIG. 39. Detox LLO Upregulates DC Maturation Markers. Bone marrow was collected from the femurs of C57BL/6 mice at 6-8 wk of age. After 7 days of culture, nonadherent cells were collected, washed, and plated at $2 \times 10^{6}$/ml and then pulsed with either E7 (10 mcg/ml), LLO (40 mcg/ml), or LLOE7 (50 mcg/ml) plus LLO (40 mcg/ml) for 16 hr in 37° C., 5% $CO_2$. Cells were stained with APC-labeled mAbs specific for mouse CD11c, or FITC-labeled mAb specific for mouse CD86, MHC class II, CD40. Isotype-matched mouse IgG was used as a negative control and subtracted from the background. Cells were incubated with mAbs for 30 min at 4° C. in the dark. Following two washes with PBS, 10 μl of 7AAD (Beckman Coulter, Marseille, France) was added 10 min before cells were analyzed on a FACS flow cytometer. The live cell population is shown as percentage of CD11c positive cells.
Figure 39B:
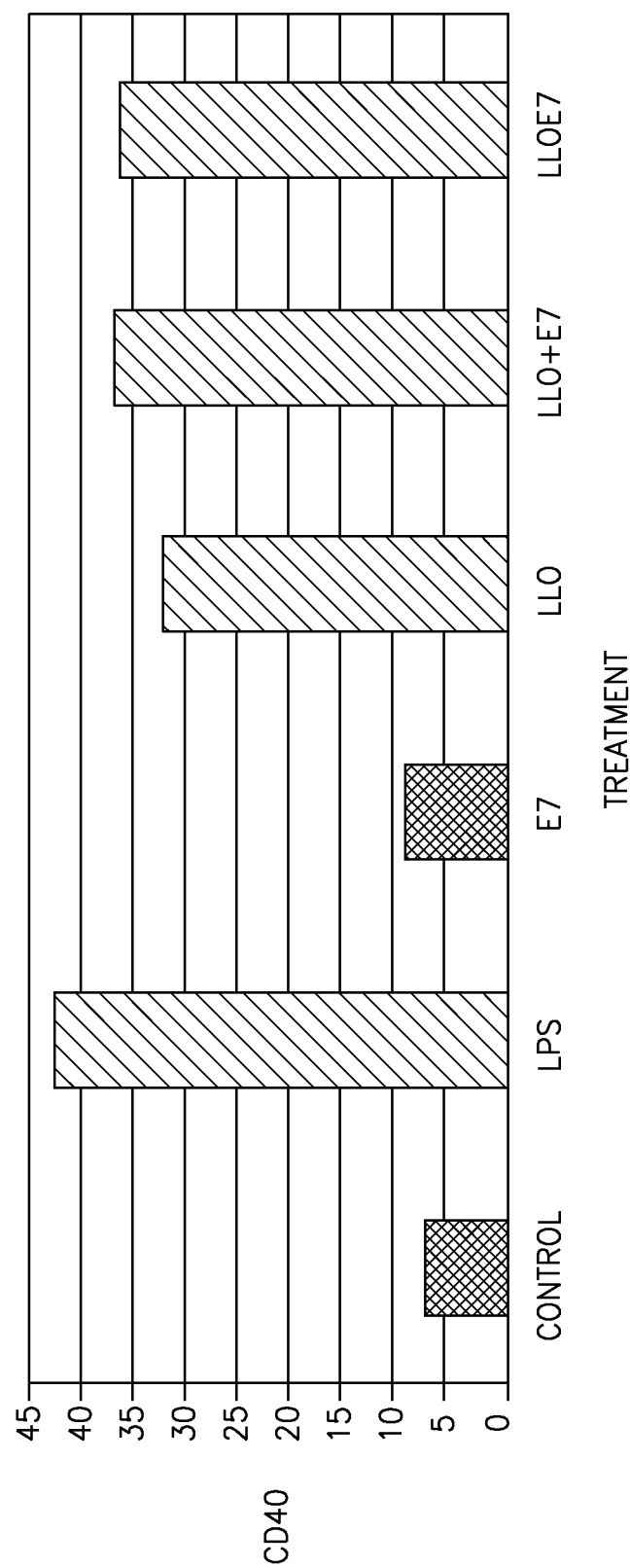
Figure 39C:
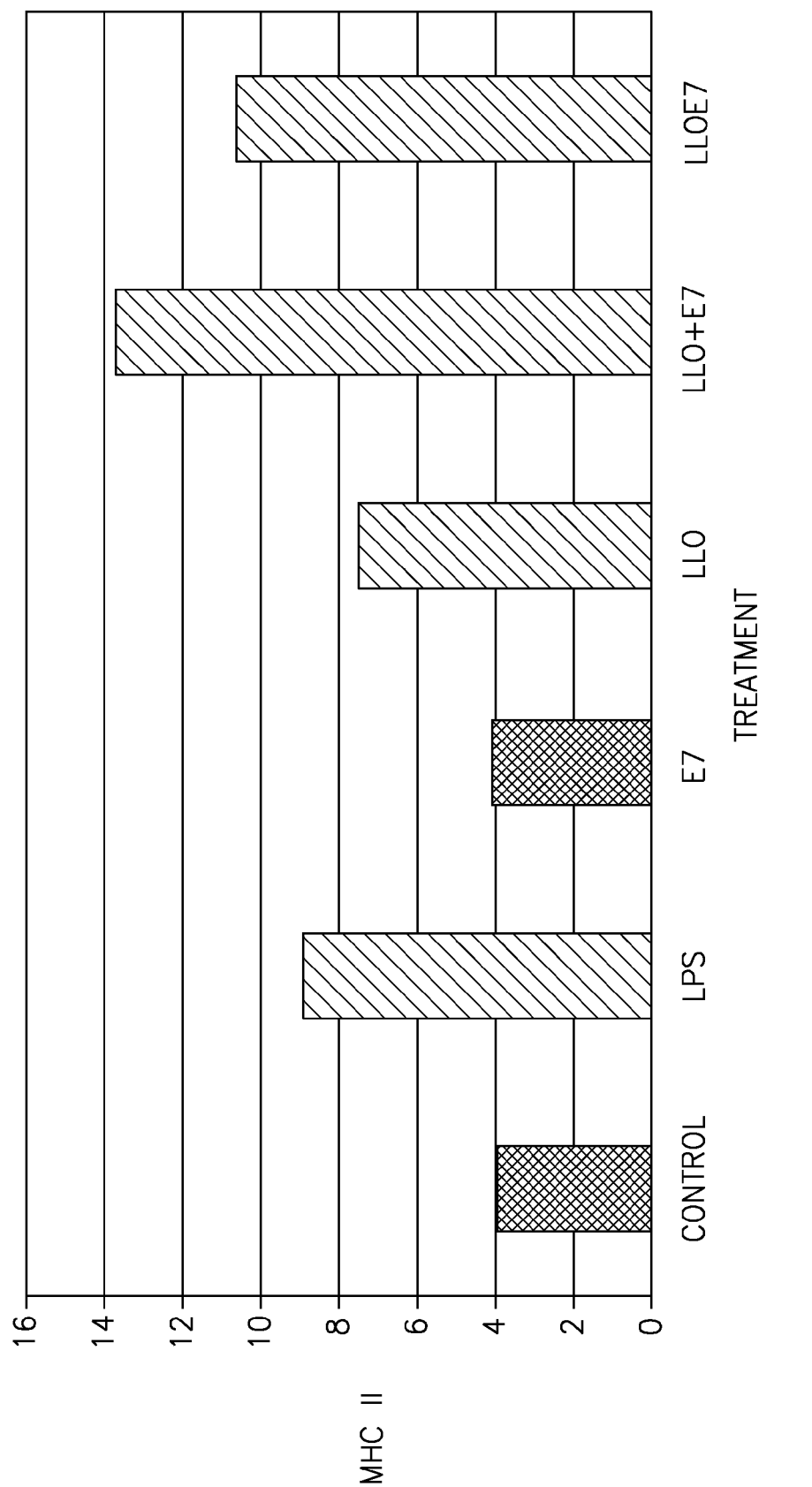

Administration of detoxLLO (in the LLO, LLO+E7 and LLOE7 groups) upregulated CD86, CD40, and MHCII (FIG. 39) compared to controls.

Example 21

Regression of TC-1 Tumors by LLO-Fused E7

2×10^5 TC-1 tumor cells were established s.c in 8 mice per vaccine group. Mice were immunized s.c. with 50 μg of E7, 200 μg of LLO, 250 μg of LLOE7, or 50 μg of E7 plus 200 μg of LLO on Days 3 and 10.

Results

Figure 40:
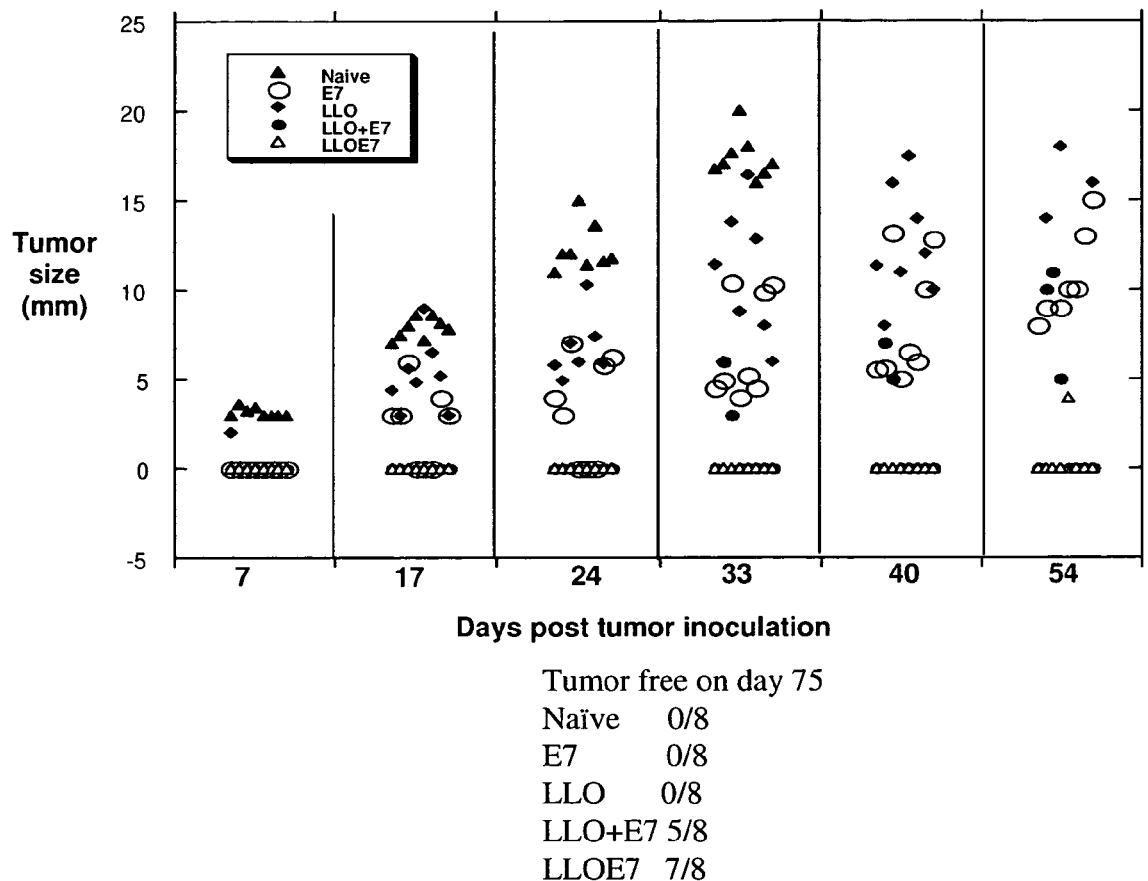
FIG. 40. Regression of TC-1 Tumors by LLO-fused E7. $2 \times 10^{5}$ TC-1 tumor cells were established s.c in 8 mice per vaccine group. Mice were immunized s.c. with 50 μg of E7, 200 μg of LLO, 250 μg of LLOE7, or 50 μg of E7 plus 200 μg of LLO on Days 3 and 10.

Mice administered conjugated LLO-E7 demonstrated an attenuated increase of tumor size compared to naïve controls. Mice administered LLO alone or LLO+E7 mixed also demonstrated an attenuated increase in tumor size (FIG. 40). While all naïve animals had tumors by day 75, 5/8 mice treated with LLO+E7 and 7/8 mice treated with LLOE7 were tumor free on day 75 (FIG. 40).

Example 22

Nuclear Translocation of NF-Kappa-B after Stimulation with DT.LLO

Figure 41:
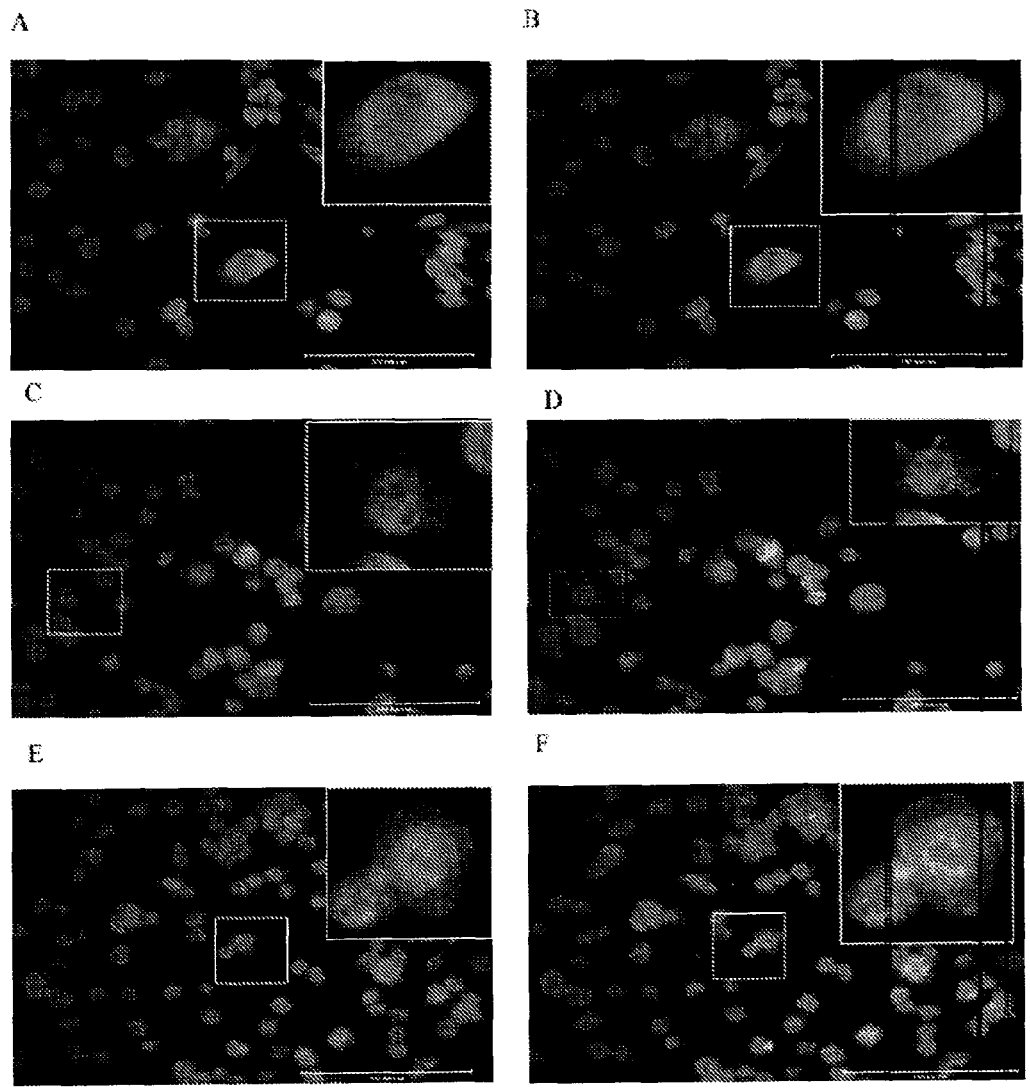
FIG. 41. Nuclear translocation of NFkappaB after stimulation with Dt.LLO. J774 macrophage cell line used as model system for antigen presenting cells (APCs). $5 \times 10^{5}$ cells per well (6 well dish) were plated in a total volume 1 ml. Cells were stained with anti-NF-κB (P65)-FITC (green fluorescence) and DAPI for nucleus (blue fluorescence). In B, D, and F, cells were also stained after 24 hours with anti-CD11B-PE (M1/170, eBioscence). The fluorescent micrograph is shown at 40× magnification. NF-kappaB is located in the cytoplasm after treatment of cells with media alone (no activation) (A). Media-treated cells demonstrate weak Cd11b staining (B). After overnight (24 hr) stimulation with Dt.LLO (30 mcg), NFkappaB moved out of the cytoplasm into the nucleus (C) and there is an increase in CD11b staining (D). Similarly, after overnight stimulation (24 hr) with LPS (10 mcg/ml, positive control), NFkappaB was translocated to the nucleus (E), which is more discernible with the halo made by the increased CD11b+ staining of the plasma membrane (F).

J774 macrophage cell line used as model system for antigen presenting cells (APCs). 5×10^5 cells per well (6 well dish) were plated in a total volume 1 ml. Cells were stained with anti-NF-κB (P65)-FITC (green fluorescence) and DAPI for nucleus (blue fluorescence). In FIGS. 41B, D, and F, cells were also stained after 24 hours with anti-CD11B-PE (M1/170, eBioscence), which is expressed on the cell surface of macrophage cells and is involved in adhesive cell interactions.

Results

NF-kappaB is located in the cytoplasm after treatment of cells with media alone (no activation) (FIG. 41A). Media-treated cells demonstrate weak Cd11b staining (FIG. 41B). After overnight (24 hr) stimulation with Dt.LLO (30 mcg), NFkappaB moved out of the cytoplasm into the nucleus (FIG. 41C) and there was an increase in CD11b staining (FIG. 41D). Similarly, after overnight stimulation (24 hr) with LPS (10 mcg/ml, positive control), NFkappaB was translocated to the nucleus (FIG. 41E), which is emphasized by the increased CD11b+ staining of the plasma membrane (FIG. 41F).

Thus, in one embodiment, the data demonstrate the ability of detox LLO to stimulate innate immunity via macrophages and DCs.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A recombinant protein comprising a listeriolysin O (LLO) protein comprising a mutation in a cholesterol-binding domain (CBD), wherein said mutation comprises a mutation of residue C484, W491, and W492 of said LLO protein set forth in SEQ ID NO: 37.

2. The recombinant protein of claim 1, wherein said LLO protein comprises a deletion of the signal peptide sequence thereof.

3. The recombinant protein of claim 1, wherein said LLO protein comprises the signal peptide sequence thereof.

4. The recombinant protein of claim 1, wherein said recombinant protein further comprises a heterologous peptide of interest.

5. The recombinant protein of claim 4, wherein said heterologous peptide of interest is an antigenic peptide.

6. The recombinant protein of claim 5, wherein said antigenic peptide is a B-cell receptor (BCR) peptide.

7. The recombinant protein of claim 5, wherein said antigenic peptide is a Human Papilloma Virus (HPV)-16-E6, HPV-16-E7, HPV-18-E6, HPV-18-E7, a Her/2-neu antigen, a Prostate Specific Antigen (PSA), Prostate Stem Cell Antigen (PSCA), a Stratum Corneum Chymotryptic Enzyme (SCCE) antigen, Wilms tumor antigen 1 (WT-1), human telomerase reverse transcriptase (hTERT), Proteinase 3, Tyrosinase Related Protein 2 (TRP2), High Molecular Weight Melanoma Associated Antigen (HMW-MAA), synovial sarcoma, X (SSX)-2, carcinoembryonic antigen (CEA), MAGE-A, interleukin-13 Receptor alpha (IL13-R alpha), Carbonic anhydrase IX (CAIX), survivin, GP100, or Testisin.

8. An immunogenic composition comprising the recombinant protein of claim 4 and an adjuvant.

9. The immunogenic composition of claim 8, wherein said adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide.

10. An immunogenic composition comprising the recombinant protein of claim 1 and a heterologous peptide of interest, wherein said recombinant protein is not covalently bound to said heterologous peptide of interest.

11. The immunogenic composition of claim 10 further comprising an adjuvant.

12. The immunogenic composition of claim 11, wherein said adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide.

13. A method for inducing an immune response in a subject, comprising administering to said subject the recombinant protein of claim 5, thereby inducing an immune response against said antigenic peptide.

14. A method for inducing an immune response in a subject, comprising administering to said subject the composition of claim 10, thereby inducing an immune response against said heterologous peptide of interest.

15. A method for inducing an immune response in a subject against a B-cell receptor (BCR)-expressing lymphoma, the method comprising the step of administering to said subject the recombinant protein of claim 6, thereby inducing an immune response against a BCR-expressing lymphoma.

16. The recombinant protein of claim 1, wherein said mutation is a deletion mutation, a point mutation or a substitution mutation.

17. The recombinant protein of claim 1, wherein said recombinant protein exhibits a greater than 100-fold reduction in hemolytic activity relative to wild-type LLO.

* * * * *